(12) United States Patent
Shipps, Jr. et al.

(10) Patent No.: US 8,318,735 B2
(45) Date of Patent: Nov. 27, 2012

(54) 2-AMINOTHIAZOLE-4-CARBOXYLIC AMIDES AS PROTEIN KINASE INHIBITORS

(75) Inventors: Gerald W. Shipps, Jr., Stoneham, MA (US); Cliff C. Cheng, Cambridge, MA (US); Xiaohua Huang, Malden, MA (US); Thierry O. Fischmann, Scotch Plains, NJ (US); Jose S. Duca, Cranford, NJ (US); Matthew Richards, Somerville, MA (US); Hongbo Zeng, Westford, MA (US); Binyuan Sun, Chestnut Hill, MA (US); Panduranga Adulla Reddy, Walpole, MA (US); Lianyun Zhao, Burlington, MA (US); Shuyi Tang, Quincy, MA (US); Tzu T. Wong, Belmont, MA (US); Praveen K. Tadikonda, Norwood, MA (US); Luis E. Torres, Medford, MA (US); M. Arshad Siddiqui, Newton, MA (US); Michael P. Dwyer, Scotch Plains, NJ (US); Kartik M. Keertikar, East Windsor, NJ (US); Timothy J. Guzi, Sudbury, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 492 days.

(21) Appl. No.: 12/447,710

(22) PCT Filed: Oct. 29, 2007

(86) PCT No.: PCT/US2007/022928
§ 371 (c)(1),
(2), (4) Date: Jan. 13, 2010

(87) PCT Pub. No.: WO2008/054749
PCT Pub. Date: May 8, 2008

(65) Prior Publication Data
US 2010/0130465 A1    May 27, 2010

Related U.S. Application Data

(60) Provisional application No. 60/855,421, filed on Oct. 31, 2006.

(51) Int. Cl.
*A61K 31/5355* (2006.01)
*A61K 31/496* (2006.01)
*C07D 401/14* (2006.01)
*C07D 403/14* (2006.01)
*C07D 413/14* (2006.01)

(52) U.S. Cl. ........... 514/235.8; 514/253.05; 514/253.06; 514/253.1; 544/121; 544/362; 544/364

(58) Field of Classification Search ........................ None
See application file for complete search history.

(56) References Cited

U.S. PATENT DOCUMENTS

| 6,107,305 | A | 8/2000 | Misra et al. |
| 6,413,974 | B1 | 7/2002 | Dumont et al. |
| 2007/0054939 | A1* | 3/2007 | Guedat et al. ................. 514/316 |

FOREIGN PATENT DOCUMENTS

| WO | WO 00/62778 | 10/2000 |
| WO | WO 02/10162 | 2/2002 |
| WO | WO 02/22610 | 3/2002 |
| WO | WO 03/097048 | 11/2003 |
| WO | WO 2004/039789 | 5/2004 |
| WO | WO 2005/003128 | * 1/2005 |
| WO | WO 2006/081172 | 8/2006 |
| WO | WO 2007/123269 | 11/2007 |
| WO | WO 2008/106692 | 9/2008 |
| WO | WO 2009/017701 | * 2/2009 |

OTHER PUBLICATIONS

F. Al-Khodairy, et al., "Identification and Characterization of New Elements Involved in Checkpoint and Feedback Controls in Fission Yeast", Molecular Biology of the Cell, vol. 5, pp. 147-160 (1994).
Stephen M. Berge, et al., "Pharmaceutical Salts", Journal of Pharmaceutical Sciences, vol. 66, No. 1, pp. 1-19 (1977).
Ann L. Bingham, et al., "Over one hundred solvates of sulfathiazole", Chem. Commun., pp. 603-604 (2001).
Carmen Birchmeier, et al., "Met, Metastasis, Motility and More", Nature Reviews, Molecular Cell Biology, vol. 4, pp. 915-925 (2003).
James R. Bischoff, et al., "A homologue of *Drosophila aurora* kinase is oncogenic and amplified in human colorectal cancers", The EMBO Journal, vol. 17, No. 11, pp. 3052-3065 (1998).
Joseph B. Bolen, "Nonreceptor tyrosine protein kinases", Oncogene, vol. 8, pp. 2025-2031 (1993).
Mino R. Caira, et al., "Preparation and Crystal Characterization of a Polymorph, a Monohydrate, and an Ethyl Acetate Solvate of the Antifungal Fluconazole", Journal of Pharmaceutical Sciences, vol. 93, No. 3, pp. 601-611 (2004).

(Continued)

*Primary Examiner* — Joseph K. McKane
*Assistant Examiner* — Alicia L Otton
(74) *Attorney, Agent, or Firm* — Peter Haeberli; David A. Muthard

(57) ABSTRACT

The present invention relates to novel Anilinopiperazine Derivatives of formula (I), compositions comprising the Anilinopiperazine Derivatives, and methods for using the Anilinopiperazine Derivatives for treating or preventing a proliferative disorder, an anti-proliferative disorder, inflammation, arthritis, a central nervous system disorder, a cardiovascular disease, alopecia, a neuronal disease, an ischemic injury, a viral disease, a fungal infection, or a disorder related to the activity of a protein kinase.

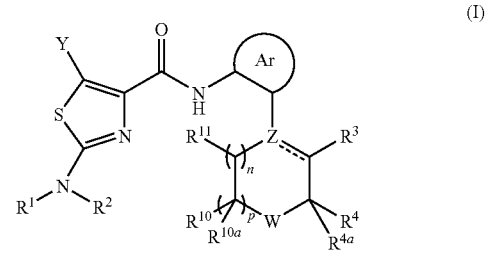

16 Claims, No Drawings

OTHER PUBLICATIONS

Jagabandhu Das, et al., "2-Aminothiazole as a Novel Kinase Inhibitor Template. Structure—Activity Relationship Studies toward the Discovery of N-(2-Chloro-6-methylphenyl)-2-[[6-[4-(2-hydroxyethyl)-1-piperazinyl)]-2-methyl-4-pyrimidinyl]amino)]-1,3-thiazole-5-carboxamide (Dasatinib, BMS-354825) as a Potent pan-Src Kinase Inhibitor", J. Med. Chem., vol. 49, pp. 6819-6832 (2006).

Maria Deak, et al., "Mitogen- and stress-activated protein kinase-1 (MSK1) is directly activated by MAPK and SAPK2/p38, and may mediate activation of CREB", The EMBO Journal, vol. 17, No. 15, pp. 4426-4441 (1998).

Philip L. Gould, "Salt selection for basic drugs", International Journal of Pharmaceutics, vol. 33, pp, 201-217 (1986).

Tomoko Hosoi, et al., "Evidence for cdk5 as a Major Activity Phosphorylating Tau Protein in Porcine Brain Extract", J. Biochem. vol. 117, pp. 741-749 (1995).

Kyoung Soon Kim, et al., "Discovery of Aminothiazole Inhibitors of Cyclin-Dependent Kinase 2: Synthesis, X-ray Crystallographic Analysis, and Biological Activities", J. Med. Chem., vol. 45, pp. 3905-3927 (2002).

Masahi Kimura, et al., "Cell Cycle-dependent Expression and Spindle Pole Localization of a Novel Human Protein Kinase, Aik, Related to Aurora of *Drosophila* and Yeast Ipl1", The Journal of Biological Chemistry, vol. 272, No. 21, pp. 13766-13771 (1997).

Peter C. Maisonpierre, et al., "Angiopoietin-2, a Natural Antagonist for Tie2 that Disrupts in vivo Angiogenesis", Science, vol. 277, pp. 55-60 (1997).

Shuhei Matsuoka, et al., "Linkage of ATM to Cell Cycle Regulation by the CHk2 Protein Kinase", Science, vol. 282, pp. 1893-1897 (1998).

Laurent Meijer, et al., "Biochemical and cellular effects of roscovitine, a potent and selective inhibitor of the cyclin-dependent kinases cdc2, cdk2 and cdk5", Eur. J. Biochem, vol. 243, pp. 527-536 (1997).

Yvette Mettey, et al., "Aloisines, a New Family of CDK/GSK-3 Inhibitors. SAR Study, Crystal Structure in Complex with CDK2, Enzyme Selectivity, and Cellular Effects", J. Med. Chem. vol. 46, pp. 222-236 (2003).

Birgit Millauer, et al., "Dominant-Negative Inhibition of Flk-1 Suppresses the Growth of Many Tumor Types in Vivo", Cancer Research, vol. 56, pp. 1615-1620 (1996).

Moosa Mohammadi, et al., "Crystal structure of an angiogenesis inhibitor bound to the FGF receptor tyrosine kinase domain", The EMBO Journal, vol. 17, No. 20, pp. 5896-5904 (1998).

Paul Nurse, "Checkpoint Pathways Come of Age", Cell, vol. 91, pp. 865-867 (1997).

Rejane Paumelle, et al., "Hepatocyte growth factor/scatter factor activates the ETS1 transcription factor by a RAS-RAF-MEK-ERK signaling pathway", Oncogene, vol. 21, pp. 2309-2319 (2002).

Cheng-Yuan Peng, et al., "Mitotic and G2 Checkpoint Control: Regulation of 14-3-3 Protein Binding by Phosphorylation of Cdc25C on Serine-216", Science, vol. 277, pp. 1501-1505 (1997).

Gregory D. Plowman, "Receptor Tyrosine Kinases as Targets for Drug Intervention", DN&P, vol. 7, No. 6, pp. 334-339 (1994).

Jeremy Saklatvala, "The p38 MAP kinase pathway as a therapeutic target in inflammatory disease", Current Opinion in Pharmacology, vol. 4, pp. 372-377 (2004).

Yolanda Sanchez et al., "Conservation of the Chk1 Checkpoint Pathway in Mammals: Linkage of DNA Damage to Cdk Regulation Through Cdc25", Science, vol. 277, pp. 1497-1501 (1997).

Jill M. Schumacher, et al., "AIR-2: An Aurora/Ipl1-related Protein Kinase Associated with Chromosomes and Midbody Microtubules is Required for Polar Body Extrusion and Cytokinesis in *Caenorhabditis elegans* Embryos", The Journal of Cell Biology, vol. 143, No. 6, pp. 1635-1646 (1998).

Adrian M. Senderowicz, et al. "Phase I Trial of Continuous Infusion Flavopiridol, a Novel Cyclin-Dependent Kinase Inhibitor, in Patients with Refractory Neoplasms", Journal of Clinical Oncology, vol. 16, No. 9, pp. 2986-2999 (1998).

Kate Petersen Shay, et al., "Pim-1 Kinase Stability is Regulated by Heat Shock Proteins and the Ubiquitin-Proteasome Pathway", Mol. Cancer Res., vol. 3, No. 3, pp. 170-181 (2005).

Yu Shi, et al., "In the Cellular Garden of Forking Paths: How p38 MAPKs Signal for Downstream Assistance", Biol. Chem., vol. 383, pp. 1519-1536 (2002).

Keisuke Shiroto, et al., "MK2-/-gene knockout mouse hearts carry anti-apoptotic signal and are resistant to ischemia reperfusion injury", Journal of Molecular and Cellular Cardiology, vol. 38, pp. 93-97 (2005).

P. Heinrich Stahl, et al., "Handbook of Pharmaceutical Salts—Properties, Selection, and Use", International Union of Pure and Applied Chemistry, 4 pages (2002).

Laurie M. Strawn, et al., "Flk-1 as a Target for Tumor Growth Inhibition", Cancer Research, vol. 56, pp. 3540-3545 (1996).

Elsa C. Van Tonder, et al., "Preparation and Physicochemical Characterization of 5 Niclosamide Solvates and 1 Hemisolvate", AAPS PharmSciTech, vol. 5, No. 1, Article 12 (2004).

Jaroslav Vesely, et al., "Inhibition of cyclin-dependent kinases by purine analogues", Eur. J. Biochem, vol. 224, pp. 771-786 (1994).

Nancy Walworth, et al., "Fission yeast chk1 protein kinase links the *rad* checkpoint pathway to *cdc2*", Nature, vol. 363, pp. 368-371 (1993).

Ted Weinert, "A DNA Damage Checkpoint Meets the Cell Cycle Engine", Science, vol. 277, No. 5331, pp. 1450-1451 (1997).

Hitoshi Yoshiji, et al., "Vascular Endothelial Growth Factor is Essential for Initial but not Continued in Vivo Growth of Human Breast Carcinoma Cells", Cancer Research, vol. 57, pp. 3924-3928 (1997).

Yan Zeng, et al., "Replication checkpoint requires phosphorylation of the phosphatase Cdc25 by Cds1 or Chk1", Nature, vol. 395, pp. 507-510 (1998).

Yu-Wein Zhang, et al., "HGF/SF-Met Signaling in the Control of Branching Morphogenesis and Invasion", Journal of Cellular Biochemistry, vol. 88, pp. 408-417 (2003).

International Search Report for corresponding International Application PCT/US2007/022829, mailed Apr. 17, 2008 (6 pages).

International Search Report for corresponding International Application PCT/US2007/022827, mailed Apr. 18, 2008 (6 pages).

International Search Report for corresponding International Application PCT/US2007/022928, mailed Apr. 18, 2008 (6 pages).

* cited by examiner

2-AMINOTHIAZOLE-4-CARBOXYLIC AMIDES AS PROTEIN KINASE INHIBITORS

FIELD OF THE INVENTION

The present invention relates to novel Anilinopiperazine Derivatives, compositions comprising the Anilinopiperazine Derivatives, and methods for using the Anilinopiperazine Derivatives for treating or preventing a proliferative disorder, an anti-proliferative disorder, inflammation, arthritis, a central nervous system disorder, a cardiovascular disease, alopecia, a neuronal disease, an ischemic injury, a viral disease, a fungal infection, or a disorder related to the activity of a protein kinase.

BACKGROUND OF THE INVENTION

Protein kinases are a family of enzymes that catalyze phosphorylation of proteins, in particular the hydroxyl group of specific tyrosine, serine, or threonine residues in proteins. Protein kinases are pivotal in the regulation of a wide variety of cellular processes, including metabolism, cell proliferation, cell differentiation, and cell survival. Uncontrolled proliferation is a hallmark of cancer cells, and can be manifested by a deregulation of the cell division cycle in one of two ways—making stimulatory genes hyperactive or inhibitory genes inactive. Protein kinase inhibitors, regulators or modulators alter the function of kinases such as cyclin-dependent kinases (CDKs), mitogen activated protein kinase (MAPK/ERK), glycogen synthase kinase 3 (GSK3beta), Checkpoint (Chk) (e.g., CHK-1, CHK-2 etc.) kinases, AKT kinases, JNK, and the like. Examples of protein kinase inhibitors are described in WO02/22610 A1 and by Y. Mettey et al., in *J. Med. Chem.*, 46:222-236 (2003).

The cyclin-dependent kinases are serine/threonine protein kinases, which are the driving force behind the cell cycle and cell proliferation. Misregulation of CDK function occurs with high frequency in many important solid tumors. Individual CDK's, such as, CDK1, CDK2, CDK3, CDK4, CDK5, CDK6 and CDK7, CDK8 and the like, perform distinct roles in cell cycle progression and can be classified as either G1S, or G2M phase enzymes. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over- or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development of cancer treatments.

A number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer. Flavopiridol (shown below) is a nonselective CDK inhibitor that is currently undergoing human clinical trials, A. M. Sanderowicz et al., *J. Clin. Oncol.* 16:2986-2999 (1998).

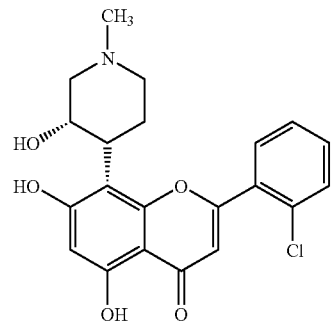

Other known inhibitors of CDKs include, for example, olomoucine (J. Vesely et al., *Eur. J. Biochem.*, 224:771-786 (1994)) and roscovitine (I. Meijer et al., *Eur. J. Biochem.*, 243:527-536 (1997)). U.S. Pat. No. 6,107,305 describes certain pyrazolo[3,4-b]pyridine compounds as CDK inhibitors. An illustrative compound from the '305 patent is:

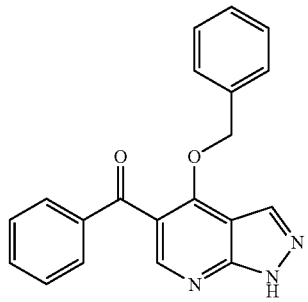

K. S. Kim et al., *J. Med. Chem.* 45:3905-3927 (2002) and WO 02/10162 disclose certain aminothiazole compounds as CDK inhibitors.

Another series of protein kinases are those that play an important role as a checkpoint in cell cycle progression. Checkpoints prevent cell cycle progression at inappropriate times, such as in response to DNA damage, and maintain the metabolic balance of cells while the cell is arrested, and in some instances can induce apoptosis (programmed cell death) when the requirements of the checkpoint have not been met. Checkpoint control can occur in the G1 phase (prior to DNA synthesis) and in G2, prior to entry into mitosis.

One series of checkpoints monitors the integrity of the genome and, upon sensing DNA damage, these "DNA damage checkpoints" block cell cycle progression in $G_1$ & $G_2$ phases, and slow progression through S phase. This action enables DNA repair processes to complete their tasks before replication of the genome and subsequent separation of this genetic material into new daughter cells takes place. Inactivation of CHK1 has been shown to transduce signals from the DNA-damage sensory complex to inhibit activation of the cyclin B/Cdc2 kinase, which promotes mitotic entry, and abrogate G.sub.2 arrest induced by DNA damage inflicted by either anticancer agents or endogenous DNA damage, as well as result in preferential killing of the resulting checkpoint defective cells. See, e.g., Peng et al., *Science,* 277:1501-1505 (1997); Sanchez et al., *Science,* 277:1497-1501 (1997), Nurse, *Cell,* 91:865-867 (1997); Weinert, *Science,* 277:1450-

1451 (1997); Walworth et al., *Nature,* 363:368-371 (1993); and Al-Khodairy et al., *Molec. Biol. Cell.,* 5:147-160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as CDS1/CHK2, a kinase recently discovered to cooperate with CHK1 in regulating S phase progression (see Zeng et al., *Nature,* 395:507-510 (1998); Matsuoka, *Science,* 282:1893-1897 (1998)), could provide valuable new therapeutic entities for the treatment of cancer.

Another group of kinases are the tyrosine kinases. Tyrosine kinases can be of the receptor type (having extracellular, transmembrane and intracellular domains) or the non-receptor type (being wholly intracellular). Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3 and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, IR, and IR-R. The PDGF subfamily includes the PDGF-alpha and beta receptors, CSFIR, c-kit and FLK-II. The FLK family is comprised of the kinase insert domain receptor (KDR), fetal liver kinase-1 (FLK-1), fetal liver kinase-4 (FLK-4) and the fms-like tyrosine kinase-1 (flt-1). For detailed discussion of the receptor-type tyrosine kinases, see Plowman et al., *DN&P* 7(6):334-339, 1994.

At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene,* 8:2025-2031 (1993). The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, *Oncogene,* 8:2025-2031 (1993).

In addition to its role in cell-cycle control, protein kinases also play a crucial role in angiogenesis, which is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. On the other hand, unwanted angiogenesis is a hallmark of several diseases, such as retinopathies, psoriasis, rheumatoid arthritis, age-related macular degeneration, and cancer (solid tumors). Protein kinases which have been shown to be involved in the angiogenic process include three members of the growth factor receptor tyrosine kinase family; VEGF-R2 (vascular endothelial growth factor receptor 2, also known as KDR (kinase insert domain receptor) and as FLK 1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al, *Cancer Res.,* 56:3540-3545 (1996)), as has been shown with mutants of VEGF-R2 which fail to mediate signal transduction. Millauer et al, *Cancer Res.,* 56:1615-1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGFR binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research,* 57: 3924-3928 (1997). Unlike VEGF-R2, however, FGF-R is expressed in a number of different cell types throughout the body and may or may not play important roles in other normal physiological processes in the adult. Nonetheless, systemic administration of a small molecule inhibitor of the kinase activity of FGF-R has been reported to block bFGF-induced angiogenesis in mice without apparent toxicity. Mohammad et al., *EMBO Journal,* 17:5996-5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre of al., *Science,* 277:55-60 (1997).

The kinase, JNK, belongs to the mitogen-activated protein kinase (MAPK) superfamily. JNK plays a crucial role in inflammatory responses, stress responses, cell proliferation, apoptosis, and tumorigenesis. JNK kinase activity can be activated by various stimuli, including the proinflammatory cytokines (TNF-alpha and interleukin-1), lymphocyte costimulatory receptors (CD28 and CD40), DNA-damaging chemicals, radiation, and Fas signaling. Results from the JNK knockout mice indicate that JNK is involved in apoptosis induction and T helper cell differentiation.

Pim-1 is a small serine/threonine kinase. Elevated expression levels of Pim-1 have been detected in lymphoid and myeloid malignancies, and recently Pim-1 was identified as a prognostic marker in prostate cancer. K. Peltola, "Signaling in Cancer: Pim-1 Kinase and its Partners", Annales Universitatis Turkuensis, Sarja—Ser. D Osa—Tom. 616, (Aug. 30, 2005), http://kirjasto.utu.fi/julkaisupalvelut/annaalit/2004/D616.html. Pim-1 acts as a cell survival factor and may prevent apoptosis in malignant cells. K. Petersen Shay et al., *Molecular Cancer Research* 3:170-181 (2005).

Aurora kinases (Aurora-A, Aurora-B, Aurora-C) are serine/threonine protein kinases that have been implicated in human cancer, such as colon, breast and other solid tumors. Aurora-A (also sometimes referred to as AIK) is believed to be involved in protein phosphorylation events that regulate the cell cycle. Specifically, Aurora-A may play a role in controlling the accurate segregation of chromosomes during mitosis. Misregulation of the cell cycle can lead to cellular proliferation and other abnormalities. In human colon cancer tissue, Aurora-A, Aurora-B, Aurora-C have been found to be overexpressed (see Bischoff et al., EMBO J., 17:3052-3065

(1998); Schumacher et al., *J. Cell Biol.* 143:1635-1646 (1998); Kimura et al., *J. Biol. Chem.*, 272:13766-13771 (1997)).

c-Met is a proto-oncogene that encodes for a tyrosine kinase receptor for hepatocyte growth factor/scatter factor (HGF/SF). The c-Met protein is expressed mostly in epithelial cells, and due to its function it is also known as hepatocyte growth factor receptor, or HGFR. When HGF/SF activates c-Met, the latter in turn may activate a number of kinase pathways, including the pathway from Ras to Raf to Mek to the mitogen-activated protein kinase ERK1 to the transcription factor ETS1. Met signaling has been implicated in the etiology and malignant progression of human cancers (see Birchmeier et al., *Nature Reviews Molecular Cell Biology*, 4:915-925 (2003); Zhang et al., *Journal of Cellular Biochemistry*, 88:408-417 (2003); and Paumelle et al., *Oncogene*, 21:2309-2319 (2002)).

Mitogen-activated protein kinase-activated protein kinase 2 (MAPKAP K2 or MK2) mediates multiple p38 MAPK-dependent cellular responses. MK2 is an important intracellular regulator of the production of cytokines, such as tumor necrosis factor alpha (TNFa), interleukin 6 (IL-6) and interferon gamma (IFNg), that are involved in many acute and chronic inflammatory diseases, e.g. rheumatoid arthritis and inflammatory bowel disease. MK2 resides in the nucleus of non-stimulated cells and upon stimulation, it translocates to the cytoplasm and phosphorylates and activates tuberin and HSP27. MK2 is also implicated in heart failure, brain ischemic injury, the regulation of stress resistance and the production of TNF-α (see Deak et al., *EMBO.* 17:4426-4441 (1998); Shi et al., *Biol. Chem.* 383:1519-1536 (2002); Staklatvala, *Curr. Opin. Pharmacol.* 4:372-377 (2004); and Shiroto et al., *J. Mol. Cell Cardiol.* 38:93-97 (2005)).

There is a need for effective inhibitors of protein kinases in order to treat or prevent disease states associated with abnormal cell proliferation. Moreover, it is desirable for kinase inhibitors to possess both high affinities for the target kinase as well as high selectivity versus other protein kinases. Small-molecule compounds that may be readily synthesized and are potent inhibitors of cell proliferation are those, for example, that are inhibitors of one or more protein kinases, such as CHK1, CHK2, VEGF (VEGF-R2), Pim-1, CDKs or CDK/cyclin complexes and both receptor and non-receptor tyrosine kinases.

SUMMARY OF THE INVENTION

In one aspect, the present invention provides compounds of Formula (I):

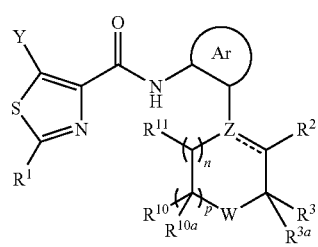

(I)

and pharmaceutically acceptable salts, solvates, esters, prodrugs and stereoisomers thereof, wherein the dashed line indicates an optional and additional bond, and wherein:

$R^1$ is nitrogen-containing heteroaryl, nitrogen-containing heterocyclyl or nitrogen-containing heterocyclenyl, wherein $R^1$ is joined to the rest of the compound of formula (I) via a ring nitrogen atom, and wherein a nitrogen-containing heteroaryl, nitrogen-containing heterocyclyl or nitrogen-containing heterocyclenyl group can be optionally and independently substituted with one or more groups selected from alkyl, cycloalkyl, -(alkylene)$_m$-heterocyclyl, -aryl, -arylene-heterocyclyl, halo, —OH, —O-alkyl, —O-alkylene-(O-alkylene)$_m$-O-alkyl, -heterocyclyl-O-alkylene-(O-alkylene)$_m$-O-alkyl, -heterocyclyl-alkylene-N(R$^8$)$_2$, -heterocyclyl-O-alkylene-N(R$^8$)$_2$, —S-alkyl, -heterocyclyl-O-heterocyclyl, -heterocyclyl-O-hydroxyalkyl, —O-heterocyclyl, —O-hydroxyalkyl, —O-alkylene-N(R$^8$)$_2$, —O-alkylene-heterocyclyl, -heterocyclyl-O-alkylene-heterocyclyl, -heterocyclyl-cyclolalkyl, —O-alkylene-N(R$^8$)$_2$, —O-aryl, —N(R$^8$)$_2$, -alkylene-N(R$^8$)$_2$, haloalkyl, -(alkylene)$_m$-heteroaryl, —O-heteroaryl, —NO$_2$, —NHSO$_2$-alkyl, —C(O)R$^8$, —C(O)OR$^8$, —C(O)N(R$^8$)$_2$, —OC(O)R$^8$ and —NHC(O)R$^8$, and wherein a nitrogen-containing heteroaryl, nitrogen-containing heterocyclyl or nitrogen-containing heterocyclenyl group can be optionally fused to an aryl, heteroaryl or heterocyclyl group;

$R^2$ is H, alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or $R^2$ and the ring carbon atom to which it is attached, form a carbonyl group;

$R^3$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or $R^3$ and $R^{3a}$, together with the common carbon atom to which each are attached, join to form a carbonyl, cycloalkyl or heterocyclyl group;

$R^{3a}$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$;

each occurrence of $R^4$ is independently H, -alkyl, -(alkylene)$_m$-aryl, -(alkylene)$_m$-heteroaryl, -(alkylene)$_m$-heterocyclyl, -(alkylene)$_m$-N(R$^8$)$_2$, -(alkylene)$_m$-OH, -(alkylene)$_m$-NHC(O)R$^8$, hydroxyalkyl, haloalkyl, —CH$_2$NH$_2$, —C(O)R$^5$, —C(O)OR$^8$, —C(O)-(alkylene)$_m$-N(R$^8$)$_2$, —C(O)NH-alkyl, —C(O)N(alkyl)$_2$, -(alkylene)$_m$-NHC(O)R$^6$, —NHC(O)OR$^8$ or —NHS(O)$_2$R$^6$;

$R^5$ is H, alkyl, aryl, -heteroaryl or —NHOH;

$R^6$ is H, -alkyl or haloalkyl;

$R^7$ is H, —OH, alkyl, —O-alkyl, or haloalkyl;

each occurrence of $R^8$ is independently H, alkyl, -(alkylene)$_m$-aryl, -(alkylene)$_m$-heterocyclyl, -(alkylene)$_m$-heteroaryl or -(alkylene)$_m$-cycloalkyl;

$R^9$ is H, alkyl, -(alkylene)$_m$-haloalkyl, -(alkylene)$_m$-hydroxyalkyl, -(alkylene)$_m$-aryl, -(alkylene)$_m$-heterocyclyl, -(alkylene)$_m$-heteroaryl or -(alkylene)$_m$-cycloalkyl;

$R^{10}$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or $R^{10}$ and $R^{10a}$, together with the common carbon atom to which each are attached, join to form a carbonyl, cycloalkyl or heterocyclyl group;

$R^{10a}$ is H, -alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$;

each occurrence of $R^{11}$ is independently H, alkyl, haloalkyl, hydroxyalkyl, -(alkylene)$_m$-C(O)N(R$^8$)$_2$, -(alkylene)$_m$-NHC(O)—R$^9$ or -(alkylene)$_m$-N(R$^9$)$_2$, or any $R^{11}$ and the ring carbon atom to which it is attached, form a carbonyl group;

each occurrence of $R^{12}$ is independently H, alkyl, -(alkylene)$_m$-aryl, -(alkylene)$_m$-heteroaryl, -(alkylene)$_m$-heterocyclyl, —S(O)$_2$-alkyl, —S(O)$_2$-aryl, —S(O)$_2$-heteroaryl, hydroxyalkyl, —C(O)R$^8$, or —C(O)OR$^8$;

Ar is arylene or heteroarylene, wherein the arylene or heteroarylene is joined via any 2 of its adjacent ring carbon atoms, and wherein the arylene or heteroarylene group can be optionally substituted with up to 4 substituents, which may be the same or different, and are independently selected from halo, alkyl, alkoxy, aryloxy, —NH$_2$, —NH-alkyl, —N(alkyl)$_2$, —SR$^8$, —S(O)R$^8$, —S(O)$_2$R$^8$, —C(O)R$^8$, —C(O)OR$^8$, —C(O)N(R$^8$)$_2$, —NHC(O)R$^8$, haloalkyl, —CN and NO$_2$, such that when Ar is tetrahydronaphthylene, R$^2$ and R$^3$ are each other than hydrogen;

W is —N(R$^{12}$)$_2$—, —S—, —O— or —C(R$^4$)$_2$—, wherein both R$^4$ groups and the common carbon atom to which they are attached can combine to form a cycloalkyl or heterocyclyl group, each of which can be further substituted;

Y is H, halo, alkyl or —CN;

Z is —C(R$^7$)— or —N—, such that when the optional additional bond is present, Z is —C(R$^7$)—;

each occurrence of m is independently 0 or 1;

n is an integer ranging from 0 to 2; and p is 0 or 1.

In one aspect, the compounds of Formula (I) (the "Anilinopiperazine Derivatives") can be useful as protein kinase inhibitors.

In another aspect, the Anilinopiperazine Derivatives can be useful for treating or preventing a proliferative disorder, an anti-proliferative disorder, inflammation, arthritis, a central nervous system disorder, a cardiovascular disease, alopecia, a neuronal disease, an ischemic injury, a viral disease, a fungal infection, or a disorder related to the activity of a protein kinase (each being a "Condition").

In another aspect, the present invention provides pharmaceutical compositions comprising an effective amount of at least one Anilinopiperazine Derivative and a pharmaceutically acceptable carrier. The compositions can be useful for treating or preventing a Condition in a patient.

In still another aspect, the present invention provides methods for treating pr preventing a Condition in a patient, the method comprising administering to the patient an effective amount of at least one Anilinopiperazine Derivative.

In another aspect, the present invention provides methods for treating a cancer in a patient, the method comprising administering to the patient an effective amount of at least one Anilinopiperazine Derivative.

In another aspect, the present invention provides methods for treating a cancer in a patient, the method comprising administering to the patient an at least one Anilinopiperazine Derivative and at least one additional anticancer agent which is not an Anilinopiperazine Derivative, wherein the amounts administered are together effective to treat the cancer.

DETAILED DESCRIPTION OF THE INVENTION

In an embodiment, the present invention provides Anilinopiperazine

Derivatives of Formula (I) and or pharmaceutically acceptable salts, solvates, esters and prodrugs thereof. The Anilinopiperazine Derivatives can be useful for treating or preventing a Condition in a patient.

DEFINITIONS AND ABBREVIATIONS

As used above, and throughout this disclosure, the following terms, unless otherwise indicated, shall be understood to have the following meanings:

"Acyl" means an H—C(O)—, alkyl-C(O)— or cycloalkyl-C(O)—, group in which the various groups are as previously described. The bond to the parent moiety is through the carbonyl. In one embodiment, acyls contain a lower alkyl. Non-limiting examples of suitable acyl groups include formyl, acetyl and propanoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Alkyl" means an aliphatic hydrocarbon group which may be straight or branched and comprising about 1 to about 20 carbon atoms in the chain. In one embodiment, an alkyl group contains from about 1 to about 12 carbon atoms in the chain. In another embodiment, an alkyl group contains from about 1 to about 6 carbon atoms in the chain. Branched means that one or more lower alkyl groups such as methyl, ethyl or propyl, are attached to a linear alkyl chain. Lower alkyl refers to a group having about 1 to about 6 carbon atoms in the chain which may be straight or branched. An alkyl group may be unsubstituted or optionally substituted by one or more substituents which may be the same or different, each substituent being independently selected from the group consisting of halo, alkyl, aryl, cycloalkyl, cyano, hydroxy, alkoxy, —S-alkyl, amino, —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl, n-butyl, sec-butyl, isobutyl, t-butyl, n-pentyl, isopentyl, neopentyl, n-hexyl, n-heptyl and n-octyl. In one embodiment, an alkyl group is a "C$_1$-C$_6$ alkyl group," having from 1 to 6 carbon atoms.

"Alkylaryl" means an alkyl-arylene- group in which the alkyl and arylene are as previously described. In one embodiment, alkylaryls comprise a lower alkyl group. Non-limiting example of a suitable alkylaryl group is tolyl. The bond to the parent moiety is through the arylene group.

"Alkylsulfonyl" means an alkyl-S(O$_2$)— group. In one embodiment, groups are those in which the alkyl group is lower alkyl. The bond to the parent moiety is through the sulfonyl.

"Alkylthio" means an alkyl-S— group in which the alkyl group is as previously described. Non-limiting examples of suitable alkylthio groups include methylthio and ethylthio. An alkylthio group is bound to the parent moiety via its sulfur atom.

"Alkenyl" means an aliphatic hydrocarbon group containing at least one carbon-carbon double bond and which may be straight or branched and comprising about 2 to about 15 carbon atoms in the chain. In one embodiment, an alkenyl group has from about 2 to about 12 carbon atoms in the chain; in another embodiment, an alkenyl group has from about 2 to about 6 carbon atoms in the chain. Branched means that one or more lower alkyl groups such as methyl, ethyl or propyl, are attached to a linear alkenyl chain. Lower alkenyl refers to about 2 to about 6 carbon atoms in the chain which may be straight or branched. An alkenyl group may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)CH_2$—. In one embodiment, an alkylene group has from 1 to about 6 carbon atoms. In another embodiment, an alkylene group is branched. In another embodiment, an alkylene group is linear.

"Alkenylene" means a difunctional group obtained by removal of a hydrogen from an alkenyl group that is defined above. Non-limiting examples of alkenylene include —CH═CH—, —C($CH_3$)═CH—, and —CH═CHCH$_2$—.

"Alkynyl" means an aliphatic hydrocarbon group containing at least one carbon-carbon triple bond and which may be straight or branched and comprising about 2 to about 15 carbon atoms in the chain. In one embodiment, an alkynyl group has from about 2 to about 12 carbon atoms in the chain; and in another embodiment, an alkynyl group has from about 2 to about 4 carbon atoms in the chain. Branched means that one or more lower alkyl groups such as methyl, ethyl or propyl, are attached to a linear alkynyl chain. Lower alkynyl refers to about 2 to about 6 carbon atoms in the chain which may be straight or branched. Non-limiting examples of suitable alkynyl groups include ethynyl, propynyl, 2-butynyl and 3-methylbutynyl. An alkynyl group may be unsubstituted or optionally substituted by one or more substituents which may be the same or different, each substituent being independently selected from the group consisting of alkyl, aryl and cycloalkyl.

"Alkynylalkyl" means an alkynyl-alkyl- group in which the alkynyl and alkyl are as previously described. In one embodiment, alkynylalkyls contain a lower alkynyl and a lower alkyl group. The bond to the parent moiety is through the alkyl. Non-limiting examples of suitable alkynylalkyl groups include propargylmethyl.

"Aralkloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Aralkyl" or "arylalkyl" means an aryl-alkylene- group in which the aryl and alkylene are as previously described. In one embodiment, aralkyls comprise a lower alkylene group. Non-limiting examples of suitable aralkyl groups include benzyl, 2-phenethyl and naphthalenylmethyl. The bond to the parent moiety is through the alkylene group.

"Aralkylthio" means an aralkyl-S— group in which the aralkyl group is as previously described. Non-limiting example of a suitable aralkylthio group is benzylthio. The bond to the parent moiety is through the sulfur.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Arylene," means an aryl group, wherein a hydrogen atom connected to one of the aryl group's ring carbon atoms is replaced with a single bond.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylsulfonyl" means an aryl-S($O_2$)— group. The bond to the parent moiety is through the sulfonyl.

"Arylthio" means an aryl-S— group in which the aryl group is as previously described. Non-limiting examples of suitable arylthio groups include phenylthio and naphthylthio. The bond to the parent moiety is through the sulfur.

"Benzofused cycloalkyl" means a cycloalkyl moiety as defined above which is fused to a benzene ring. Non-limiting examples of a benzofused cycloalkyl are indanyl and tetrahydronaphthylenyl.

"Benzofused cycloalkenyl" means a cycloalkenyl moiety as defined above which is fused to a benzene ring. Non-limiting examples of a benzofused cycloalkyl include indenyl.

"Benzofused heterocyclyl" means a heterocyclyl moiety as defined above which is fused to a benzene ring. Non-limiting examples of a benzofused heterocyclyl include indolinyl and 2,3-dihydrobenzofuran.

"Benzofused heteroaryl" means a heteroaryl moiety as defined above which is fused to a benzene ring. Non-limiting examples of a benzofused heteroaryl are indolyl, indazolyl, benzofuranyl, quinolinyl, isoquinolinyl, benzthiazolyl, indolyl, benzimidazolyl and benzothiophenyl.

"Composition" means a product comprising the specified ingredients in the specified amounts, as well as any product which results, directly or indirectly, from combination of the specified ingredients in the specified amounts.

"Cycloalkyl" means a non-aromatic mono- or multicyclic ring system comprising about 3 to about 10 carbon atoms, preferably about 5 to about 10 carbon atoms. In one embodiment, cycloalkyl rings contain about 5 to about 7 ring atoms. A cycloalkyl group can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising from 3 to about 10 carbon atoms and having at least one endocyclic carbon-carbon double bond. In one embodiment, a cycloalkenyl group has from about 5 to about 10 ring carbon atoms. In another embodiment, a cycloalkenyl group has from about 5 to about 7 ring carbon atoms. A cycloalkenyl group can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Effective amount" or "therapeutically effective amount" means an amount of Anilinopiperazine Derivative and/or an additional therapeutic agent, or a composition thereof that is effective in producing the desired therapeutic, ameliorative, inhibitory or preventative effect when administered to a patient suffering from a Condition. In the combination therapies of the present invention, an effective amount can refer to each individual agent or to the combination as a whole, wherein the amounts of all agents administered are together effective, but wherein the component agent of the combination may not be present individually in an effective amount.

"Halo" means —F, —Cl, —Br or —I. In one embodiment, halo refers to —Cl or —Br. In another embodiment, halo refers to —F.

"Haloalkyl" means an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$.

"Heteroaryl" means an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, that is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. In one embodiment, a heteroaryl group is unsubstituted. In another embodiment, a heteroaryl group is a 5-membered heteroaryl. In another embodiment, a heteroaryl group is a 6-membered heteroaryl.

The term "heteroarylene," as used herein, refers to a heteroaryl group, wherein a hydrogen atom connected to one of the heteroaryl group's ring atoms is replaced with a single bond.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising 3 to about 10 ring atoms, wherein from 1 to 4 of the ring atoms are independently O, S or N and the remainder of the ring atoms are carbon atoms. In one embodiment, a heterocyclyl group has from about 5 to about 10 ring atoms. In another embodiment, a heterocyclyl group has 5 or 6 ring atoms. There are no adjacent oxygen and/or sulfur atoms present in the ring system. Any —NH group in a heterocyclyl ring may exist protected such as, for example, as an —N(BOC), —N(Cbz), —N(Tos) group and the like; such protected heterocyclyl groups are considered part of this invention. The term "heterocyclyl" also encompasses a heterocyclyl group, as defined above, that is fused to an aryl (e.g., benzene) or heteroaryl ring. A heterocyclyl group can be optionally substituted by one or more "ring system substituents" which may be the same or different, and are as defined herein below. The nitrogen or sulfur atom of the heterocyclyl can be optionally oxidized to the corresponding N-oxide, S-oxide or S,S-dioxide. Non-limiting examples of monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. A ring carbon atom of a heterocyclyl group may be functionalized as a carbonyl group. An illustrative example of such a heterocyclyl group is pyrrolidonyl:

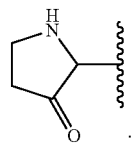

In one embodiment, a heterocyclyl group is unsubstituted. In another embodiment, a heterocyclyl group is a 5-membered heterocyclyl. In another embodiment, a heterocyclyl group is a 6-membered heterocyclyl.

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a heterocyclyl group, as defined above, wherein the heterocyclyl group contains from 3 to 10 ring atoms, and at least one endocyclic carbon-carbon or carbon-nitrogen double bond. In one embodiment, a heterocyclenyl group has from 5 to 10 ring atoms. In another embodiment, a heterocyclenyl group is monocyclic and has 5 or 6 ring atoms. A heterocyclenyl group can optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. A ring carbon atom of a heterocyclenyl group may be functionalized as a carbonyl group. An illustrative example of such a heterocyclenyl group is:

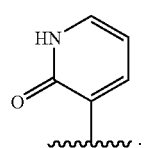

In one embodiment, a heterocyclenyl group is unsubstituted. In another embodiment, a heterocyclenyl group is a 5-membered heterocyclenyl.

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

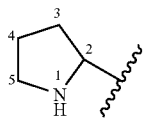

there is no —OH attached directly to carbons marked 2 and 5.

It should also be noted that tautomeric forms such as, for example, the moieties:

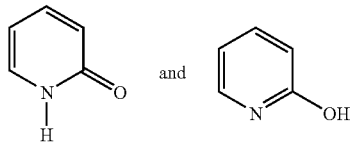

are considered equivalent in certain embodiments of this invention.

"Heteroaralkyl" means a heteroaryl-alkyl- group in which the heteroaryl and alkyl are as previously described. In one embodiment, heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$.

"Nitrogen-containing heteroaryl" means a heteroaryl group, as defined above, having at least one ring nitrogen atom. In one embodiment, a nitrogen-containing heteroaryl group is 5-membered. In another embodiment, a nitrogen-containing heteroaryl group is 6-membered. In another embodiment, a nitrogen-containing heteroaryl group is fused to a benzene ring. In still another embodiment, a nitrogen-containing heteroaryl group is fused to a cycloalkyl ring. In another embodiment, a nitrogen-containing heteroaryl group is fused to a heterocyclyl ring. In a further embodiment, a nitrogen-containing heteroaryl group is fused to a heteroaryl ring. Illustrative examples of nitrogen-containing heteroaryl groups include all examples of heteroaryl groups, as listed above in the definition of "heteroaryl," which contain at least one ring nitrogen atom.

"Nitrogen-containing heterocyclyl" means a heterocyclyl group, as defined above, having at least one ring nitrogen atom. In one embodiment, a nitrogen-containing heterocyclyl group is 5-membered. In another embodiment, a nitrogen-containing heterocyclyl group is 6-membered. In another embodiment, a nitrogen-containing heterocyclyl group is fused to a benzene ring. In still another embodiment, a nitrogen-containing heterocyclyl group is fused to a cycloalkyl ring. In another embodiment, a nitrogen-containing hetero-cyclyl group is fused to a heterocyclyl ring. In a further embodiment, a nitrogen-containing heterocyclyl group is fused to a heteroaryl ring. Illustrative examples of nitrogen-containing heterocyclyl groups include all examples of heterocyclyl groups, as listed above in the definition of "heterocyclyl," which contain at least one ring nitrogen atom.

"Nitrogen-containing heterocyclenyl" means a heterocyclenyl group, as defined above, having at least one ring nitrogen atom. In one embodiment, a nitrogen-containing heterocyclenyl group is 5-membered. In another embodiment, a nitrogen-containing heterocyclenyl group is 6-membered. In another embodiment, a nitrogen-containing heterocyclenyl group is fused to a benzene ring. In still another embodiment, a nitrogen-containing heterocyclenyl group is fused to a cycloalkyl ring. In another embodiment, a nitrogen-containing heterocyclenyl group is fused to a heterocyclyl ring. In a further embodiment, a nitrogen-containing heterocyclenyl group is fused to a heteroaryl ring. Illustrative examples of nitrogen-containing heterocyclenyl groups include all examples of heterocyclenyl groups, as listed above in the definition of "heterocyclenyl," which contain at least one ring nitrogen atom.

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

"Ring system substituent" means a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkyl-aryl, -aryl-alkyl, -alkylene-heteroaryl, -alkenylene-heteroaryl, -alkynylene-heteroaryl, hydroxy, hydroxyalkyl, haloalkyl, —O-alkyl, —O-haloalkyl, -alkylene-O-alkyl, —O-aryl, aralkoxy, acyl, —C(O)-aryl, halo, nitro, cyano, carboxy, —C(O)O-alkyl, —C(O)O-aryl, —C(O)O-alkelene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)— and Y$_1$Y$_2$NSO$_2$—, wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$—, —O-alkylene-O—, and the like which form moieties such as, for example:

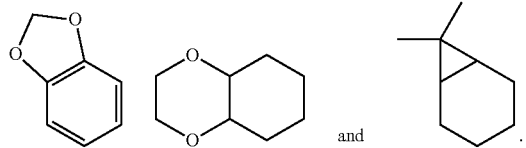 and

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent. The term "optionally substituted" means optional substitution with the specified groups, radicals or moieties.

It should also be noted that any carbon atom or heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any variable (e.g., aryl, heterocycle, R$^2$, etc.) occurs more than one time in any constituent or any chemical structure or formula herein, its definition on each occurrence is independent of its definition at every other occurrence.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield an Anilinopiperazine Derivative or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if an Anilinopiperazine Derivative or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl (such as β-dimethylaminoethyl), carbamoyl-(C$_1$-C$_2$)alkyl, N,N-di (C$_1$-C$_2$)alkylcarbamoyl-(C$_1$-C$_2$)alkyl and piperidino-, pyrrolidino- or morpholino(C$_2$-C$_3$)alkyl, and the like.

Similarly, if an Anilinopiperazine Derivative contains an alcohol functional group, a prodrug can be formed by the replacement of the hydrogen atom of the alcohol group with a group such as, for example, (C$_1$-C$_6$)alkanoyloxymethyl, 1-((C$_1$-C$_6$)alkanoyloxy)ethyl, 1-methyl-1-((C$_1$-C$_6$)alkanoyloxy)ethyl, (C$_1$-C$_6$)alkoxycarbonyloxymethyl, N—(C$_1$-C$_6$) alkoxycarbonylaminomethyl, succinoyl, (C$_1$-C$_6$)alkanoyl, α-amino(C$_1$-C$_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O(C$_1$-C$_6$)alkyl)$_2$ or glycosyl (the radical resulting from the removal of a hydroxyl group of the hemiacetal form of a carbohydrate), and the like.

If an Anilinopiperazine Derivative incorporates an amine functional group, a prodrug can be formed by the replacement of a hydrogen atom in the amine group with a group such as, for example, R-carbonyl, RO-carbonyl, NRR'-carbonyl where R and R' are each independently (C$_1$-C$_{10}$)alkyl, (C$_3$-C$_7$) cycloalkyl, benzyl, or R-carbonyl is a natural α-aminoacyl or natural α-aminoacyl, —C(OH)C(O)OY$^1$ wherein Y$^1$ is H, (C$_1$-C$_6$)alkyl or benzyl, —C(OY$^2$)Y$^3$ wherein Y$^2$ is (C$_1$-C$_4$) alkyl and Y$^3$ is (C$_1$-C$_6$)alkyl, carboxy (C$_1$-C$_6$)alkyl, amino(C$_1$-C$_4$)alkyl or mono-N— or di-N,N—(C$_1$-C$_6$)alkylaminoalkyl, —C(Y$^4$)Y$^5$ wherein Y$^4$ is H or methyl and Y$^5$ is mono-N— or di-N,N—(C$_1$-C$_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid.

"Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describes the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

The Anilinopiperazine Derivatives can form salts which are also within the scope of this invention. Reference to an Anilinopiperazine Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when an Anilinopiperazine Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting an Anilinopiperazine Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Anilinopiperazine Derivatives, and salts, solvates, esters and prodrugs thereof, may exist in their tautomeric form (for example, as an amide or imino ether). All such tautomeric forms are contemplated herein as part of the present invention.

The Anilinopiperazine Derivatives may contain asymmetric or chiral centers, and, therefore, exist in different stereoisomeric forms. It is intended that all stereoisomeric forms of the Anilinopiperazine Derivatives as well as mixtures thereof, including racemic mixtures, form part of the present invention. In addition, the present invention embraces all geometric and positional isomers. For example, if an Anilinopiperazine Derivative incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the Anilinopiperazine Derivatives may be atropisomers (e.g., substituted biaryls) and are considered as part of this invention. Enantiomers can also be separated by use of chiral HPLC column.

It is also possible that the Anilinopiperazine Derivatives may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if an Anilinopiperazine Derivative incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled Anilinopiperazine Derivatives (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled Anilinopiperazine Derivatives can generally be prepared by following procedures analogous to those disclosed in the Schemes and/or in the Examples hereinbelow, by substituting an appropriate isotopically labelled reagent for a non-isotopically labelled reagent.

Polymorphic forms of the Anilinopiperazine Derivatives, and of the salts, solvates, esters, prodrugs and stereoisomers of the Anilinopiperazine Derivatives, are intended to be included in the present invention.

The following abbreviations are used below and have the following meanings: Boc is tert-butoxycarbonyl, dba is dibenzylideneacetone, DMF is N,N-dimethylformamide, DMSO is dimethylsulfoxide, EtOAc is ethyl acetate, LCMS is liquid chromatography mass spectrometry, MeOH is methanol, NMR is nuclear magnetic resonance, PBS is phosphate buffered saline, SPA is scintillation proximity assay, Tf is triflate, TFA is trifluoroacetic acid and Xantphos is 9,9-Dimethyl-4,5-bis(diphenylphosphino)xanthene.

The Anilinopiperazine Derivatives of Formula (I)

The present invention provides Anilinopiperazine Derivatives of Formula (I):

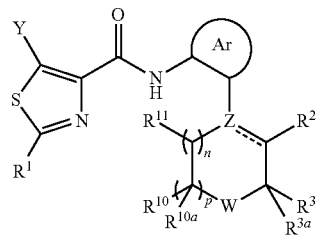

and pharmaceutically acceptable salts, solvates, esters, prodrugs and stereoisomers thereof, wherein the dashed lines indicate an optional and additional bond and wherein $R^1$, $R^2$, $R^3$, $R^{3a}$, $R^{10}$, $R^{10a}$, $R^{11}$, Ar, n, p, W, X, Y and Z are as defined above for formula (I).

In one embodiment, $R^1$ is nitrogen-containing heteroaryl.
In another embodiment, $R^1$ is nitrogen-containing heterocyclyl.
In another embodiment, $R^1$ is nitrogen-containing benzofused heteroaryl.
In still another embodiment, $R^1$ is nitrogen-containing benzofused heterocyclyl.
In one another embodiment, $R^1$ is N-morpholinyl.
In another embodiment, $R^1$ is N-pyrrolinyl.
In another embodiment, $R^1$ is N-imidazolyl.
In still another embodiment, $R^1$ is N-imidazolinyl.
In yet another embodiment, $R^1$ is N-pyrazolyl.
In another embodiment, $R^1$ is N-pyrazolinyl.
In a further embodiment, $R^1$ is N-pyrazolidinyl.
In one another embodiment, $R^1$ is N-isoxazolyl.
In another embodiment, $R^1$ is N-isothiazolyl.
In another embodiment, $R^1$ is N-oxadiazolyl.
In still another embodiment, $R^1$ is N-triazolyl.
In yet another embodiment, $R^1$ is N-thiadiazolyl.
In another embodiment, $R^1$ is N-thiomorpholinyl.
In a further embodiment, $R^1$ is N-piperazinyl.
In one another embodiment, $R^1$ is N-indolyl.
In another embodiment, $R^1$ is N-isoindolyl.
In another embodiment, $R^1$ is N-indolinyl.
In still another embodiment, $R^1$ is N-indazolyl.
In yet another embodiment, $R^1$ is N-benzimidazolyl.
In another embodiment, $R^1$ is N-benzthiazolyl.
In a further embodiment, $R^1$ is N-quinolinyl.
In a further embodiment, $R^1$ is N-1,2,3,4-tetrahydroquinolinyl.
In one another embodiment, $R^1$ is N-isoquinolinyl.
In another embodiment, $R^1$ is N-1,2,3,4-tetrahydroisoquinolinyl.
In another embodiment, $R^1$ is N-cinnolinyl.
In another embodiment, $R^1$ is N-phthalizinyl.
In still another embodiment, $R^1$ is N-quinazolinyl.
In yet another embodiment, $R^1$ is N-quinoxalinyl.
In another embodiment, $R^1$ is N-naphthyridinyl.
In a further embodiment, $R^1$ is N-pteridinyl.
In another embodiment, $R^1$ is N-carbazolyl.
In one embodiment, $R^1$ is

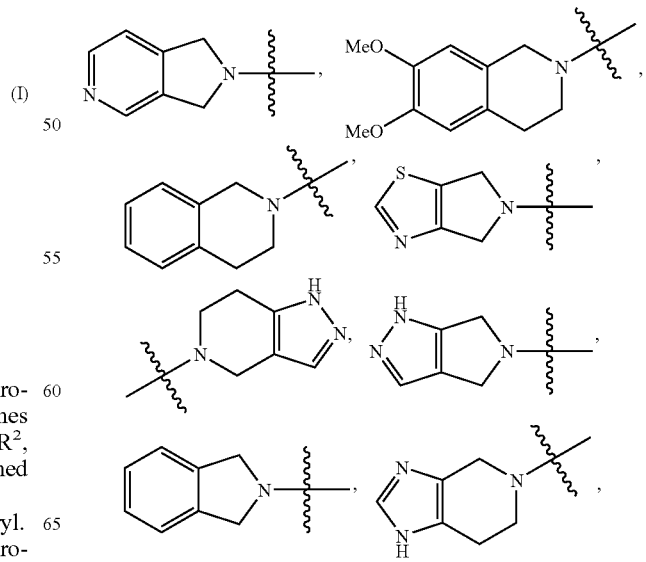

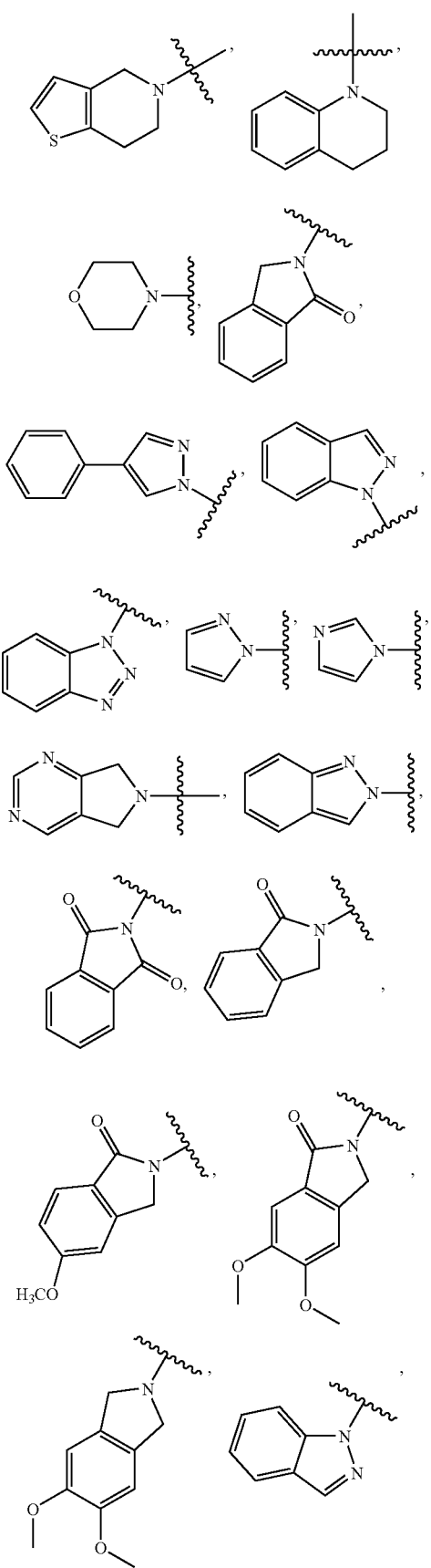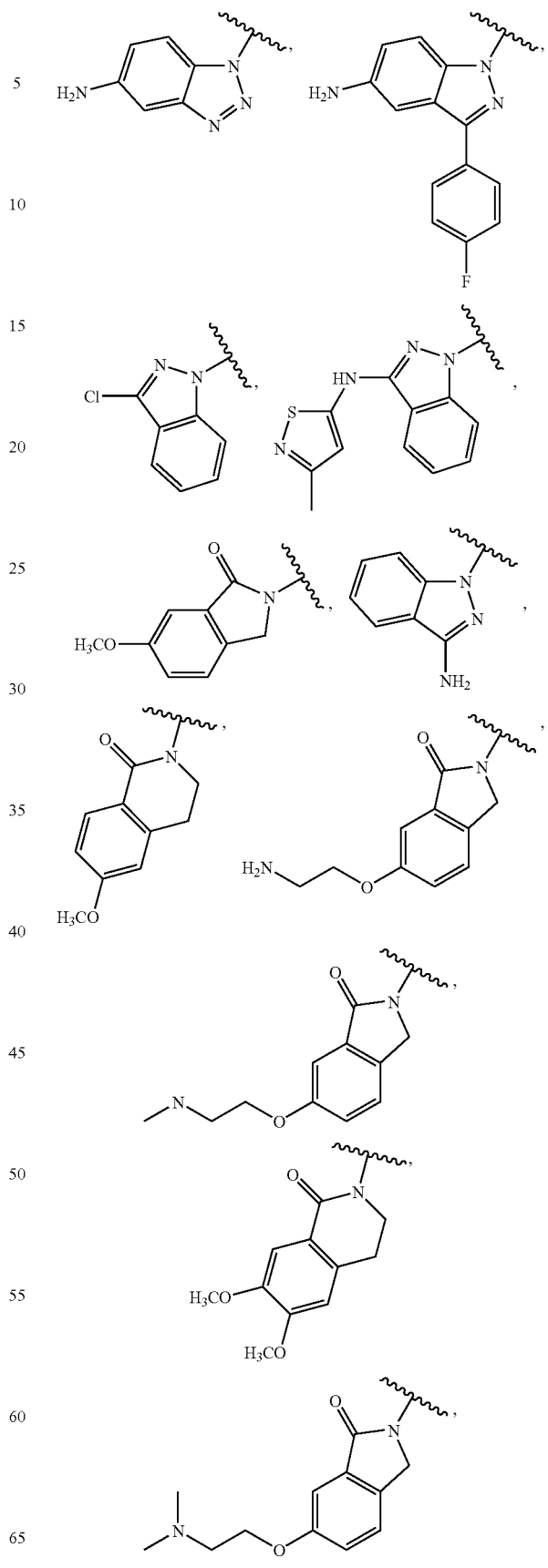

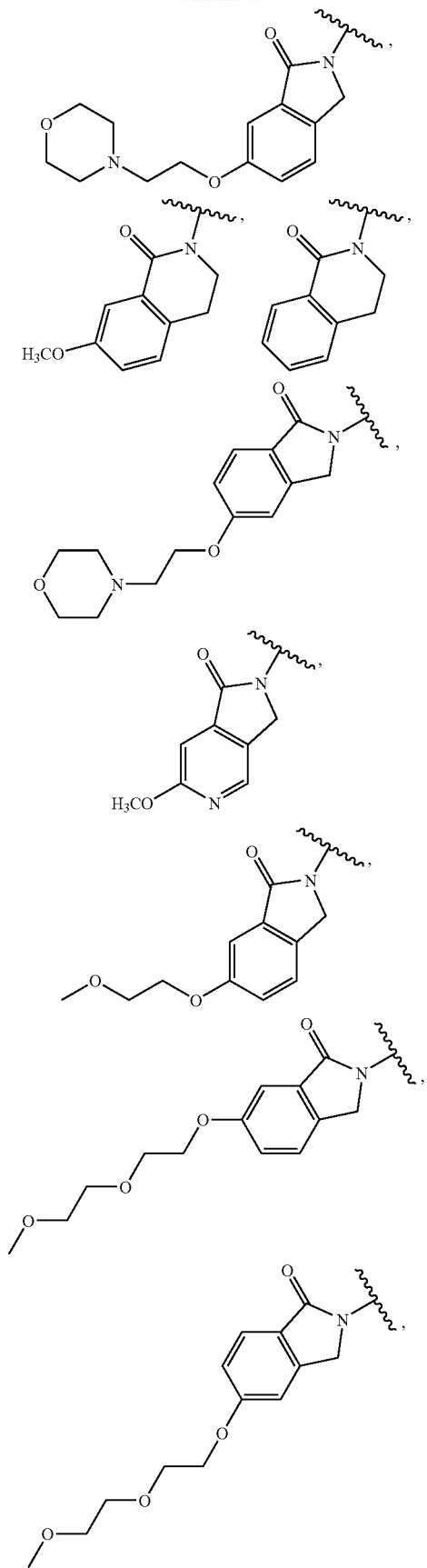
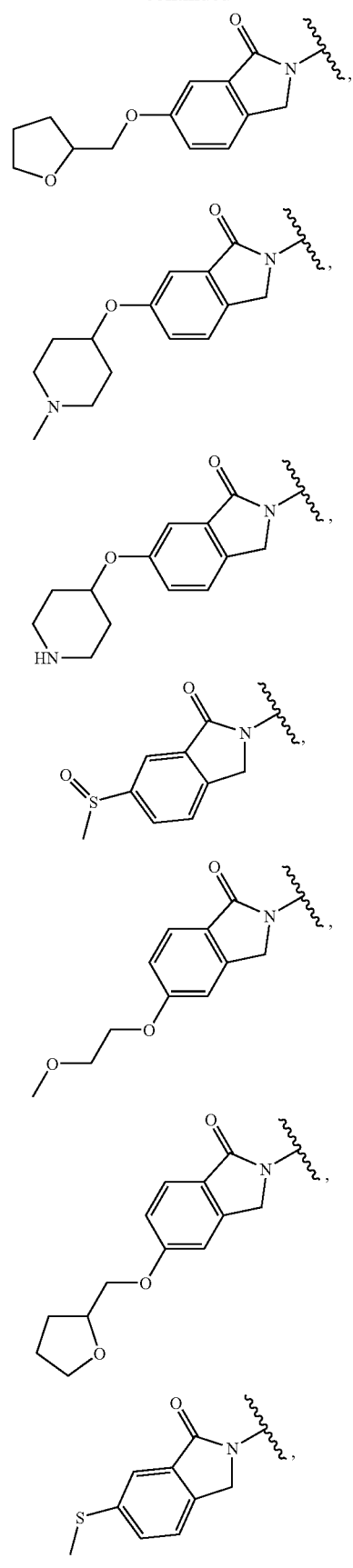

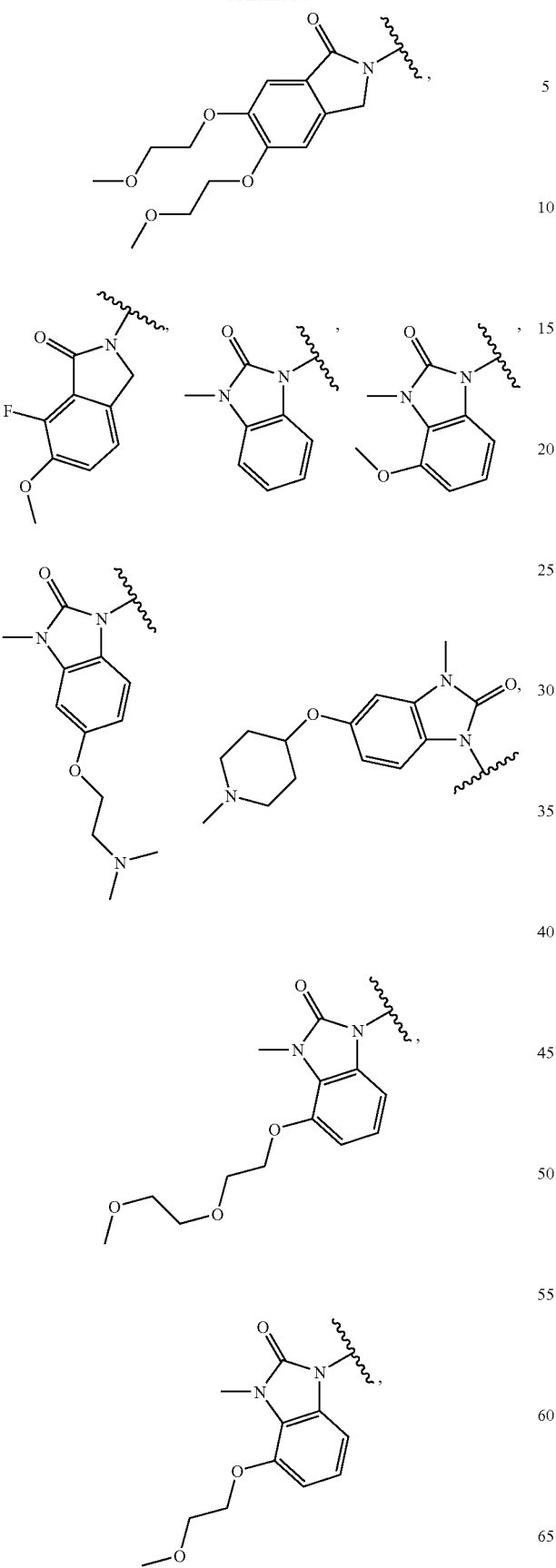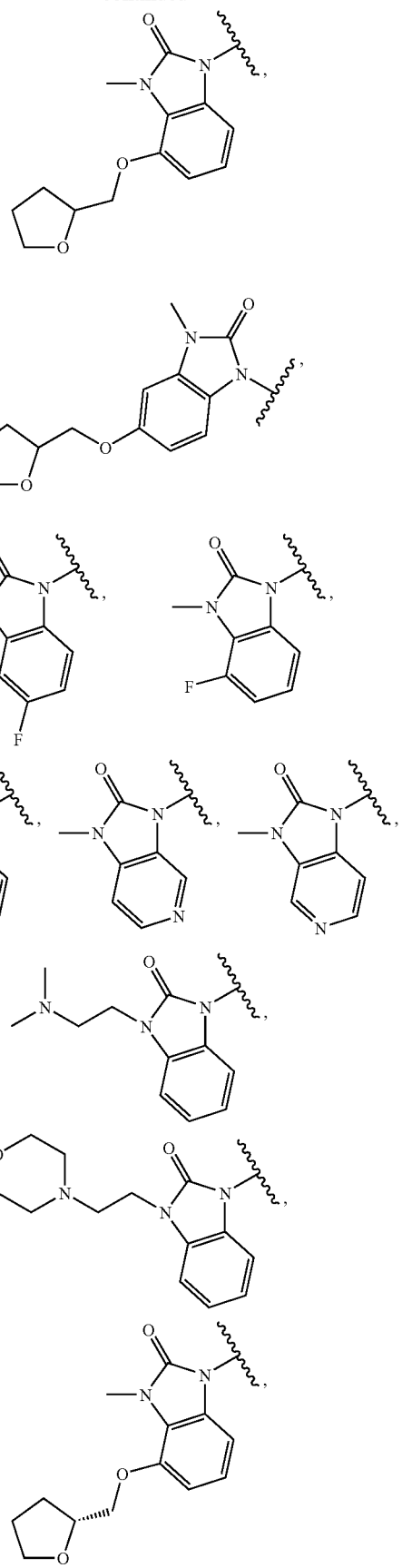

27
-continued
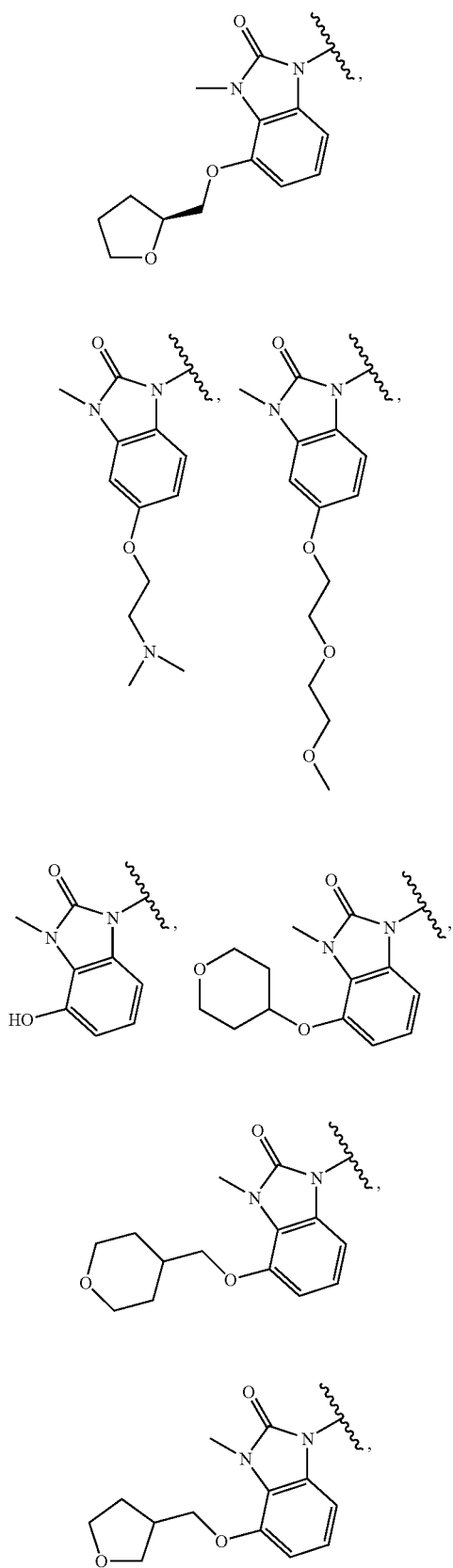
28
-continued
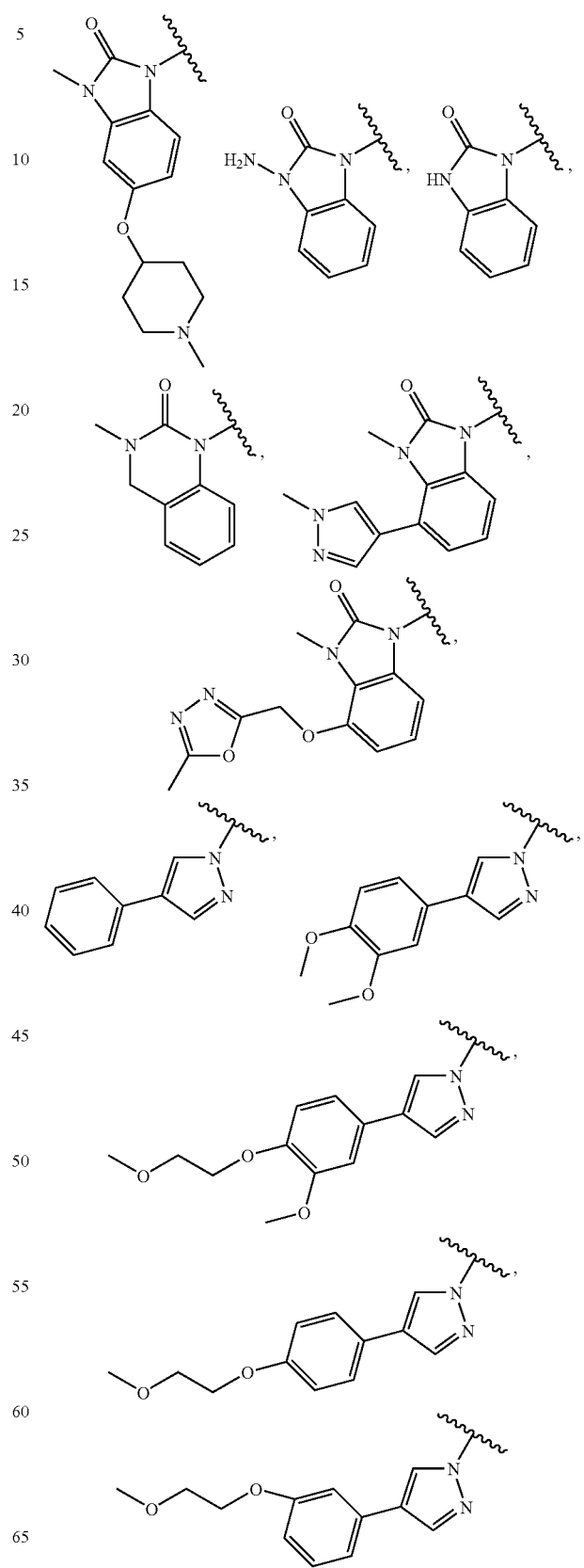

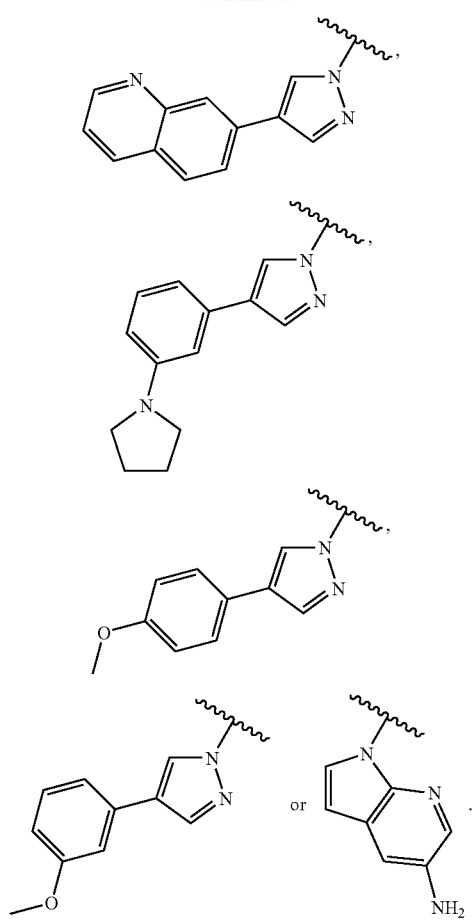
In another embodiment, R[1] is:
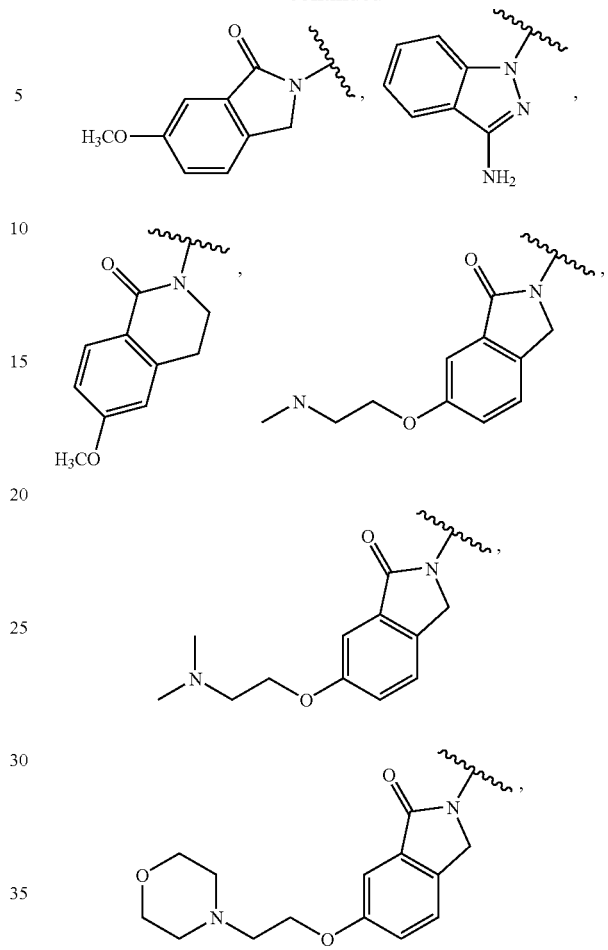

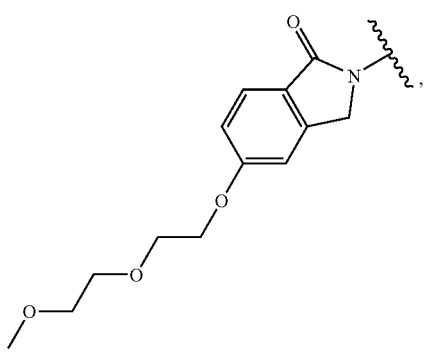
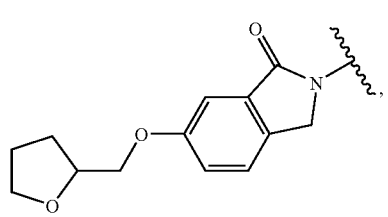
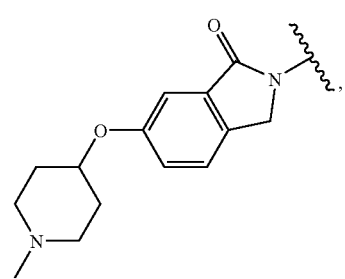
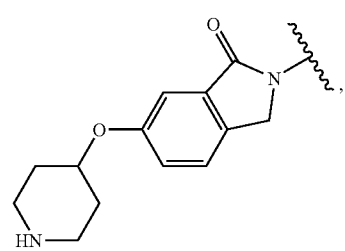
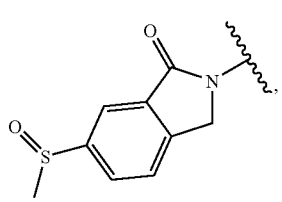
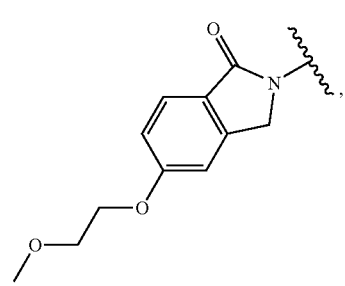
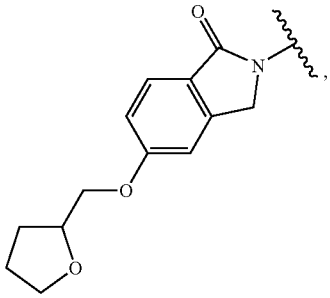
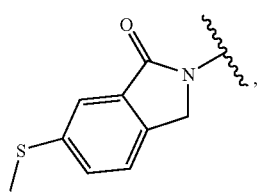
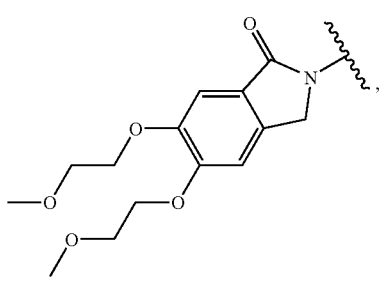
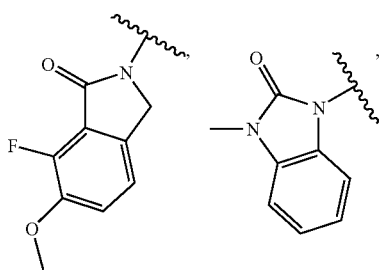
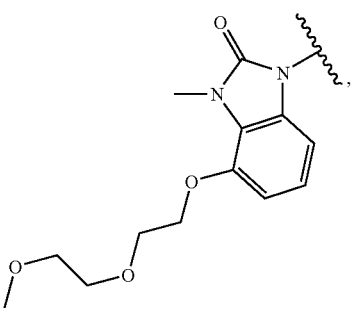
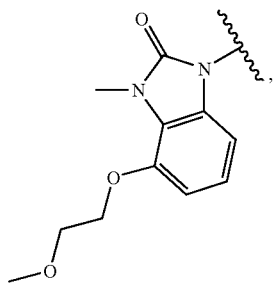

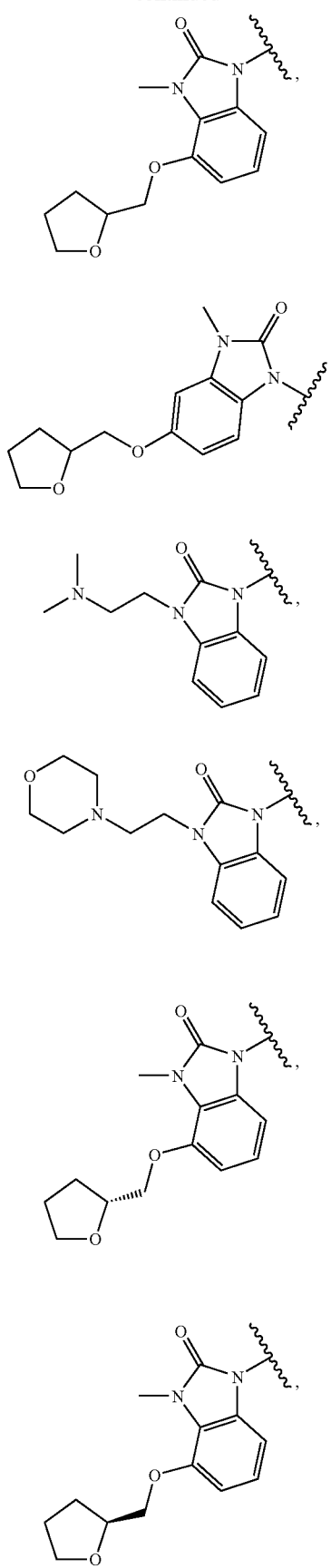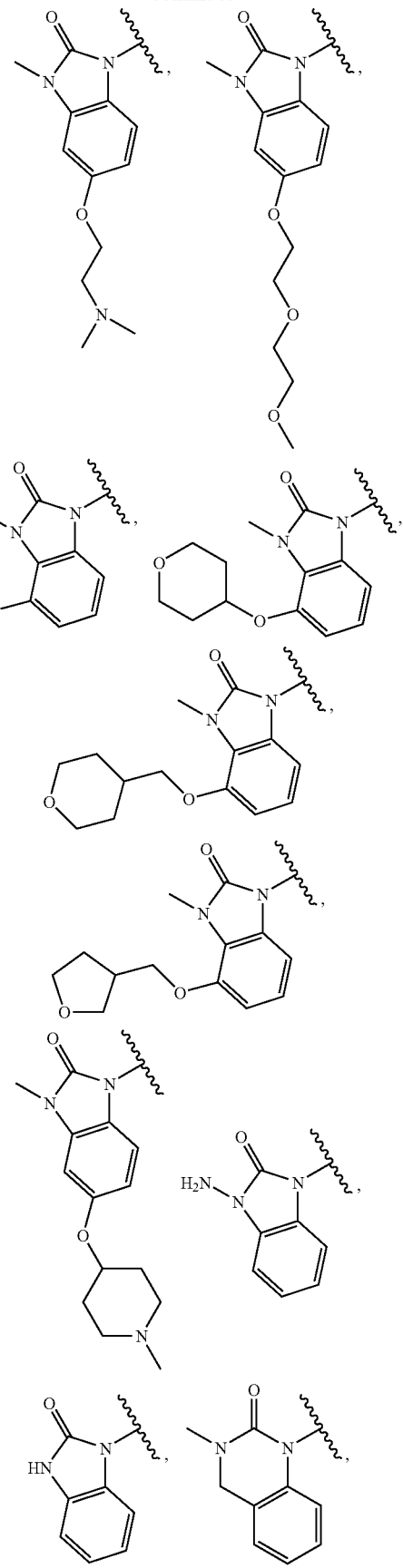

-continued

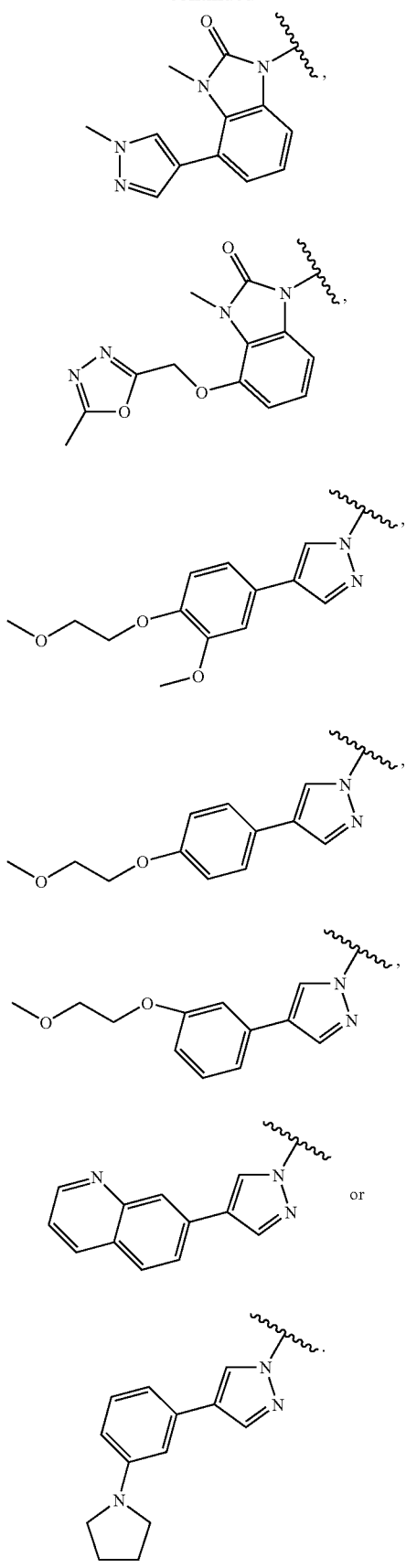

In one embodiment, $R^1$ is

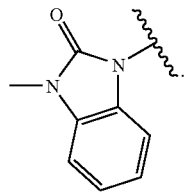

In one embodiment, $R^2$ is —H.
In another embodiment, $R^2$ is -alkyl.
In one embodiment, $R^2$ is —$CH_3$.
In another embodiment, $R^2$ is -α-$CH_3$.
In another embodiment, $R^2$ is -β-$CH_3$.
In a further embodiment, $R^2$ is -alkylene-$NH_2$.
In one embodiment, $R^2$ is —$NH_2$.
In another embodiment, $R^2$ is -α-$NH_2$.
In another embodiment, $R^2$ is -β-$NH_2$.
In a further embodiment, $R^2$ is -alkylene-$NH_2$.
In yet another embodiment, $R^2$ is —$CH_2NH_2$.
In one embodiment, $R^2$ and the carbon atom to which it is attached, form a carbonyl group.
In one embodiment, $R^3$ is —H.
In another embodiment, $R^a$ is —H.
In another embodiment, $R^3$ and $R^{3a}$ are each —H.
In still another embodiment, $R^3$ is -alkyl.
In another embodiment, $R^3$ is haloalkyl.
In yet another embodiment, $R^3$ is hydroxyalkyl.
In one embodiment, $R^3$ is -(alkylene)$_m$-C(O)N($R^8$)$_2$.
In another embodiment, $R^3$ is -(alkylene)$_m$-NHC(O)—$R^9$.
In another embodiment, $R^3$ is -(alkylene)$_m$-N($R^9$)$_2$.
In one embodiment, $R^3$ is —$CH_3$.
In another embodiment, $R^3$ is -α-$CH_3$.
In another embodiment, $R^3$ is -β-$CH_3$.
In one embodiment, $R^3$ is —$NH_2$.
In another embodiment, $R^3$ is -α-$NH_2$.
In another embodiment, $R^3$ is -β-$NH_2$.
In a further embodiment, $R^3$ is -alkylene-$NH_2$.
In yet another embodiment, $R^3$ is —$CH_2NH_2$.
In one embodiment, $R^3$ and $R^{3a}$ and the common carbon atom to which they are attached, join to form a carbonyl group.
In another embodiment, $R^3$ and $R^{3a}$ and the common carbon atom to which they are attached, join to form a cycloalkyl group.
In another embodiment, $R^3$ and $R^{3a}$ and the common carbon atom to which they are attached, join to form a heterocycyl group.
In one embodiment, $R^2$ and $R^3$ are each —H.
In another embodiment, $R^2$ is alkyl and $R^3$ is —H.
In another embodiment, $R^2$ is —H and $R^3$ is alkyl.
In one embodiment, $R^{10}$ is —H.
In another embodiment, $R^{10a}$ is —H.
In another embodiment, $R^{10}$ and $R^{10a}$ are each —H.
In still another embodiment, $R^{10}$ is -alkyl.
In another embodiment, $R^{10}$ is haloalkyl.
In yet another embodiment, $R^{10}$ is hydroxyalkyl.
In one embodiment, $R^{10}$ is -(alkylene)$_m$-C(O)N($R^8$)$_2$.
In another embodiment, $R^{10}$ is -(alkylene)$_m$-NHC(O)—$R^9$.
In another embodiment, $R^{10}$ is -(alkylene)$_m$-N($R^9$)$_2$.
In one embodiment, $R^{10}$ is —$CH_3$.
In another embodiment, $R^{10}$ is -α-$CH_3$.
In another embodiment, $R^{10}$ is -β-$CH_3$.
In one embodiment, $R^{10}$ is —$NH_2$.

In another embodiment, $R^{10}$ is -α-NH$_2$.
In another embodiment, $R^{10}$ is -β—NH$_2$.
In a further embodiment, $R^{10}$ is -alkylene-NH$_2$.
In yet another embodiment, $R^{10}$ is —CH$_2$NH$_2$.
In one embodiment, $R^{10}$ and $R^{10a}$ and the common carbon atom to which they are attached, join to form a carbonyl group.
In another embodiment, $R^{10}$ and $R^{10a}$ and the common carbon atom to which they are attached, join to form a cycloalkyl group.
In another embodiment, $R^{10}$ and $R^{10a}$ and the common carbon atom to which they are attached, join to form a heterocycyl group.
In one embodiment, $R^{11}$ is —H.
In another embodiment, $R^{11}$ is -alkyl.
In one embodiment, $R^{11}$ is —CH$_3$.
In another embodiment, $R^{11}$ is -α-CH$_3$.
In another embodiment, $R^{11}$ is -β-CH$_3$.
In a further embodiment, $R^{11}$ is -alkylene-NH$_2$.
In one embodiment, $R^{11}$ is —NH$_2$.
In another embodiment, $R^{11}$ is -α-NH$_2$.
In another embodiment, $R^{11}$ is -β—NH$_2$.
In a further embodiment, $R^{11}$ is -alkylene-NH$_2$.
In yet another embodiment, $R^{11}$ is —CH$_2$NH$_2$.
In another embodiment, $R^{11}$ and the carbon atom to which it is attached, form a carbonyl group.
In one embodiment, n and p are each 1 and $R^{10}$, $R^{10a}$ and $R^{11}$ are each H.
In another embodiment, n and p are each 1 and $R^2$, $R^{10}$, $R^{10a}$ and $R^{11}$ are each H
In still another embodiment, n and p are each 1 and $R^2$, $R^{3a}$, $R^{10}$, $R^{10a}$ and $R^{11}$ are each H.
In one embodiment, Z is —N—; n and p are each 1; and $R^{10}$, $R^{10a}$ and $R^{11}$ are each H.
In another embodiment, Z is —N—; n and p are each 1; and $R^2$, $R^{10}$, $R^{10a}$ and $R^{11}$ are each H
In still another embodiment, Z is —N—; n and p are each 1; and $R^2$, $R^{3a}$, $R^{10}$, $R^{10a}$ and $R^{11}$ are each H.
In one embodiment, Ar is aryl.
In another embodiment, Ar is:

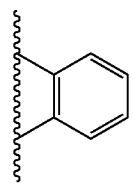

In one embodiment, Ar is heteroaryl.
In another embodiment, Ar is

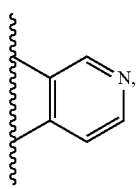 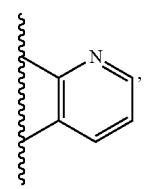 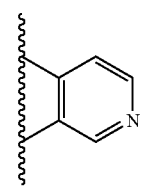 or

-continued

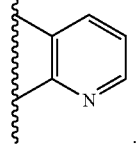

.

In another embodiment, Ar is

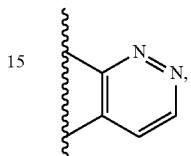 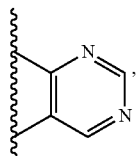 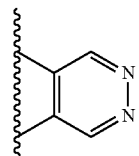 or

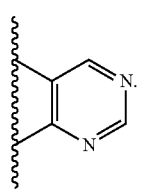

In one embodiment, W is —C($R^4$)$_2$—.
In another embodiment, W is —N($R^{12}$)—.
In another embodiment, W is —O—.
In still another embodiment, W is —S—.
In one embodiment, W is —C($R^4$)$_2$— and both $R^4$ groups, together with the common carbon atom to which they are attached, join to form a cycloalkyl group.
In another embodiment, W is —C($R^4$)$_2$— and both $R^4$ groups, together with the common carbon atom to which they are attached, join to form a heterocyclyl group.
In another embodiment, W is —C($R^4$)$_2$— and both $R^4$ groups, together with the common carbon atom to which they are attached, join to form a group having the formula:

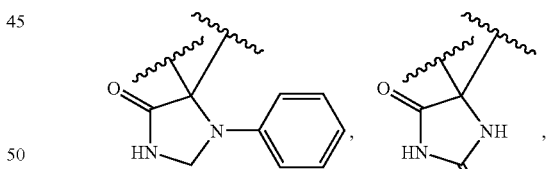

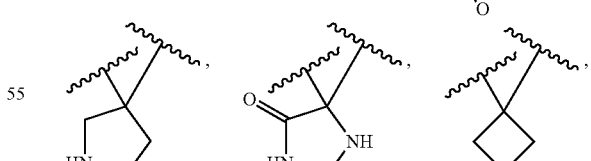

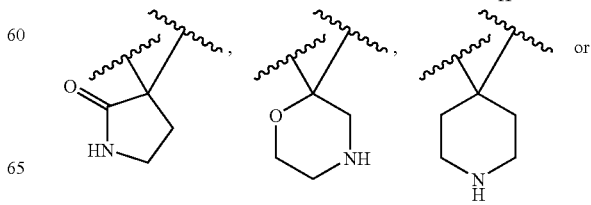

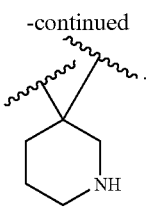

In one embodiment, W is —C(R⁴)₂—, wherein each R⁴ group is independently selected from H, -(alkylene)$_m$-NH₂, —NH-alkyl, —N(alkyl)₂, —C(O)NH₂, —OH, —C(O)O-alkyl, 5 or 6 membered heteroaryl or hydroxyalkyl.

In another embodiment, W is —C(R⁴)₂—, wherein each R⁴ group is independently selected from H, -(alkylene)$_m$-NH₂, —NH-alkyl, —N(alkyl)₂ or —C(O)NH₂.

In one embodiment, W is —C(NH₂)(C(O)NH₂)—.

In another embodiment, W is —C(NH₂)(alkyl)-.

In another embodiment, W is —C(NH₂)(CH₃)—.

In still another embodiment, W is —C(NH₂)(—C(O)NHOH)—.

In one embodiment, W is —CH(—NC(O)CF₃)—.

In another embodiment, W is —CH(—NS(O)₂alkyl)-.

In still another embodiment, W is —C(NH₂)(—C(O)NHOH)—.

In one embodiment, W is —CH(—CH₂NH₂)—.

In another embodiment, W is —C(—C(O)NH₂)(—NHalkyl)-.

In another embodiment, W is —CH(—C(O)NH₂)—.

In still another embodiment, W is —CH₂—.

In yet another embodiment, W is —NH—.

In still another embodiment, W is —CH(OH)—.

In a further embodiment, W is —CH(NH₂)—.

In one embodiment, W is —CH(CH₃)—.

In another embodiment, W is —CH(—C(O)CH₃)—.

In another embodiment, W is —C(OH)(alkyl)-.

In another embodiment, W is —C(OH)(-alkylene-OH)—.

In another embodiment, n is 0; p is 1 or 2; Z is —N—; R², R³, R³ᵃ, R¹⁰, R¹⁰ᵃ and R¹¹ are each H; W is —C(R⁴)₂—; and both R⁴ groups, together with the common carbon atom to which they are attached, join to form a group having the formula:

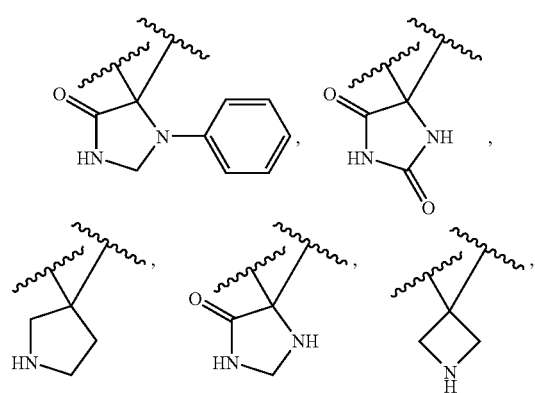

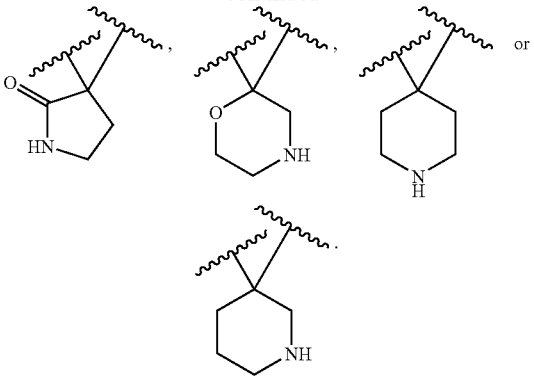

In one embodiment, n is 0; p is 1 or 2; Z is —N—; R², R³, R³ᵃ, R¹⁰, R¹⁰ᵃ and R¹¹ are each H; W is —C(R⁴)₂—, wherein each R⁴ group is independently selected from H, -(alkylene)$_m$-NH₂, —NH-alkyl, —N(alkyl)₂, —C(O)NH₂, —OH, —C(O)O-alkyl, 5 or 6 membered heteroaryl or hydroxyalkyl.

In another embodiment, n is 0; p is 1 or 2; Z is —N—; R², R³, R³ᵃ, R¹⁰, R¹⁰ᵃ and R¹¹ are each H; W is —C(R⁴)₂—, wherein each R⁴ group is independently selected from H, -(alkylene)$_m$-NH₂, —NH-alkyl, —N(alkyl)₂ or —C(O)NH₂.

In one embodiment, Y is —H.

In another embodiment, Y is -halo, -alkyl or —CN.

In another embodiment, Y is methyl.

In one embodiment, Z is —C(R⁷)—.

In another embodiment, Z is —C— and the optional and additional bond is present.

In another embodiment, Z is —CH—.

In still another embodiment, Z is —C(alkyl)-.

In yet another embodiment, Z is —C(OH)—.

In another embodiment, Z is —C(—O-alkyl)-.

In still another embodiment, Z is —C(—CF₃)—.

In a further embodiment, Z is —N—.

In one embodiment, n is 0.

In another embodiment, n is 1.

In another embodiment, n is 2.

In one embodiment, n is 0, W is —CH₂— and Z is —N—.

In another embodiment, n is 1, W is —CH₂— and Z is —N—.

In another embodiment, n is 0, W is —CH₂—, Z is —N—, R² is H and R³ is H.

In still another embodiment, n is 1, W is —C(NH₂)(C(O)NH₂)—, Z is —N—, R² is H and R³ is —H.

In yet another embodiment, n is 1, W is —CH₂—, Z is —N—, R³ is —H and R³ᵃ is —NH₂.

In another embodiment, n is 1, W is —CH₂—, Z is —N—, R² is —H and R³ is -β-NH₂.

In a further embodiment, n is 0, W is —CH₂—, Z is —N—, R² is —H and R³ is —NH₂.

In a further embodiment, n is 0, W is —CH₂—, Z is —N—, R² is —H and R³ is -α-NH₂.

In another embodiment, n is 1, W is —CH(NH₂)—, Z is —N—, R² is —H and R³ is —H.

In another embodiment, n is 1, W is —CH(OH)—, Z is —N—, R² is —H and R³ is —H.

In still another embodiment, n is 1, W is —CH(NH₂)(alkyl)-, Z is —N—, R² is —H and R³ is —H.

In one embodiment, Y is —H.

In another embodiment, Y is -halo, -alkyl or —CN.

In one embodiment, R² is —H and Z is —N—.

In another embodiment, R² is —H, Y is —H and Z is —N—.
In one embodiment, Ar is phenyl, R² is —H and Z is —CH—.
In one embodiment, the optional double bond is present.
In another embodiment, the optional double bond is absent.
In one embodiment, the group
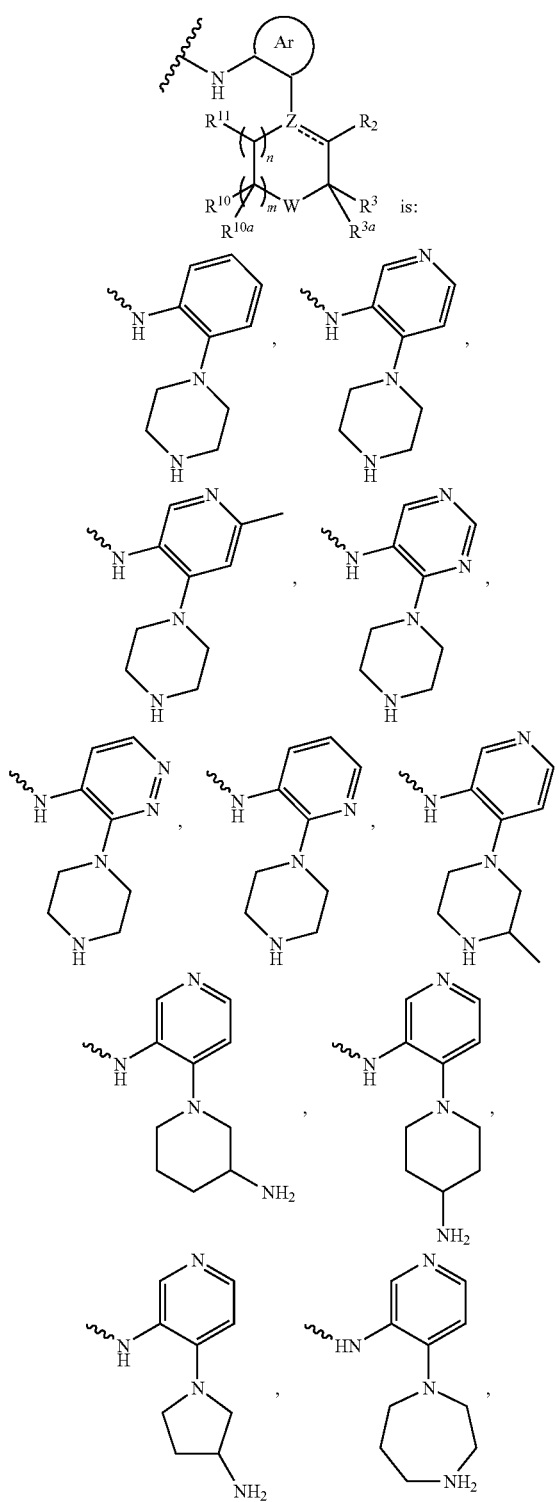
is:
-continued
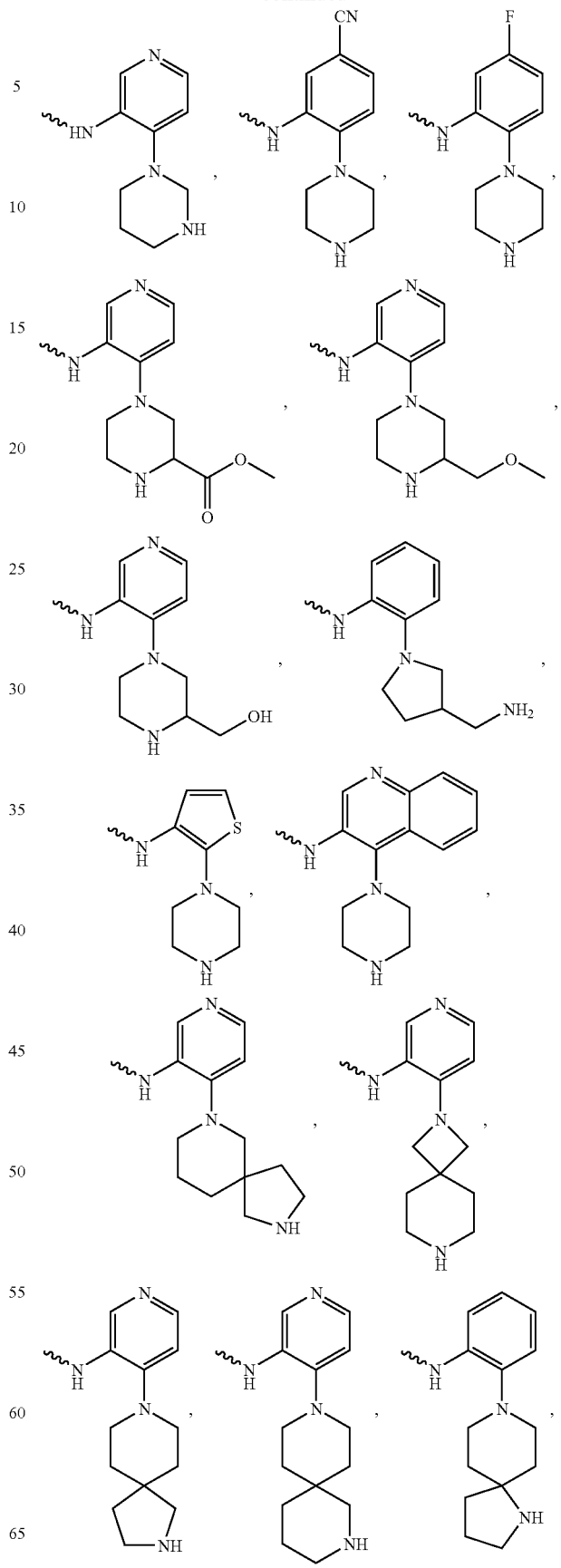

-continued
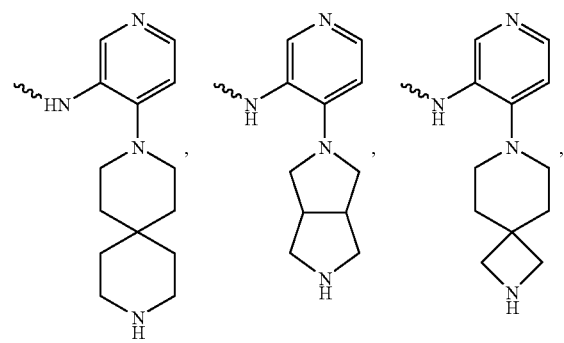
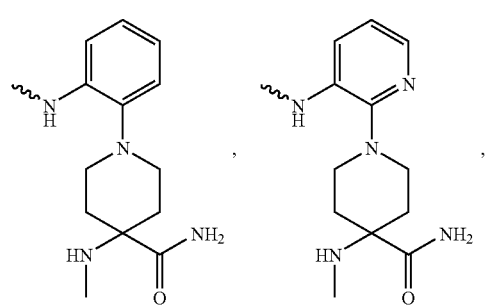
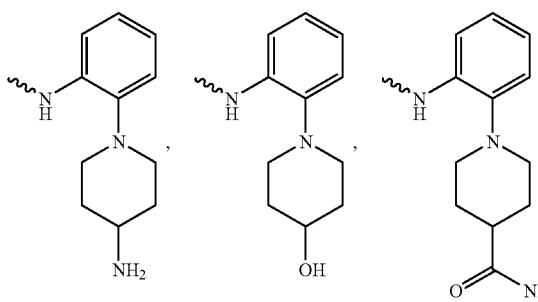
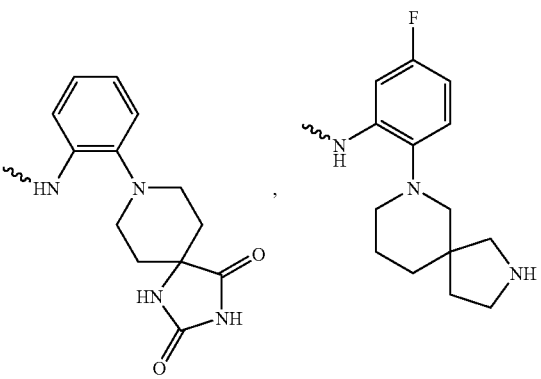
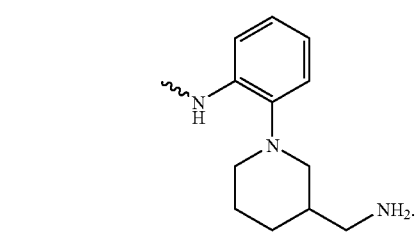
In another embodiment, the group
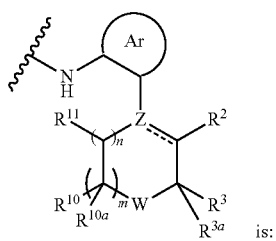
is:
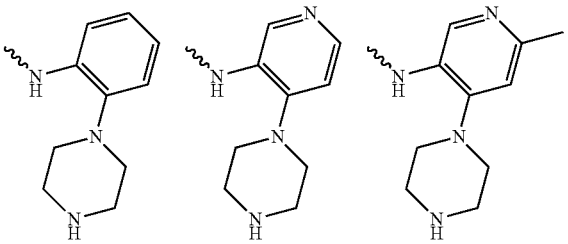
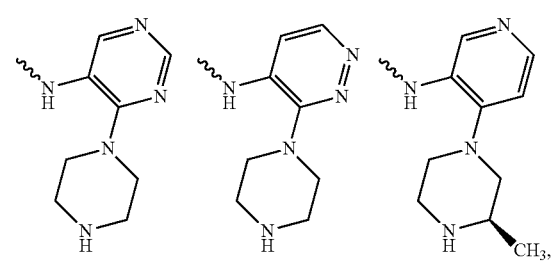
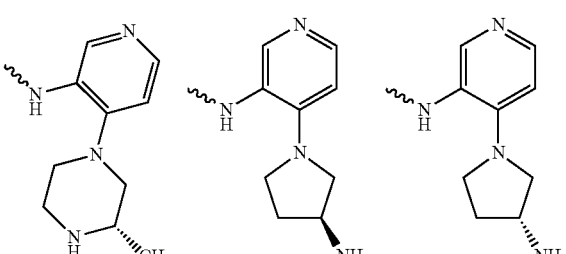
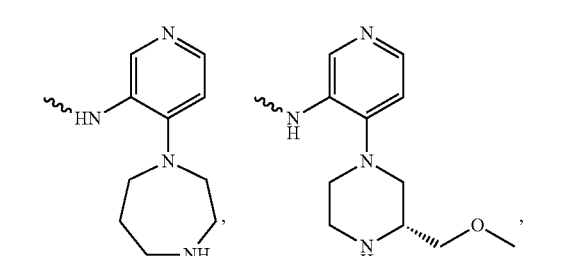
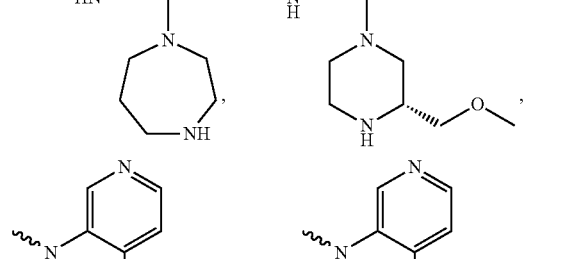

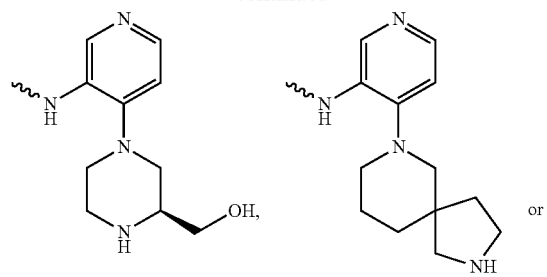
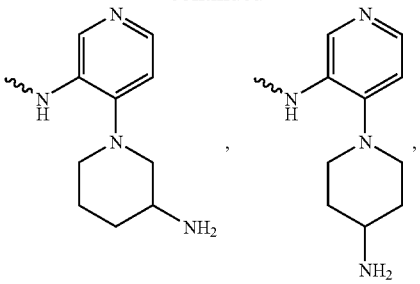
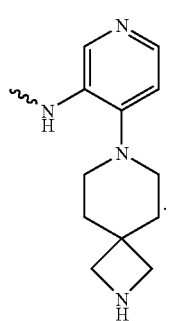
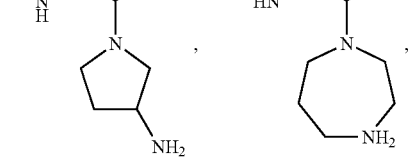
In one embodiment, the group
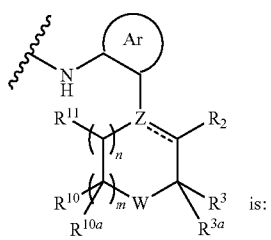 is:
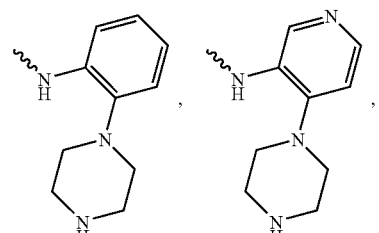
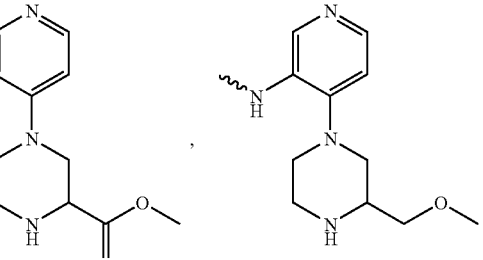
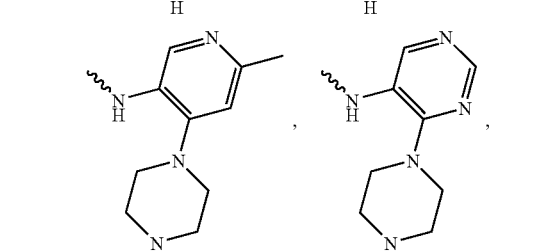
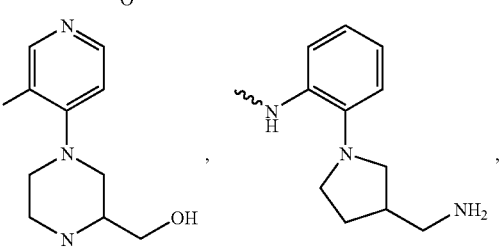
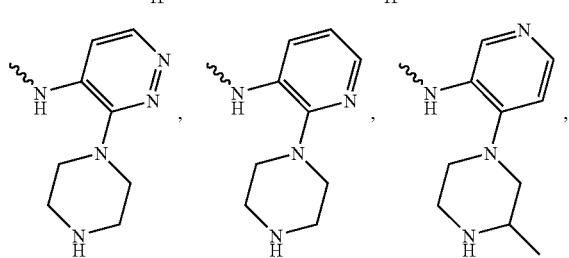
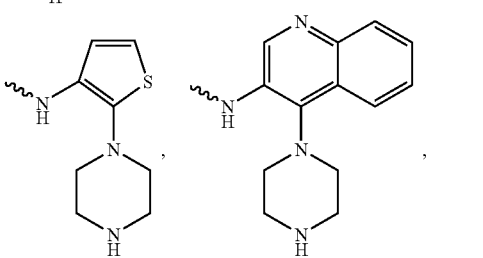

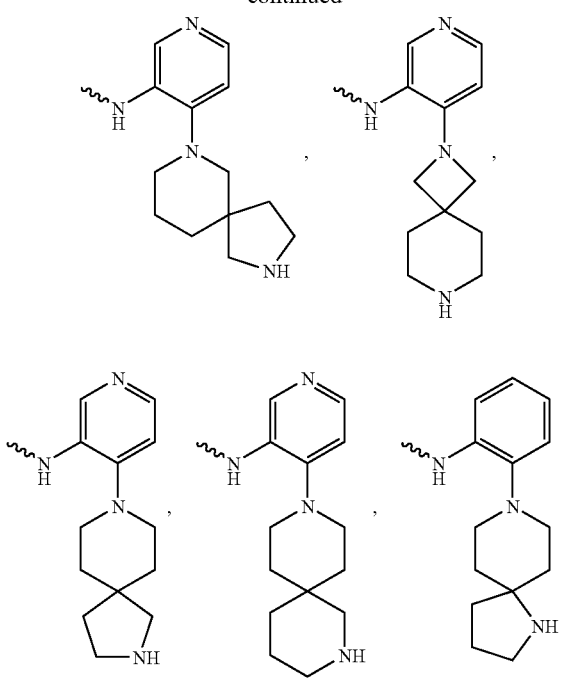
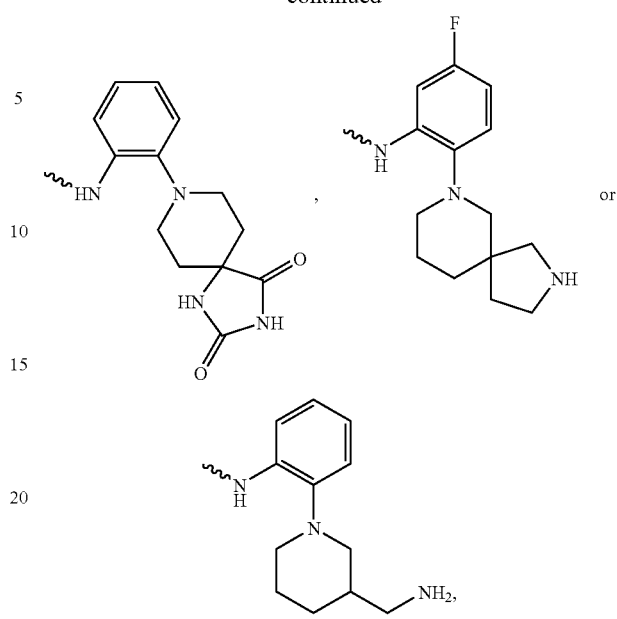
and the group R[1] is:
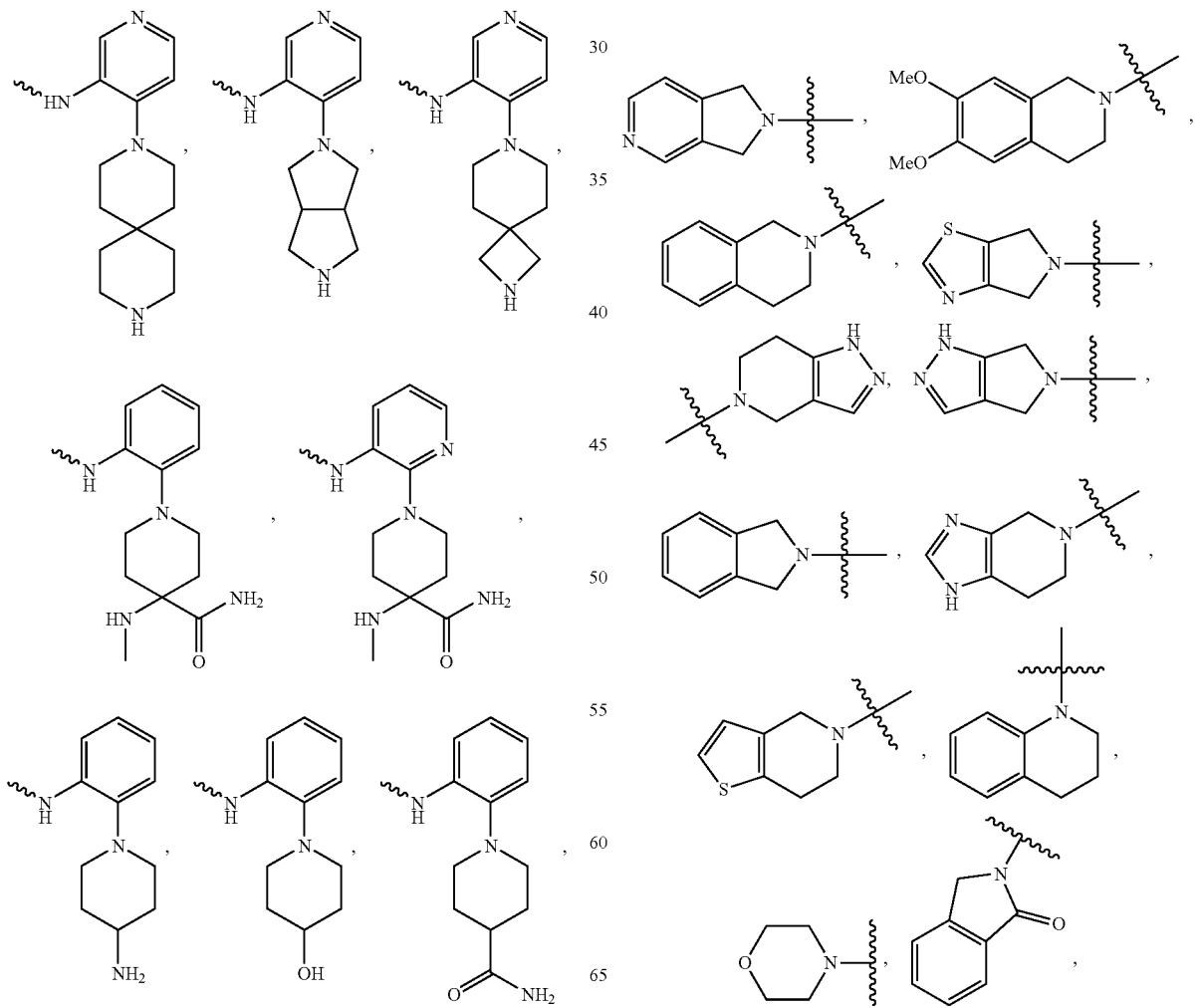

-continued
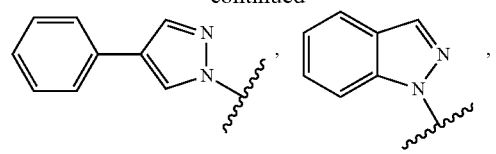
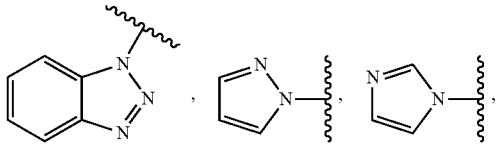
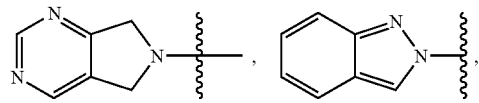
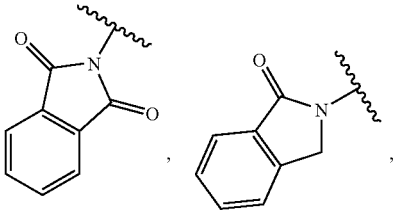
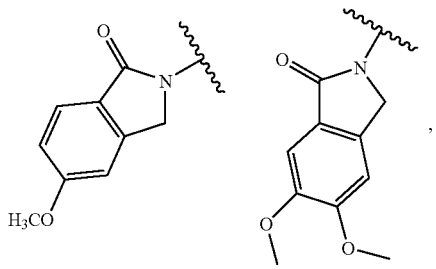
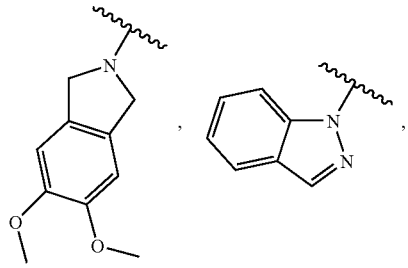
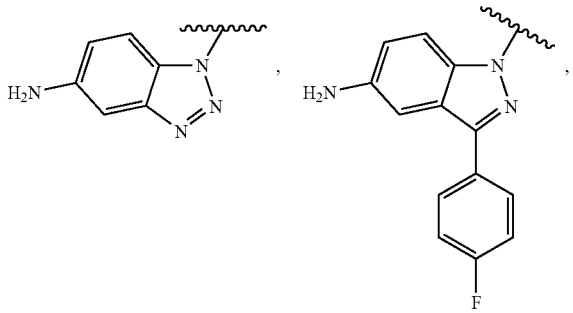
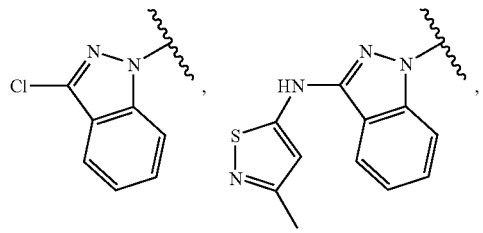
-continued
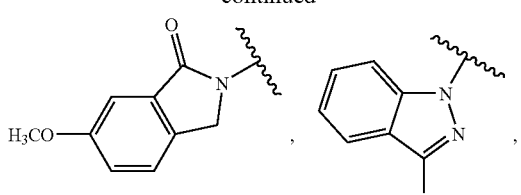
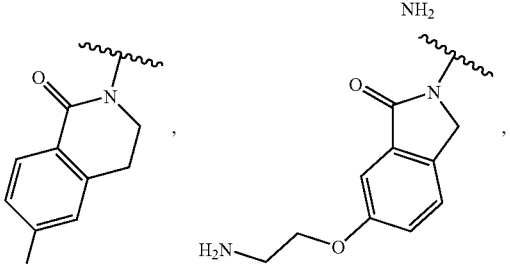
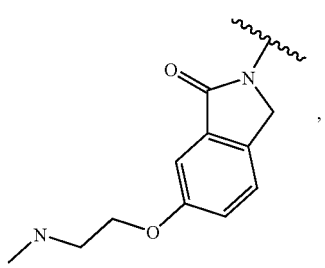
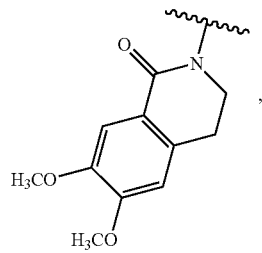
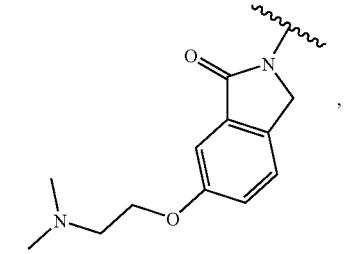
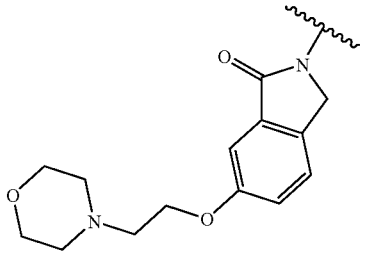
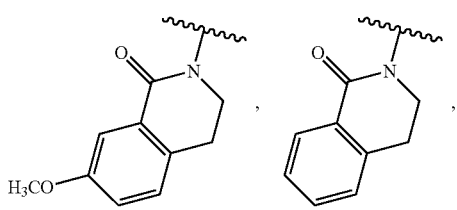

51
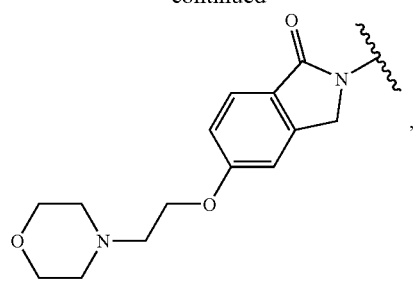
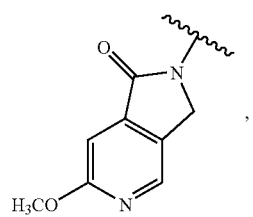
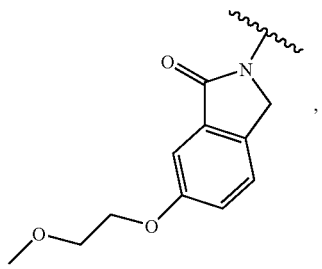
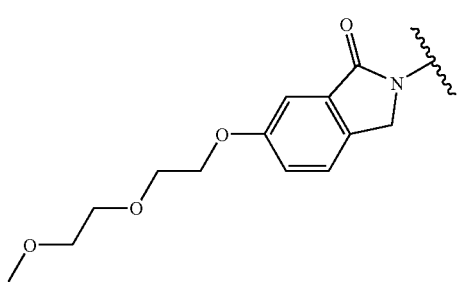
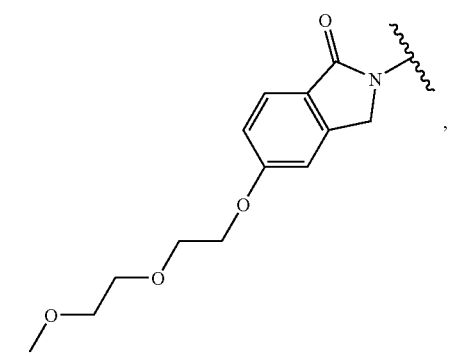
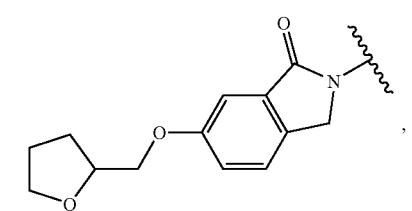
52
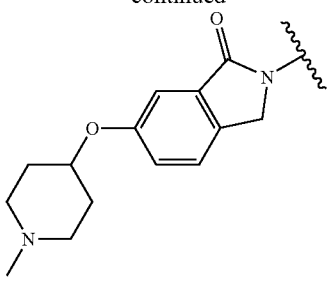
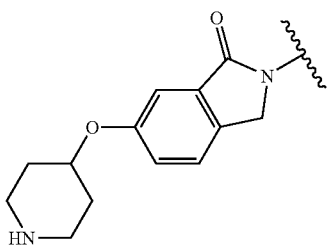
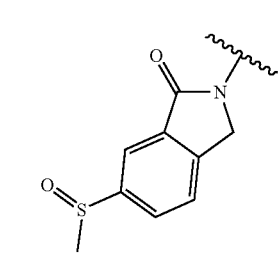
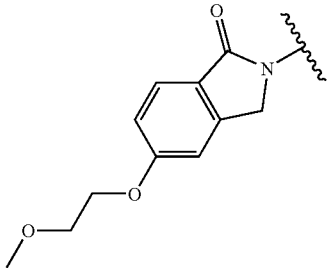
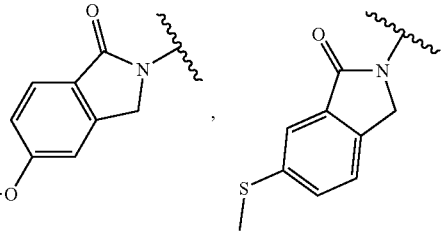
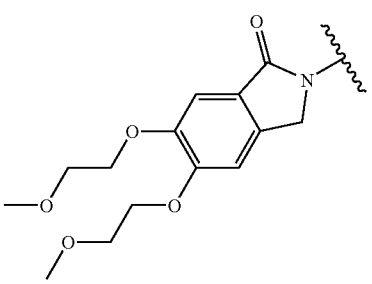

53
-continued
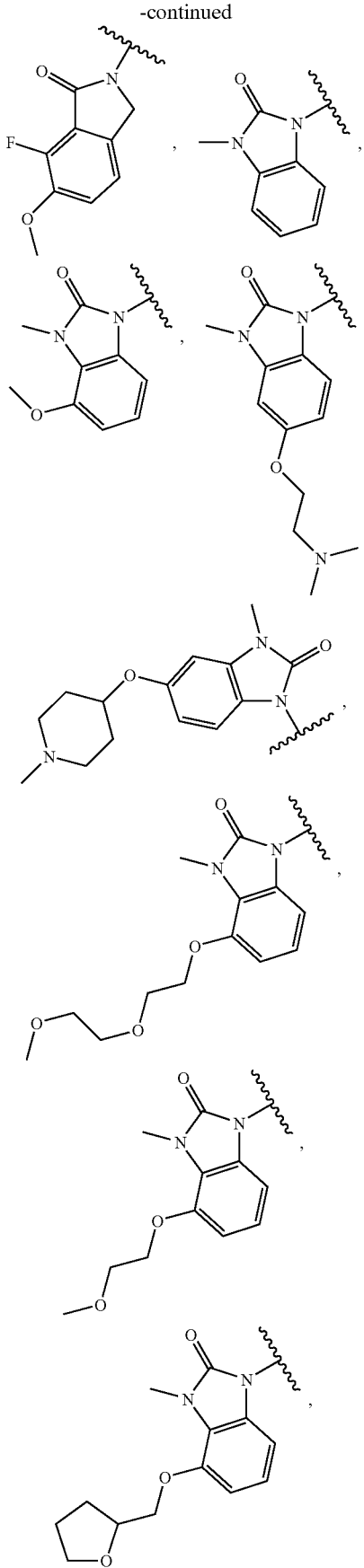
54
-continued
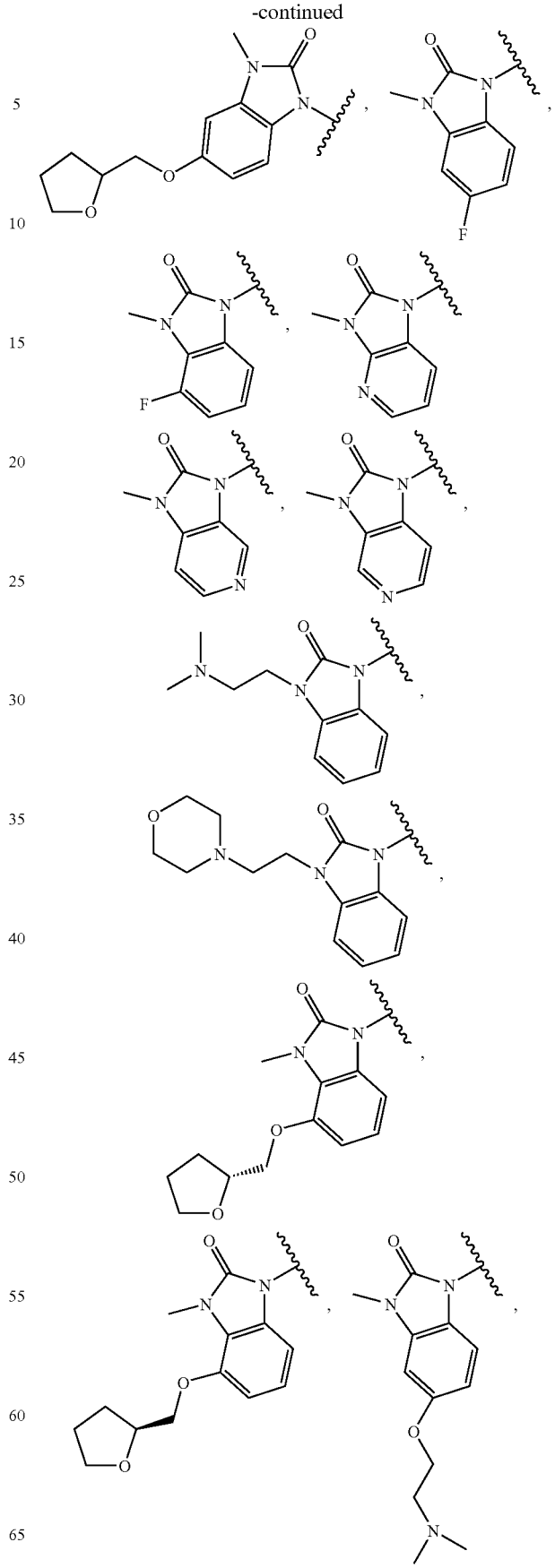

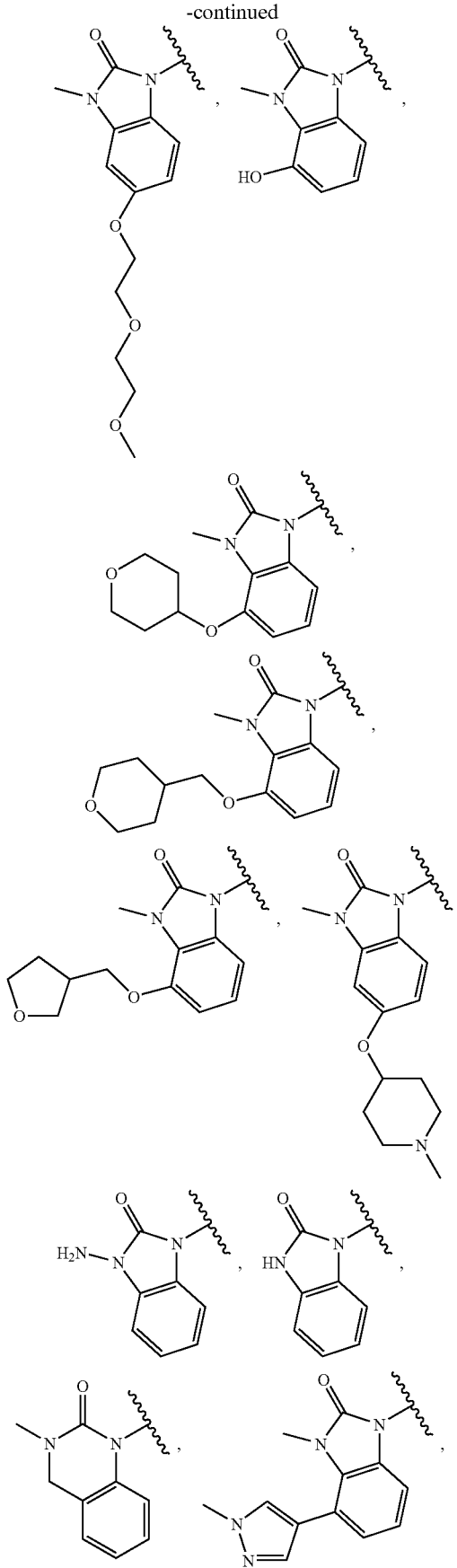
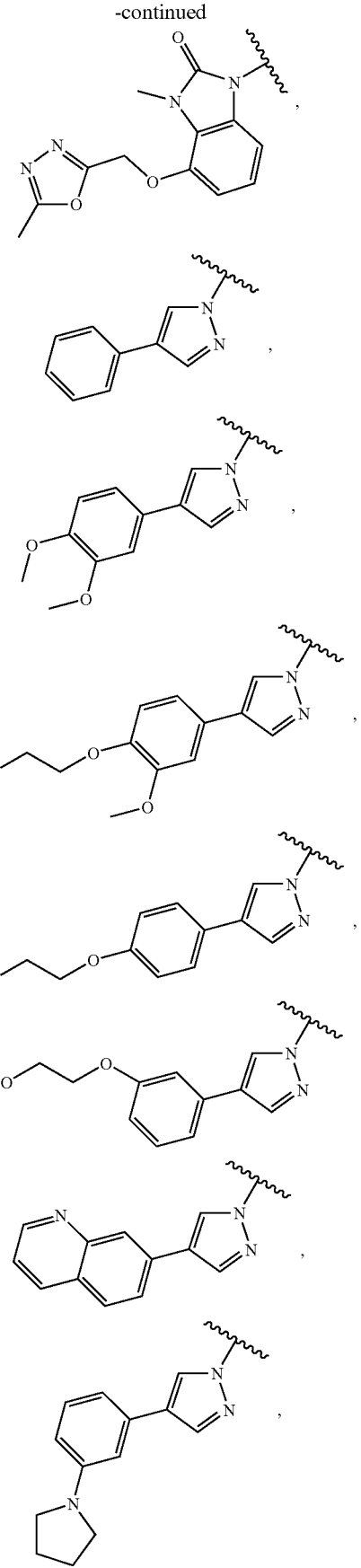

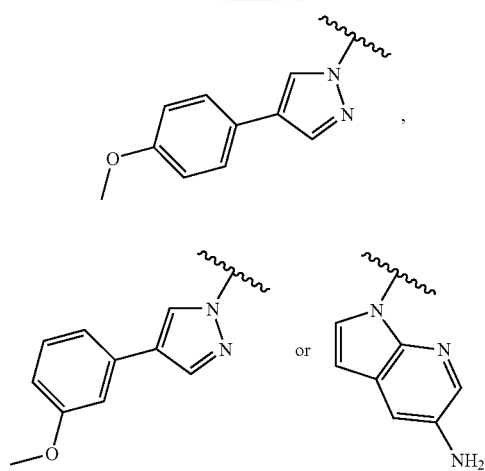
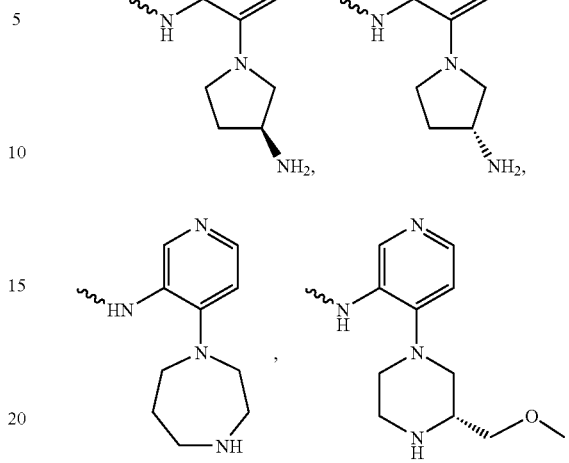
In another embodiment, the group
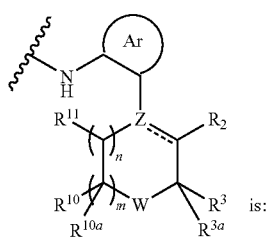 is:
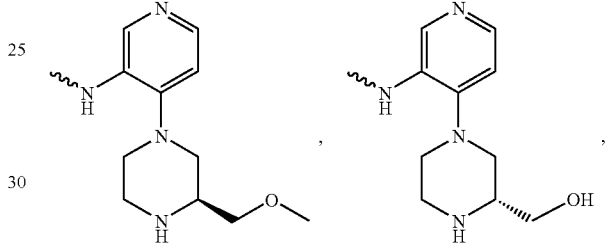
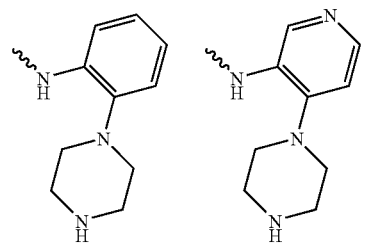
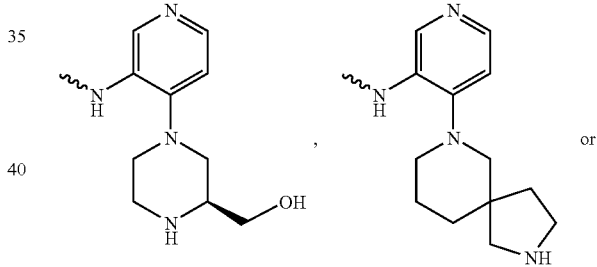
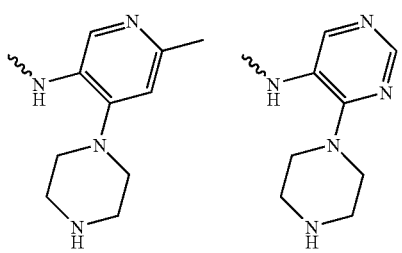
and the group R¹ is:
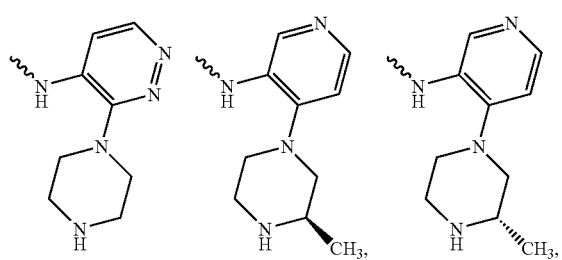
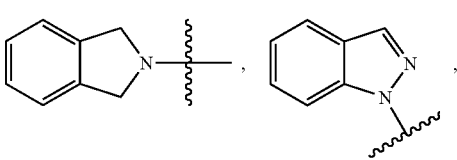

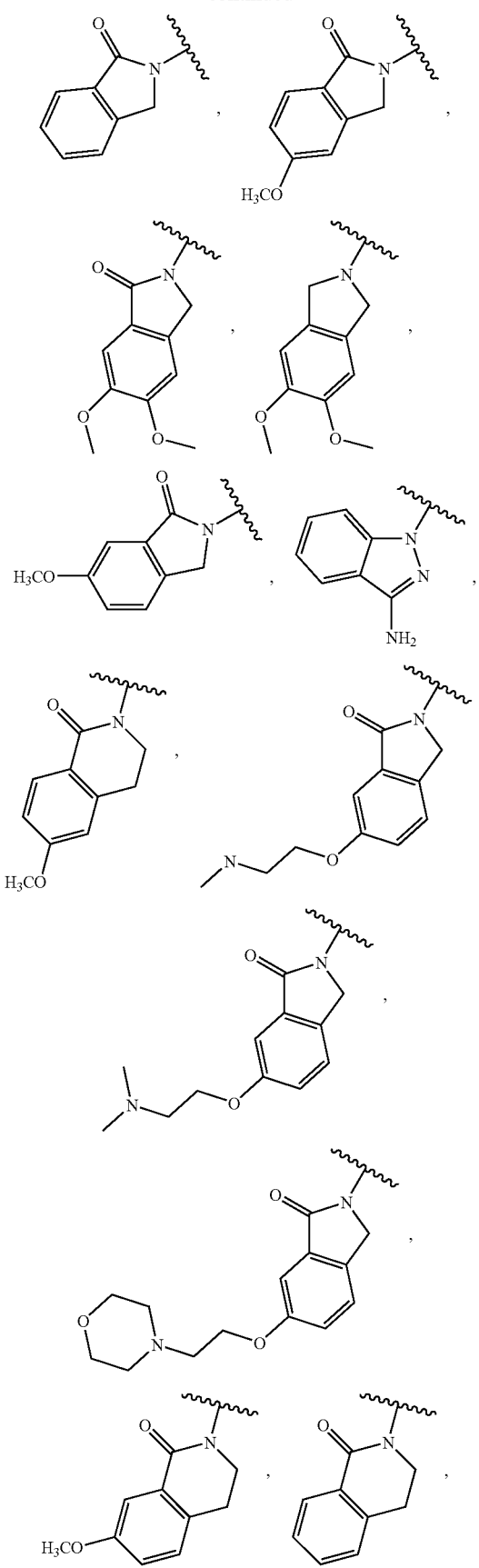
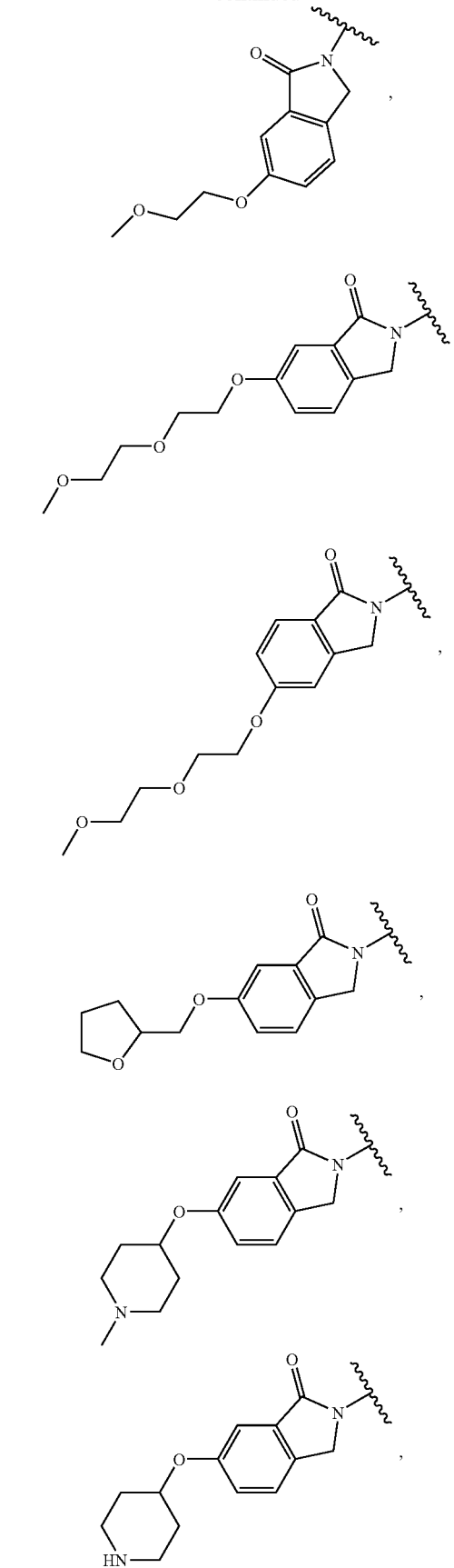

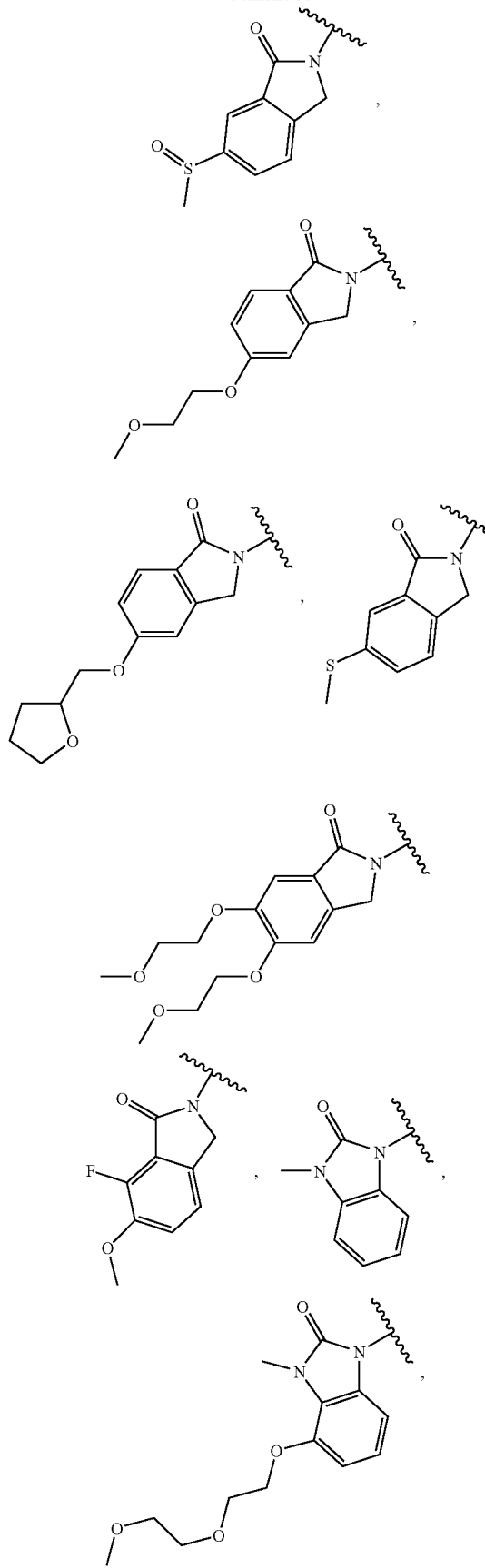
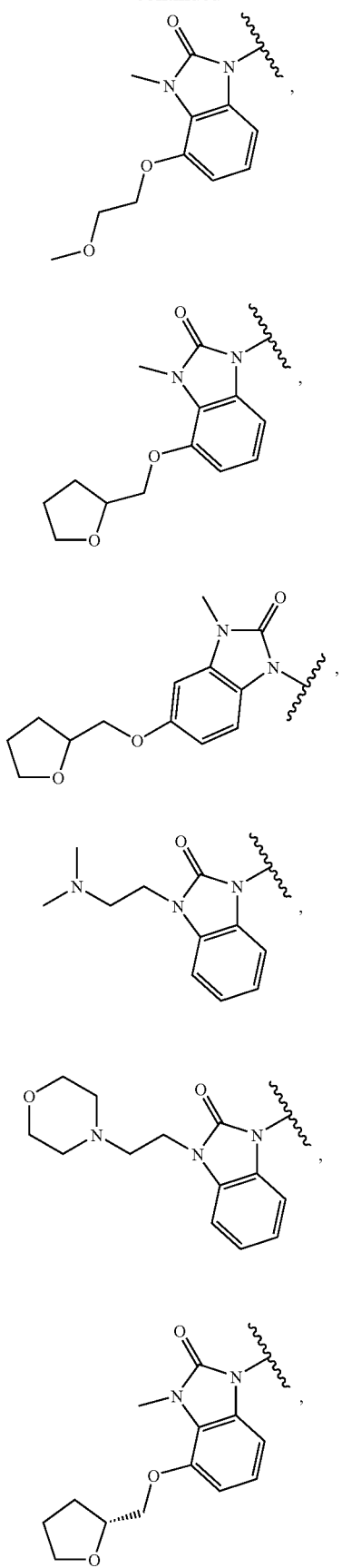

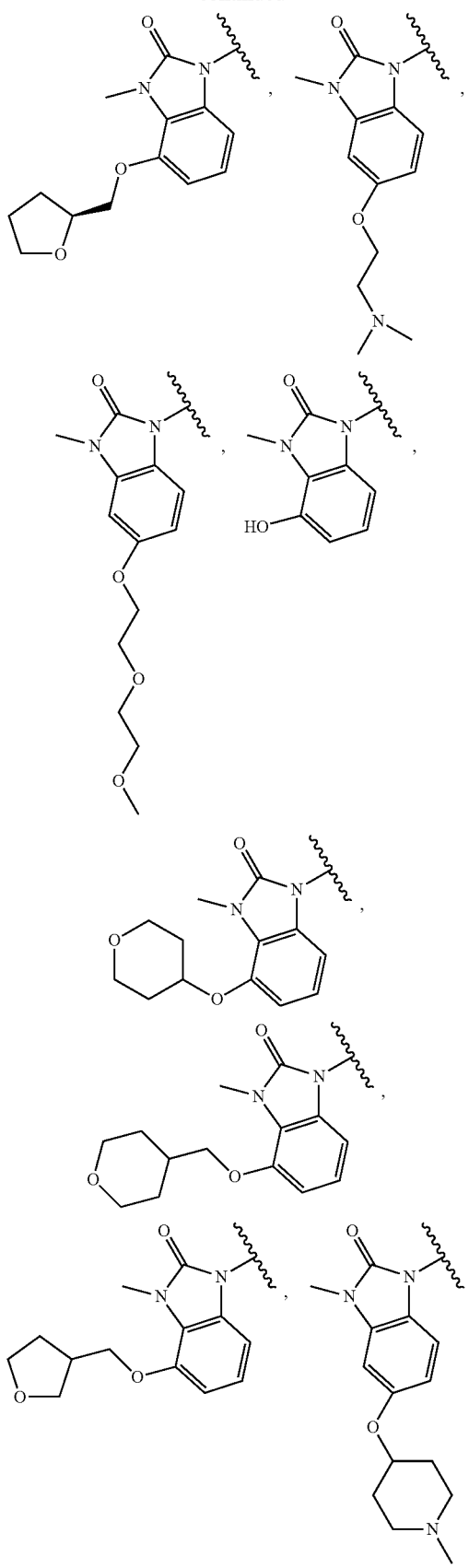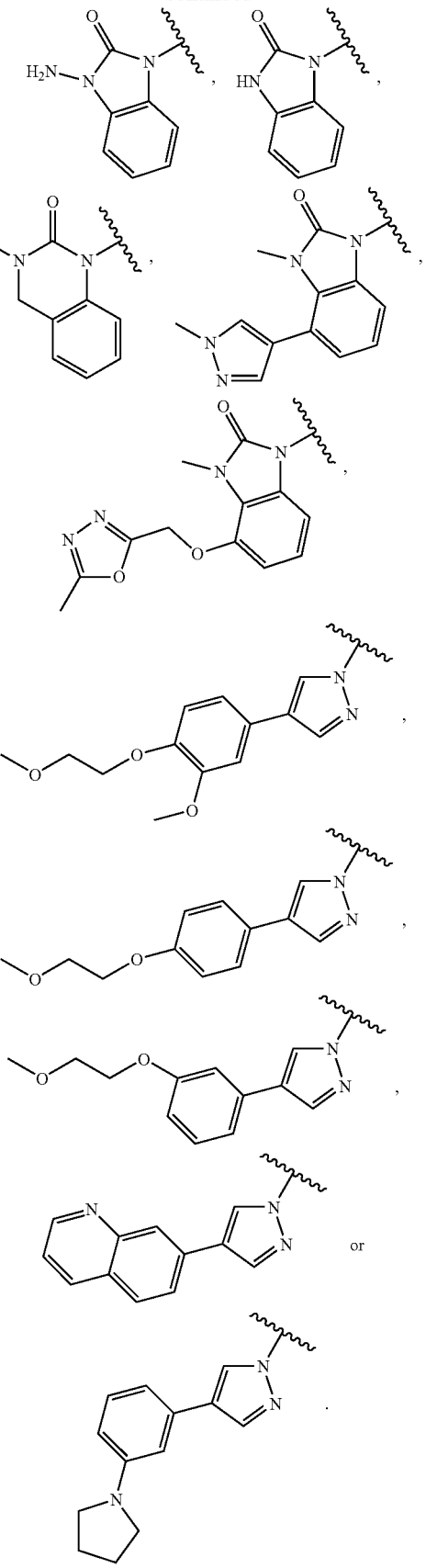

In one embodiment, $R^2$, $R^3$, $R^{3a}$, $R^{10}$, $R^{10a}$ and each occurrence of $R^{11}$ are each —H; Z is —N—; n is 1; and p is 1.

In another embodiment, $R^2$, $R^3$, $R^{3a}$, $R^{10}$, $R^{10a}$ and each occurrence of $R^{11}$ are each —H; Z is —N—; n is 1; p is 1; and W is —(CR$^4$)$_2$— or —N(R$^{12}$)—.

In one embodiment, p is 1 and n is 0.

In another embodiment, p is 1 and n is 1.

In another embodiment, p is 1 and n is 2.

In one embodiment, $R^2$, $R^3$, $R^{3a}$, $R^{10}$, $R^{10a}$ and each occurrence of $R^{11}$ are each —H; Z is —N—; n is 1; p is 1; and W is NH.

In another embodiment, $R^2$, $R^3$, $R^{3a}$, $R^{10}$, $R^{10a}$ and each occurrence of $R^{11}$ are each —H; Z is —N—; n is 1; p is 1; and W is —CH(NH$_2$)—, —C(R$^4$)(NH$_2$)— or —CH(OH)—

In another embodiment, $R^2$, $R^3$, $R^{3a}$, $R^{10}$, $R^{10a}$ and each occurrence of $R^{11}$ are each —H; Z is —N—; n is 1; p is 1; and W is —C(R$^4$)$_2$—, wherein both R$^4$ groups and the carbon atom to which they are attached, join to form a –4- to –7-membered heterocyclyl group.

In one embodiment, $R^2$, $R^3$, $R^{3a}$, $R^{10}$, $R^{10a}$ and each occurrence of $R^{11}$ are each —H; Z is —N—; n is 1; p is 1; W is —(CR$^4$)$_2$— or —N(R$^{12}$)—; and Ar is:

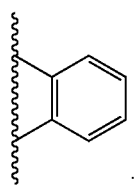

In another embodiment, $R^2$, $R^3$, $R^{3a}$, $R^{10}$, $R^{10a}$ and each occurrence of $R^{11}$ are each —H; Z is —N—; n is 1; p is 1; W is —(CR$^4$)$_2$— or —N(R$^{12}$)—; and Ar is:

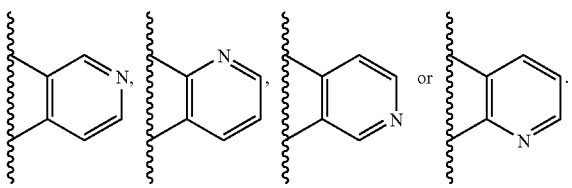

In another embodiment, $R^2$, $R^3$, $R^{3a}$, $R^{10}$, $R^{10a}$ and each occurrence of $R^{11}$ are each —H; Z is —N—; n is 1; p is 1; W is —(CR$^4$)$_2$— or —N(R$^{12}$)—; and Ar is:

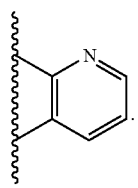

In one embodiment, the present invention provides a compound of formula (I) or a pharmaceutically acceptable salt, solvate, ester, prodrug or stereoisomer thereof, wherein R$^1$, R$^2$, R$^3$, R$^{3a}$, R$^{10}$, R$^{10a}$, R$^{11}$, Ar, n, p, W, X, Y and Z are selected independently of each other.

In one embodiment, the Anilinopiperazine Derivatives have the formula (IA):

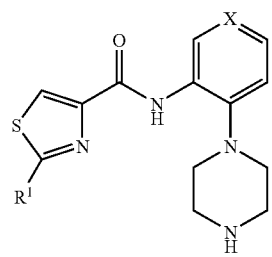

(IA)

wherein X is CH or N, and R$^1$ is defined above for the compounds of formula (I).

In one embodiment, the Anilinopiperazine Derivatives have the formula (IA) wherein X is CH.

In another embodiment, the Anilinopiperazine Derivatives have the formula (IA) wherein X is N.

In another embodiment, the Anilinopiperazine Derivatives have the formula (IA) wherein R$^1$ is nitrogen-containing heteroaryl, which may be optionally substituted as set forth above for the compounds of formula (I).

In another embodiment, the Anilinopiperazine Derivatives have the formula (IA) wherein R$^1$ is nitrogen-containing heterocyclyl, which may be optionally substituted as set forth above for the compounds of formula (I).

In another embodiment, the Anilinopiperazine Derivatives have the formula (IA) wherein R$^1$ is nitrogen-containing benzofused heteroaryl, which may be optionally substituted as set forth above for the compounds of formula (I).

In another embodiment, the Anilinopiperazine Derivatives have the formula (IA) wherein R$^1$ is nitrogen-containing benzofused heterocyclyl, which may be optionally substituted as set forth above for the compounds of formula (I).

In one embodiment, R$^1$ is

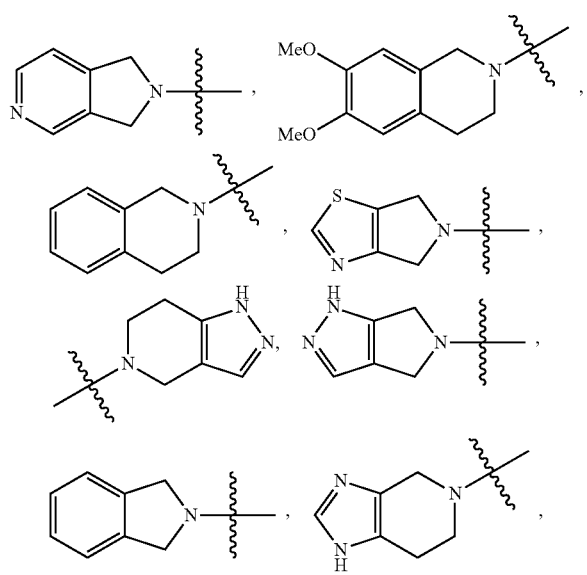

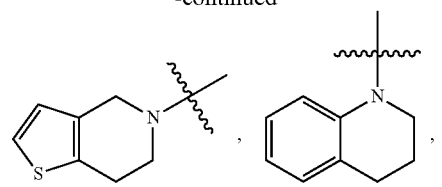
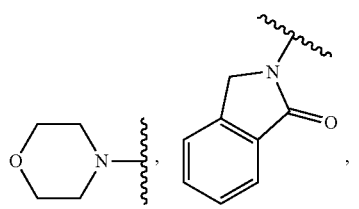
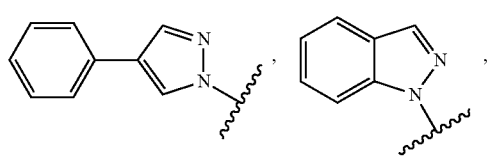
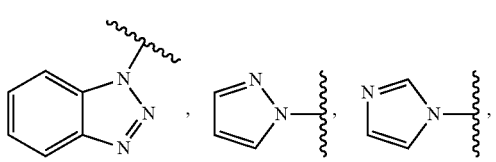
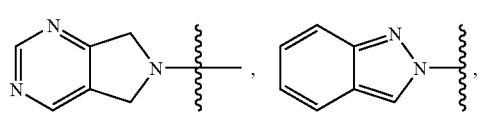
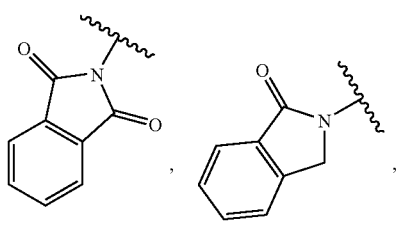
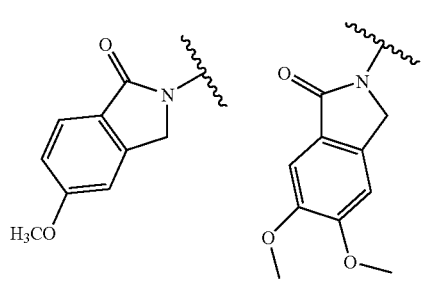
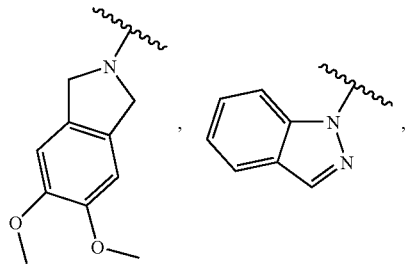
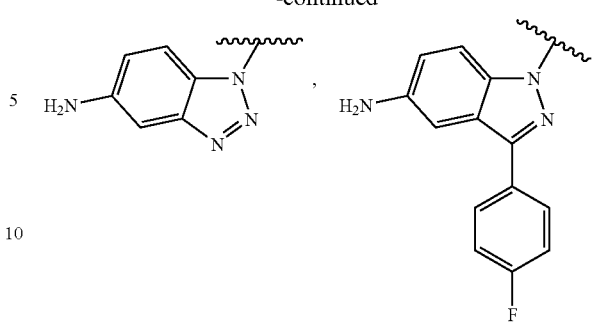
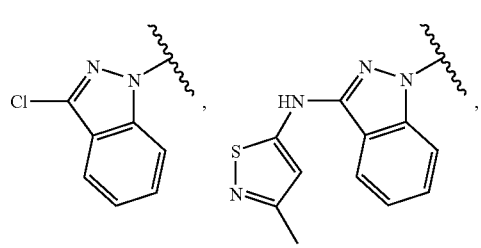
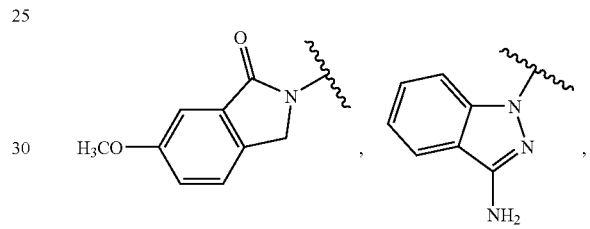
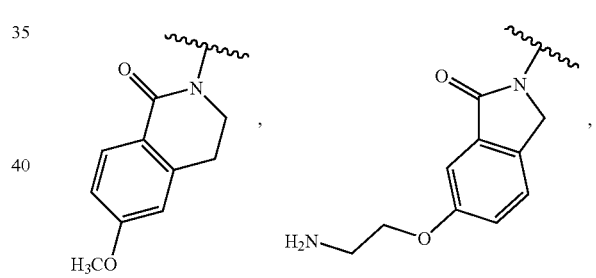
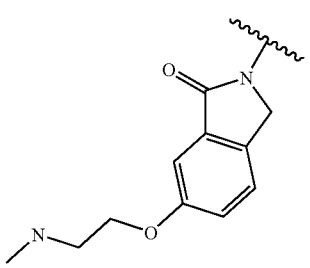
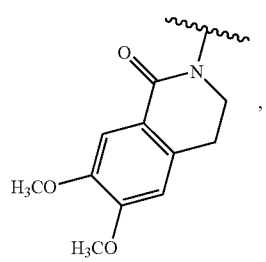

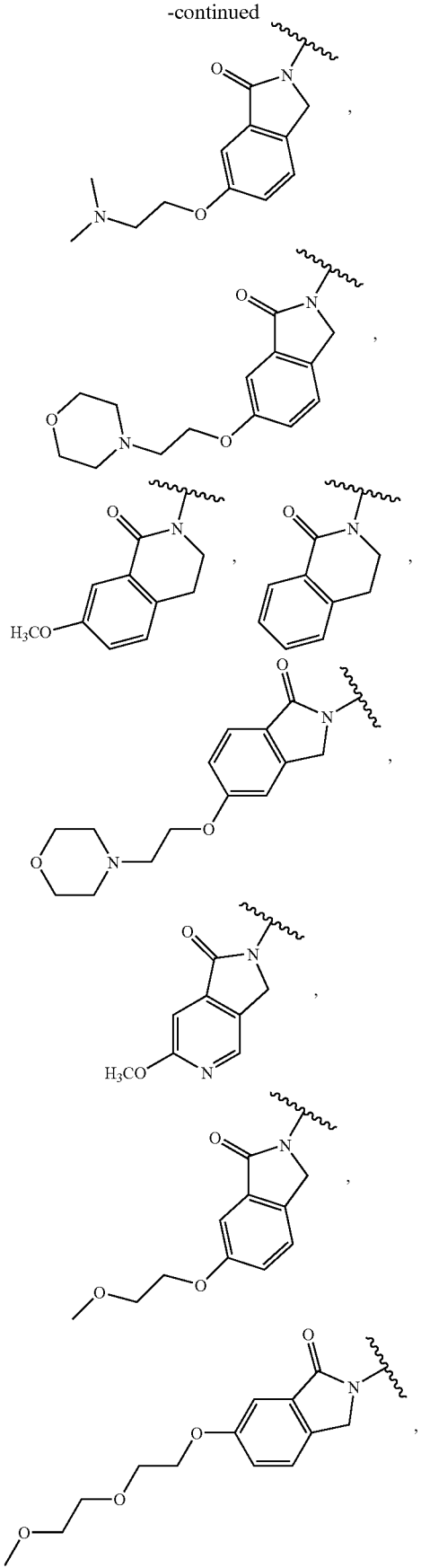
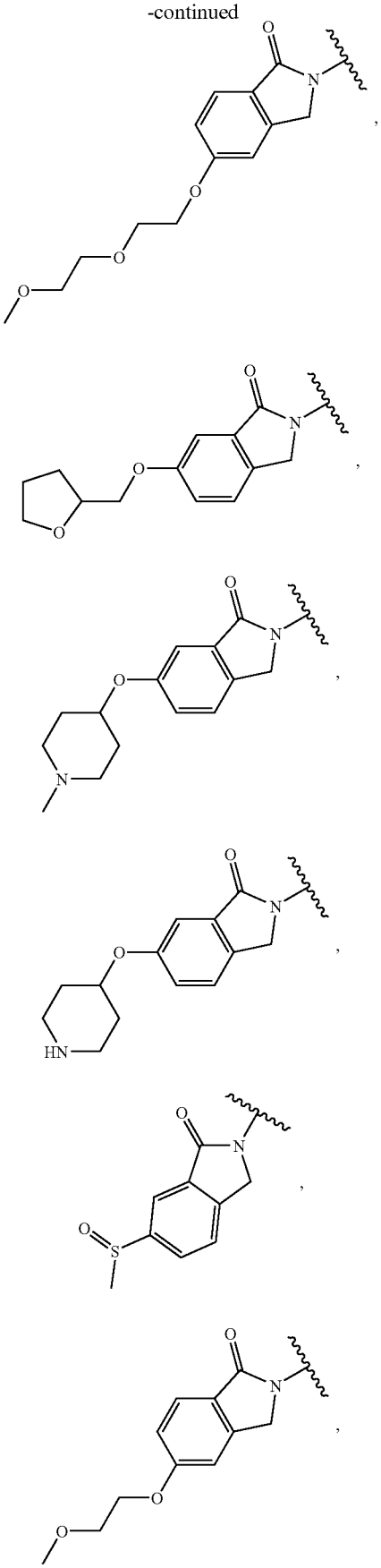

71
-continued
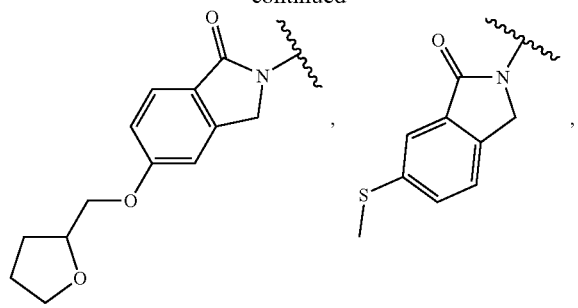
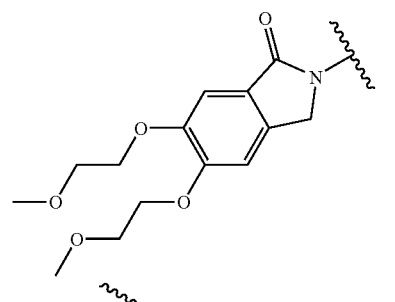
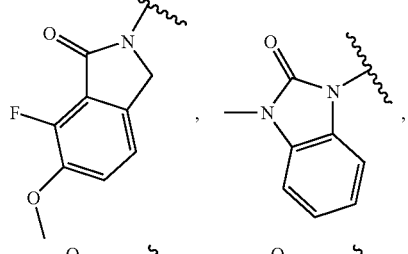
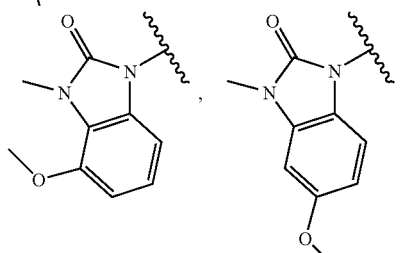
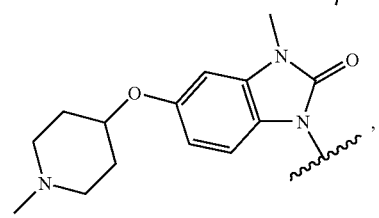
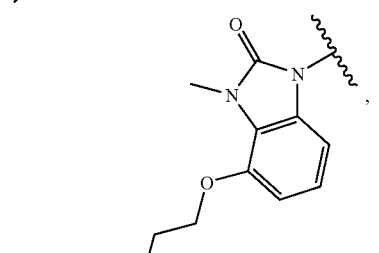
72
-continued
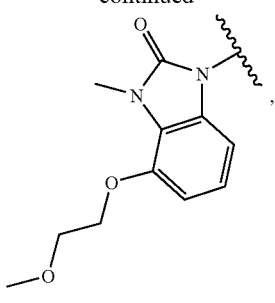
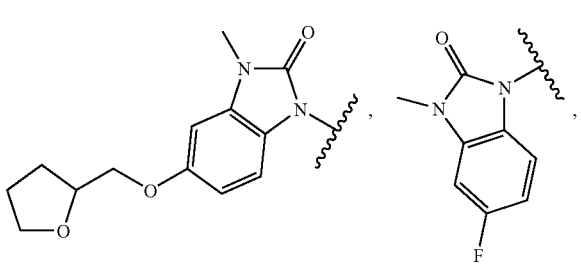
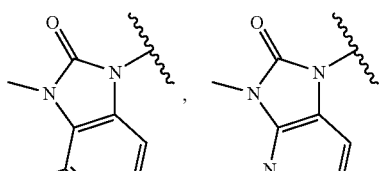
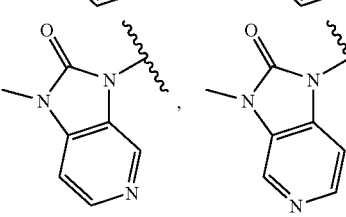
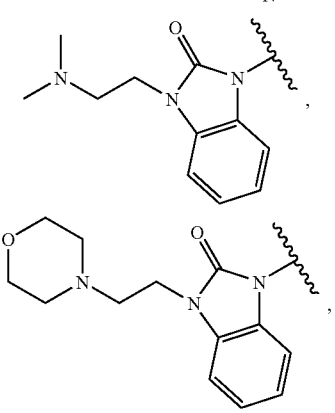

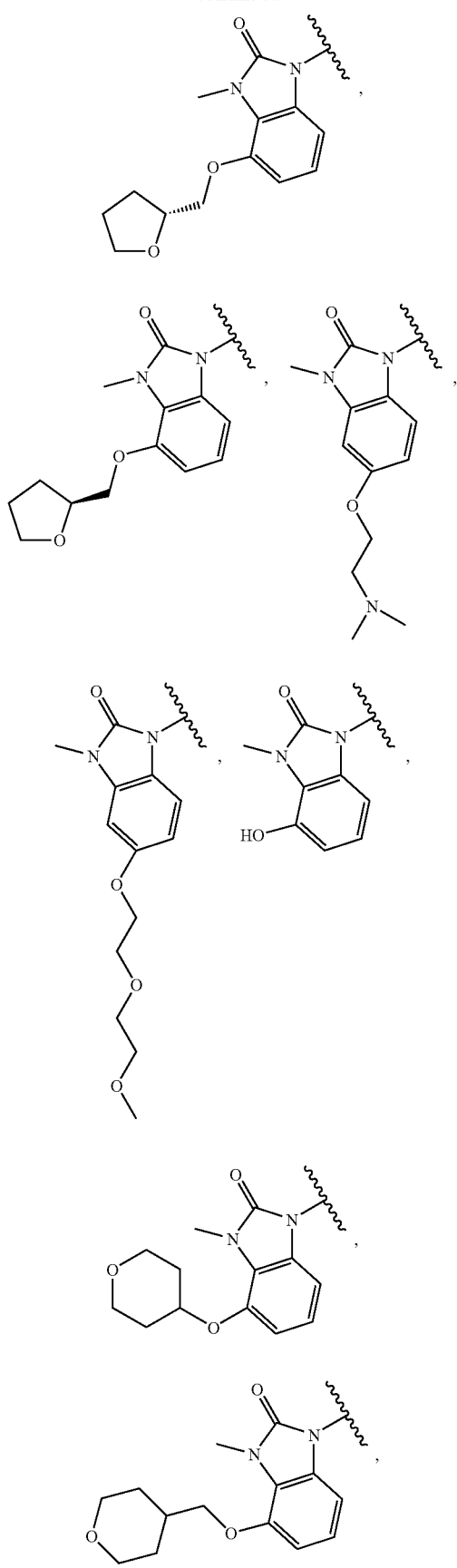
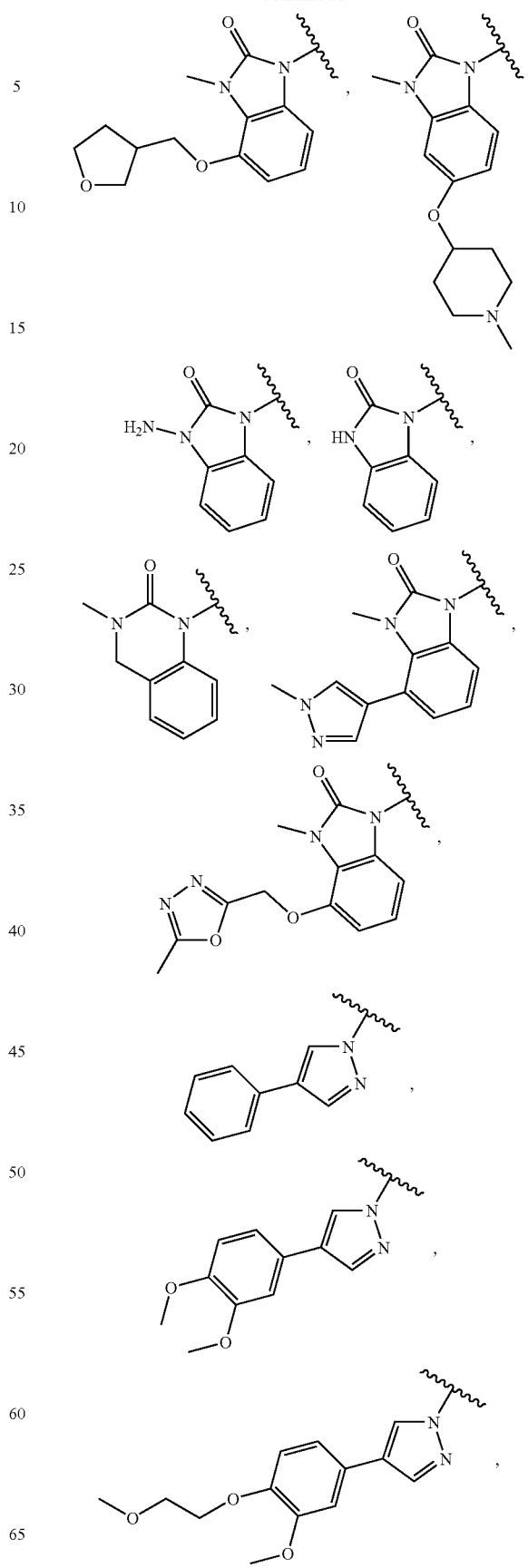

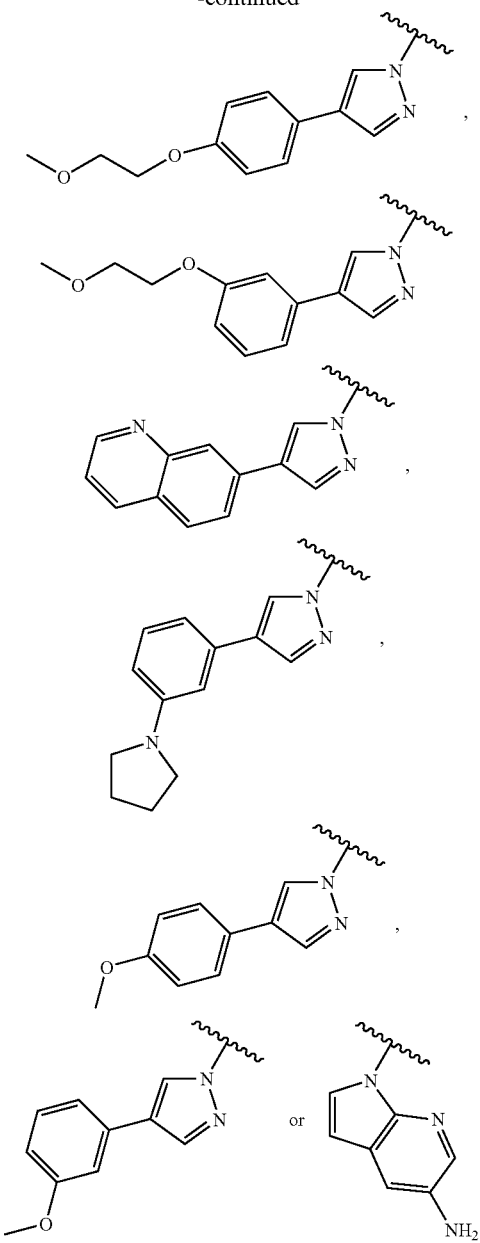
In another embodiment, $R^1$ is:
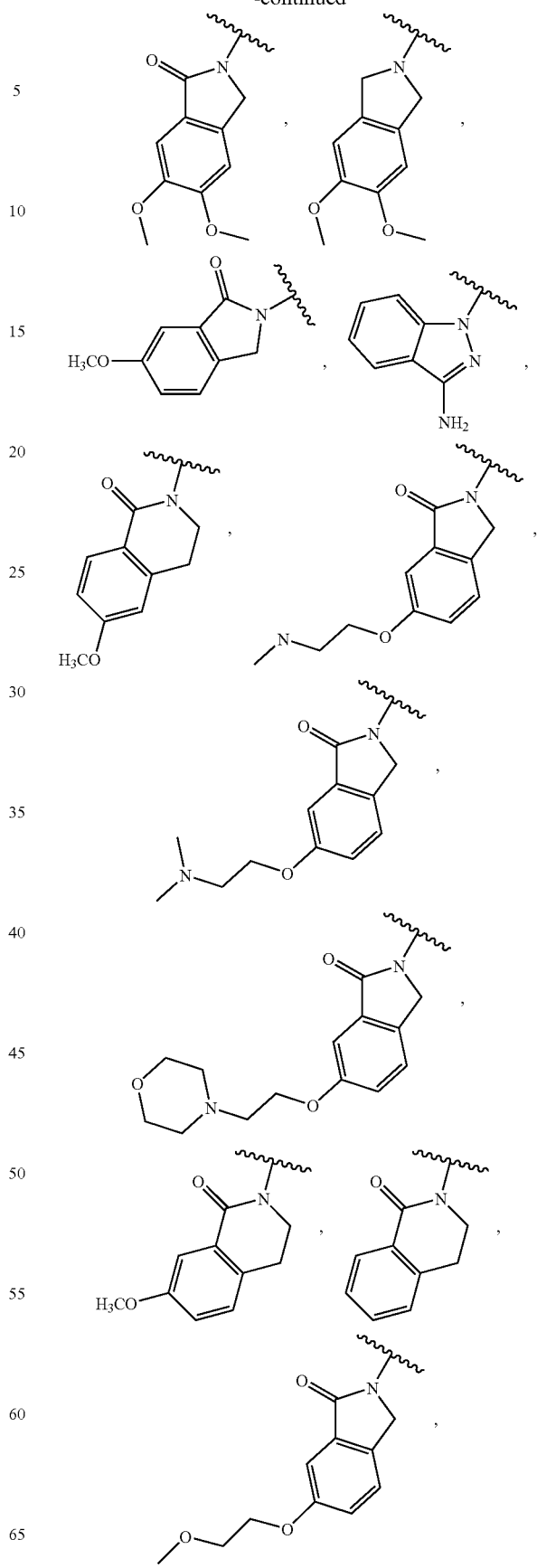

77
-continued
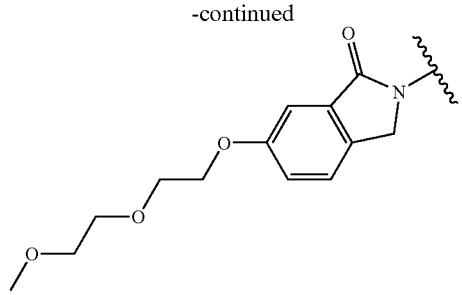,
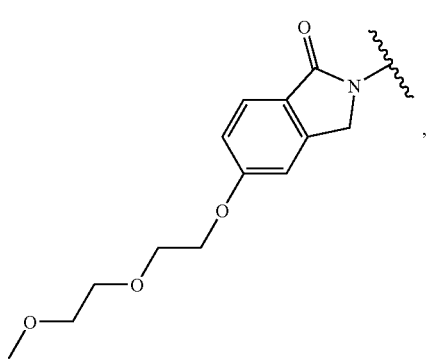,
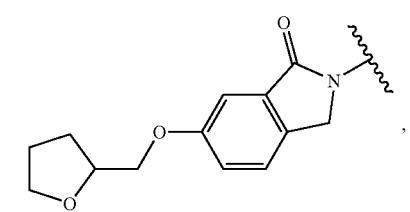,
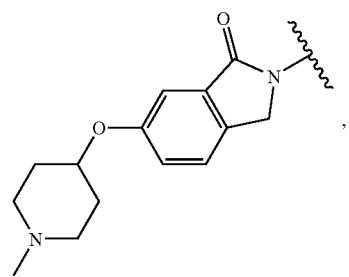,
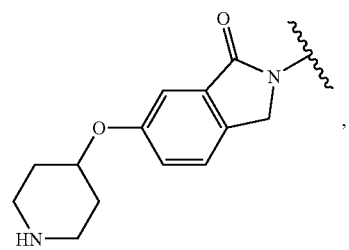,
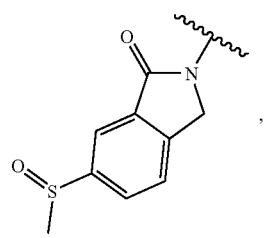,
78
-continued
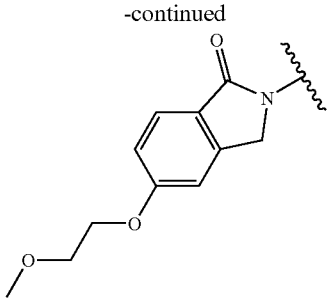,
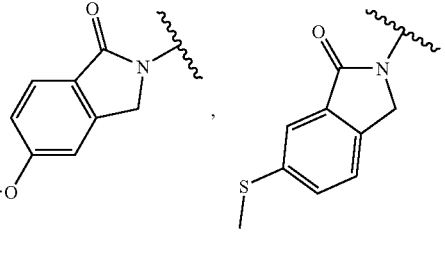,
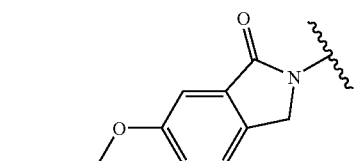,
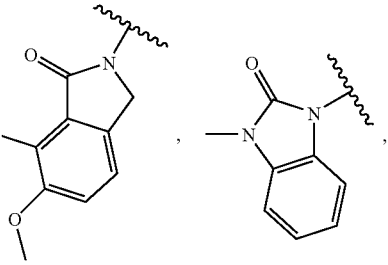,
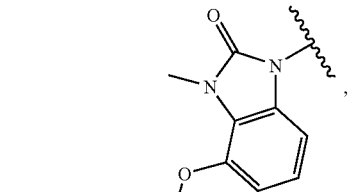,
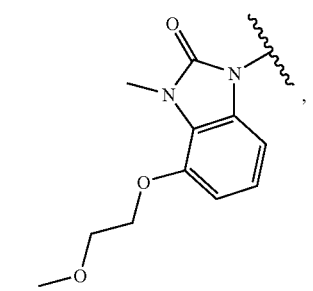,

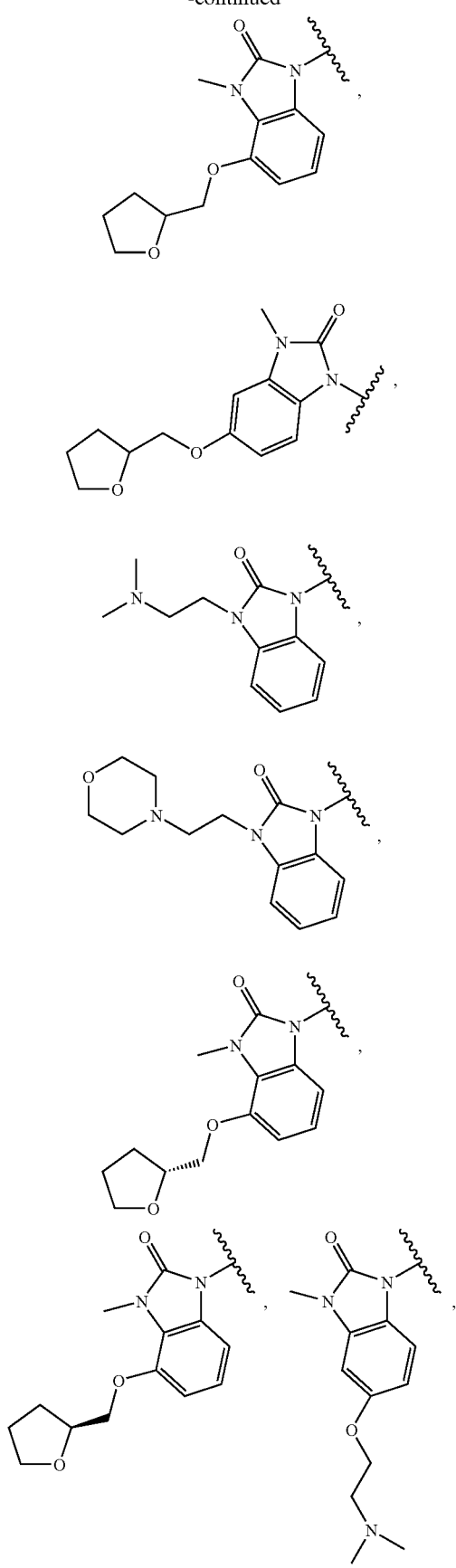
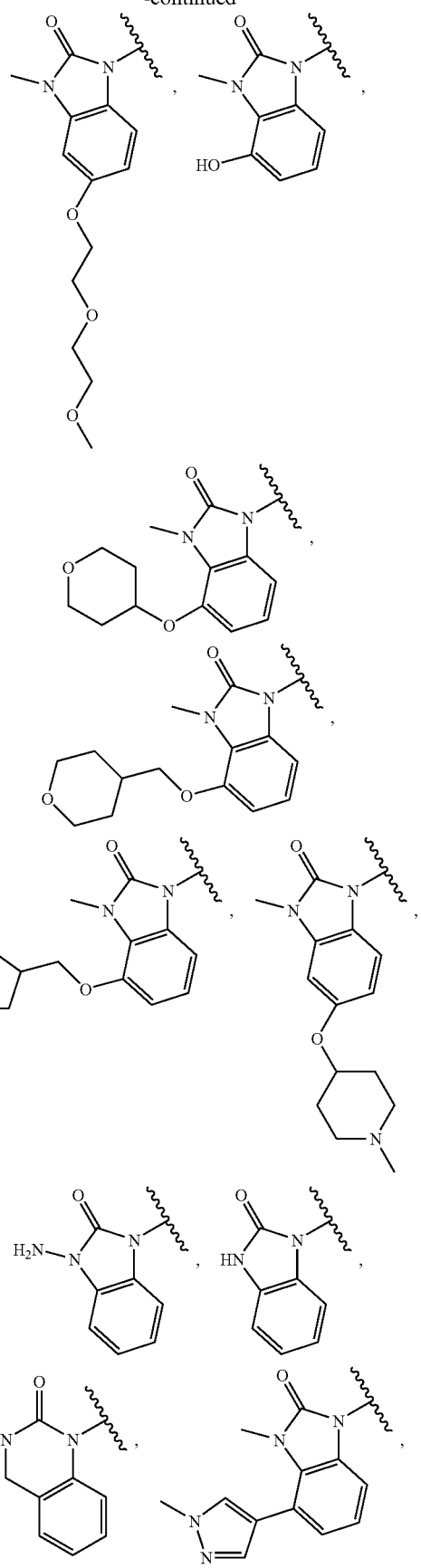

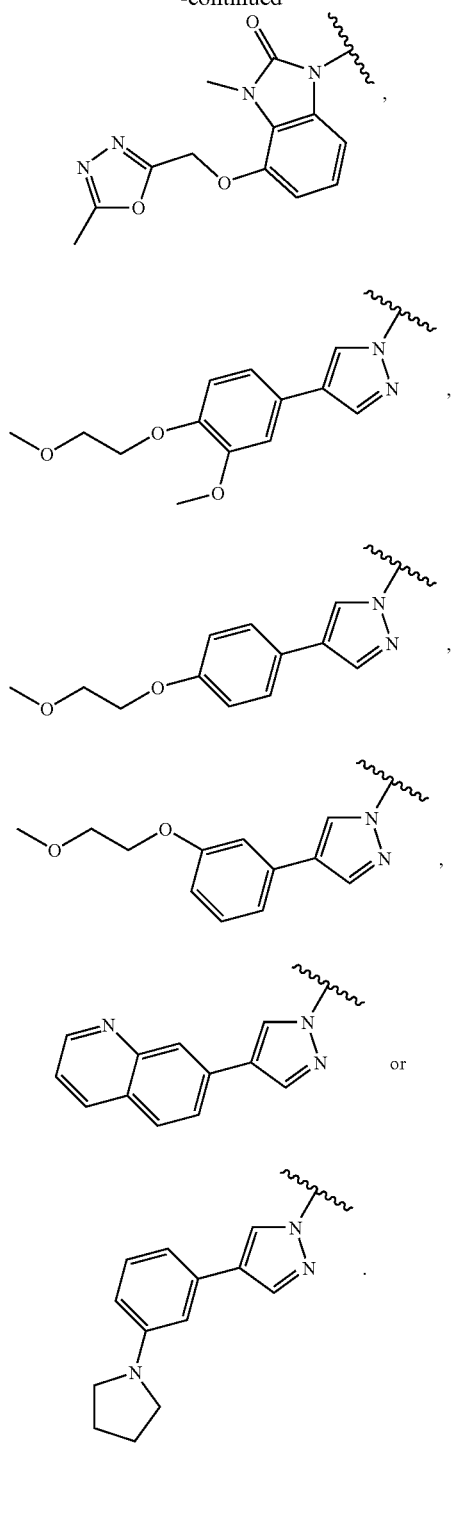
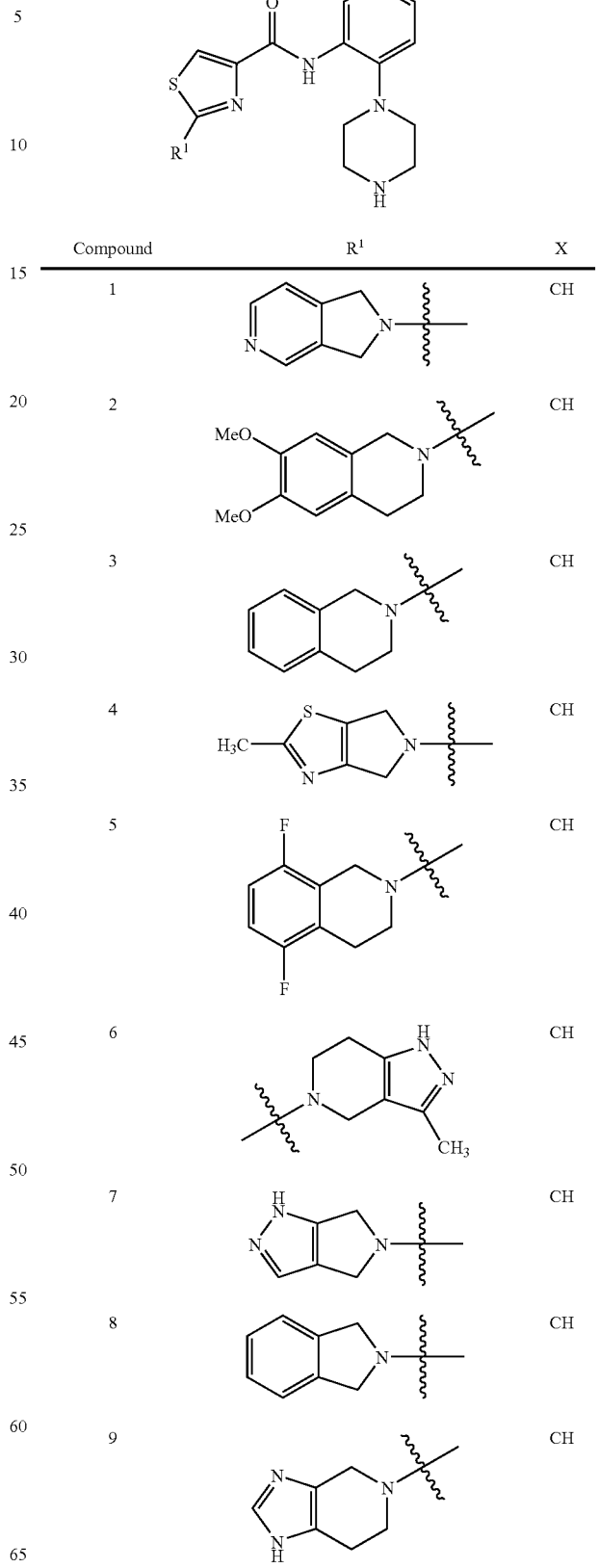
In one embodiment, the present invention provides a compound of formula (IA) or a pharmaceutically acceptable salt, solvate, ester, prodrug or stereoisomer thereof, wherein $R^1$ and X are selected independently of each other.
Illustrative examples of compounds of formula (I) include, but are not limited to, the compounds of formula (IA) listed below:

-continued
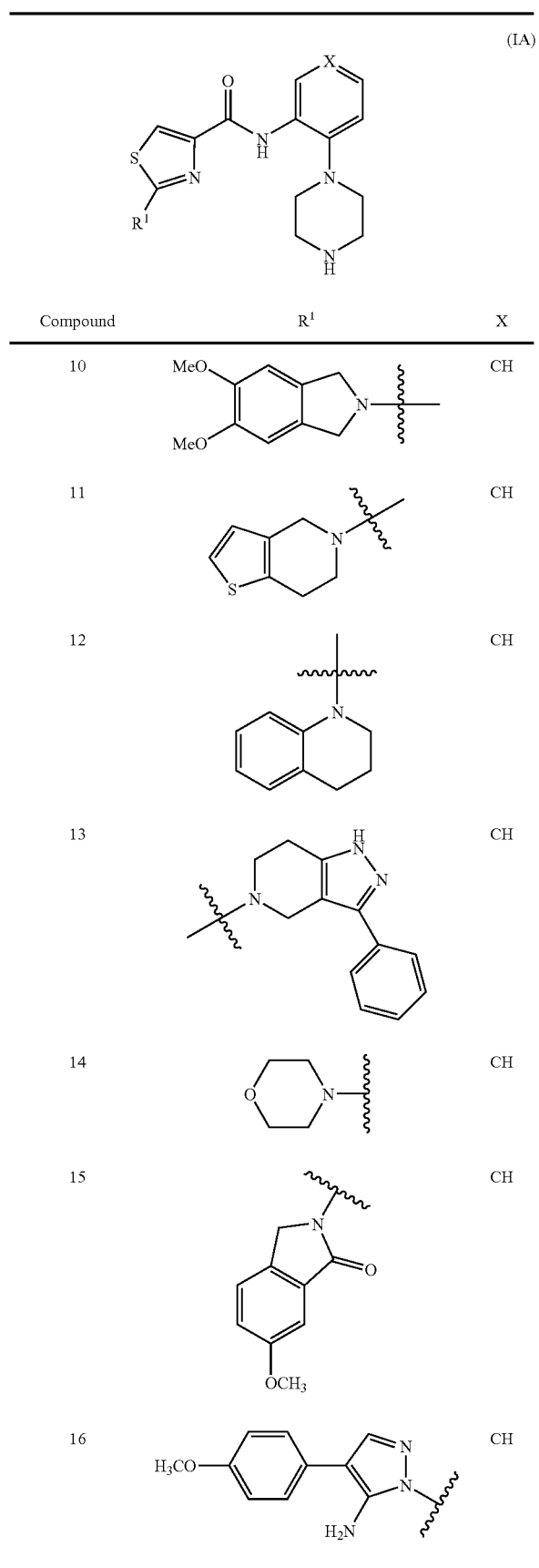
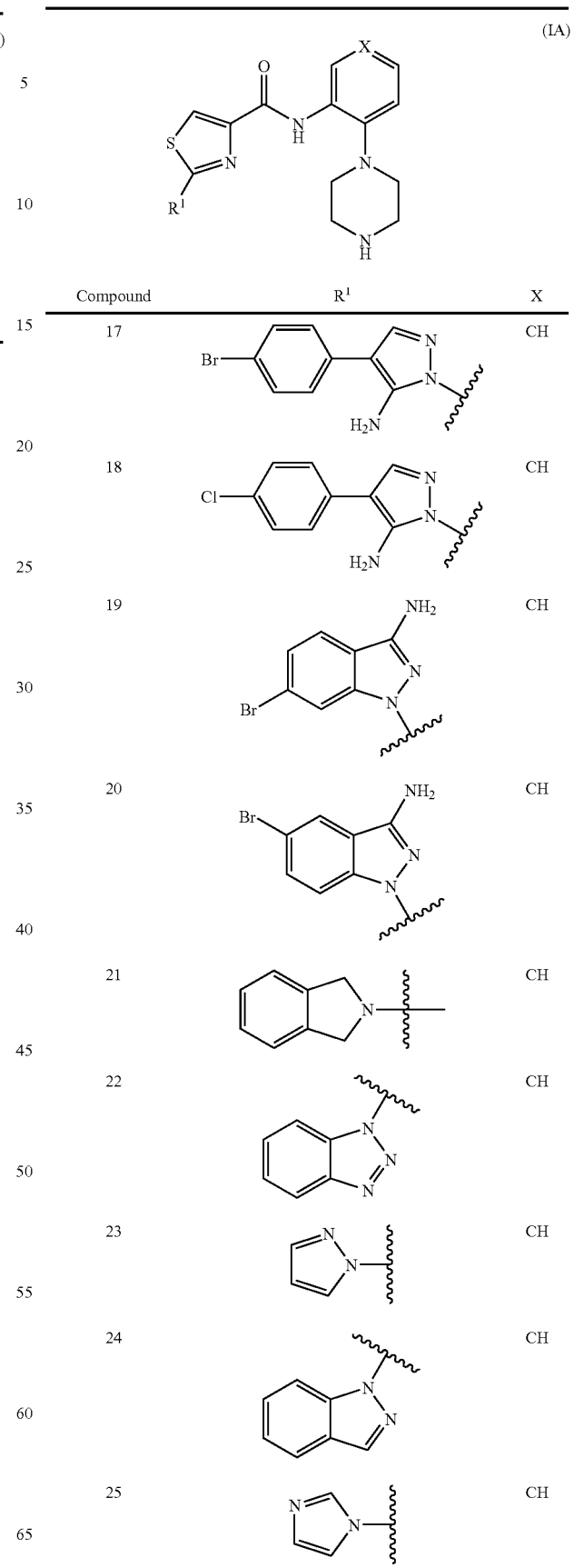

| Compound | R¹ | X |
|---|---|---|
| 26 | 2-methyl-pyrrolo[3,4-d]pyrimidine | CH |
| 27 | 3-amino-1H-indazol-1-yl | CH |
| 28 | 1H-indazol-1-yl | CH |
| 29 | 2H-indazol-2-yl | CH |
| 30 | 5-(trifluoromethyl)-1,3,4-thiadiazol-2-yl piperazine | CH | and pharmaceutically acceptable salts, solvates, esters, prodrugs and stereoisomers thereof.

Additional non-limiting illustrative examples of compounds of formula (I) include the following compounds:

| Compound No. | Structure |
|---|---|
| 31 | 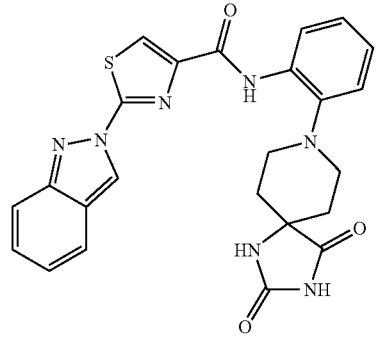 |
| 32 | 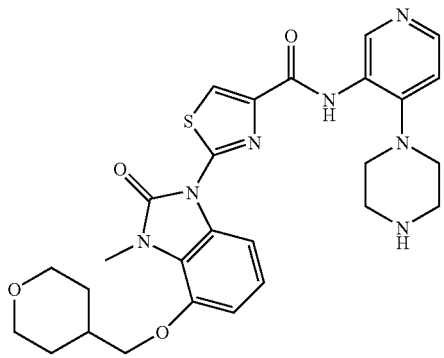 |

-continued
| Compound No. | Structure |
|---|---|
| 33 | 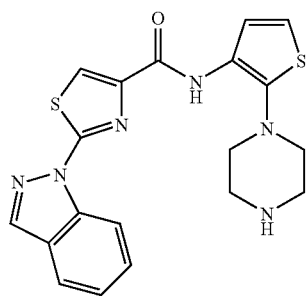 |
| 34 | 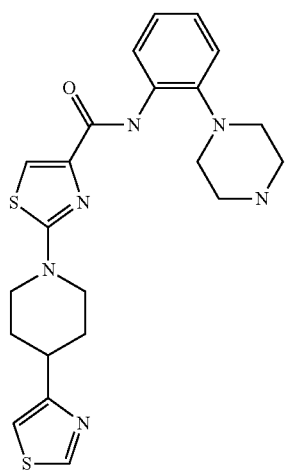 |
| 35 | 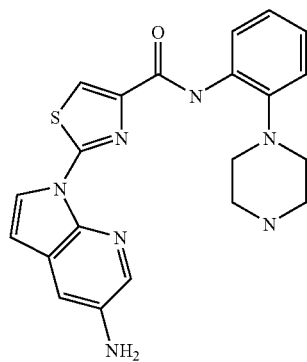 |
| 36 | 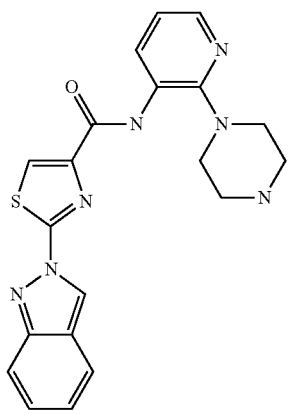 |

| Compound No. | Structure |
|---|---|
| 37 | 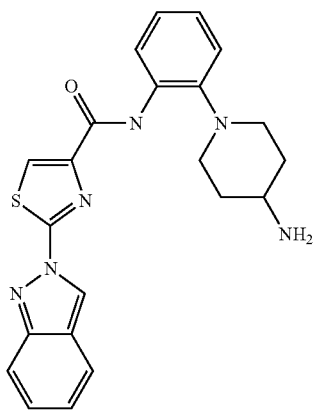 |
| 38 | 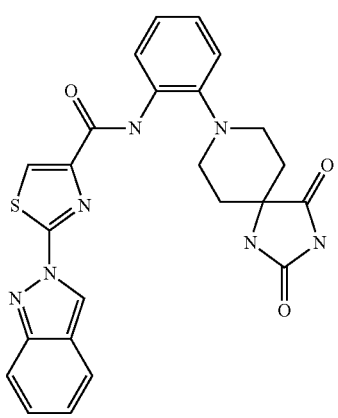 |
| 39 | 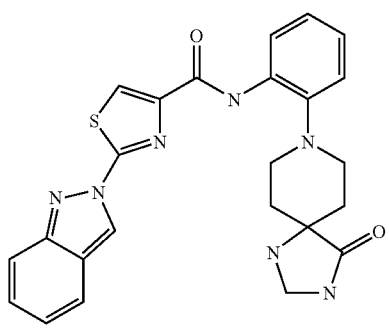 |
| 40 | 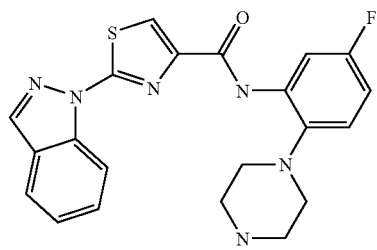 |

-continued
| Compound No. | Structure |
|---|---|
| 41 | |
| 42 | 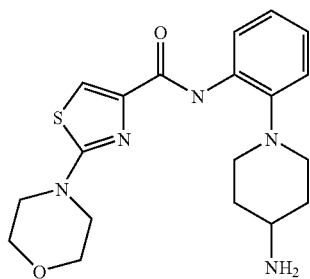 |
| 43 | 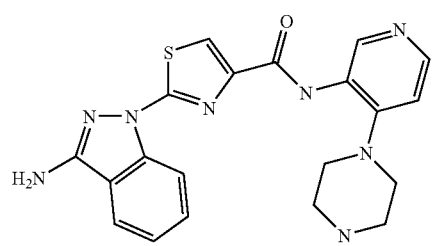 |
| 44 | 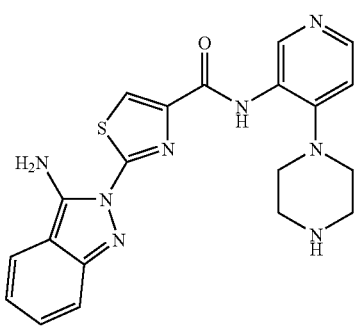 |
| 45 | 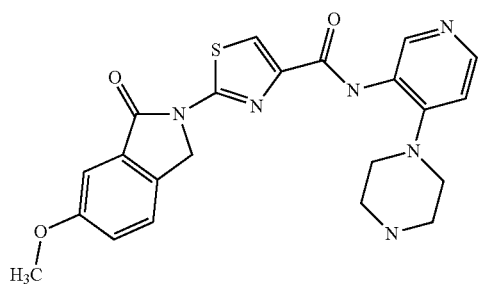 |
| 46 | 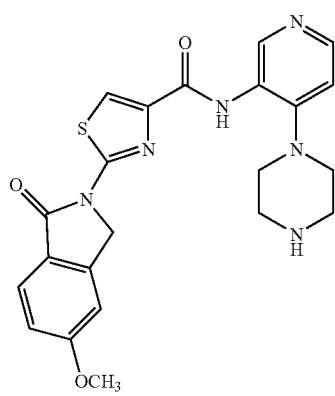 |

-continued
| Compound No. | Structure |
|---|---|
| 47 | 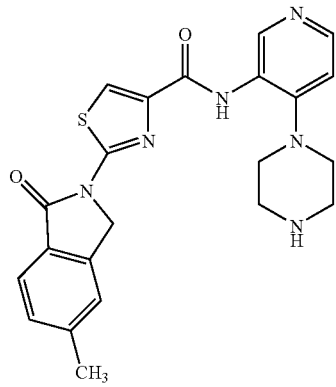 |
| 48 | 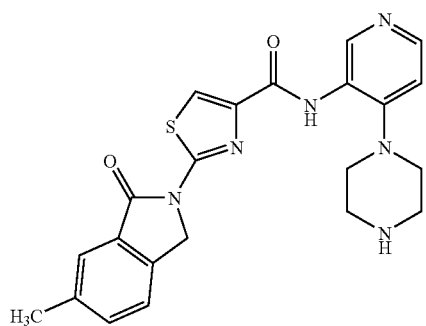 |
| 49 | 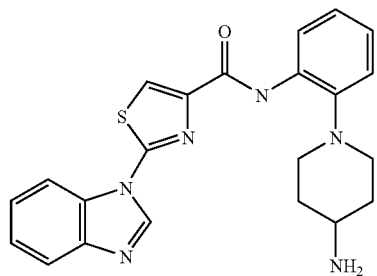 |
| 50 | 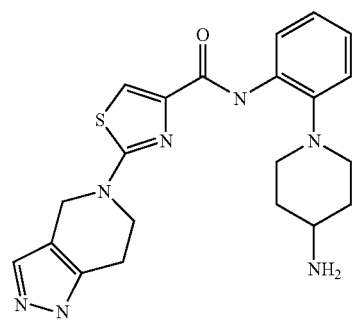 |

| Compound No. | Structure |
|---|---|
| 51 | 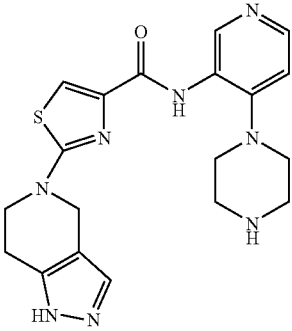 |
| 52 | 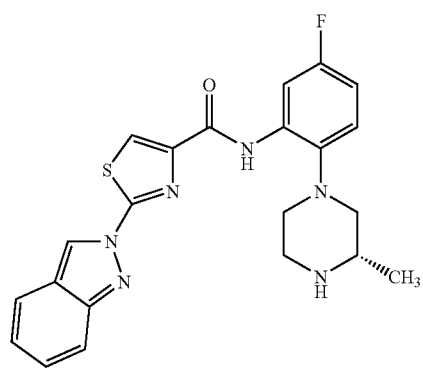 |
| 53 | 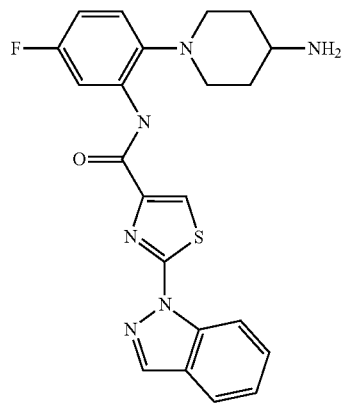 |
| 54 | 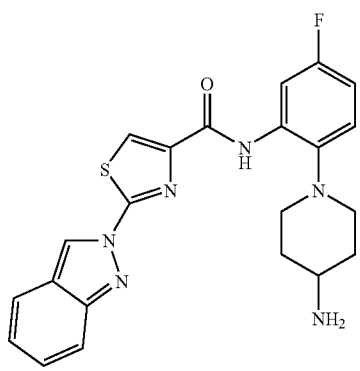 |

-continued
| Compound No. | Structure |
|---|---|
| 55 | 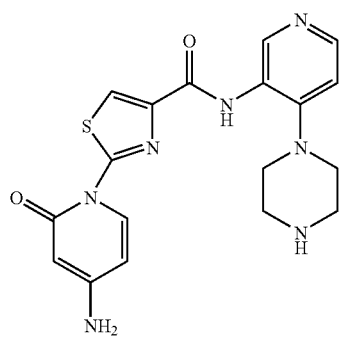 |
| 56 | 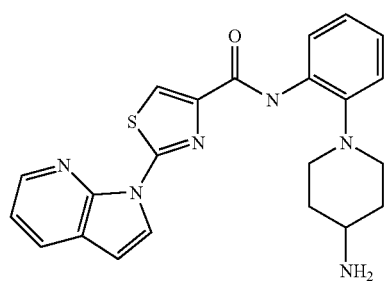 |
| 57 | 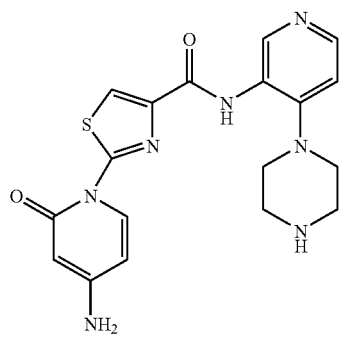 |
| 58 | 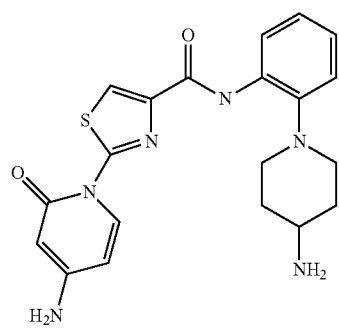 |
| 59 | 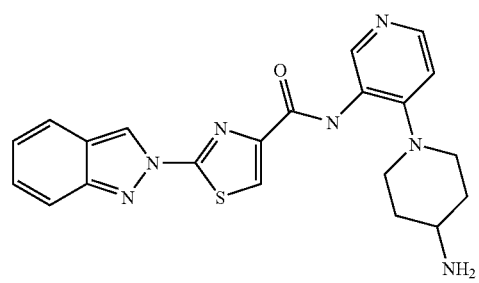 |

-continued
| Compound No. | Structure |
|---|---|
| 60 | 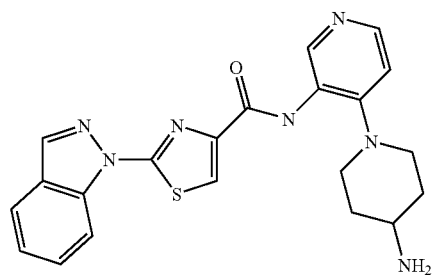 |
| 61 | 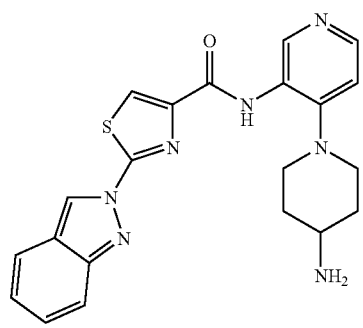 |
| 62 | 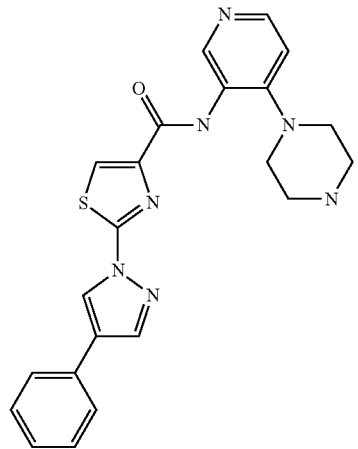 |
| 63 | 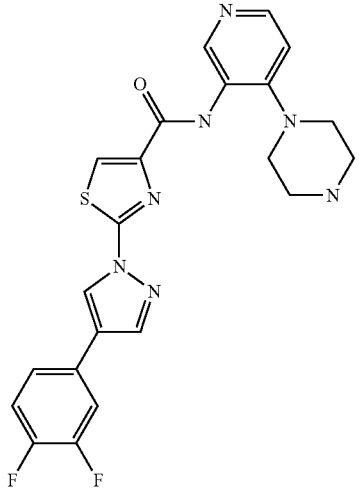 |

-continued
| Compound No. | Structure |
|---|---|
| 64 | 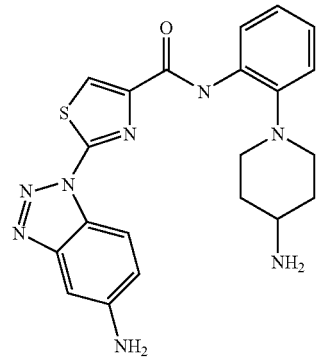 |
| 65 | 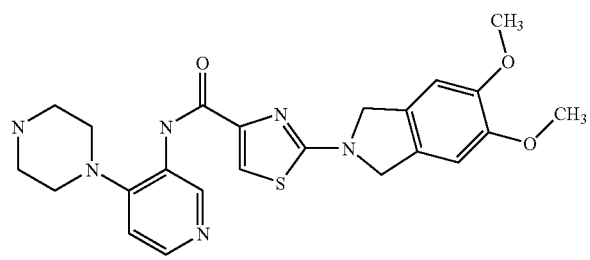 |
| 66 | 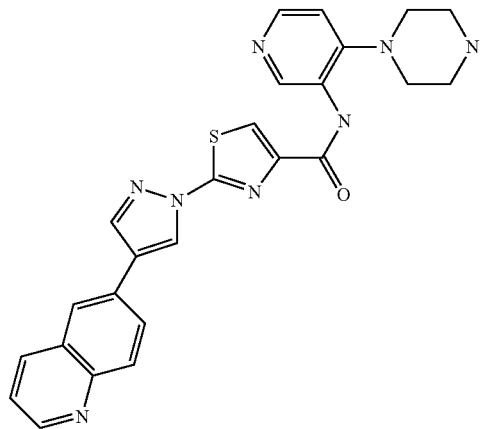 |
| 67 | 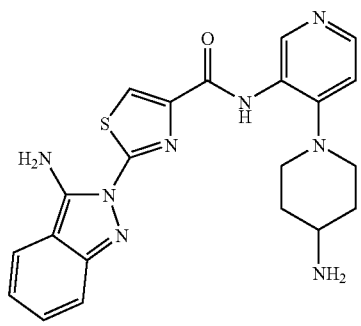 |

| Compound No. | Structure |
|---|---|
| 68 | 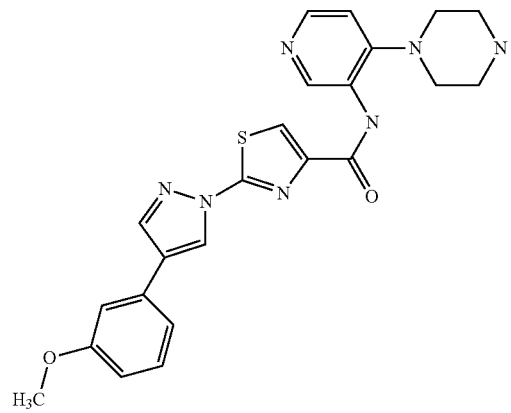 |
| 69 | 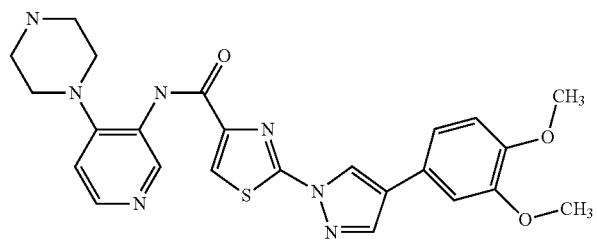 |
| 70 | 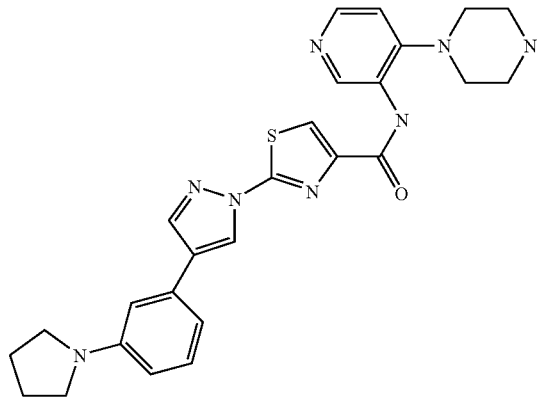 |
| 71 | 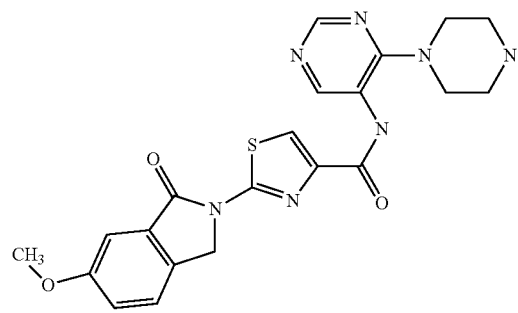 |

-continued
| Compound No. | Structure |
|---|---|
| 72 | 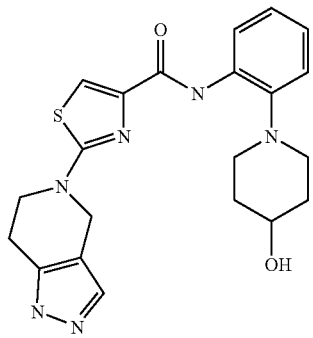 |
| 73 | 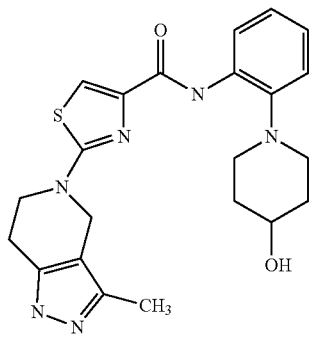 |
| 74 | 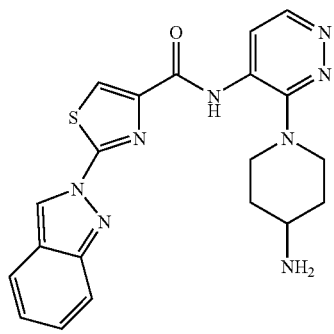 |
| 75 | 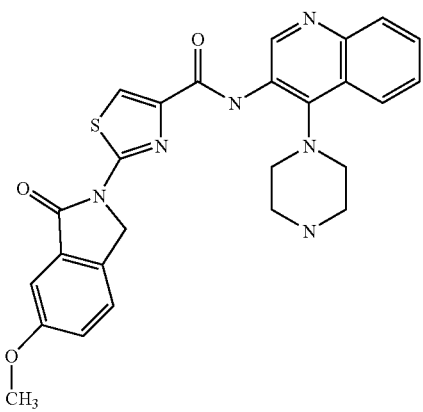 |

-continued
| Compound No. | Structure |
|---|---|
| 76 | 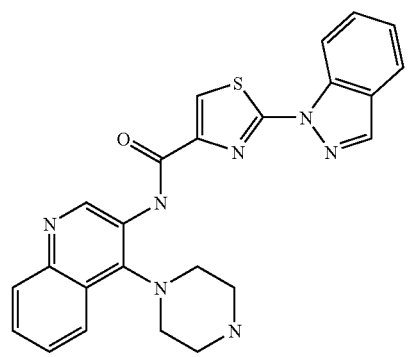 |
| 77 | 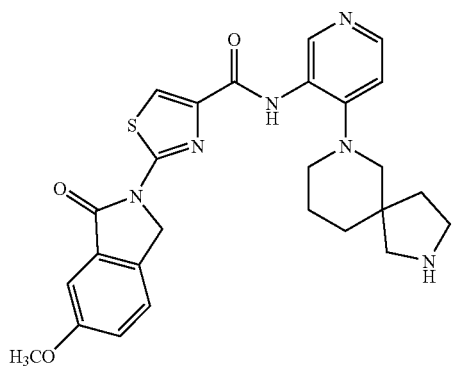 |
| 78 | 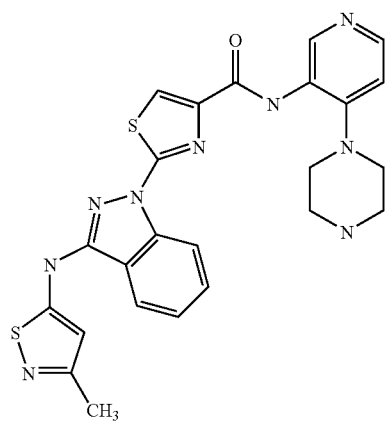 |
| 79 | 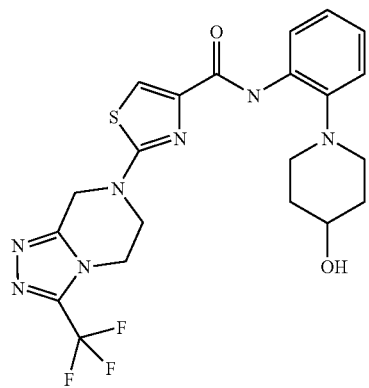 |

-continued
| Compound No. | Structure |
|---|---|
| 80 | 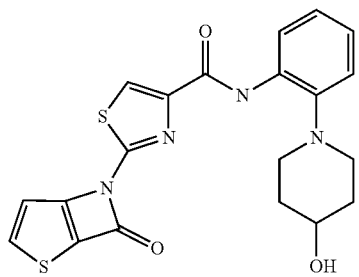 |
| 81 | 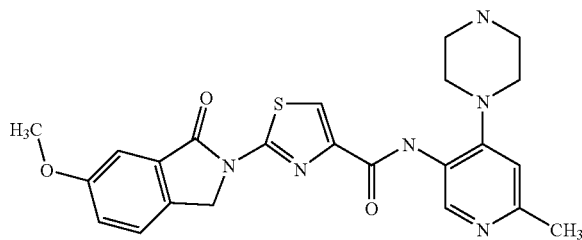 |
| 82 | 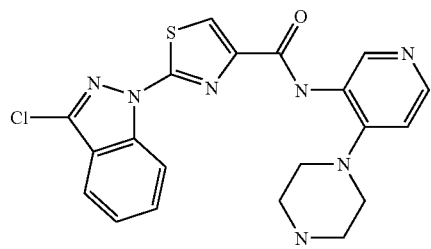 |
| 83 | 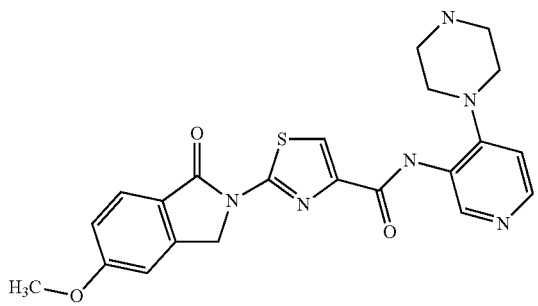 |
| 84 | 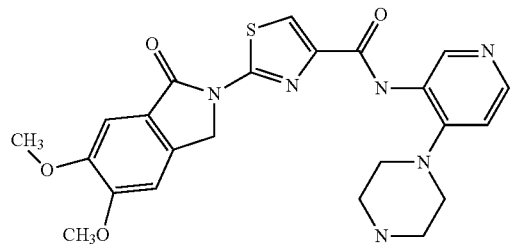 |
| 85 | 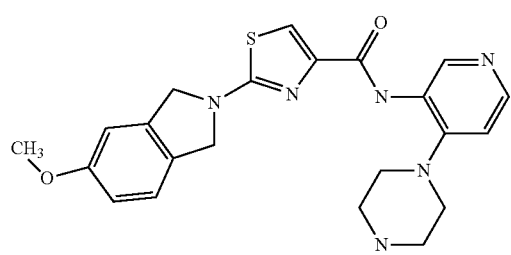 |

-continued
| Compound No. | Structure |
|---|---|
| 86 | 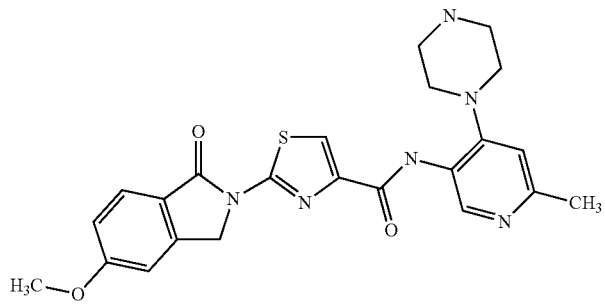 |
| 87 | 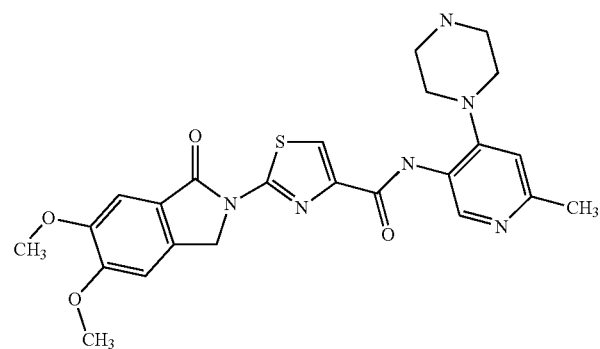 |
| 88 | 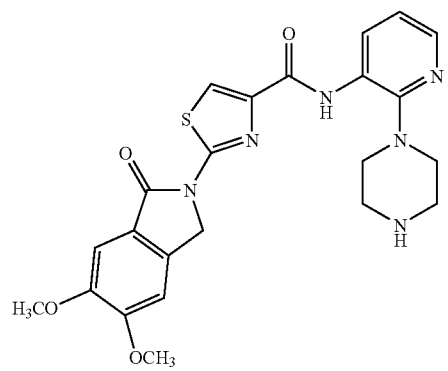 |
| 89 | 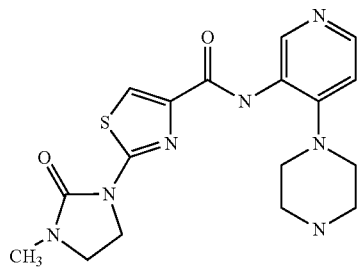 |
| 90 | 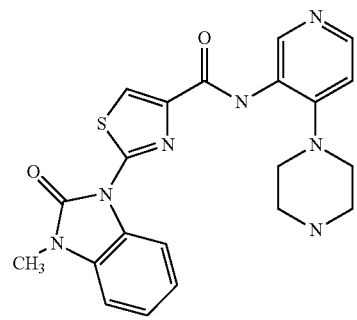 |

-continued
| Compound No. | Structure |
|---|---|
| 91 | 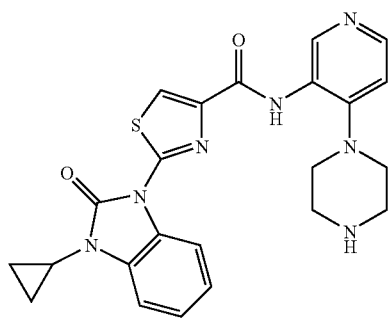 |
| 92 | 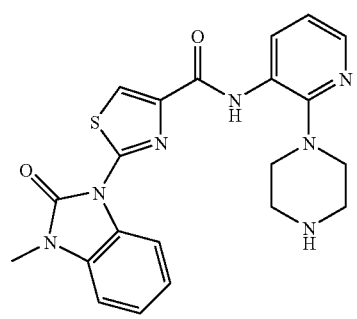 |
| 93 | 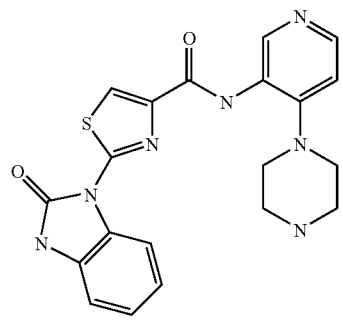 |
| 94 | 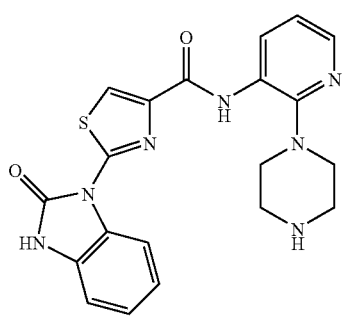 |
| 95 | 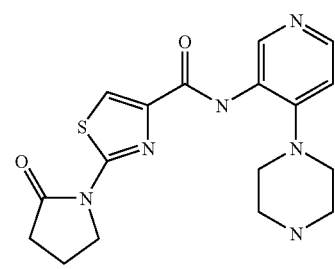 |

-continued
| Compound No. | Structure |
|---|---|
| 96 | 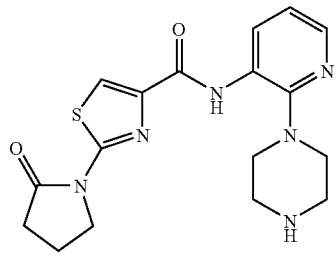 |
| 97 | 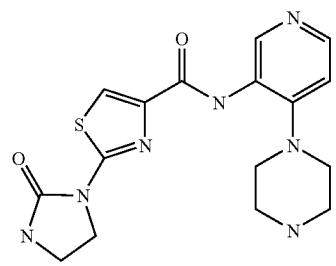 |
| 98 | 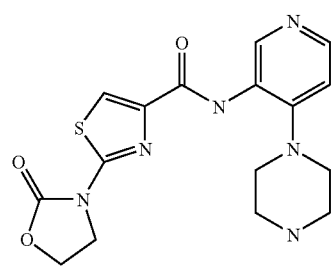 |
| 99 | 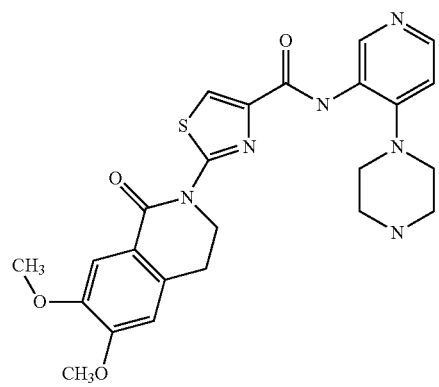 |
| 100 | 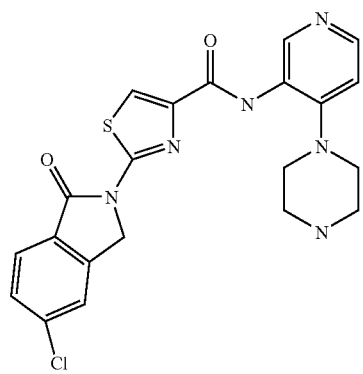 |

-continued
| Compound No. | Structure |
|---|---|
| 101 | 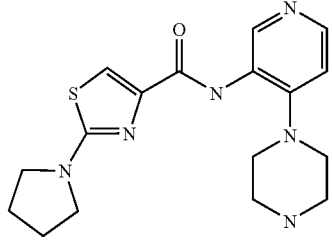 |
| 102 | 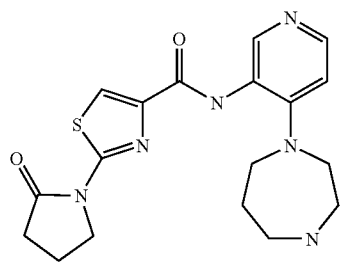 |
| 103 | 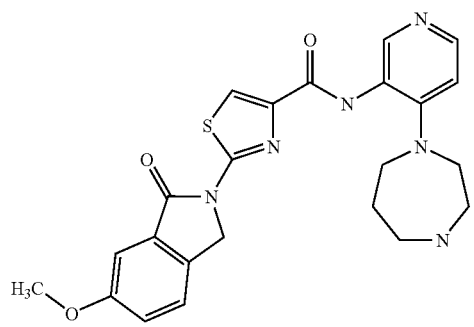 |
| 104 | 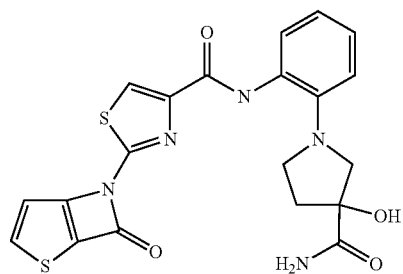 |
| 105 | 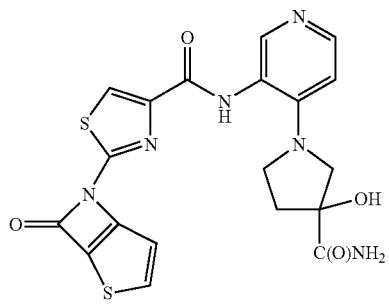 |

-continued
| Compound No. | Structure |
| --- | --- |
| 106 | 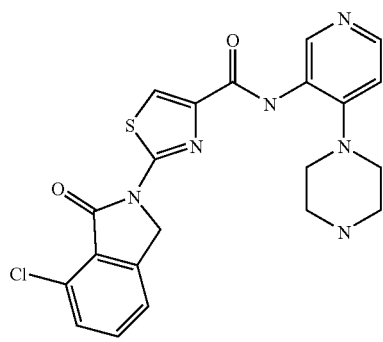 |
| 107 | 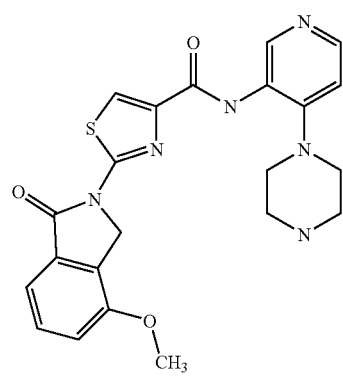 |
| 108 | 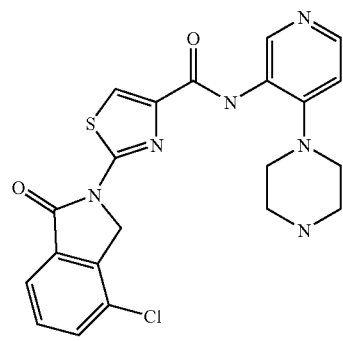 |
| 109 | 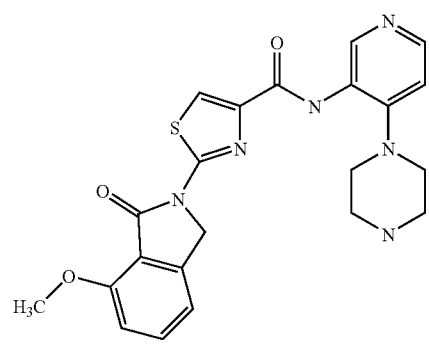 |

-continued
| Compound No. | Structure |
|---|---|
| 110 | 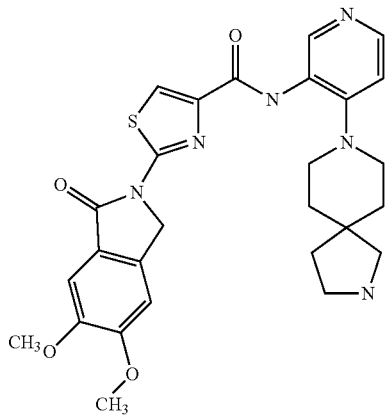 |
| 111 | 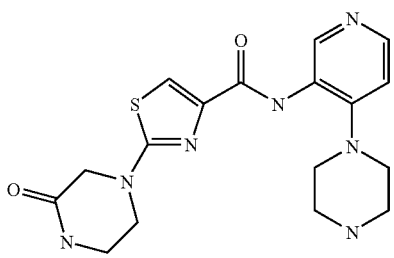 |
| 112 | 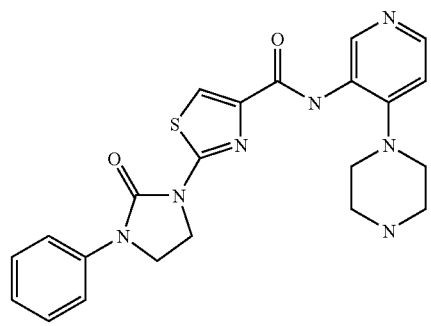 |
| 113 | 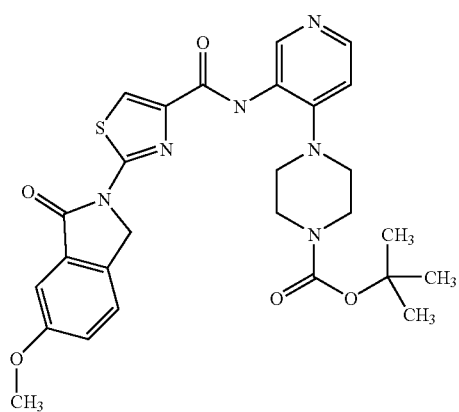 |

| Compound No. | Structure |
|---|---|
| 114 | 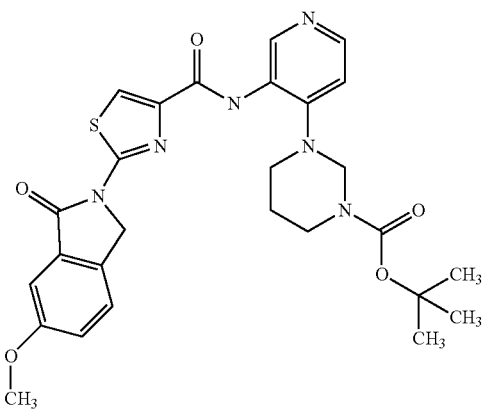 |
| 115 | 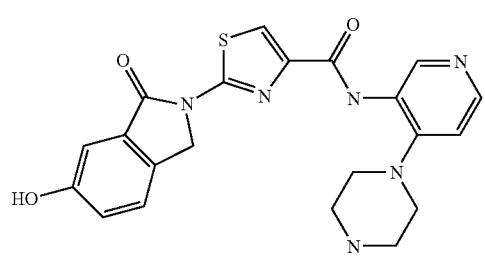 |
| 116 | 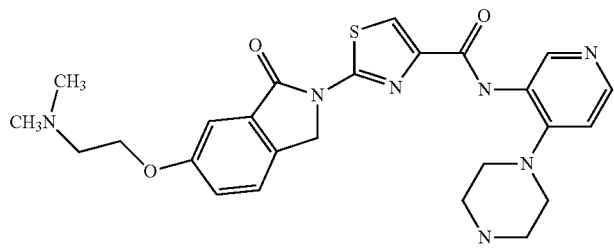 |
| 117 | 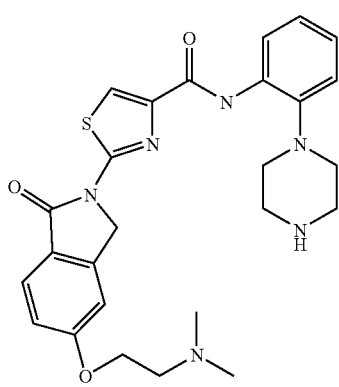 |

-continued
| Compound No. | Structure |
|---|---|
| 118 | 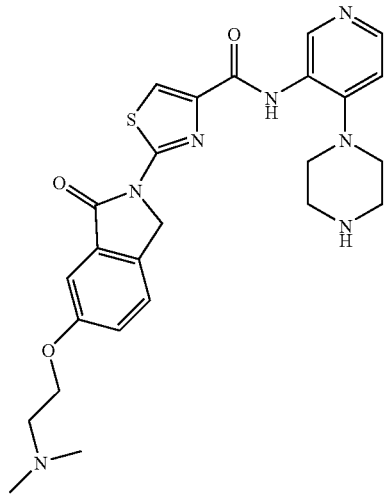 |
| 119 | 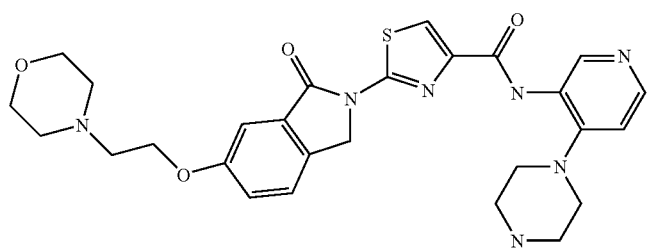 |
| 123 | 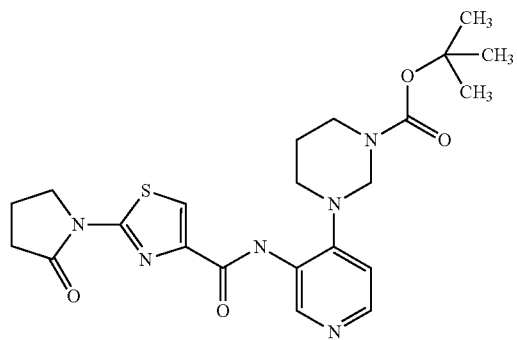 |
| 124 | 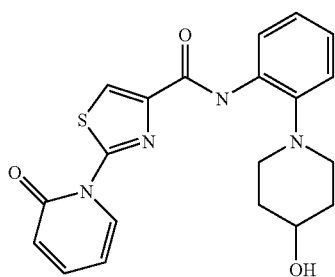 |

| Compound No. | Structure |
|---|---|
| 125 | 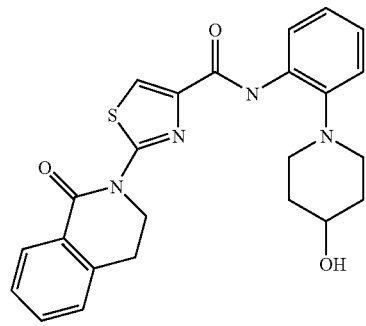 |
| 126 | 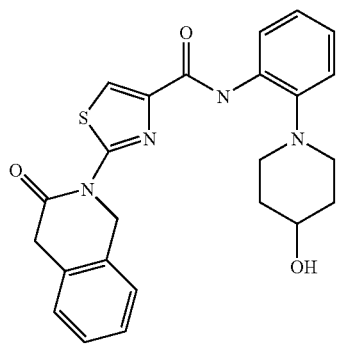 |
| 127 | 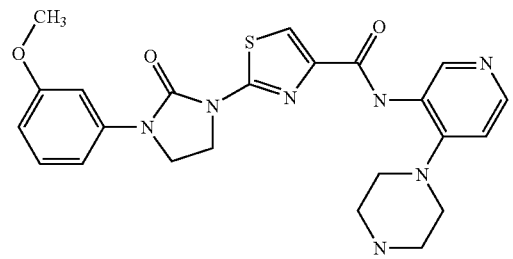 |
| 128 | 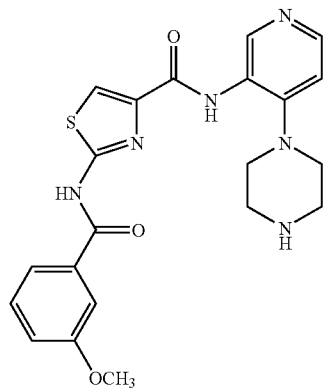 |

| Compound No. | Structure |
|---|---|
| 129 | 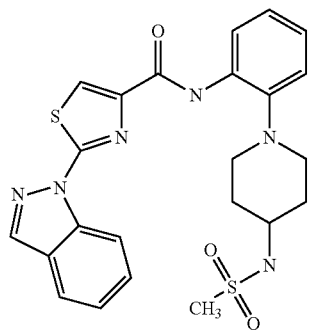 |
| 130 | 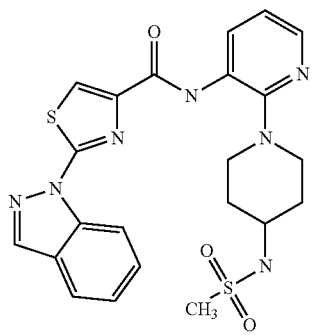 |
| 131 | 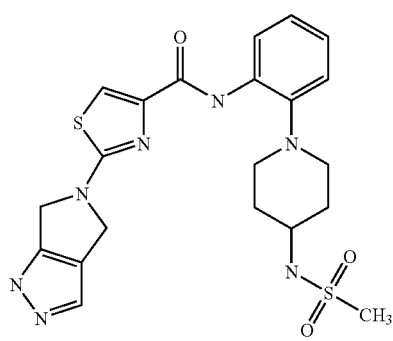 |
| 132 | 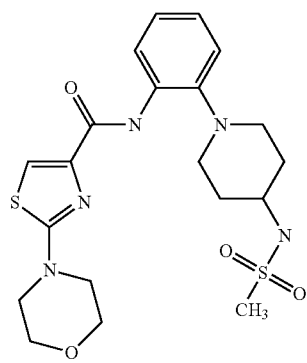 |

| Compound No. | Structure |
|---|---|
| 133 | 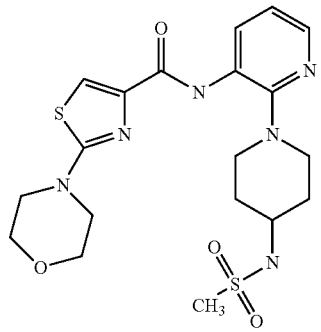 |
| 134 | 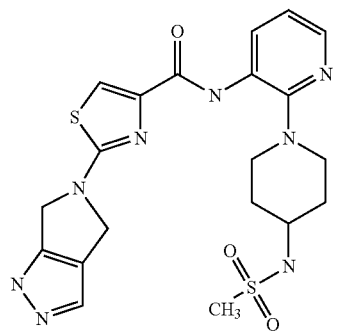 |
| 135 | 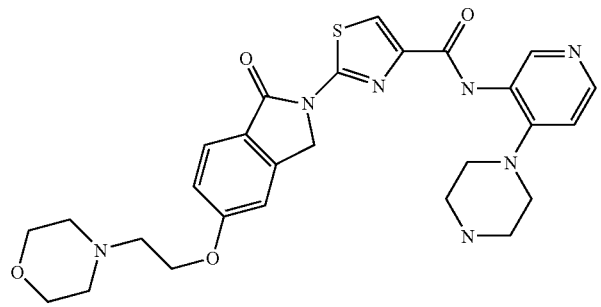 |
| 136 | 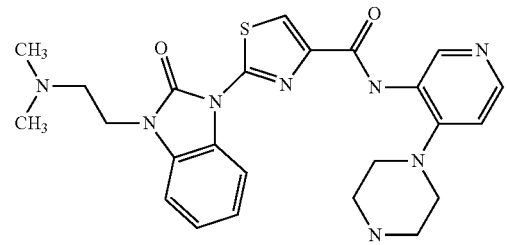 |
| 137 | 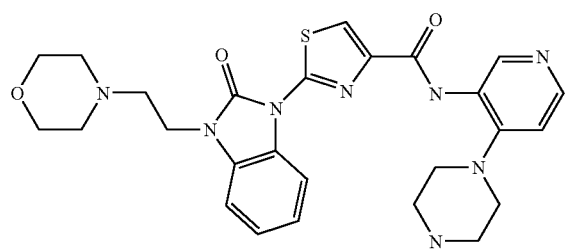 |

-continued
| Compound No. | Structure |
|---|---|
| 138 | 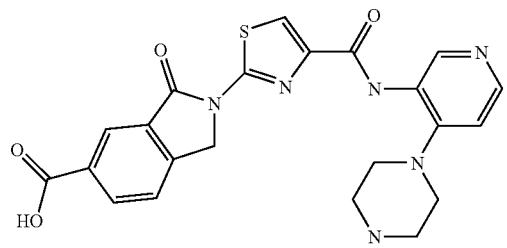 |
| 139 | 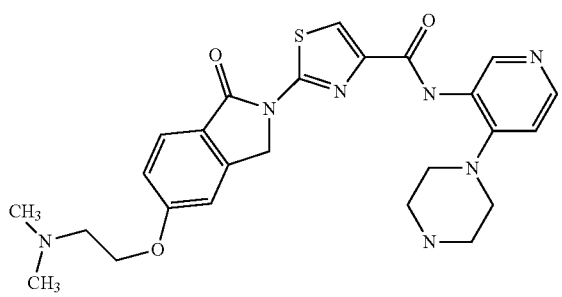 |
| 140 | 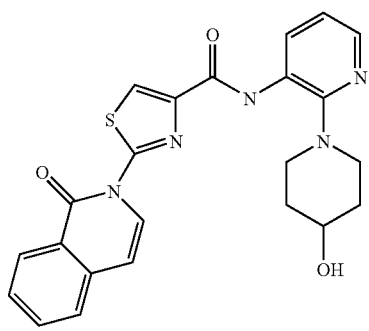 |
| 141 | 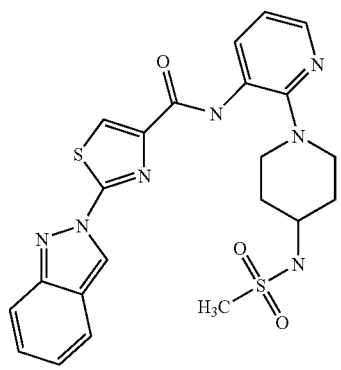 |
| 142 | 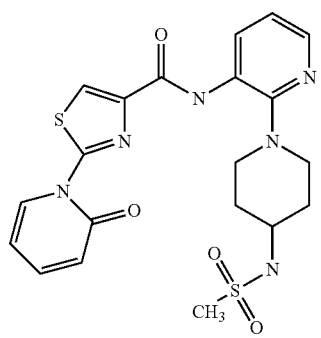 |

-continued
| Compound No. | Structure |
|---|---|
| 143 | 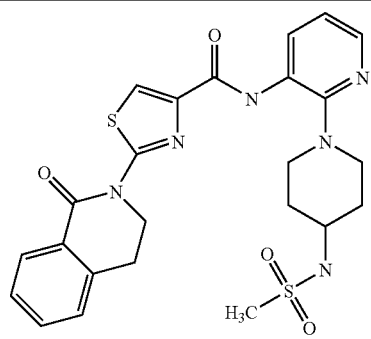 |
| 144 | 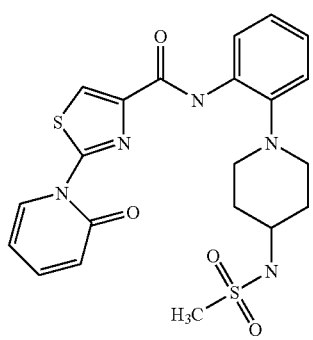 |
| 145 | 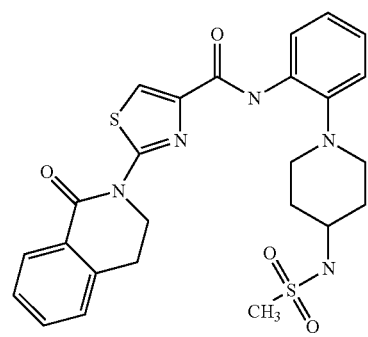 |
| 146 | 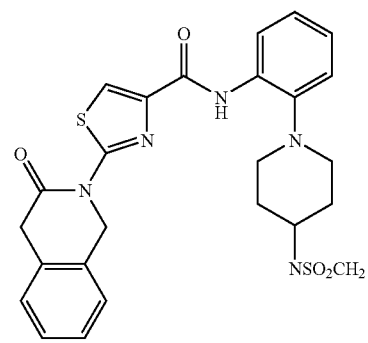 |
| 147 | 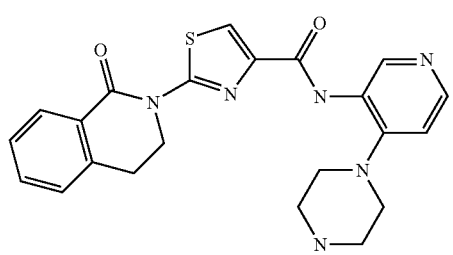 |

| Compound No. | Structure |
|---|---|
| 148 | 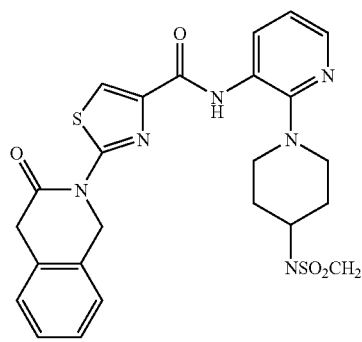 |
| 149 | 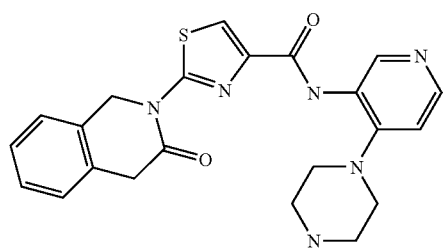 |
| 150 | 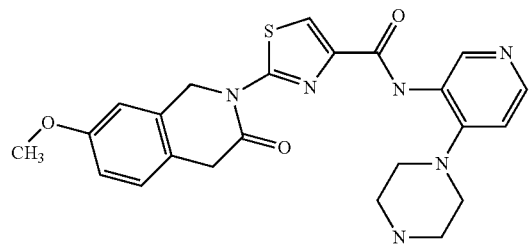 |
| 151 | 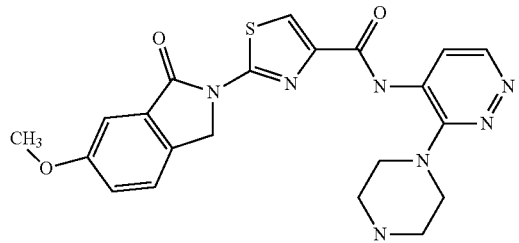 |
| 152 | 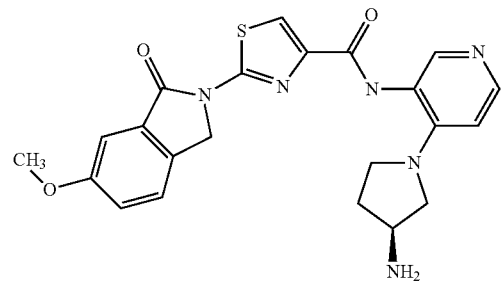 |

-continued
| Compound No. | Structure |
|---|---|
| 153 | 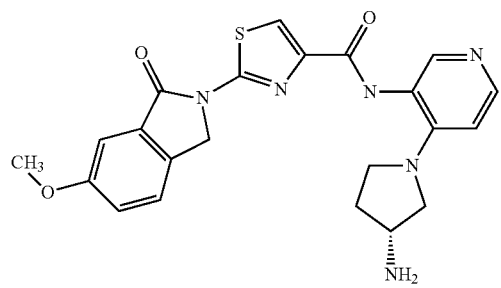 |
| 154 | 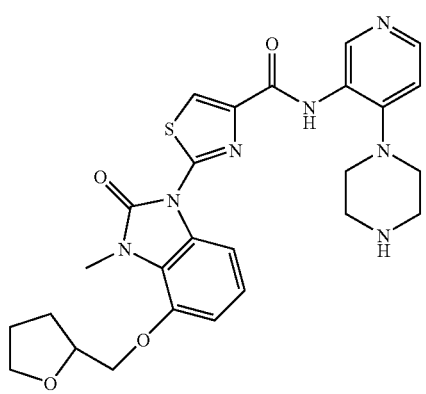 |
| 155 | 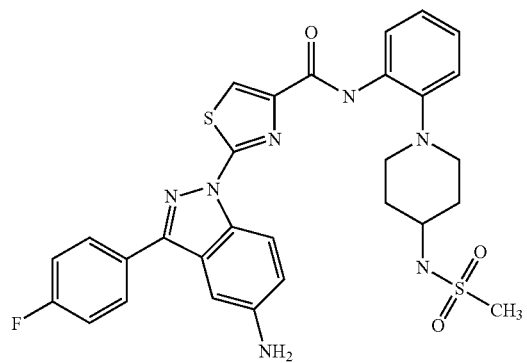 |
| 156 | 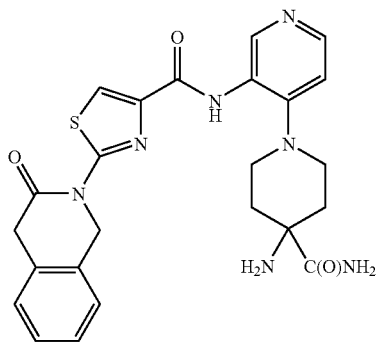 |

| Compound No. | Structure |
|---|---|
| 157 | 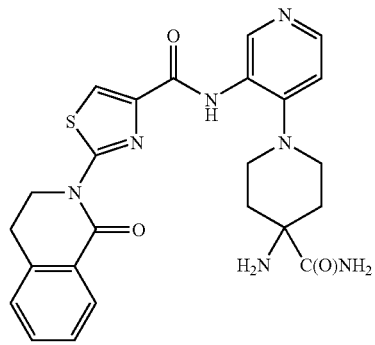 |
| 158 | 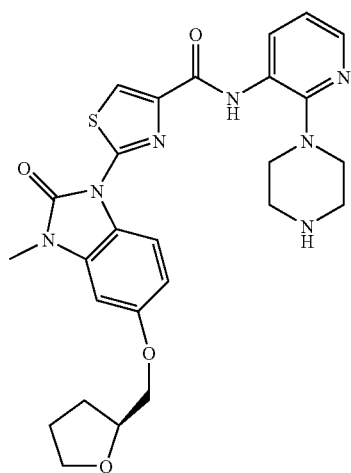 |
| 159 | 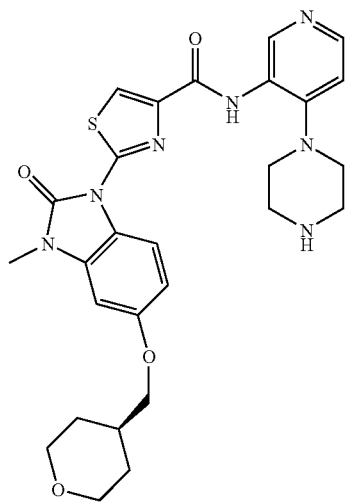 |

| Compound No. | Structure |
|---|---|
| 160 | 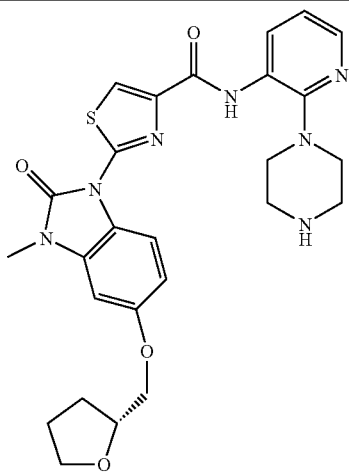 |
| 161 | 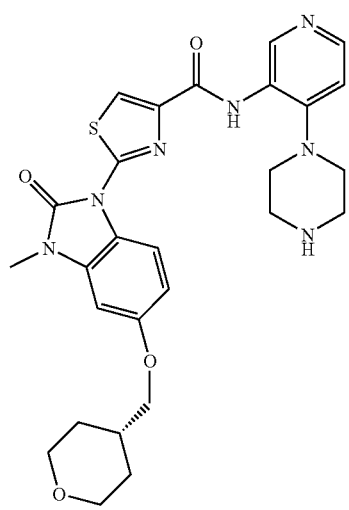 |
| 162 | 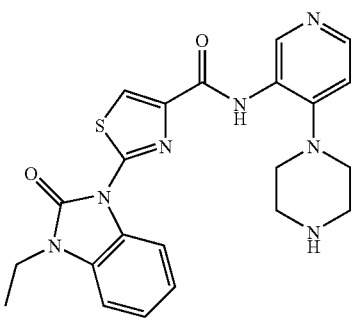 |
| 163 | 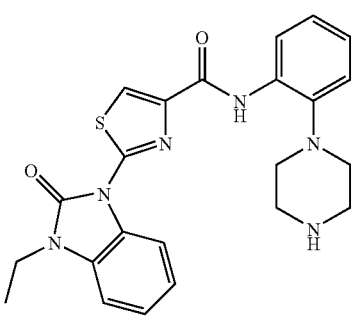 |

-continued
| Compound No. | Structure |
|---|---|
| 164 | 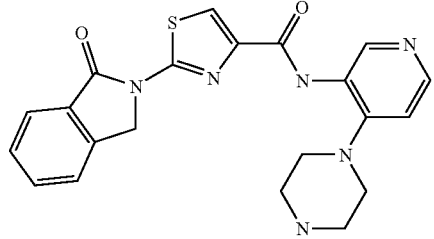 |
| 165 | 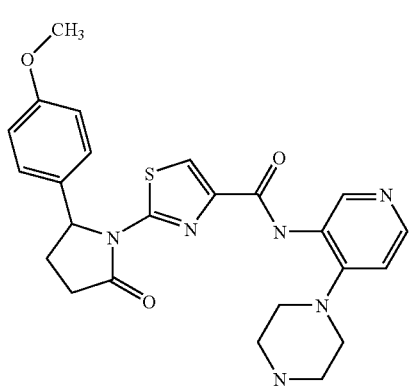 |
| 166 | 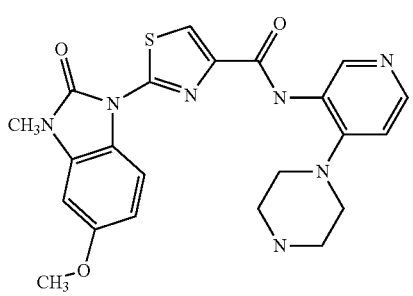 |
| 167 | 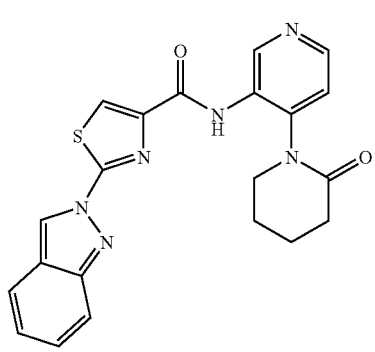 |
| 168 | 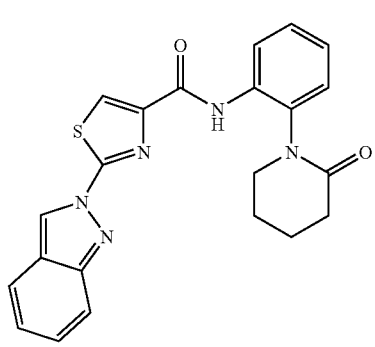 |

-continued
| Compound No. | Structure |
|---|---|
| 169 | 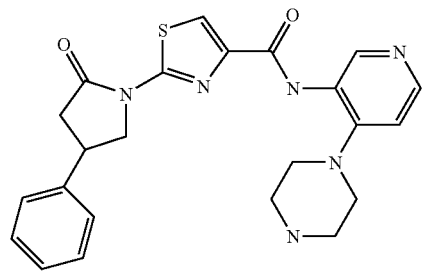 |
| 170 | 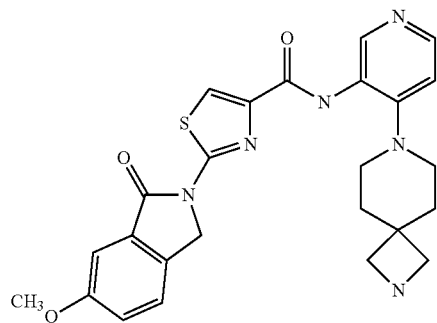 |
| 171 | 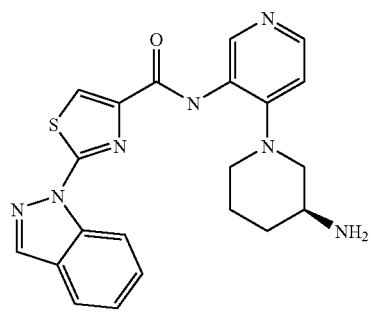 |
| 172 | 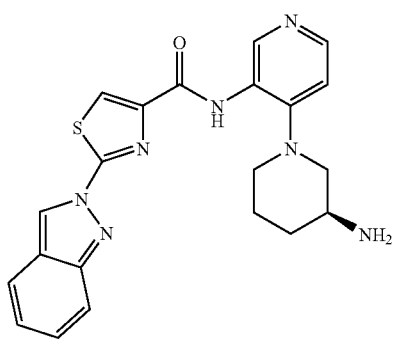 |
| 173 | 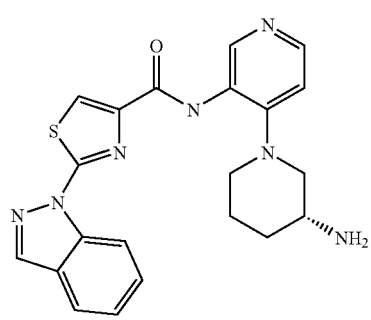 |

| Compound No. | Structure |
|---|---|
| 174 | 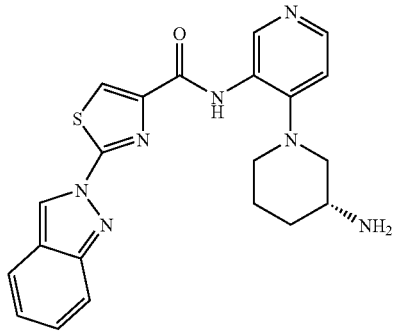 |
| 175 | 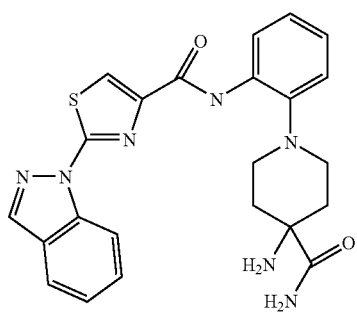 |
| 176 | 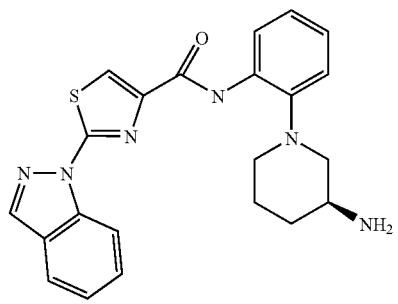 |
| 177 | 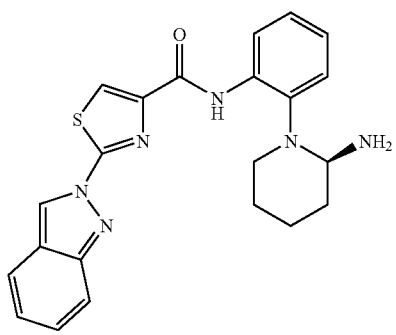 |

151
-continued
| Compound No. | Structure |
|---|---|
| 178 | 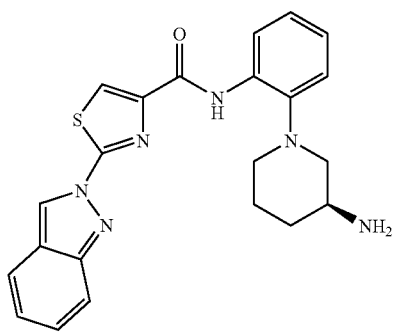 |
| 179 | 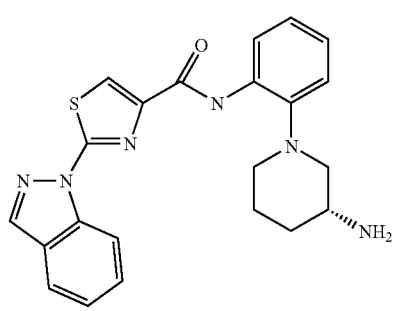 |
| 180 | 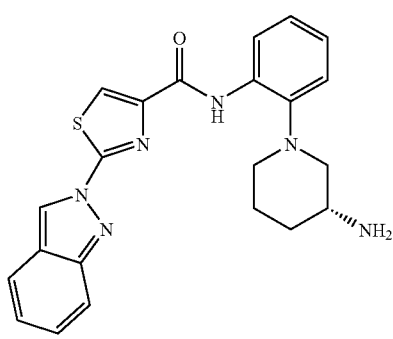 |
| 181 | 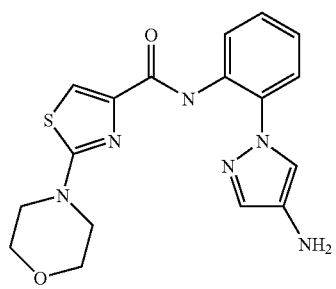 |
| 182 | 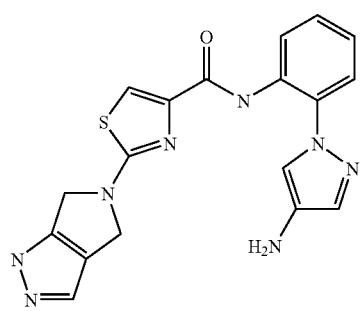 |

US 8,318,735 B2
| Compound No. | Structure |
|---|---|
| 183 | 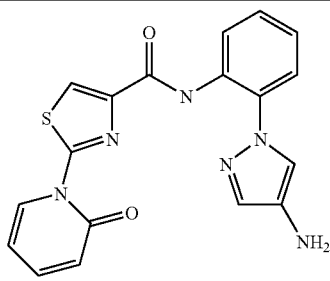 |
| 184 | 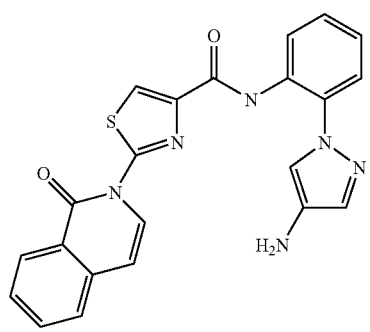 |
| 185 | 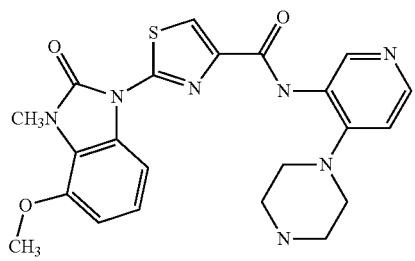 |
| 186 | 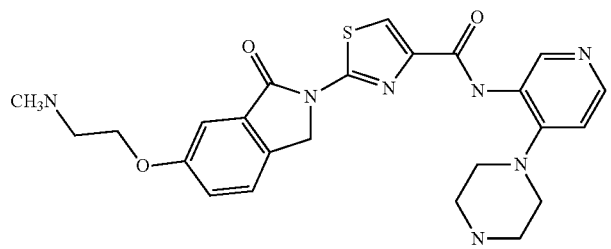 |
| 187 | 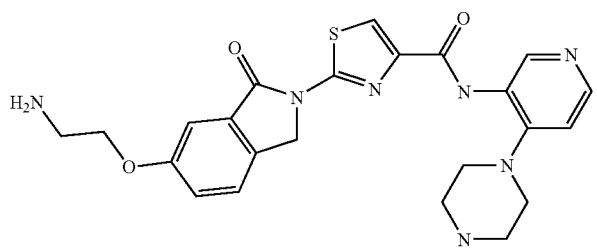 |

| Compound No. | Structure |
|---|---|
| 188 | 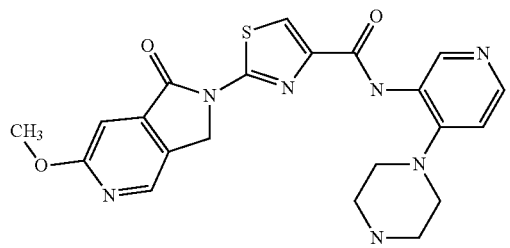 |
| 189 | 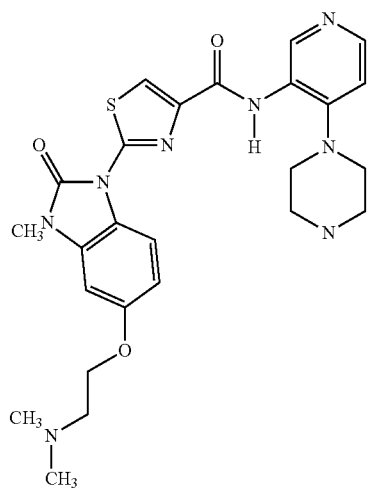 |
| 190 | 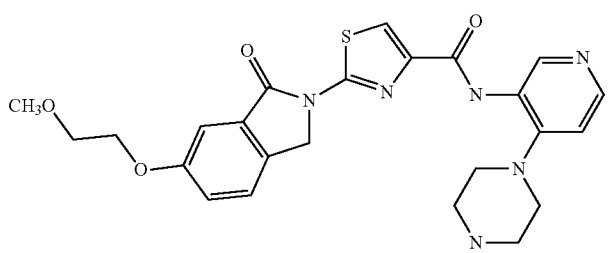 |
| 191 | 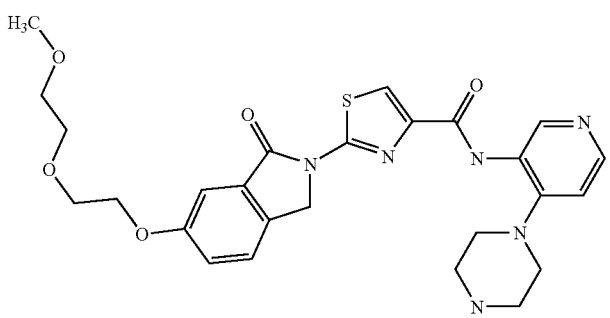 |
| 192 | 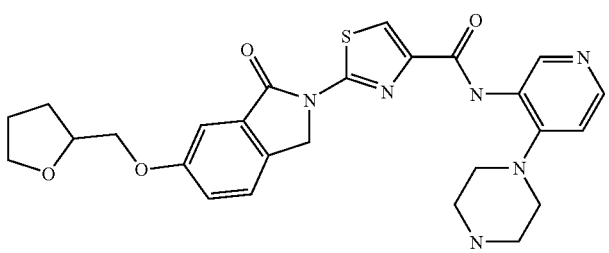 |

| Compound No. | Structure |
|---|---|
| 193 | 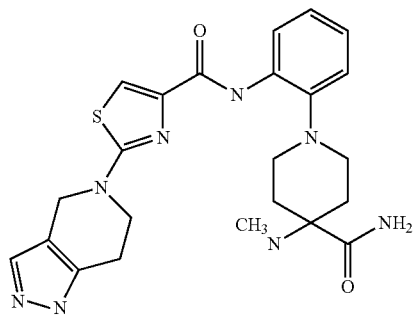 |
| 194 | 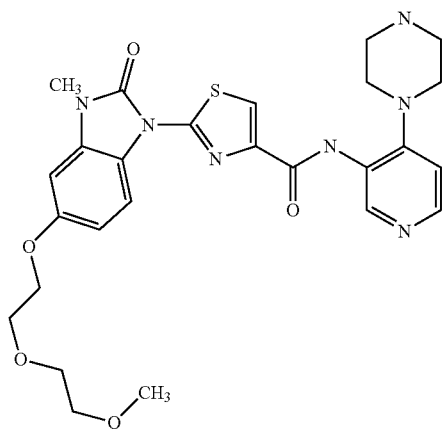 |
| 195 | 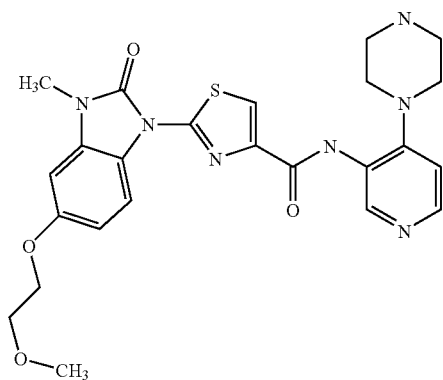 |
| 196 | 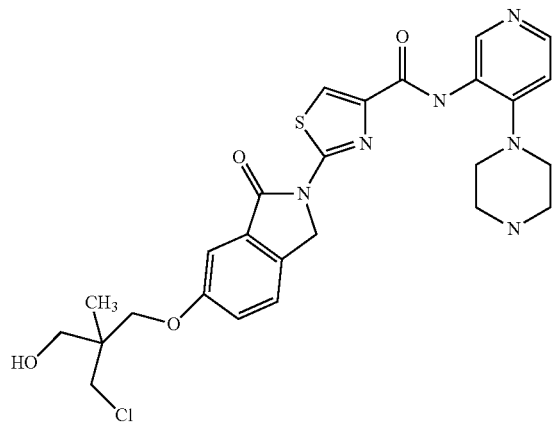 |

| Compound No. | Structure |
|---|---|
| 197 | 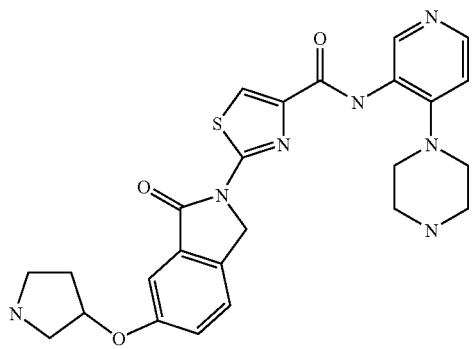 |
| 198 | 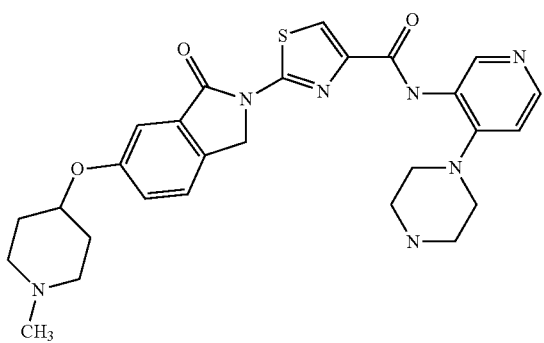 |
| 199 | 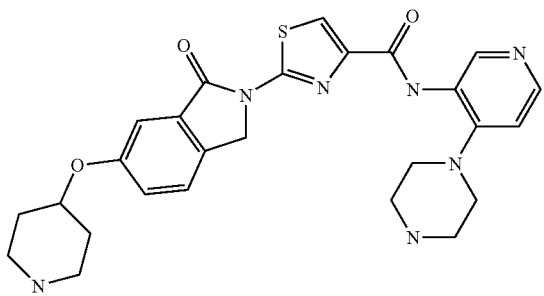 |
| 200 | 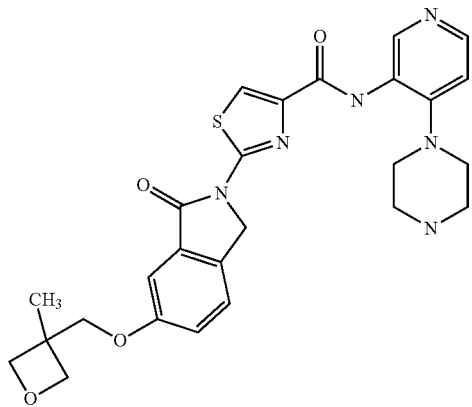 |

-continued
| Compound No. | Structure |
|---|---|
| 201 | 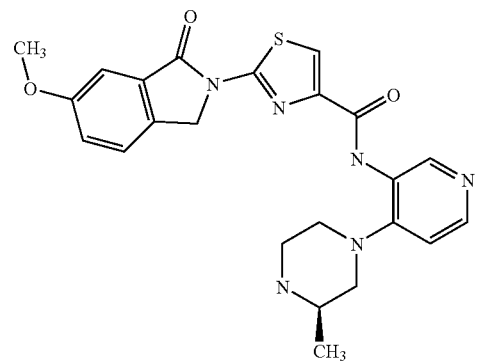 |
| 202 | 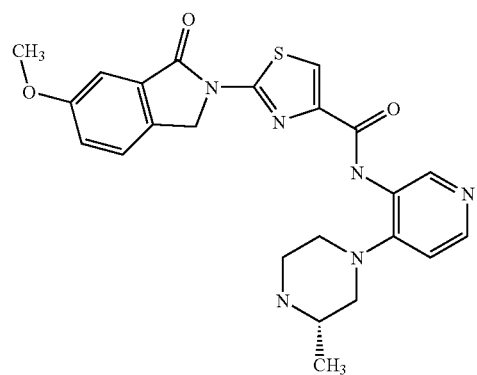 |
| 203 | 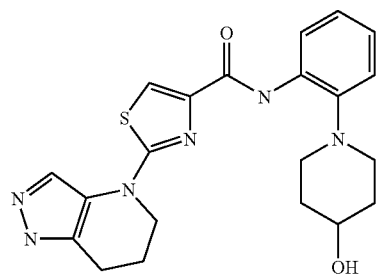 |
| 204 | 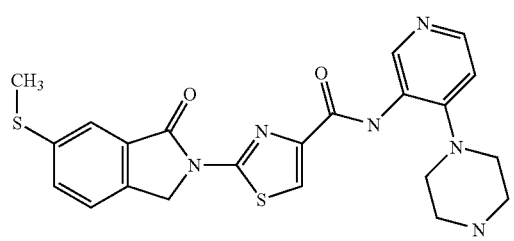 |

| Compound No. | Structure |
|---|---|
| 205 | 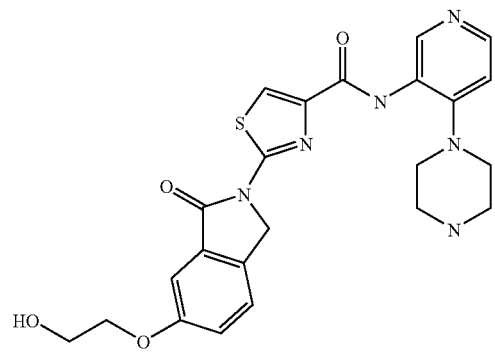 |
| 206 | 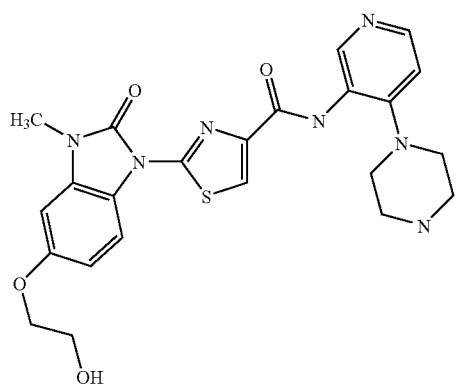 |
| 207 | 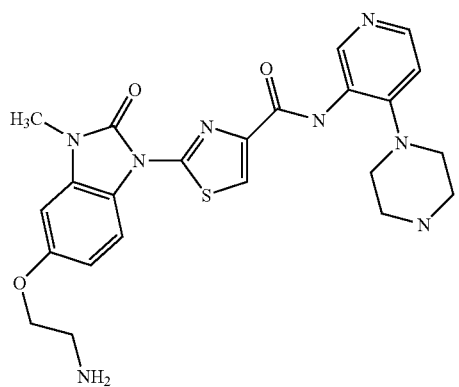 |
| 208 | 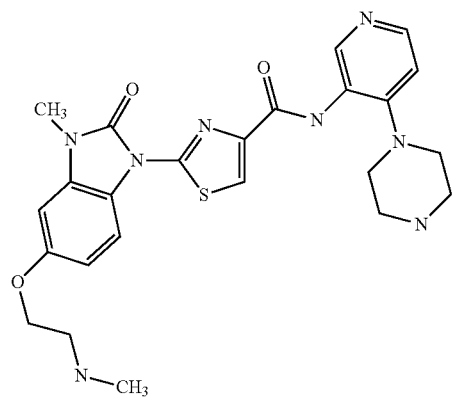 |

| Compound No. | Structure |
|---|---|
| 209 | *(structure)* |
| 210 | *(structure)* |
| 211 | *(structure)* |
| 212 | *(structure)* |
| 213 | *(structure)* |

-continued
| Compound No. | Structure |
|---|---|
| 214 | 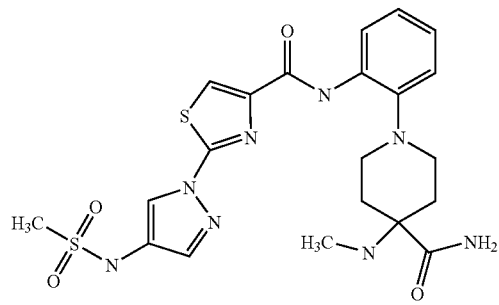 |
| 215 | 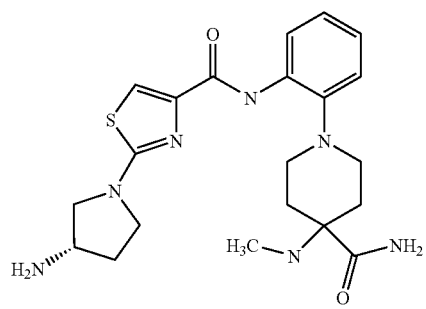 |
| 216 | 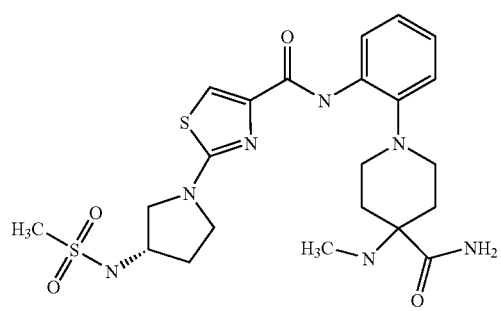 |
| 217 | 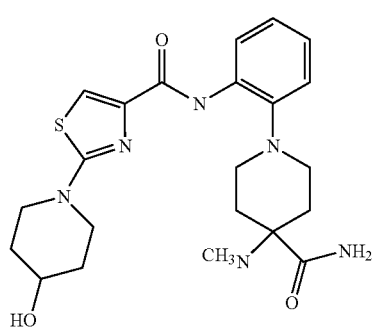 |
| 218 | 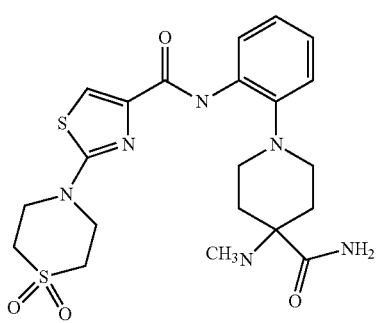 |

| Compound No. | Structure |
|---|---|
| 219 | 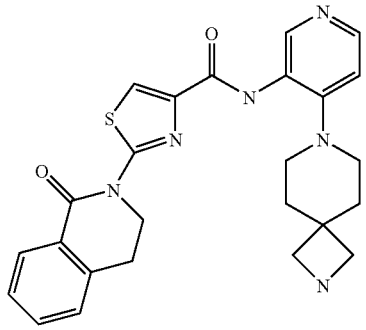 |
| 220 | 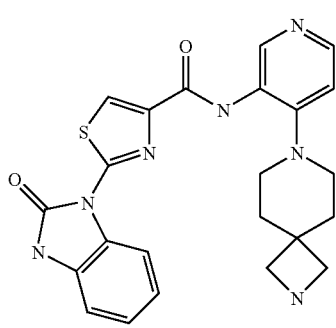 |
| 221 | 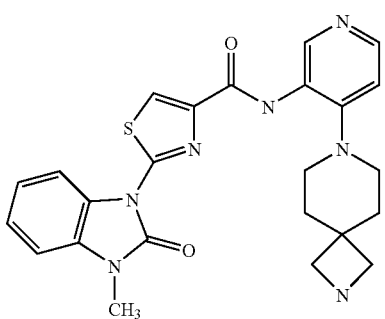 |
| 222 | 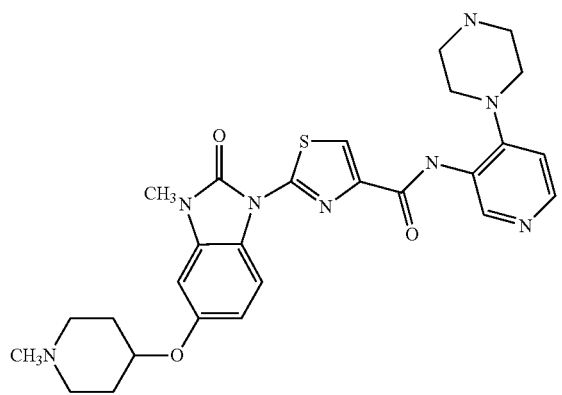 |

| Compound No. | Structure |
|---|---|
| 223 | 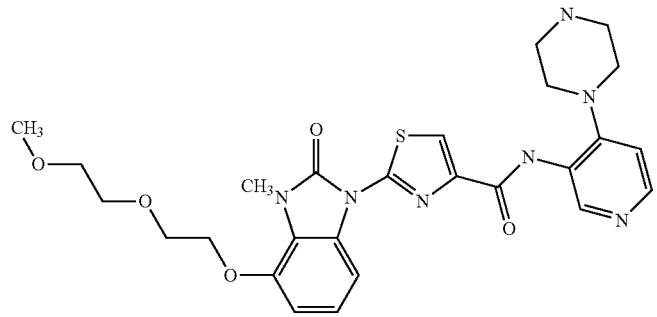 |
| 224 | 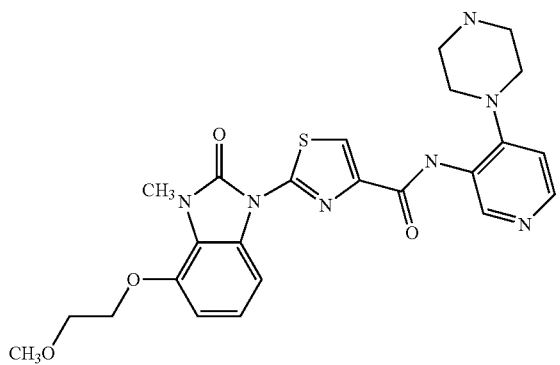 |
| 225 | 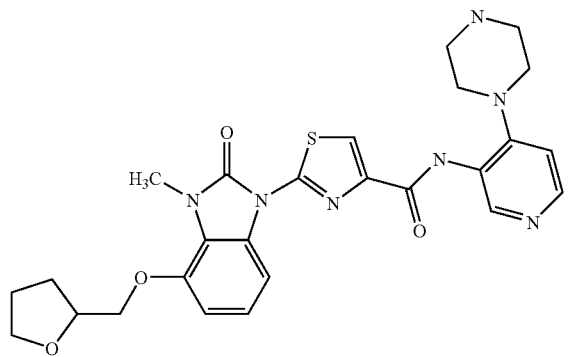 |
| 226 | 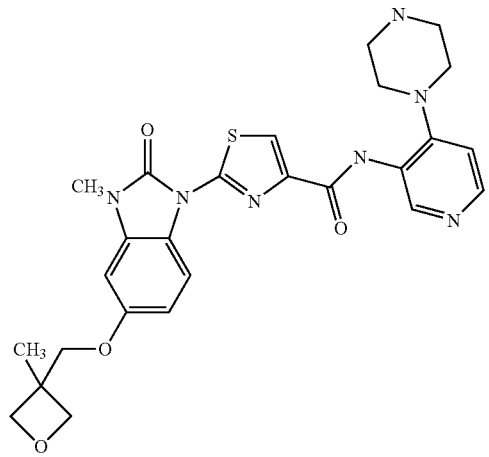 |

| Compound No. | Structure |
|---|---|
| 227 | 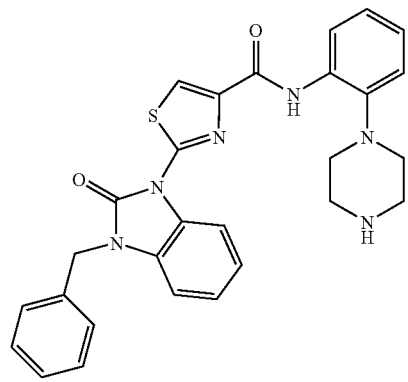 |
| 228 | 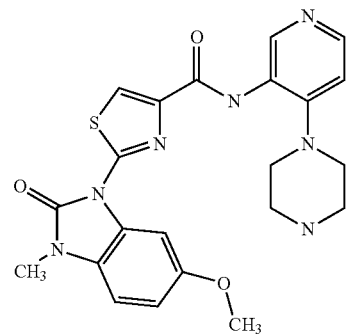 |
| 229 | 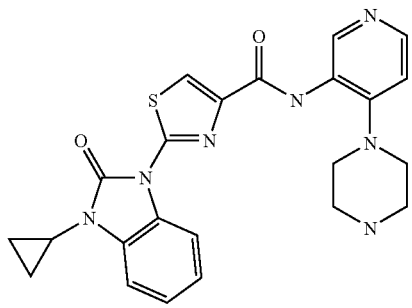 |
| 230 | 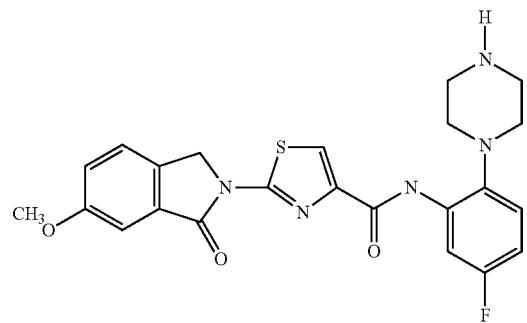 |

| Compound No. | Structure |
|---|---|
| 231 | 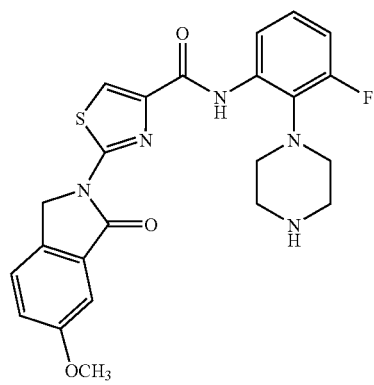 |
| 232 | 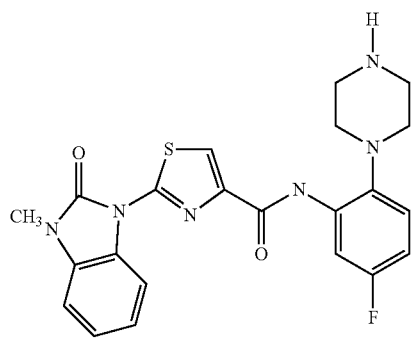 |
| 233 | 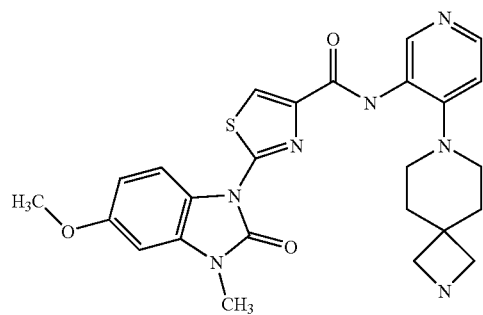 |
| 234 | 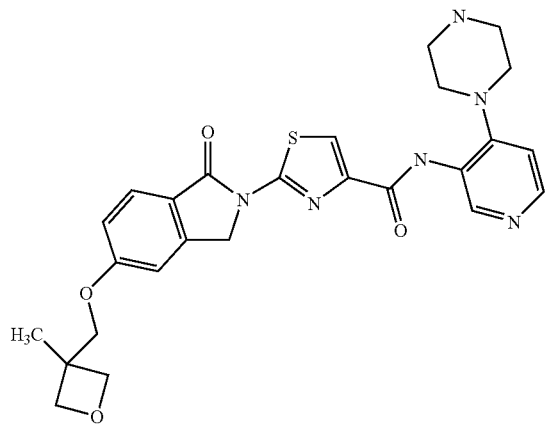 |

| Compound No. | Structure |
|---|---|
| 235 | 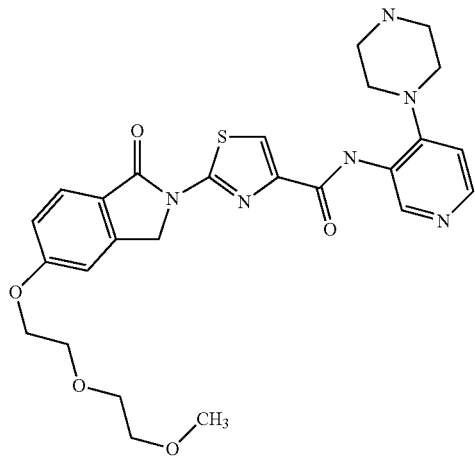 |
| 236 | 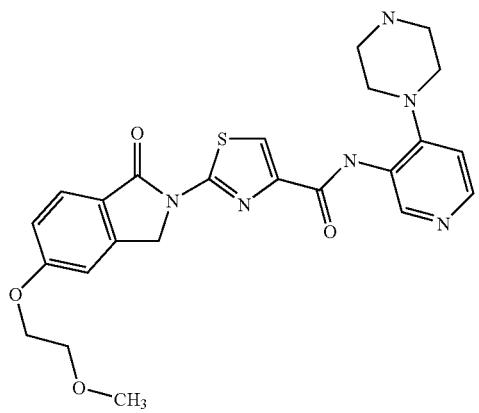 |
| 237 | 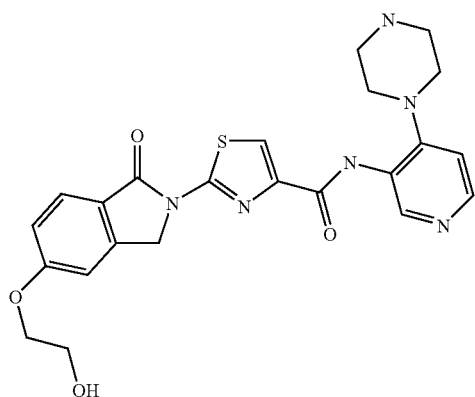 |

| Compound No. | Structure |
|---|---|
| 238 | 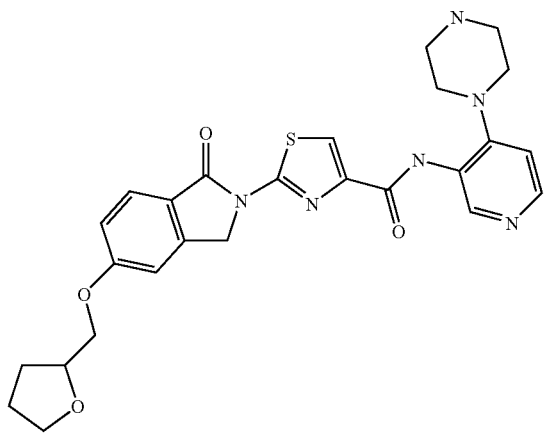 |
| 239 | 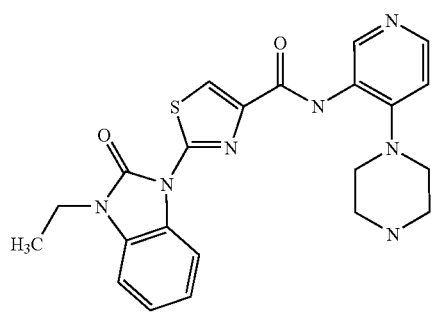 |
| 240 | 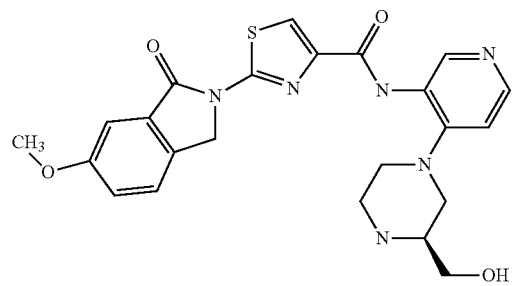 |
| 241 | 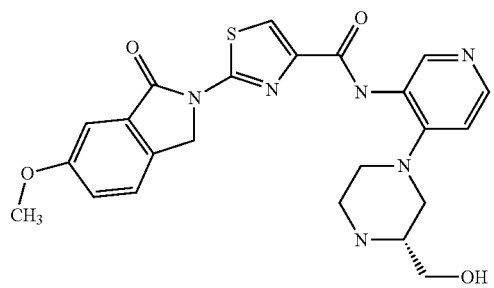 |

| Compound No. | Structure |
|---|---|
| 242 | 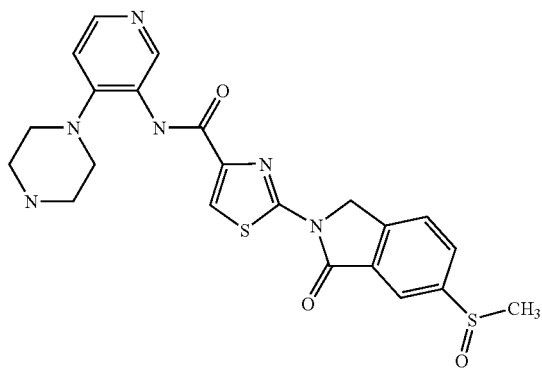 |
| 243 | 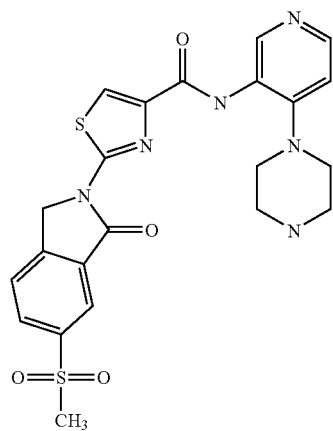 |
| 244 | 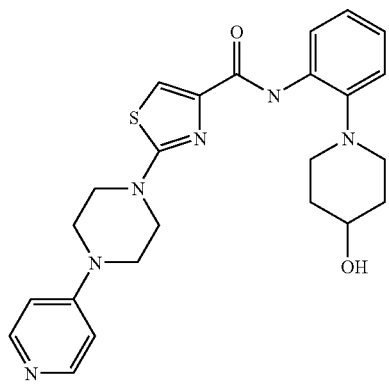 |
| 245 | 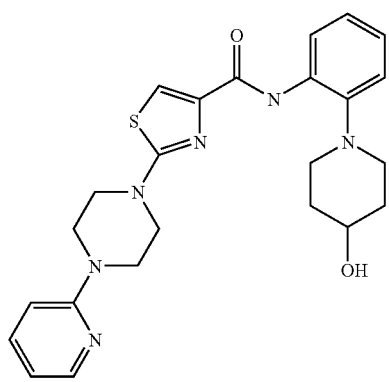 |

| Compound No. | Structure |
|---|---|
| 246 | 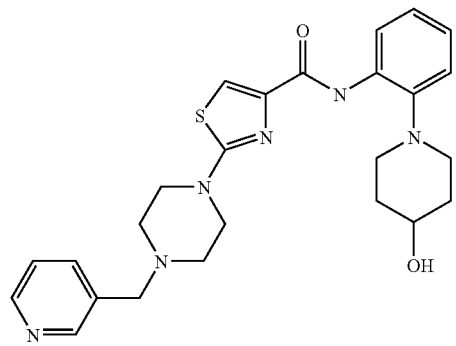 |
| 247 | 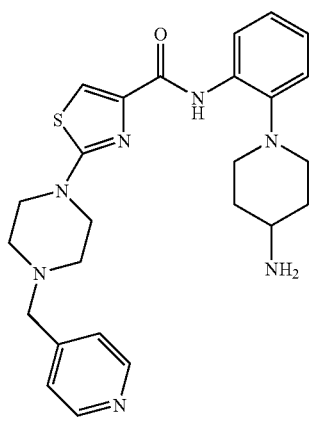 |
| 248 | 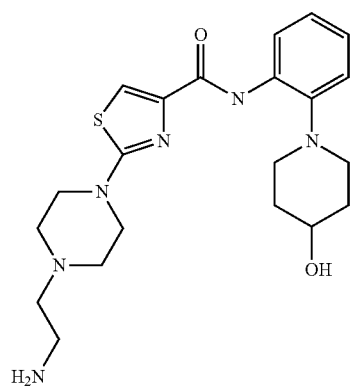 |
| 249 | 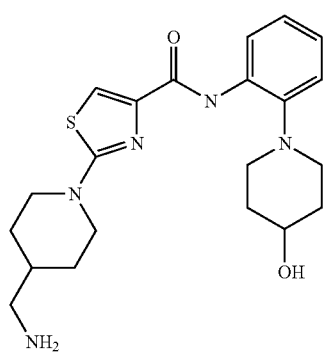 |

-continued
| Compound No. | Structure |
|---|---|
| 250 | 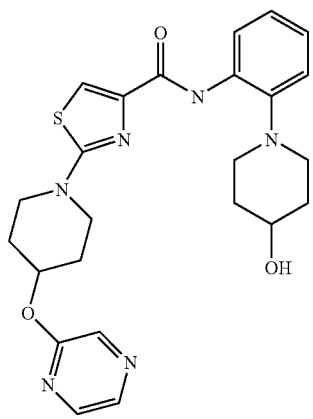 |
| 251 | 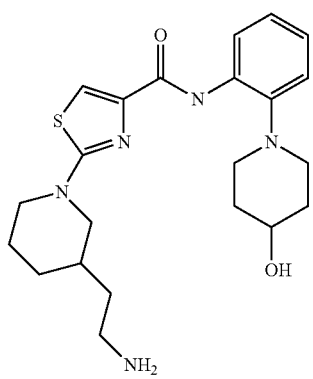 |
| 252 | 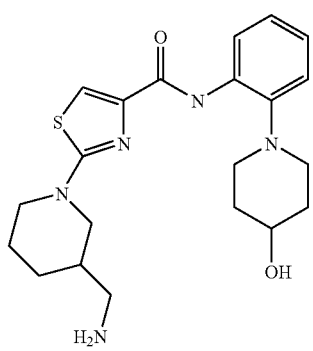 |
| 253 | 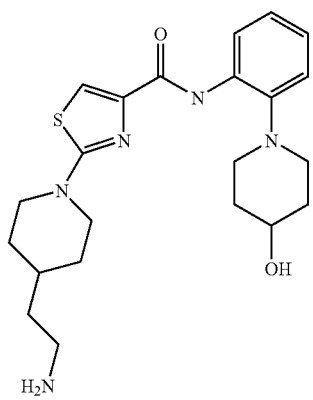 |

| Compound No. | Structure |
|---|---|
| 254 | 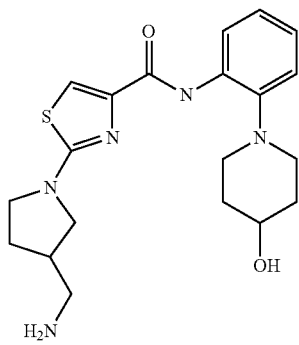 |
| 255 | 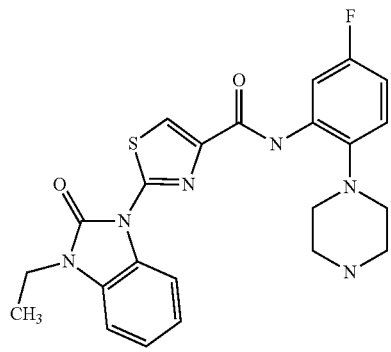 |
| 256 | 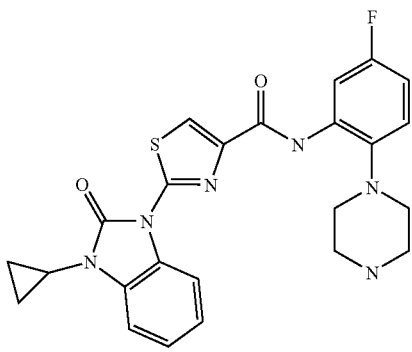 |
| 257 | 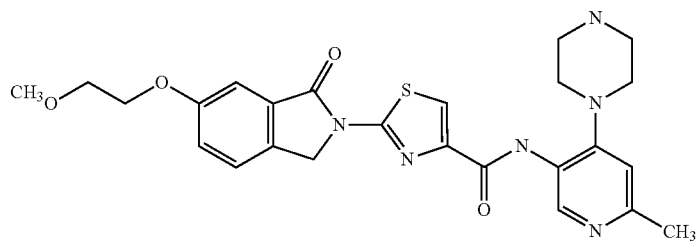 |

| Compound No. | Structure |
|---|---|
| 258 | 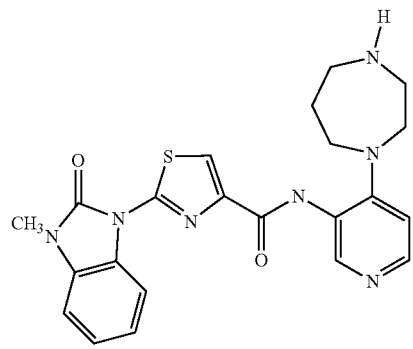 |
| 259 | 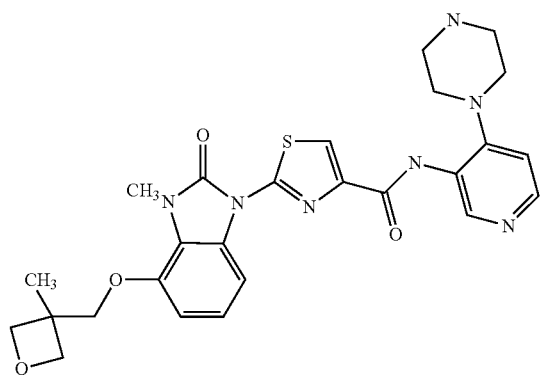 |
| 260 | 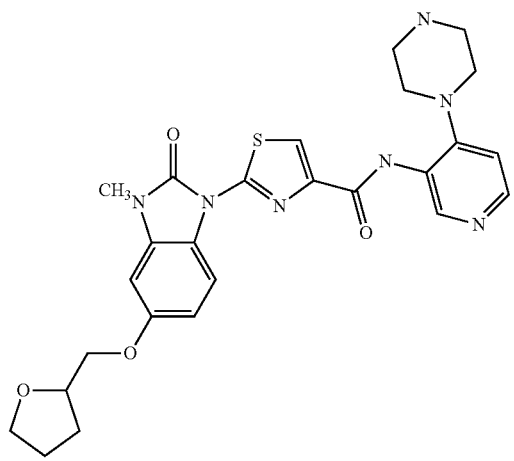 |
| 261 | 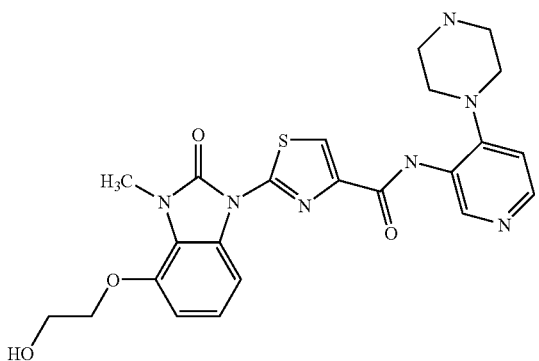 |

-continued
| Compound No. | Structure |
|---|---|
| 262 | 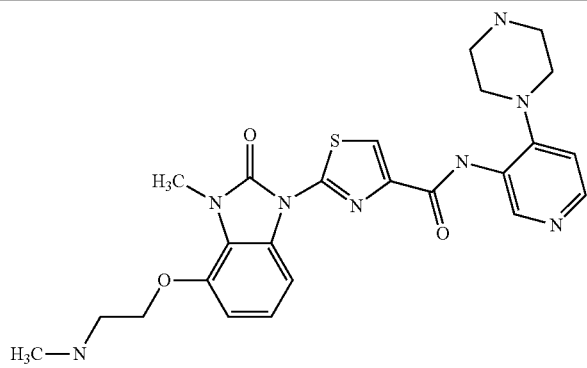 |
| 263 | 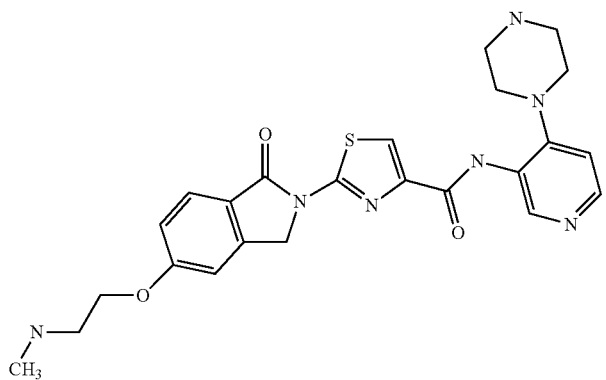 |
| 264 | 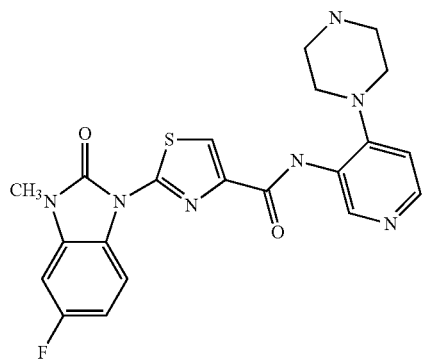 |
| 265 | 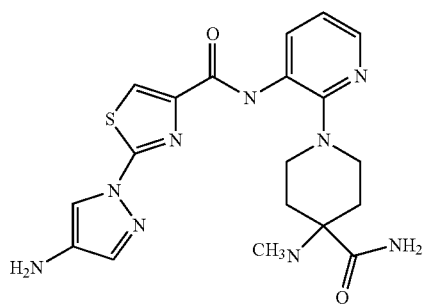 |

| Compound No. | Structure |
|---|---|
| 266 | 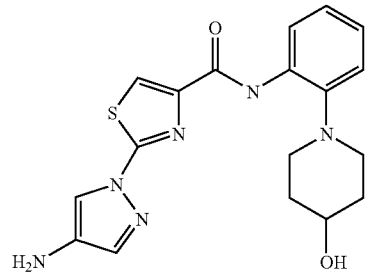 |
| 267 | 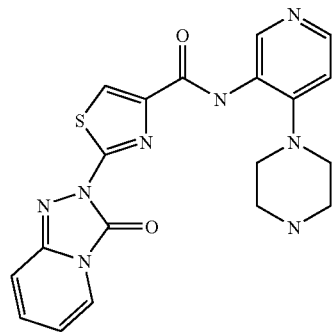 |
| 268 | 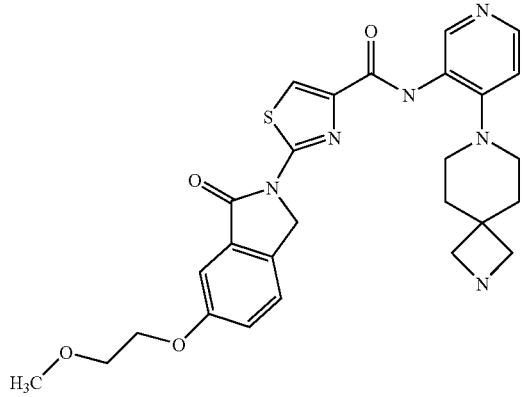 |
| 269 | 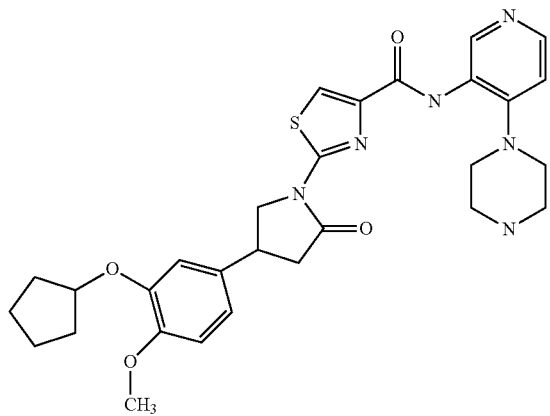 |

| Compound No. | Structure |
|---|---|
| 270 | 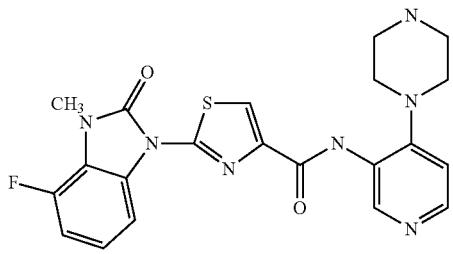 |
| 271 | 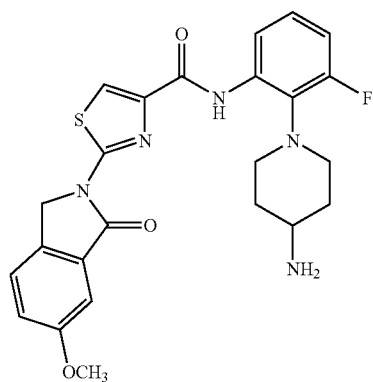 |
| 272 | 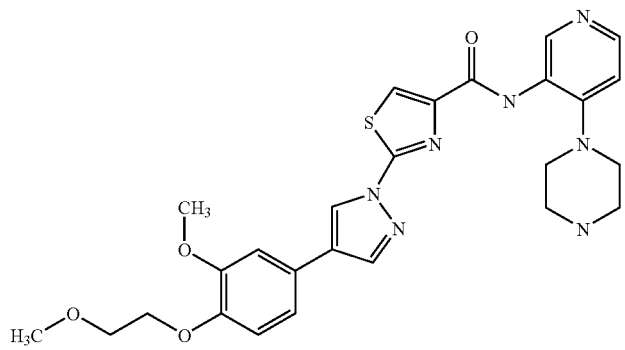 |
| 273 | 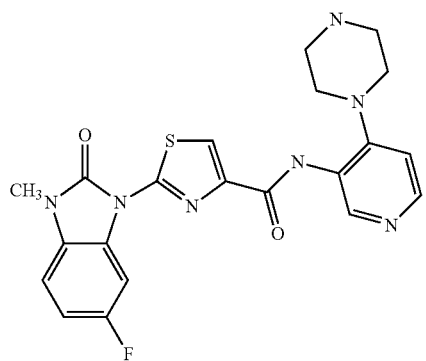 |

-continued
| Compound No. | Structure |
|---|---|
| 274 | 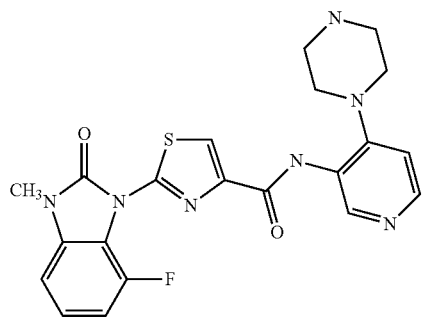 |
| 275 | 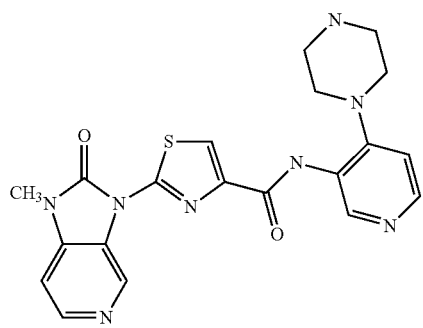 |
| 276 | 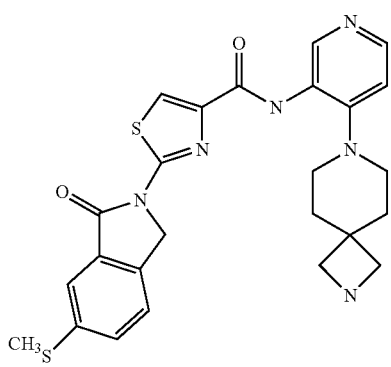 |
| 277 | 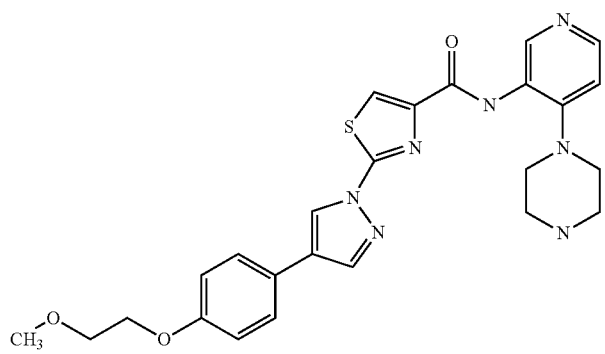 |
| 278 | 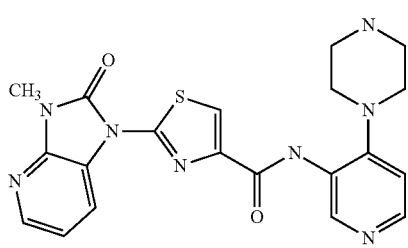 |

| Compound No. | Structure |
|---|---|
| 279 | 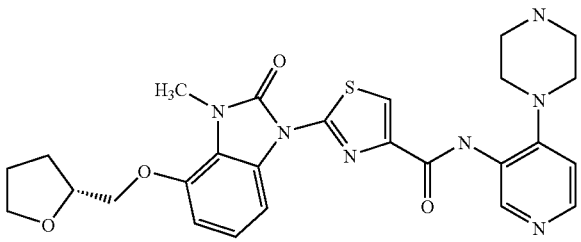 |
| 280 | 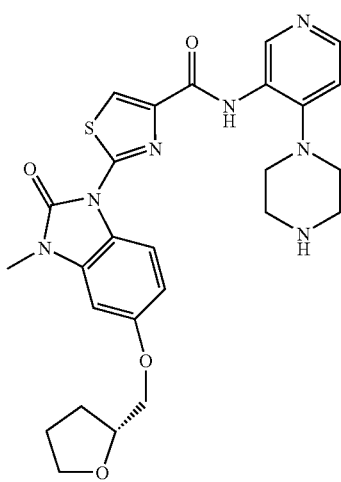 |
| 281 | 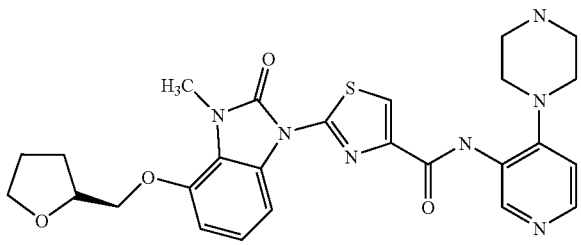 |
| 282 | 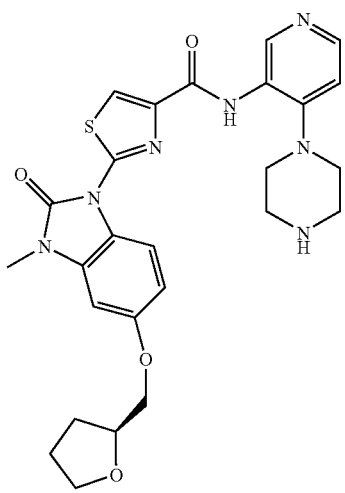 |

-continued
| Compound No. | Structure |
|---|---|
| 283 | 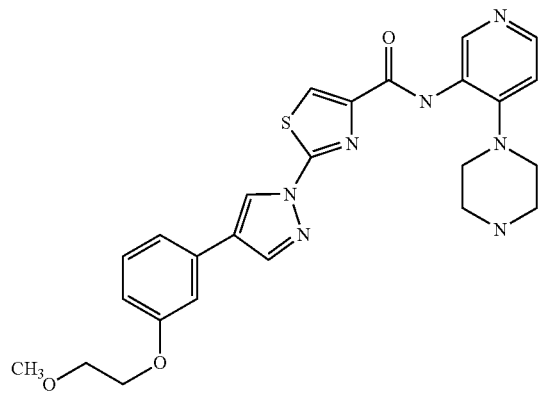 |
| 284 | 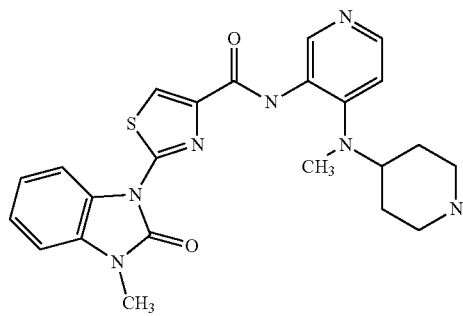 |
| 285 | 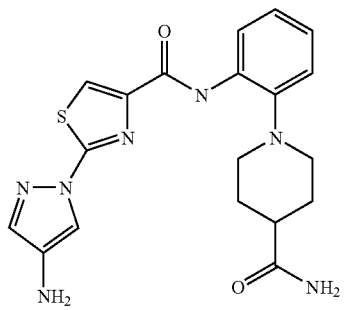 |
| 286 | 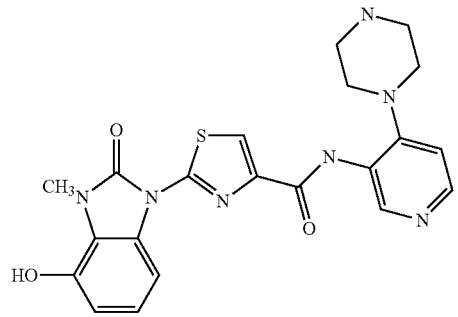 |

| Compound No. | Structure |
|---|---|
| 287 | 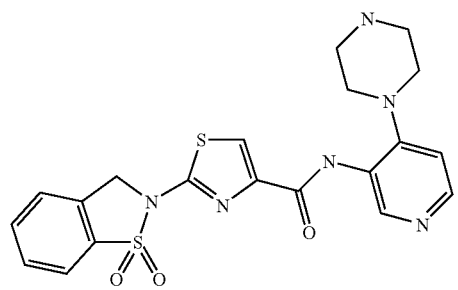 |
| 288 | 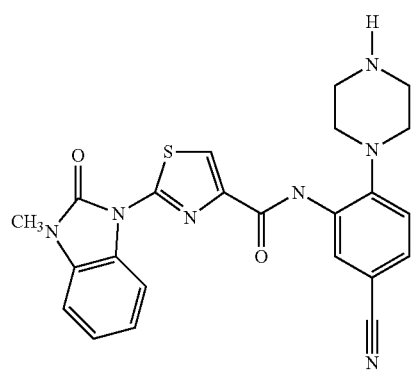 |
| 289 | 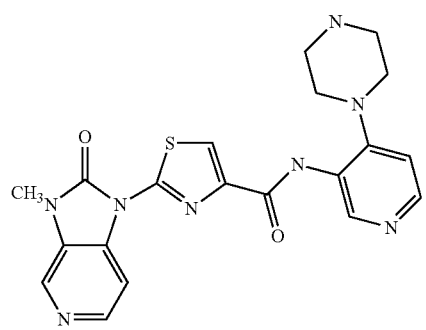 |
| 290 | 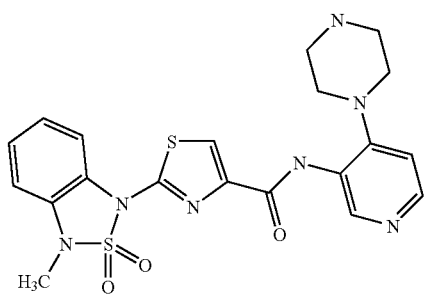 |
| 291 | 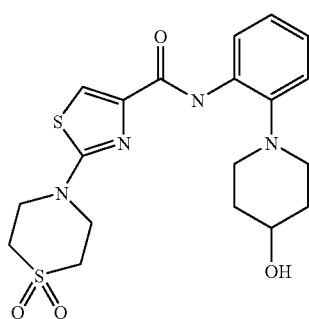 |

-continued
| Compound No. | Structure |
|---|---|
| 292 | 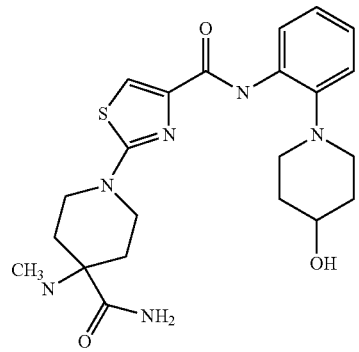 |
| 293 | 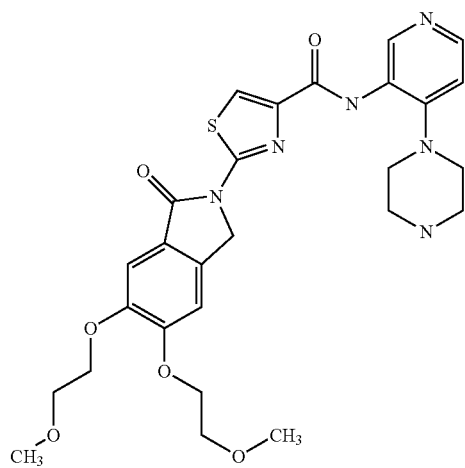 |
| 294 | 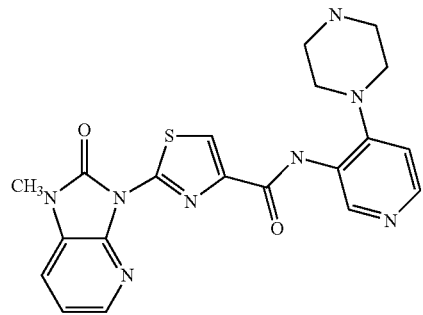 |
| 295 | 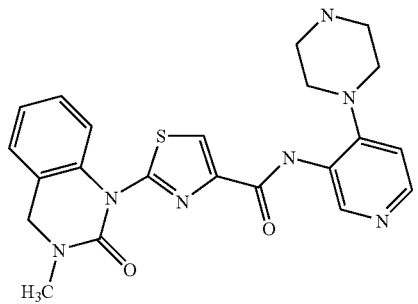 |

| Compound No. | Structure |
| --- | --- |
| 296 | 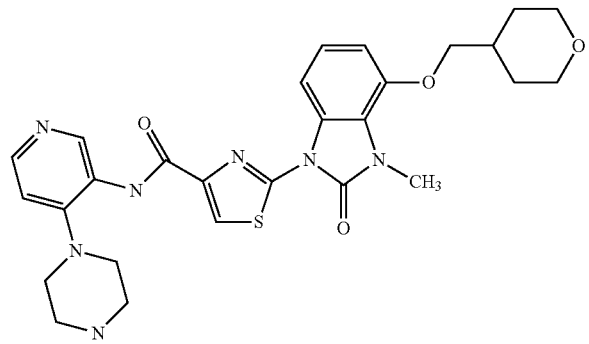 |
| 297 | 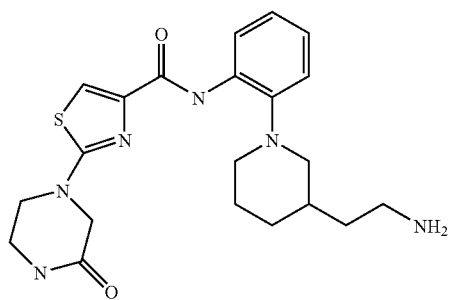 |
| 298 | 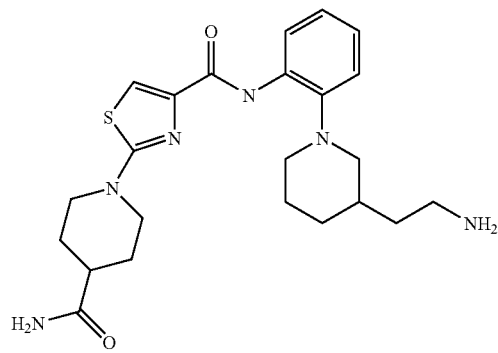 |
| 299 | 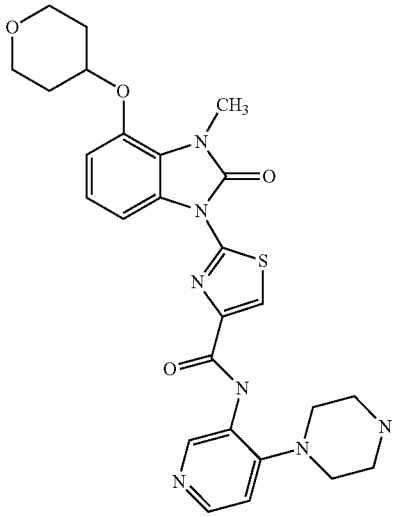 |

-continued
| Compound No. | Structure |
|---|---|
| 300 | 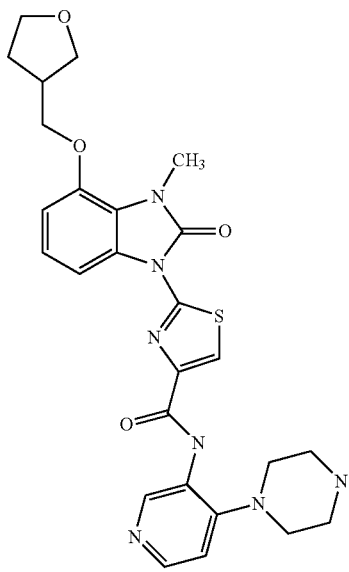 |
| 301 | 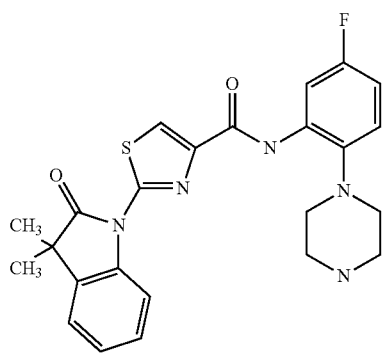 |
| 302 | 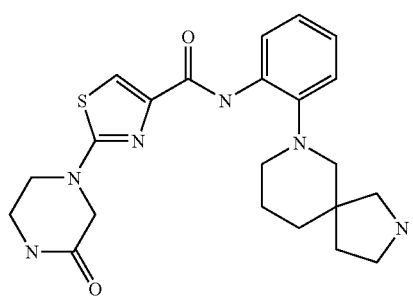 |
| 303 | 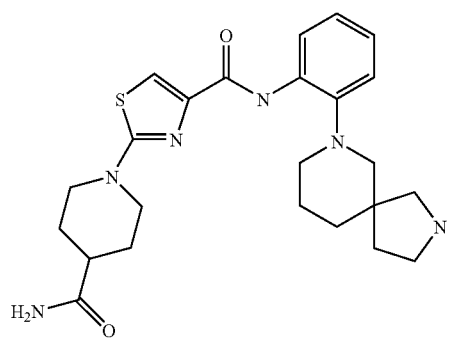 |

-continued
| Compound No. | Structure |
|---|---|
| 304 | 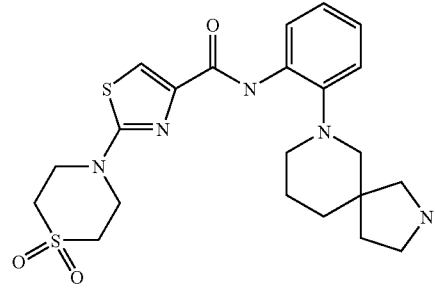 |
| 305 | 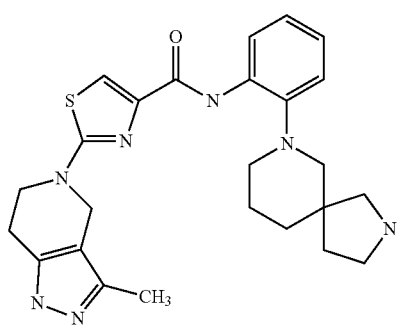 |
| 306 | 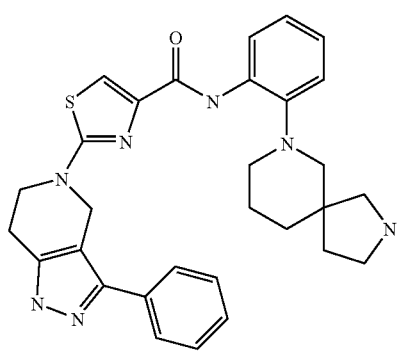 |
| 307 | 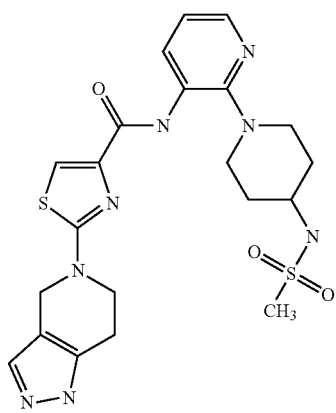 |

-continued
| Compound No. | Structure |
|---|---|
| 308 | 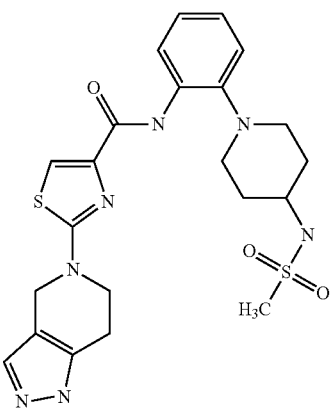 |
| 309 | 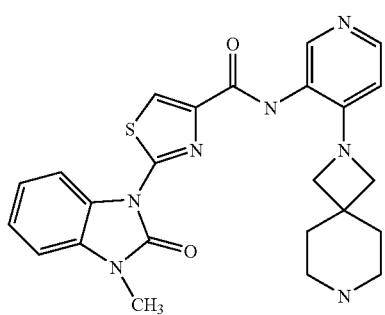 |
| 310 | 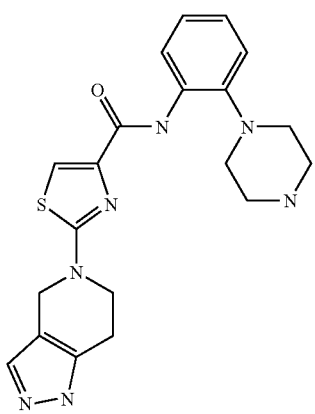 |
| 311 | 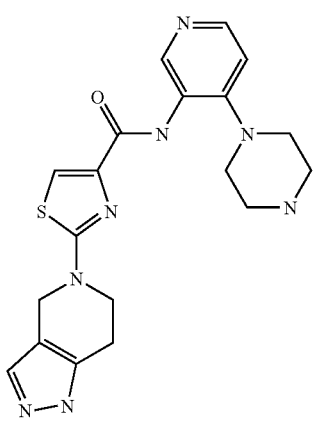 |

-continued
| Compound No. | Structure |
|---|---|
| 312 | 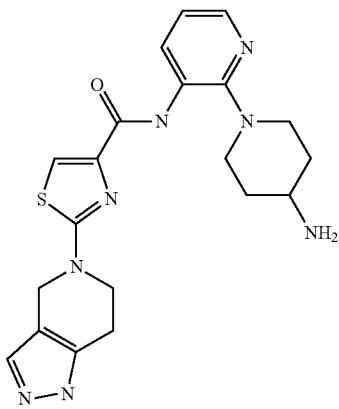 |
| 313 | 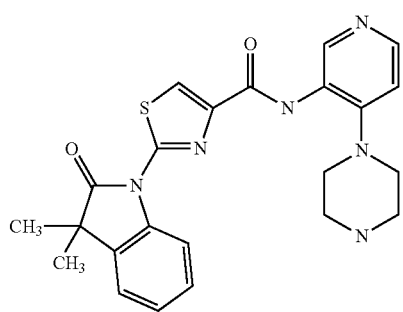 |
| 314 | 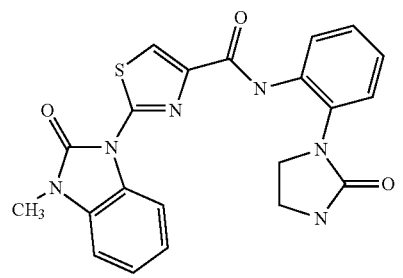 |
| 315 | 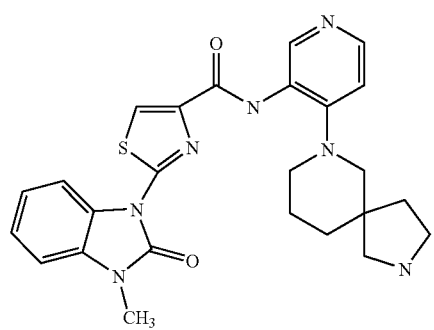 |

| Compound No. | Structure |
|---|---|
| 316 | 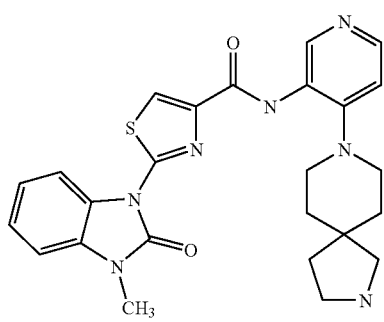 |
| 317 | 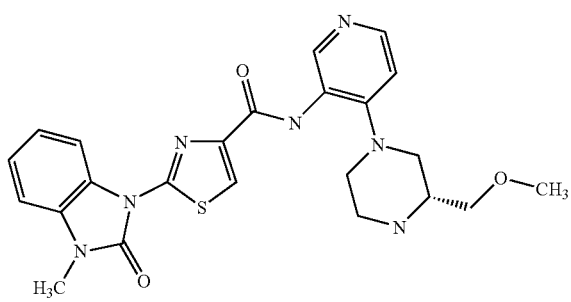 |
| 318 | 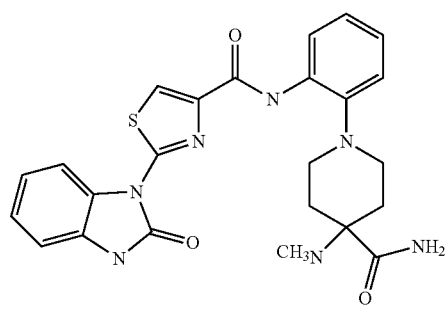 |
| 319 | 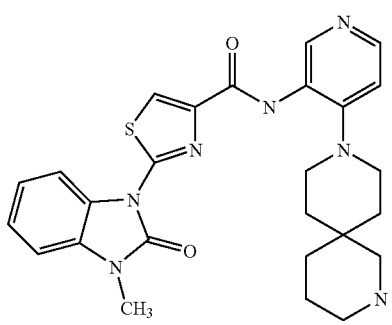 |
| 320 | 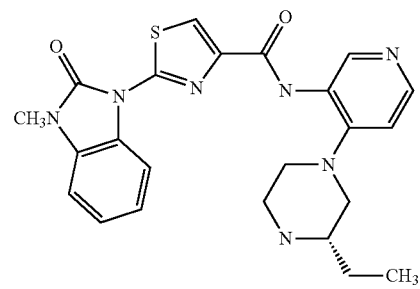 |

| Compound No. | Structure |
|---|---|
| 321 | 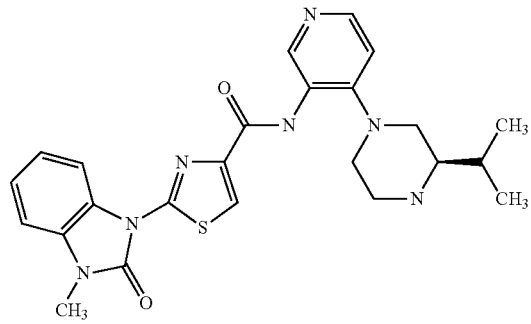 |
| 322 | 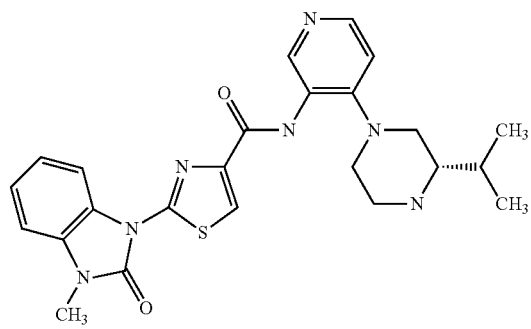 |
| 323 | 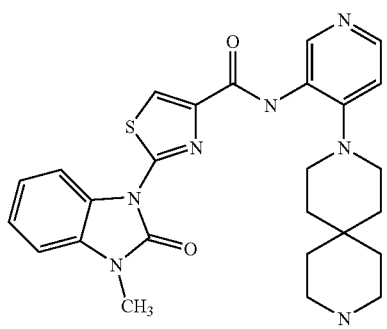 |
| 324 | 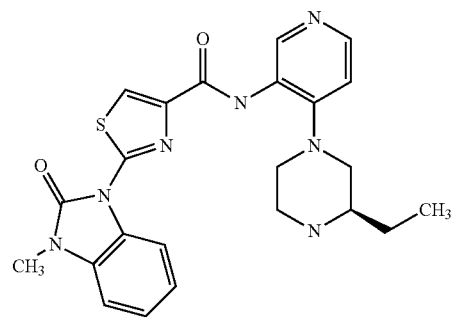 |

-continued
| Compound No. | Structure |
|---|---|
| 325 | 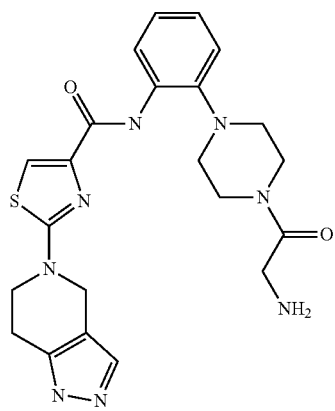 |
| 326 | 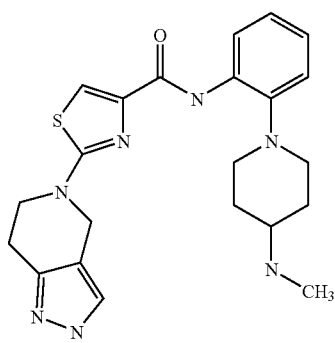 |
| 327 | 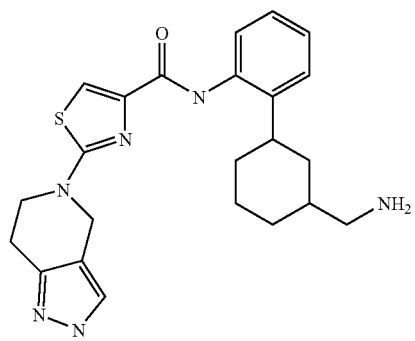 |
| 328 | 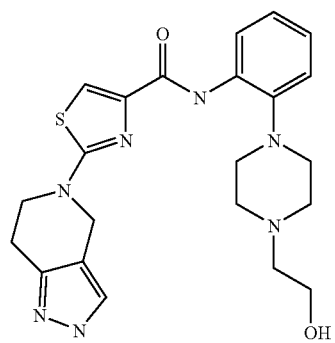 |

| Compound No. | Structure |
|---|---|
| 329 | 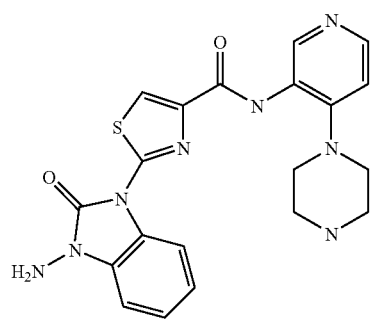 |
| 330 | 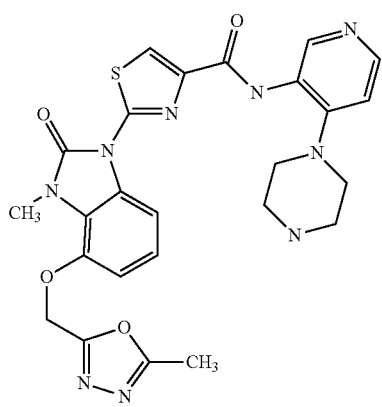 |
| 331 | 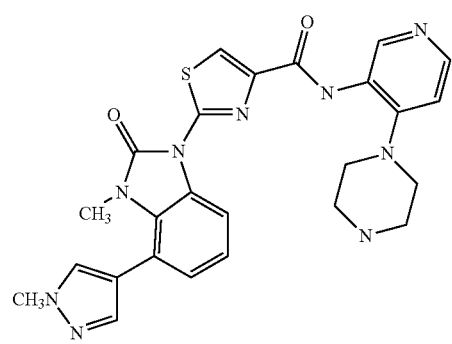 |
| 332 | 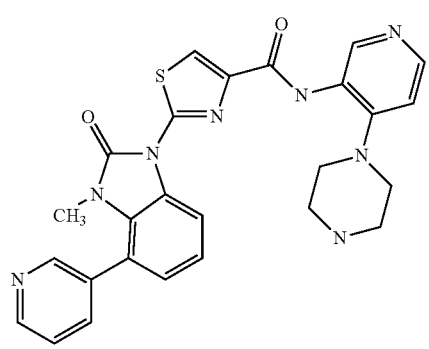 |

-continued
| Compound No. | Structure |
|---|---|
| 333 | 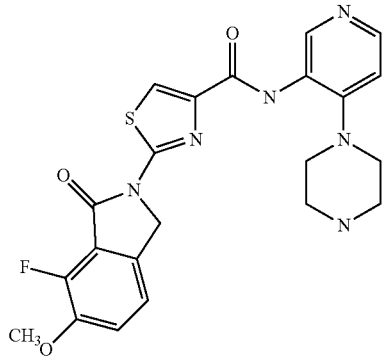 |
| 334 | 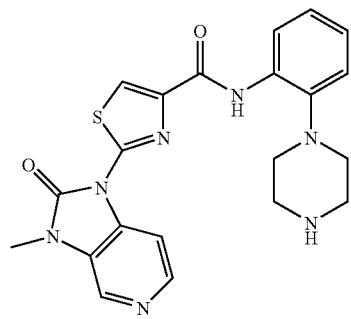 |
| 335 | 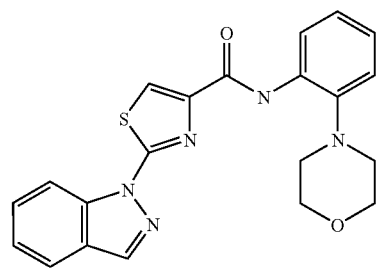 |
| 336 | 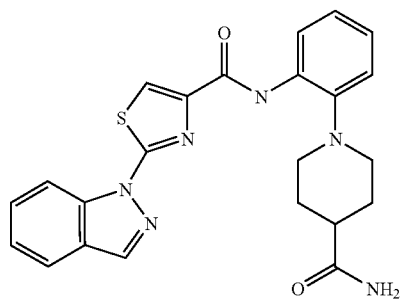 |
| 337 | 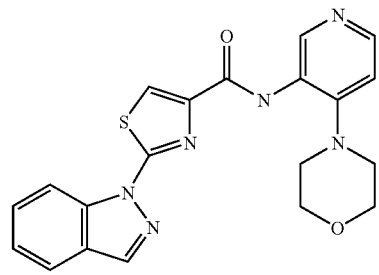 |

| Compound No. | Structure |
|---|---|
| 338 | 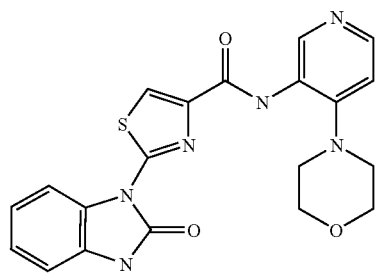 |
| 339 | 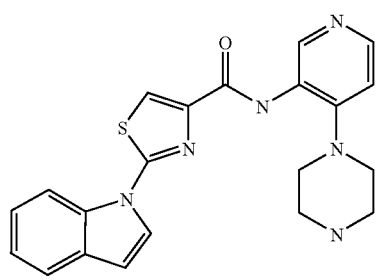 |
| 340 | 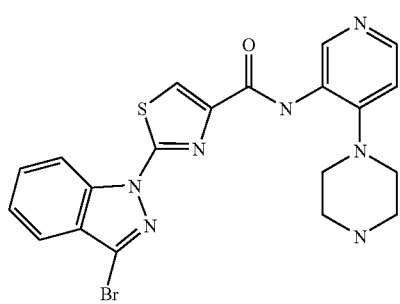 |
| 341 | 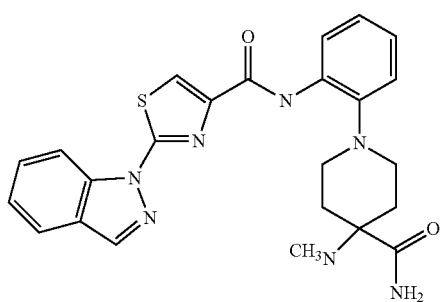 |
| 342 | 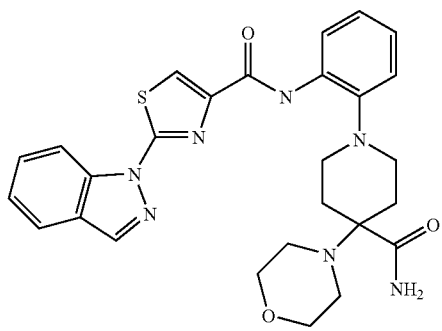 |

| Compound No. | Structure |
|---|---|
| 343 | 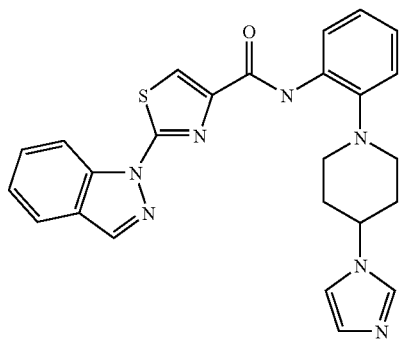 |
| 344 | 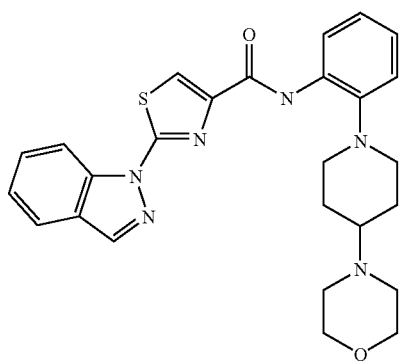 |
| 345 | 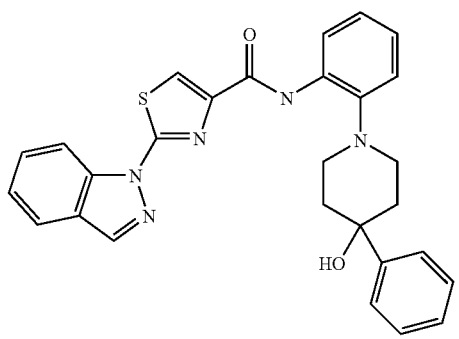 |
| 346 | 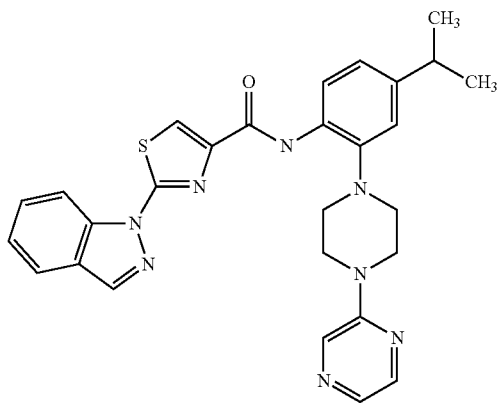 |

-continued
| Compound No. | Structure |
|---|---|
| 347 | 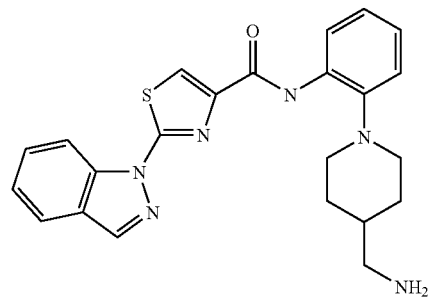 |
| 348 | 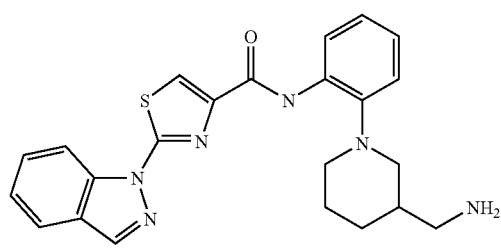 |
| 349 | 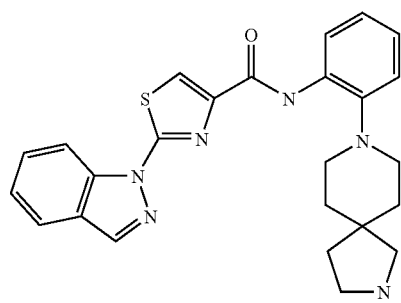 |
| 350 | 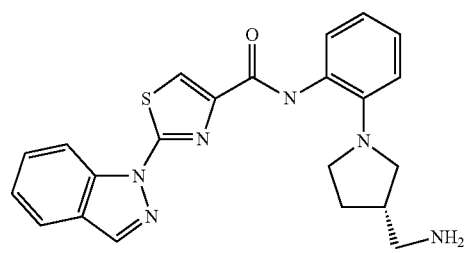 |
| 351 | 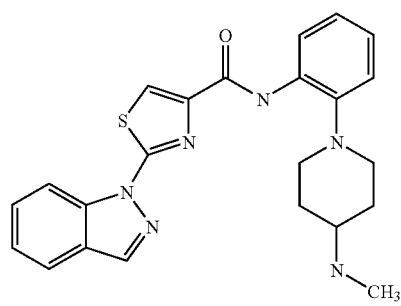 |

-continued
| Compound No. | Structure |
|---|---|
| 352 | 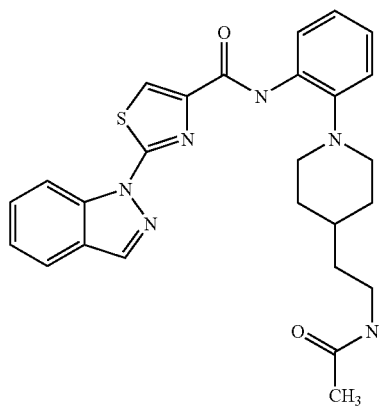 |
| 353 | 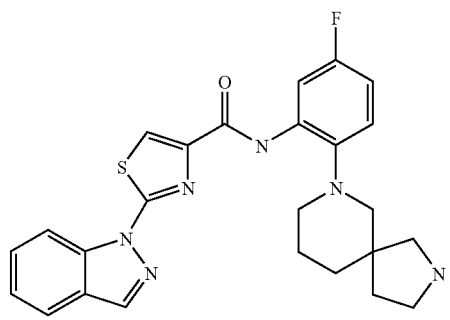 |
| 354 | 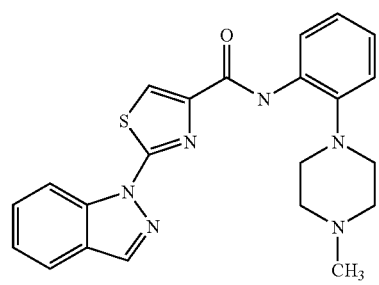 |
and pharmaceutically acceptable salts, solvates, esters, prodrugs and stereoisomers thereof.
In one embodiment, the present invention provides the following compounds of
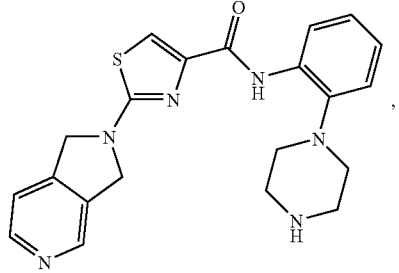
-continued
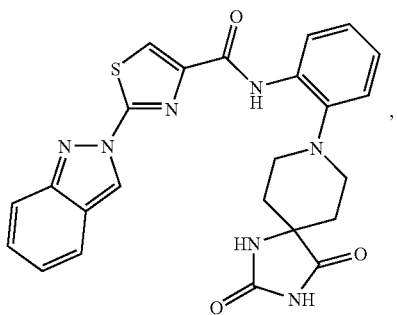

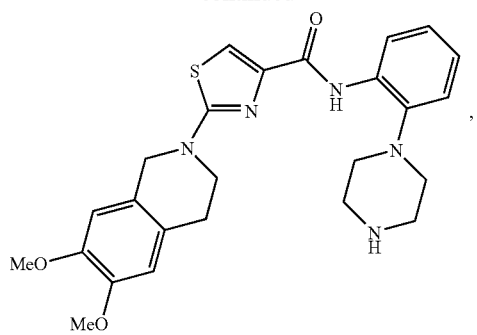,
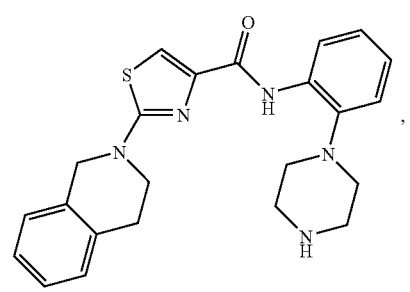,
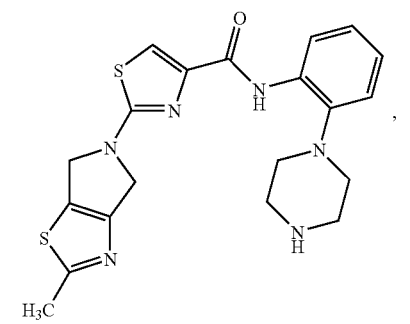,
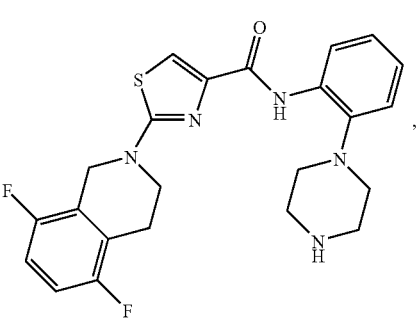,
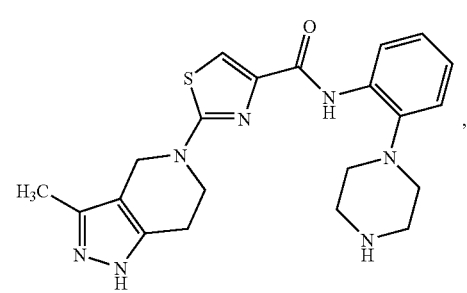,
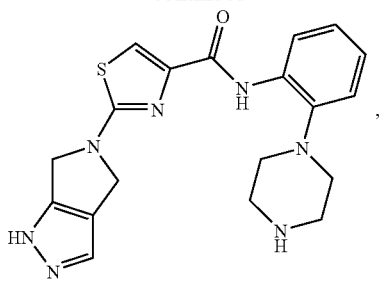,
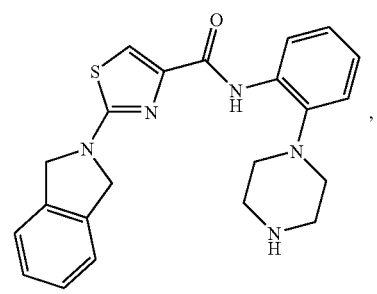,
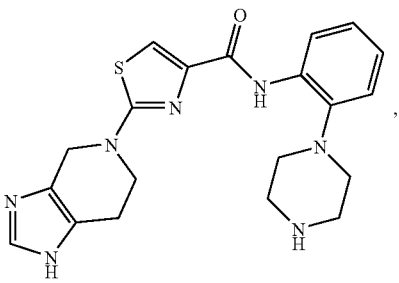,
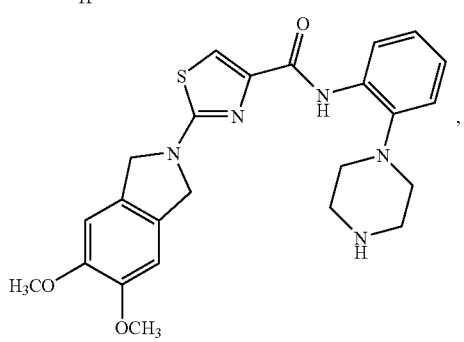,
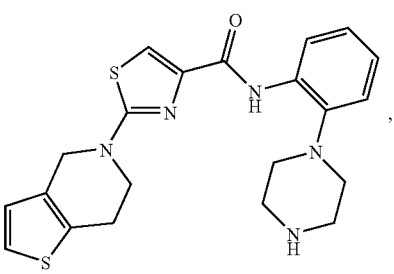,
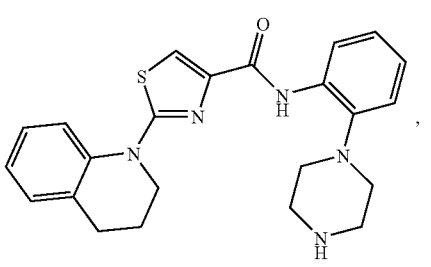, 237
-continued
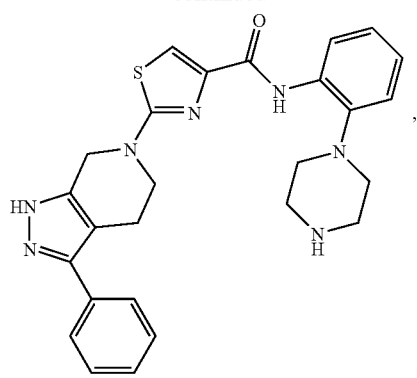
,
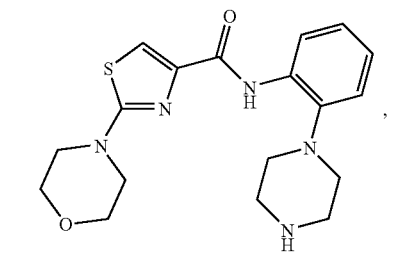
,
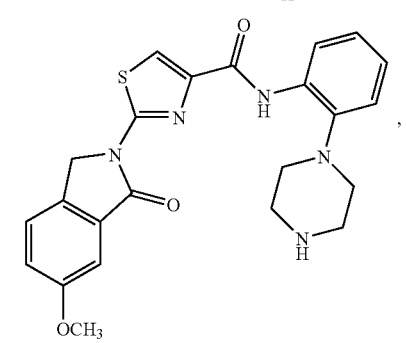
,
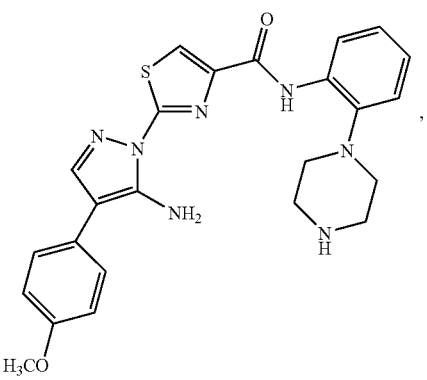
,
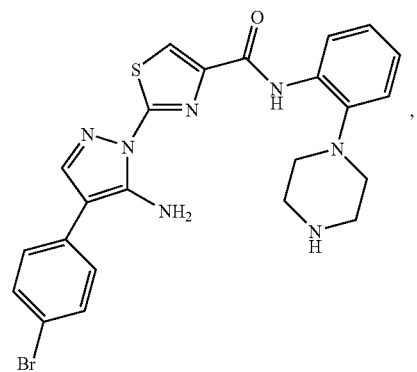
,
238
-continued
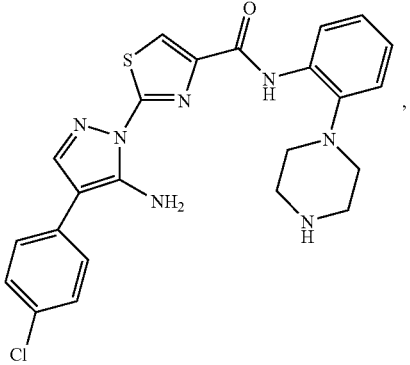
,
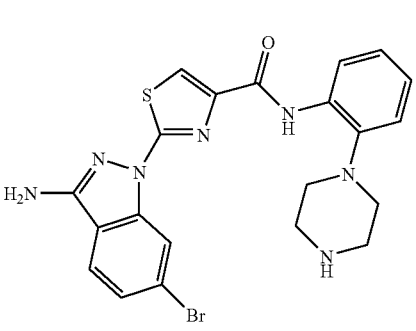
,
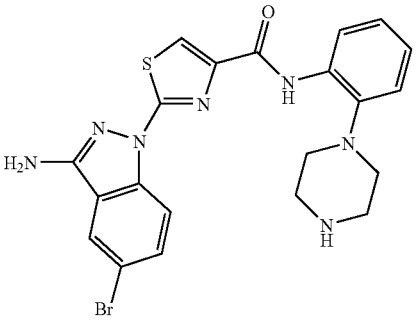
,
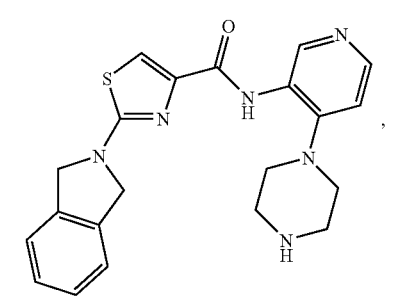
,
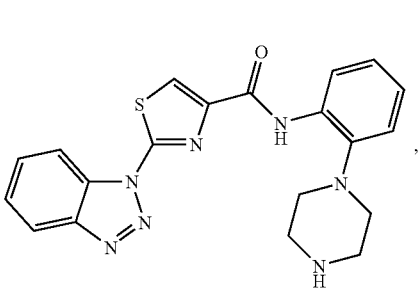
, -continued
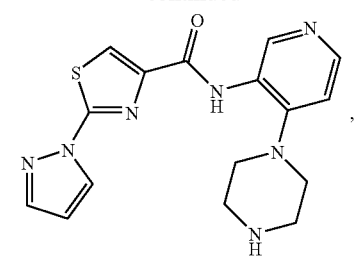,
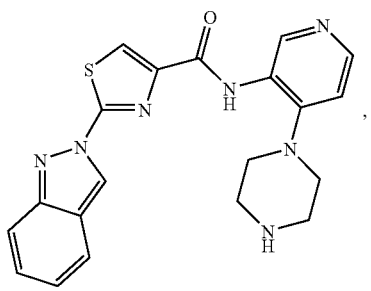,
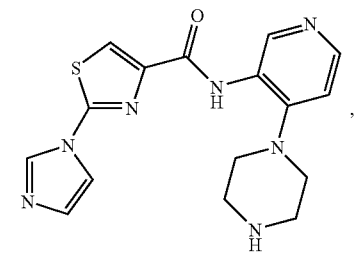,
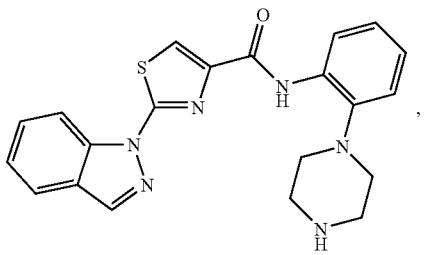,
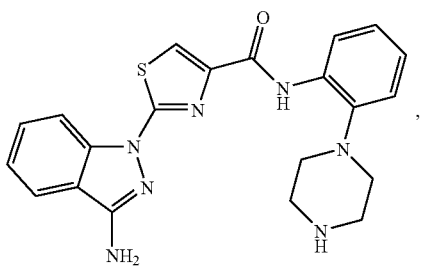,
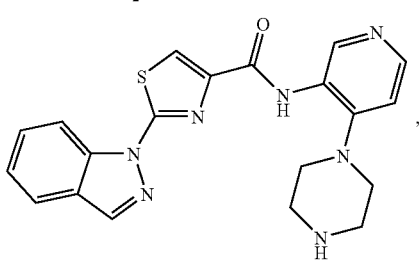,
-continued
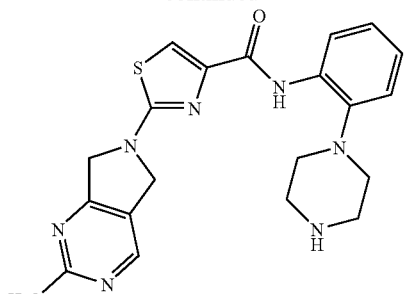,
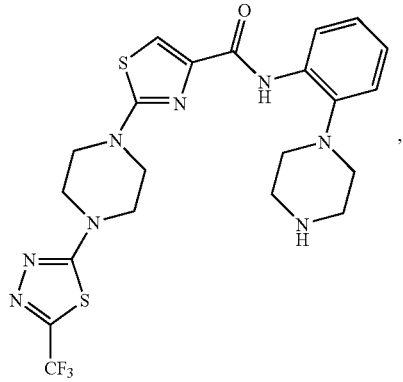,
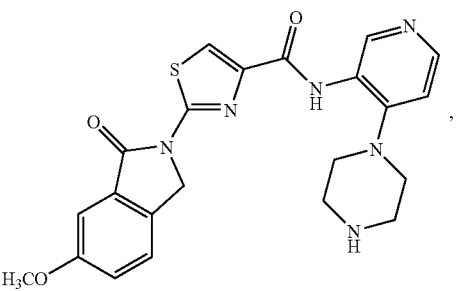,
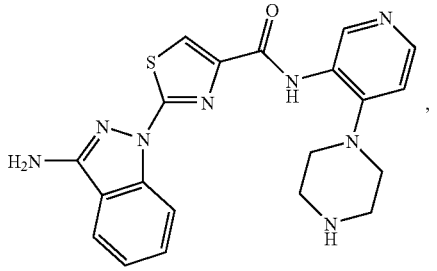,
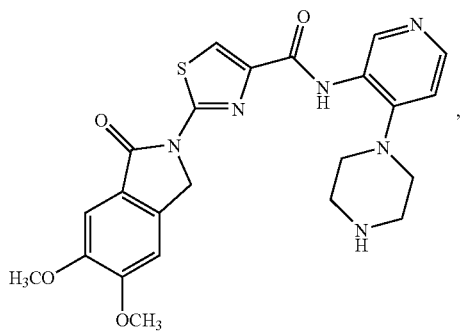, 241
-continued
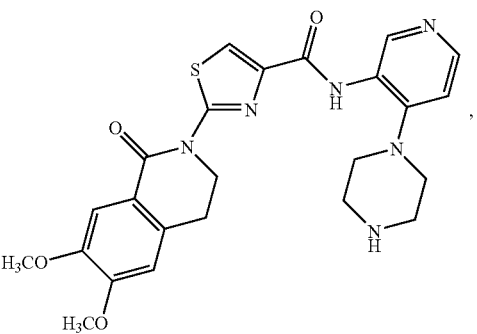
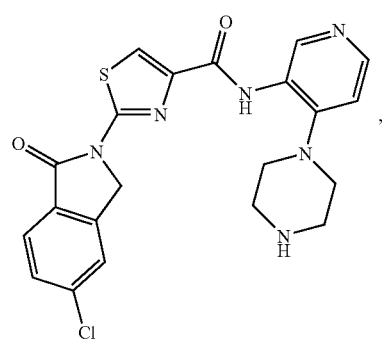
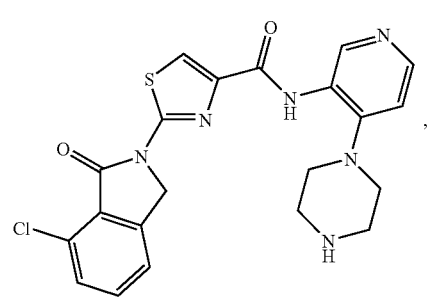
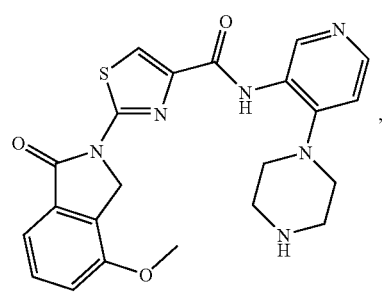
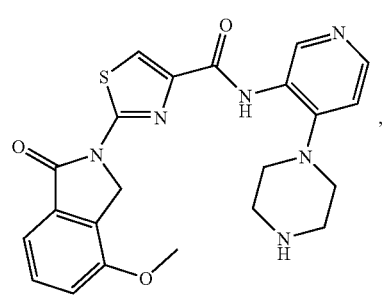
242
-continued
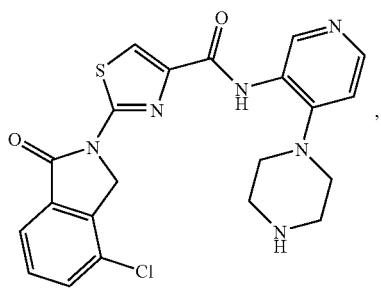
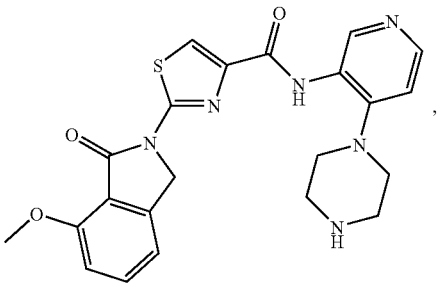
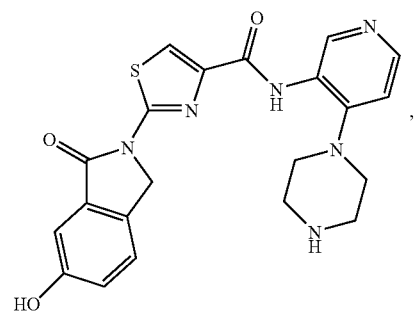
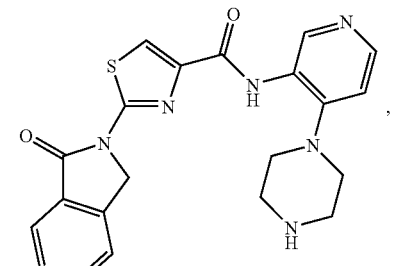
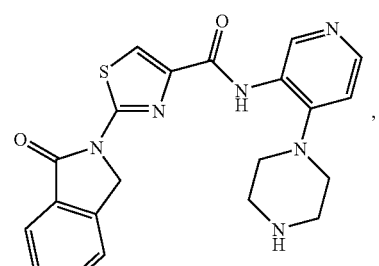

243
-continued
244
-continued
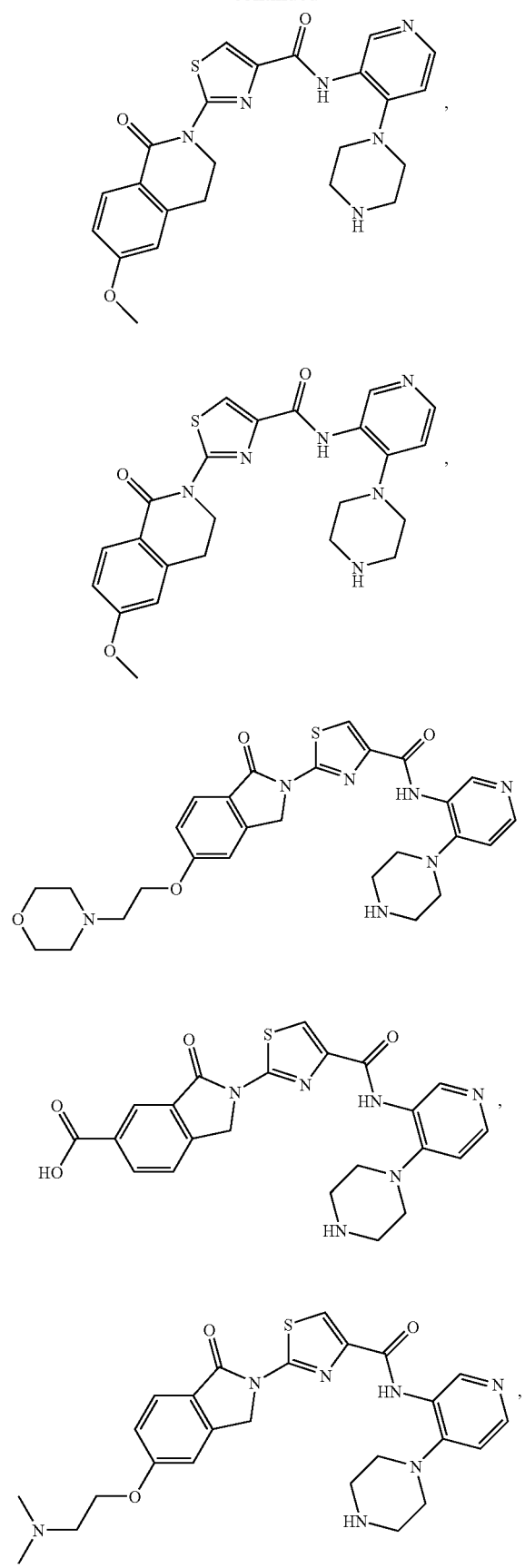
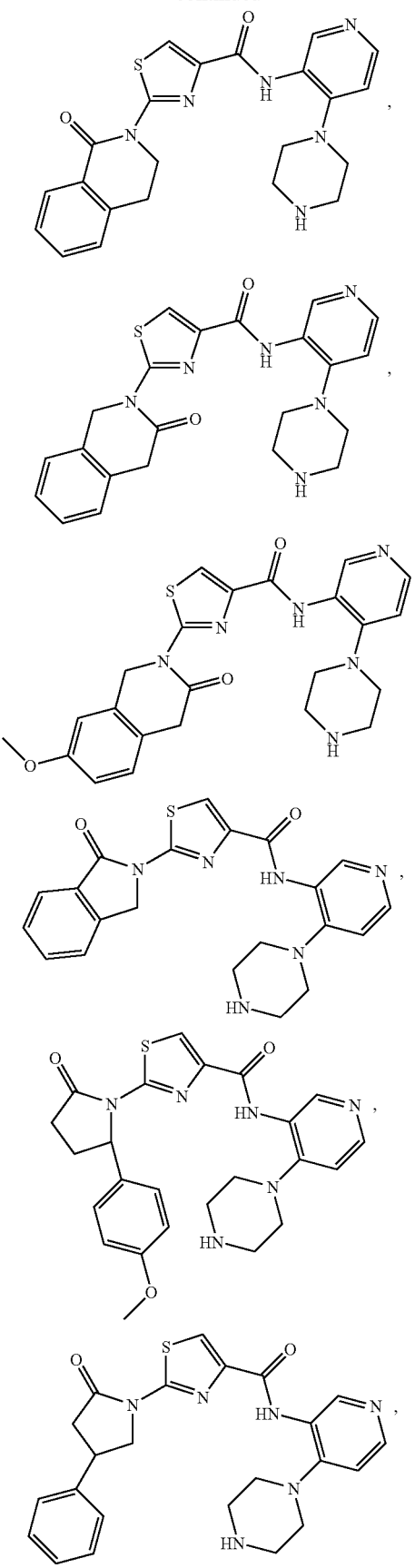

245
-continued
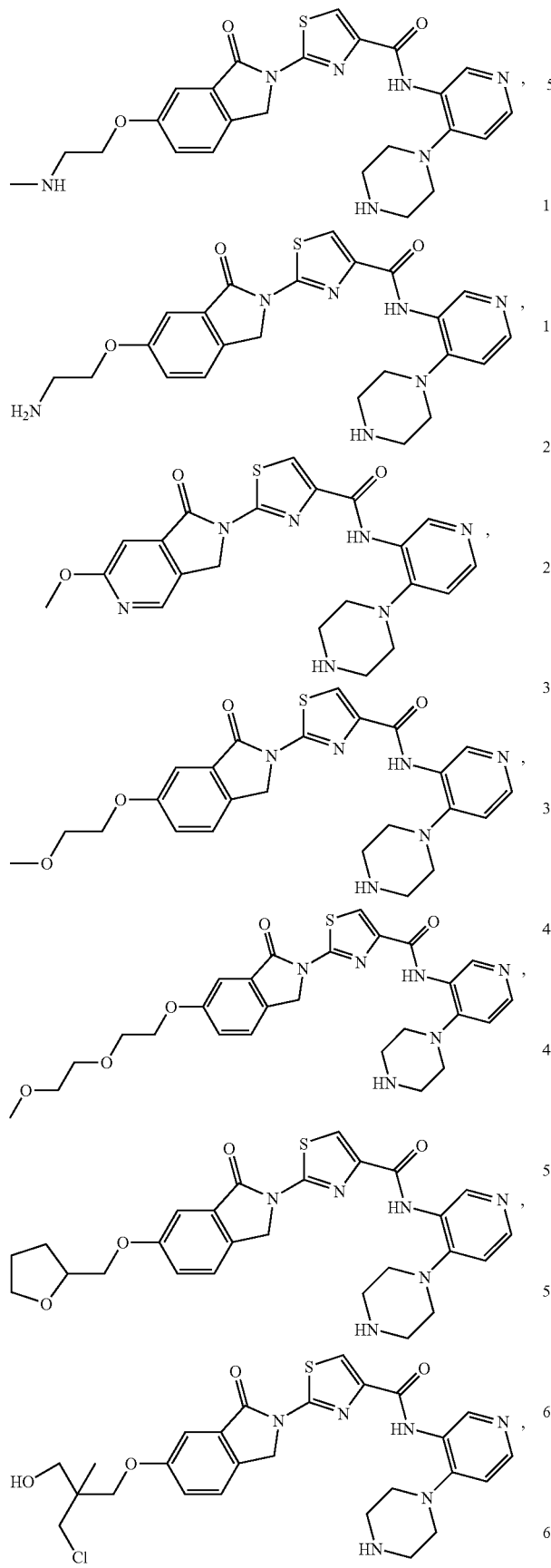
246
-continued
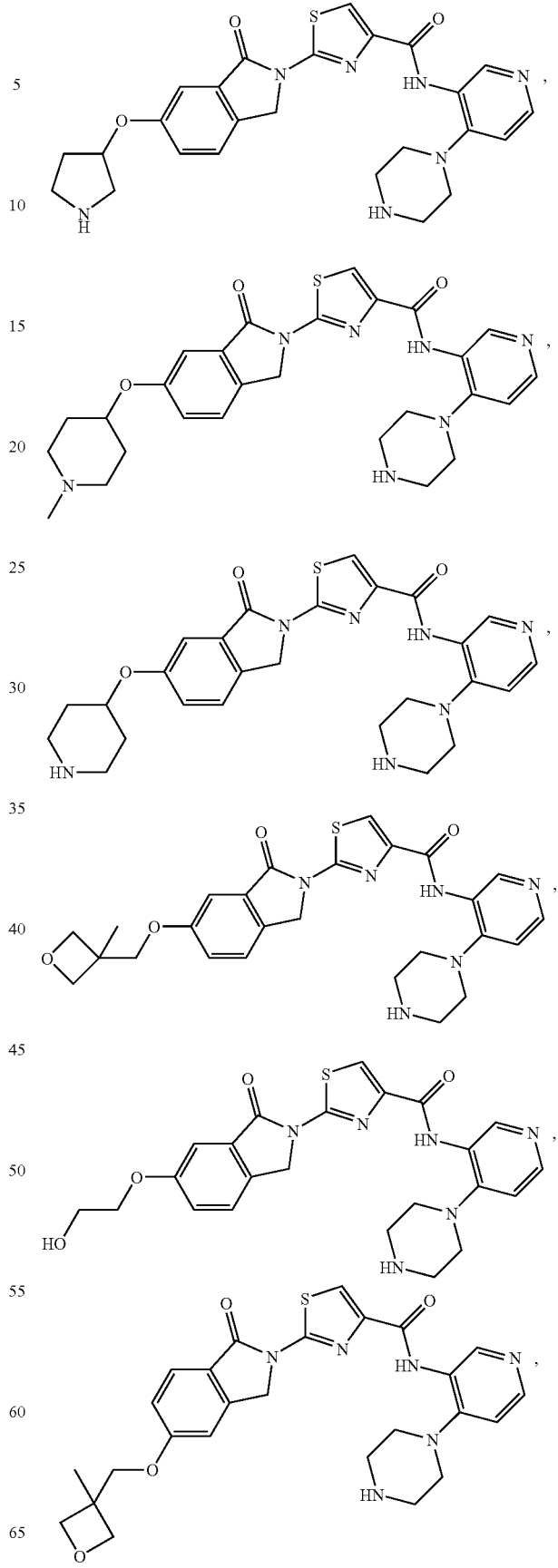

247
-continued
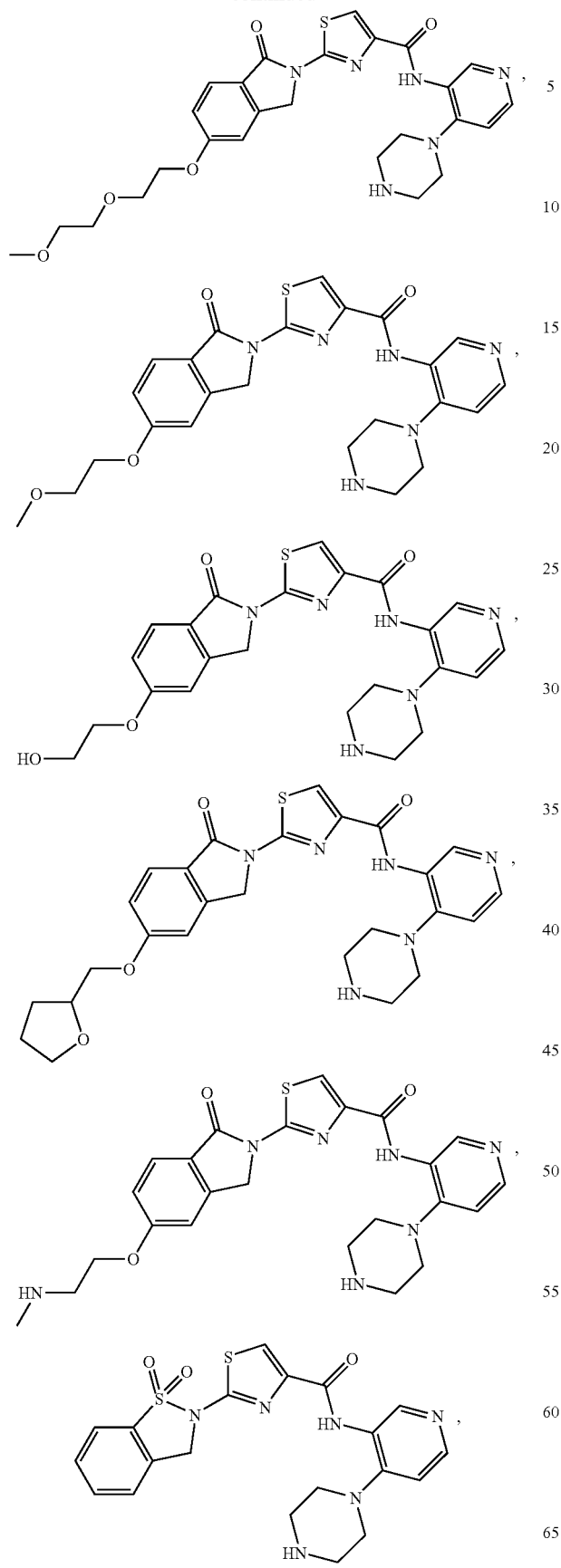
248
-continued
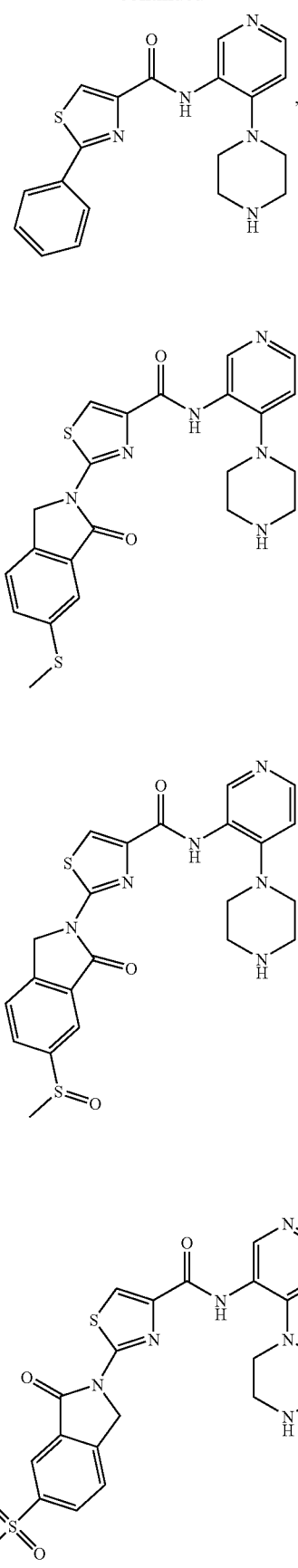

249
-continued
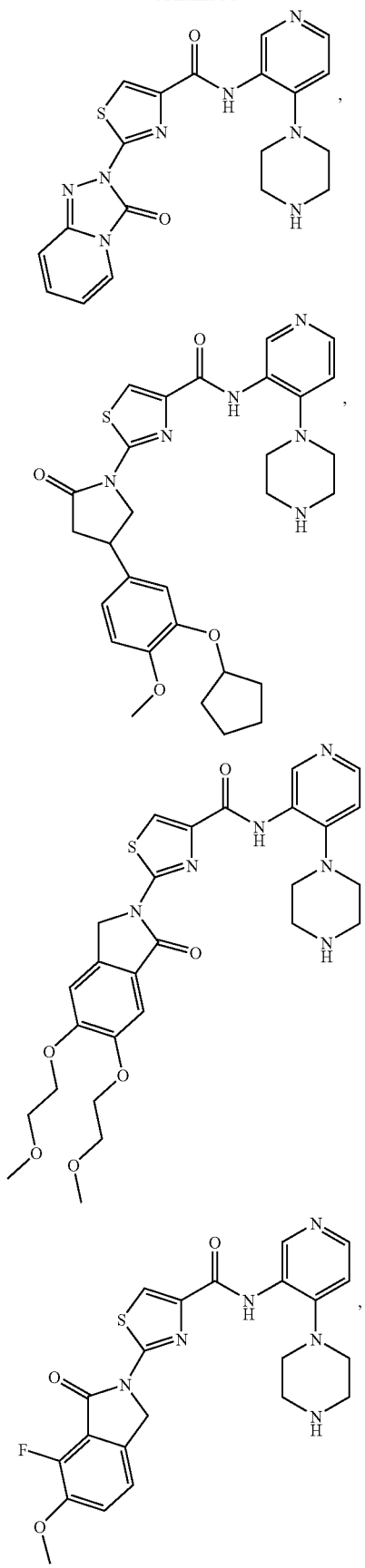
250
-continued
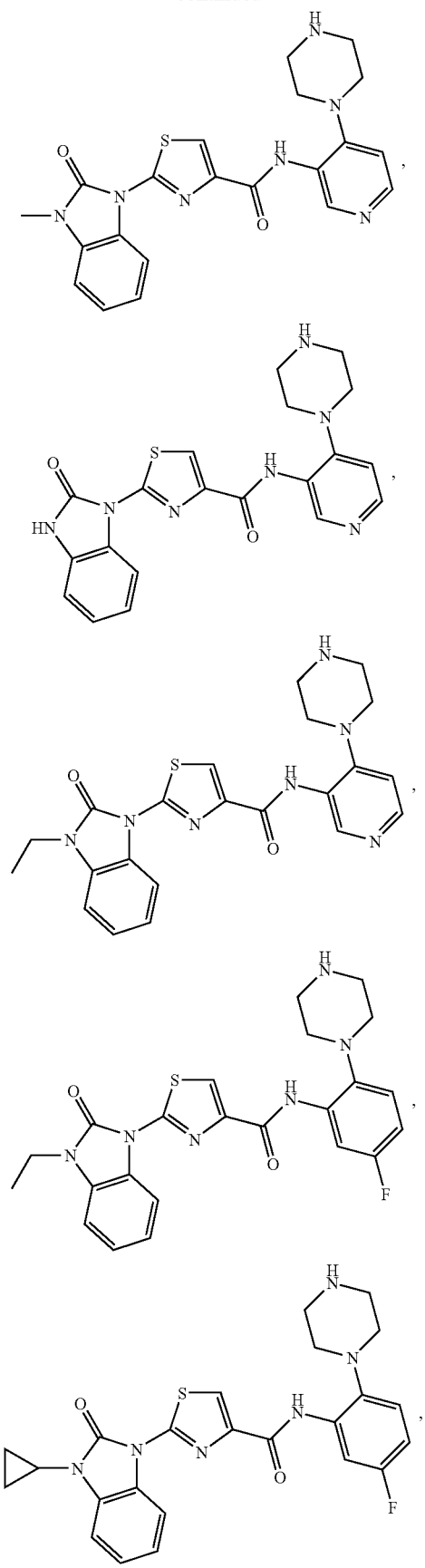

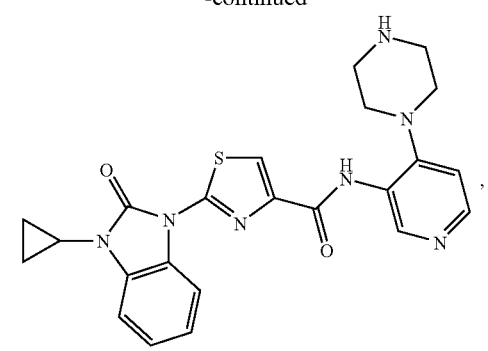
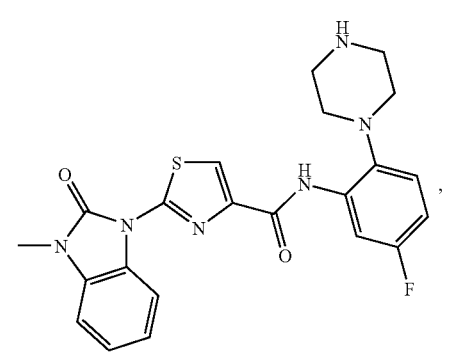
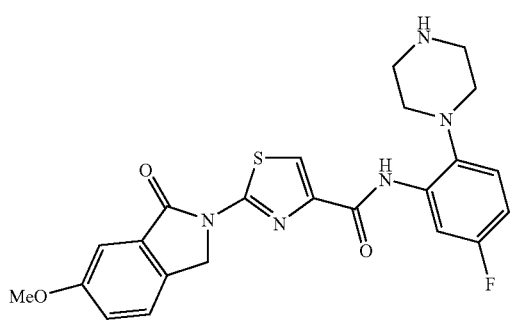
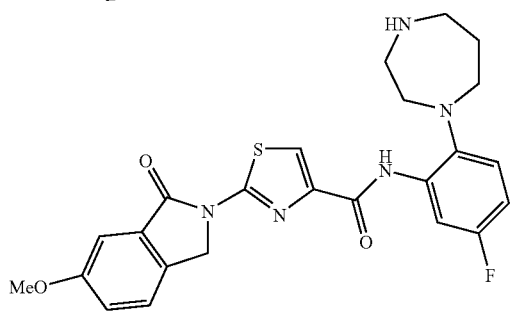
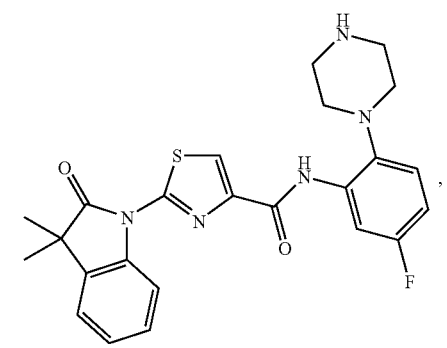
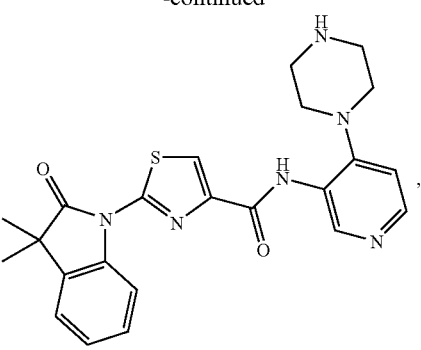
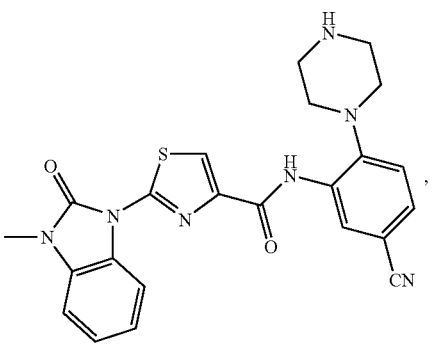
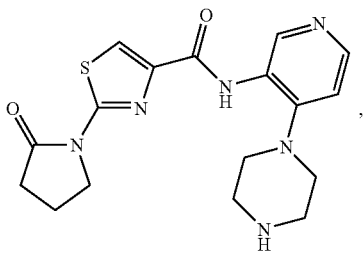
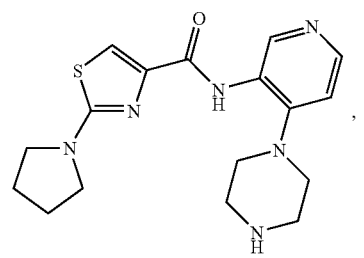
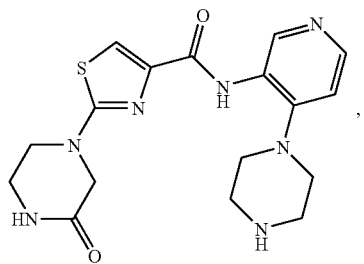
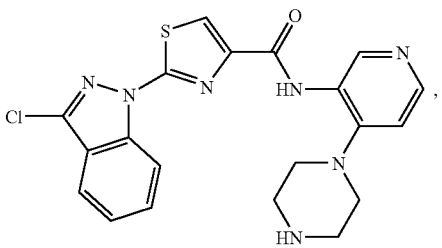

253
-continued
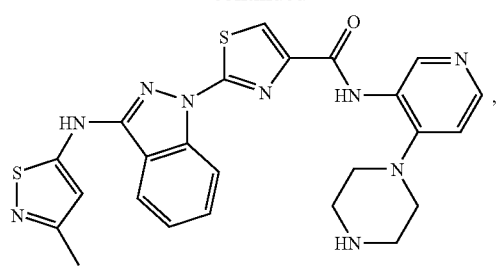
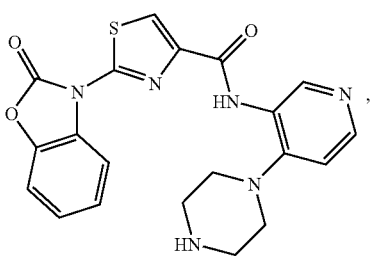
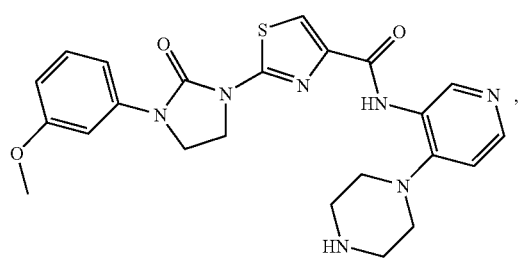
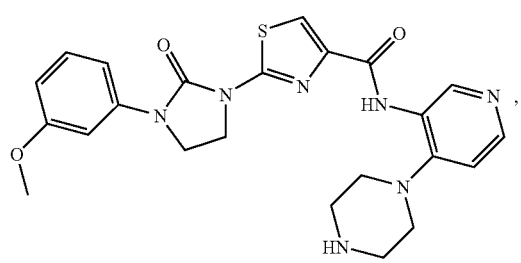
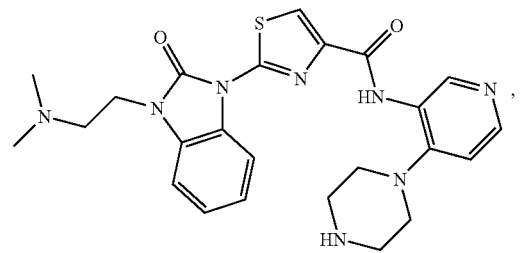
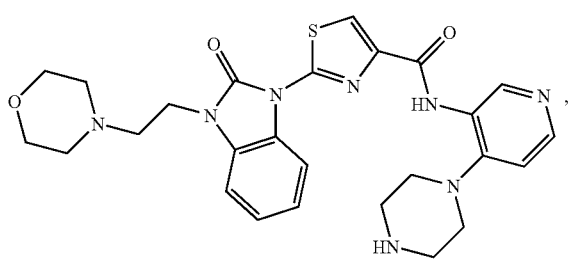
254
-continued
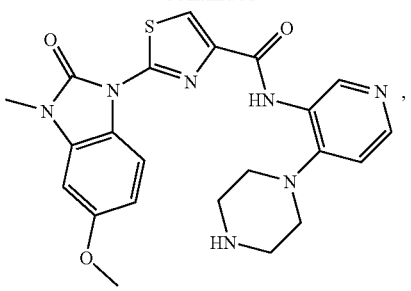
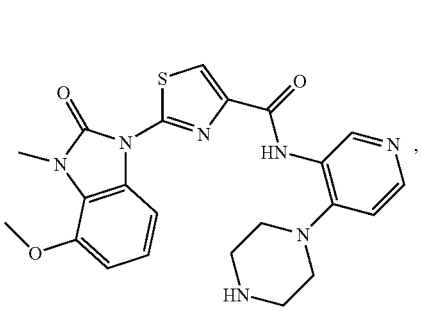
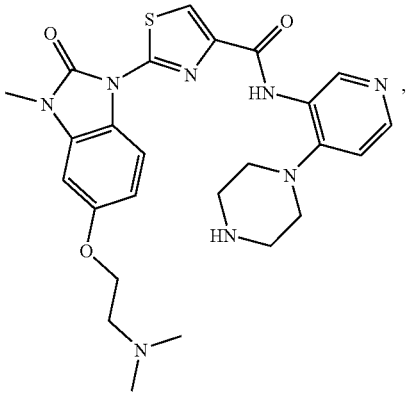
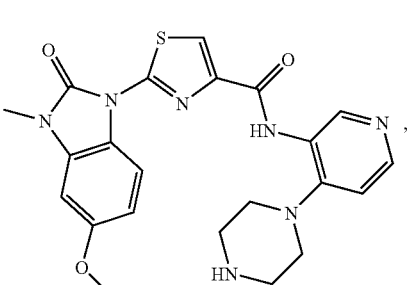

255
-continued
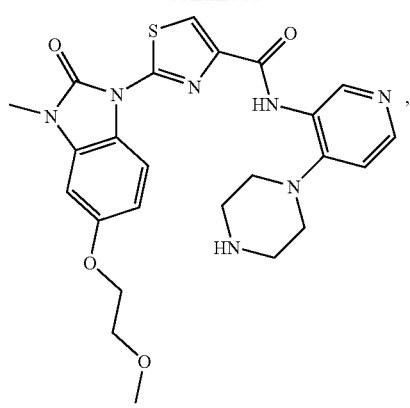
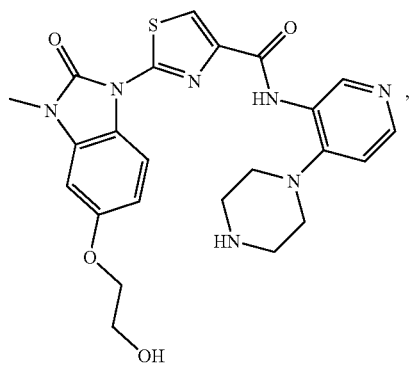
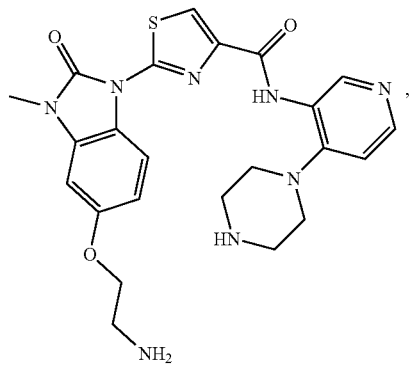
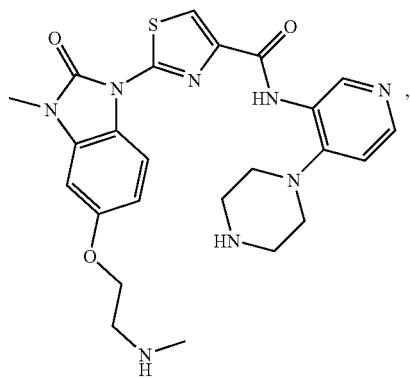
256
-continued
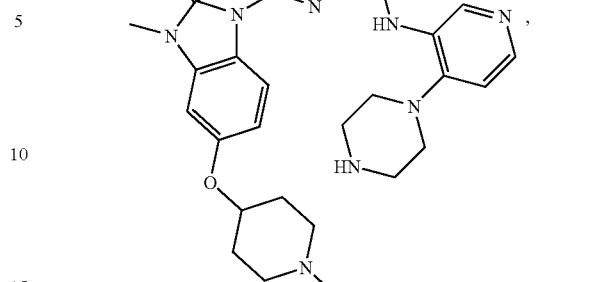
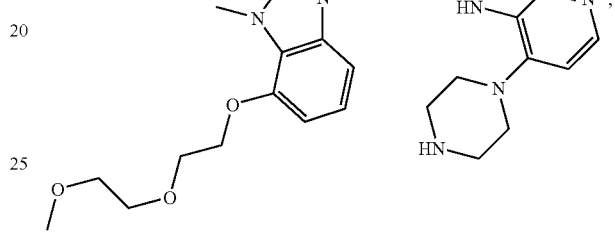
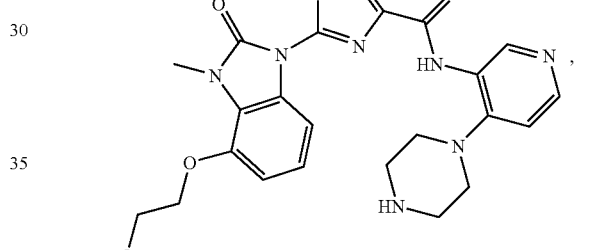
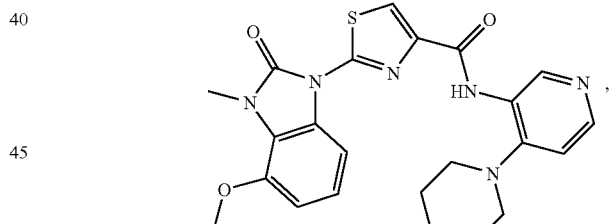
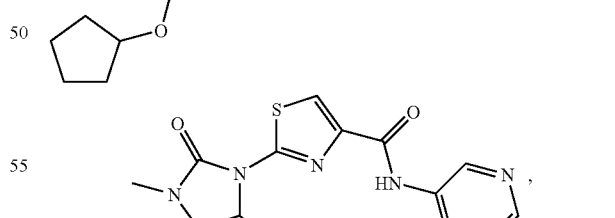
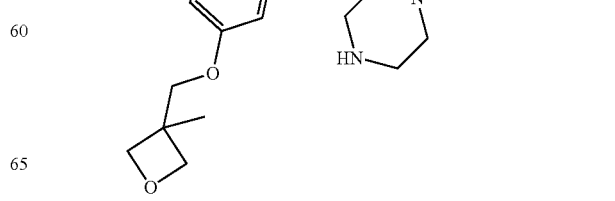

257
-continued
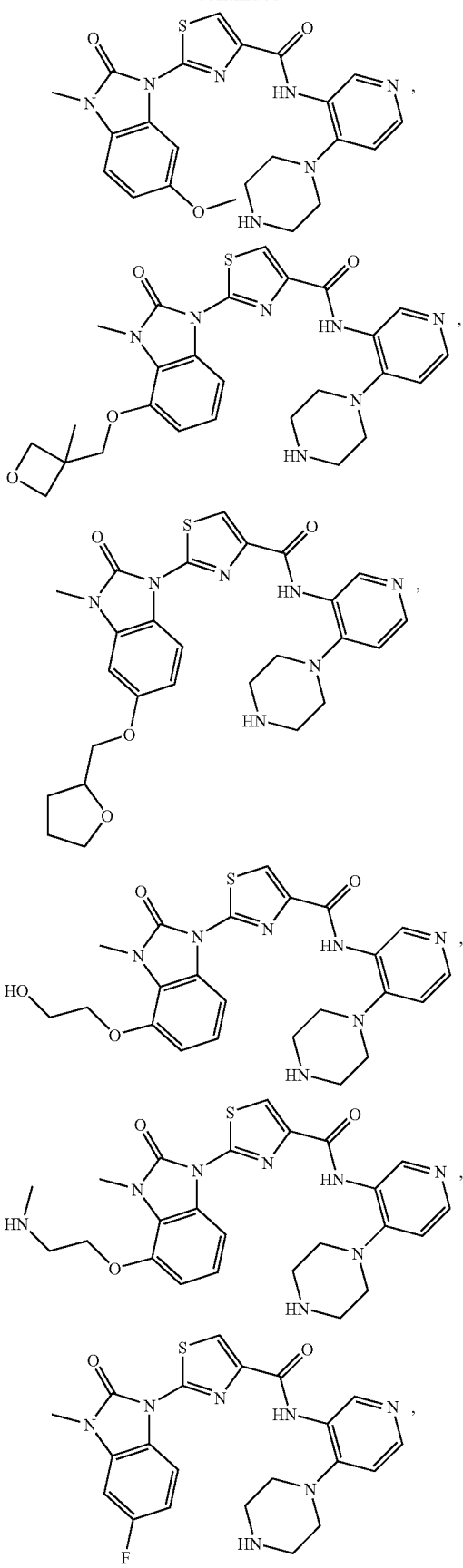
258
-continued
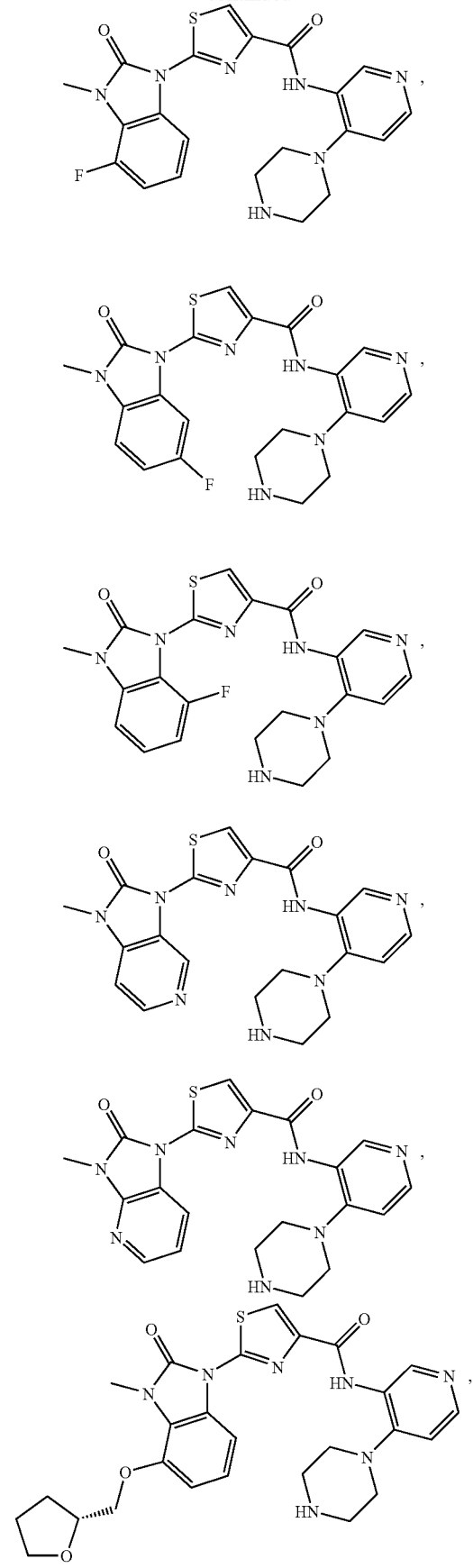

259
-continued
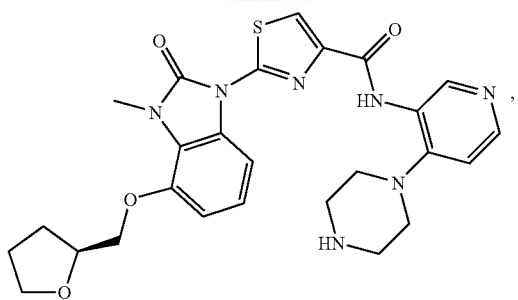
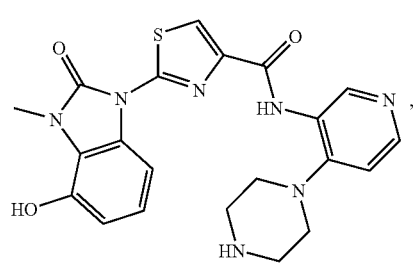
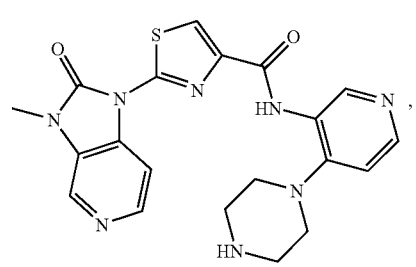
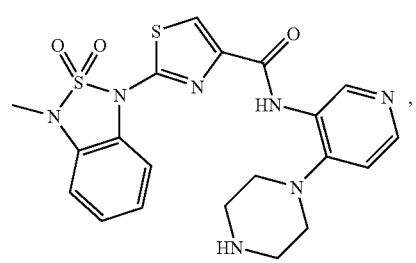
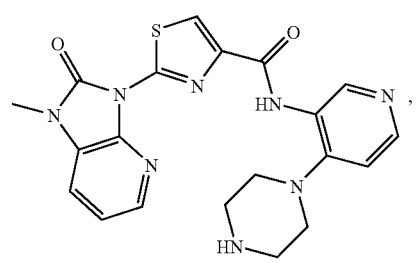
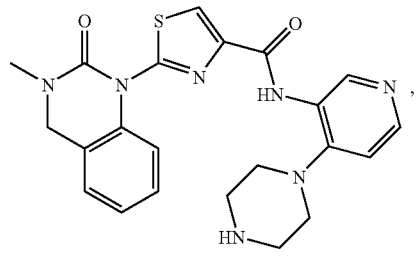
260
-continued
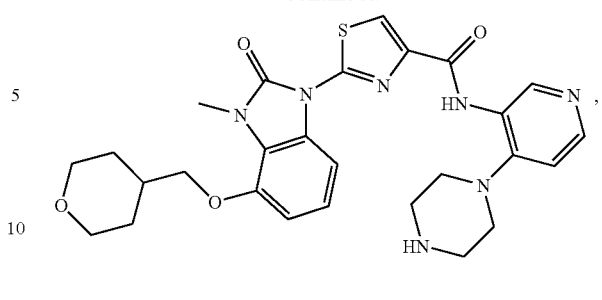
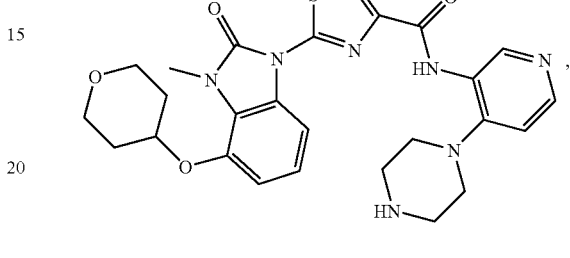
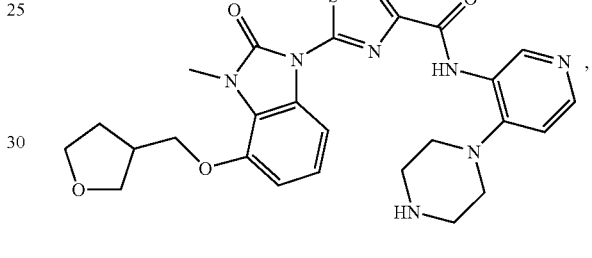
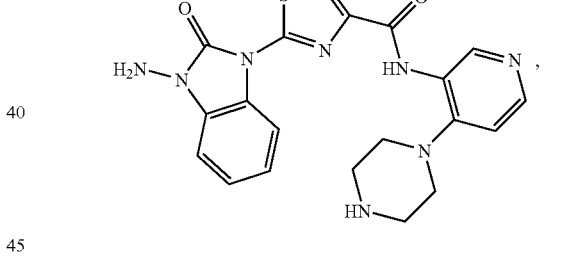
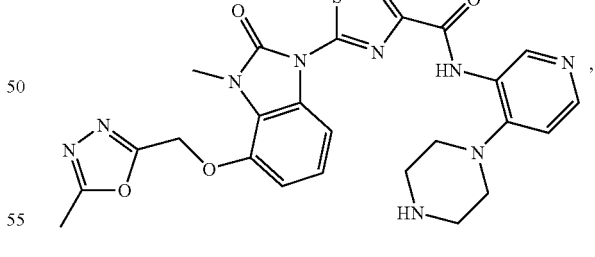
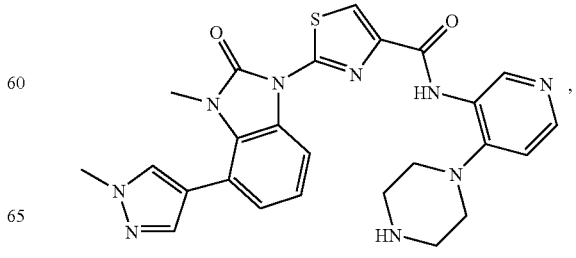

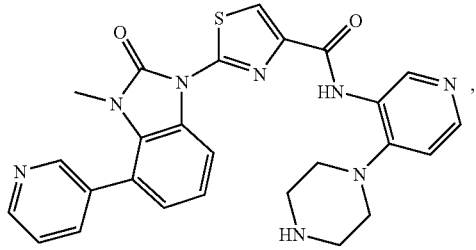
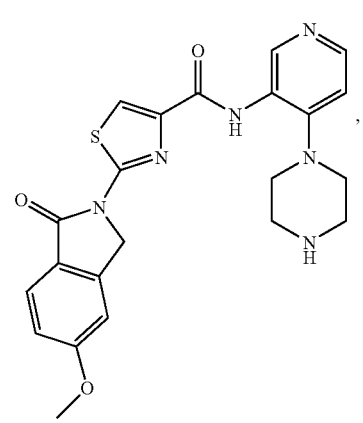
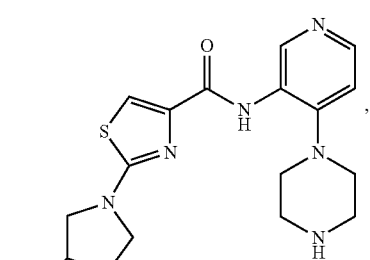
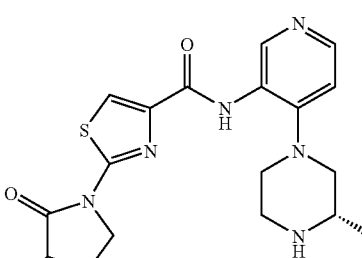
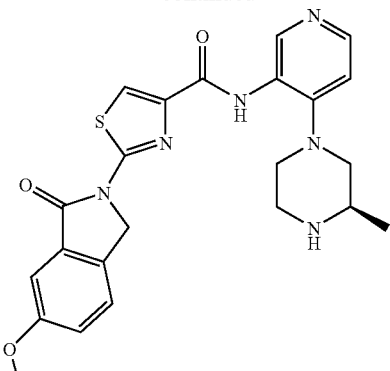
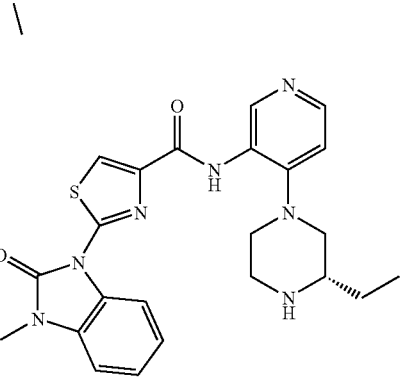
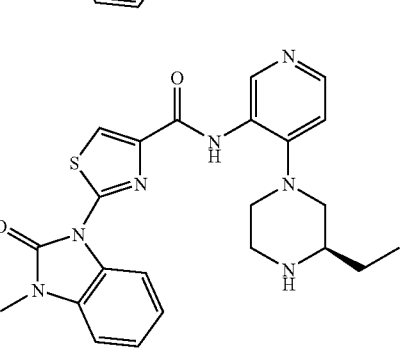
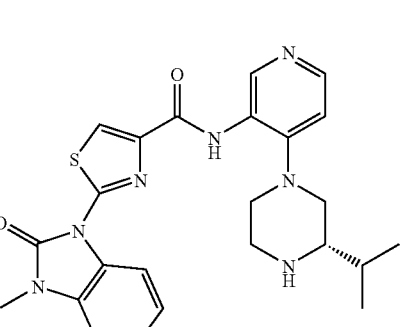
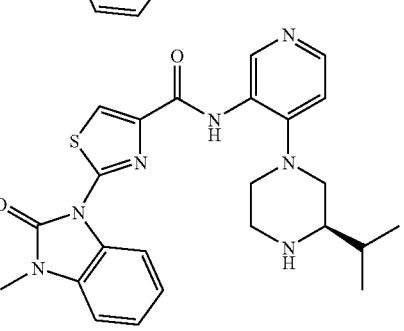

263
-continued
264
-continued
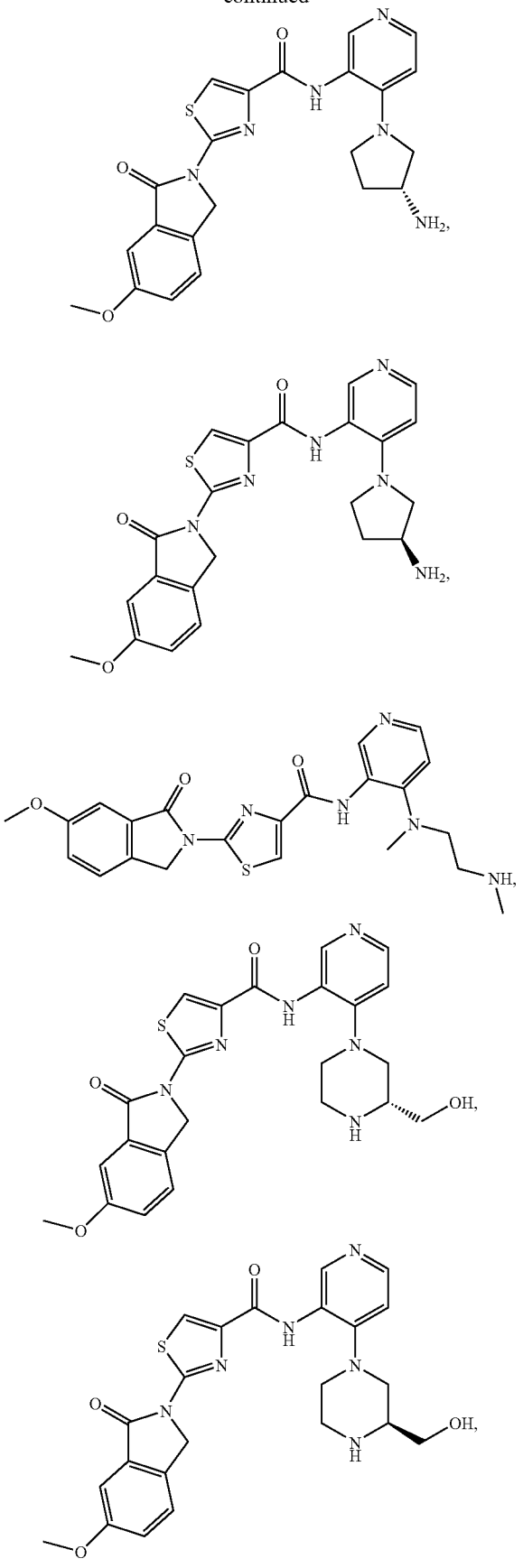
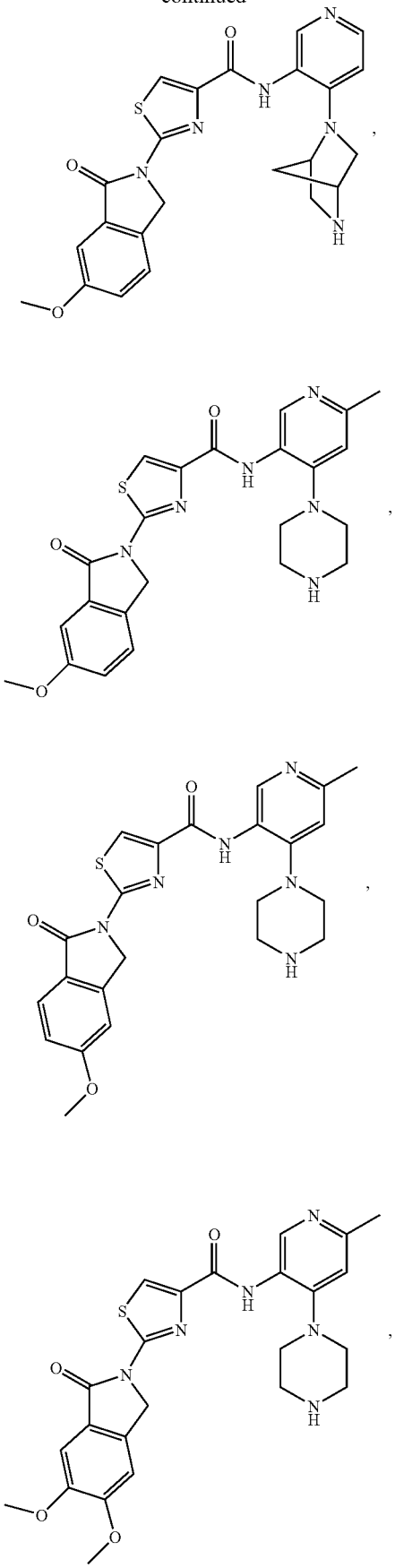

265
-continued
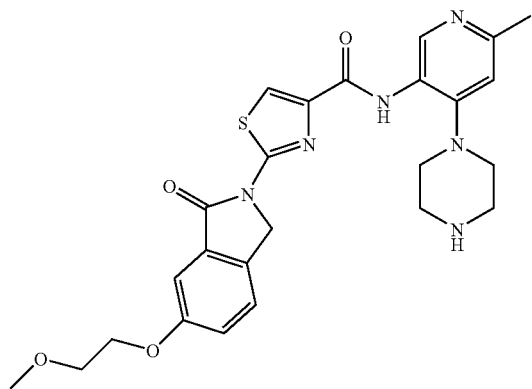
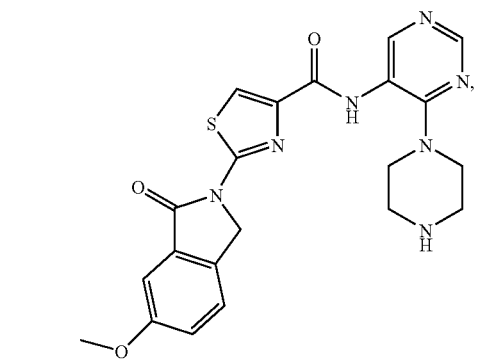
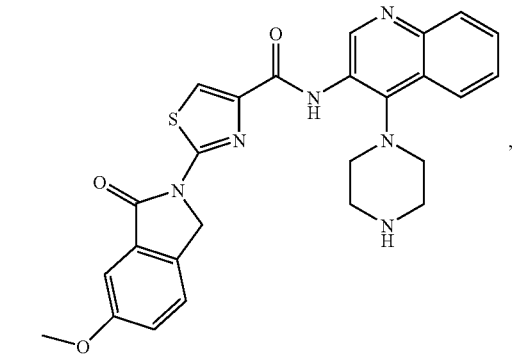
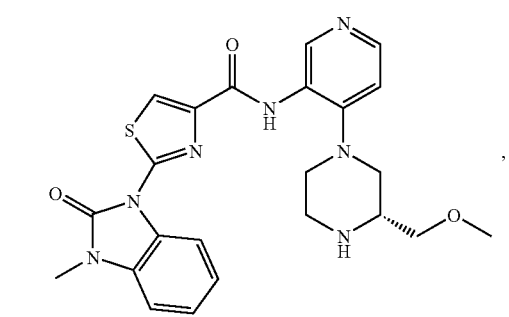
266
-continued
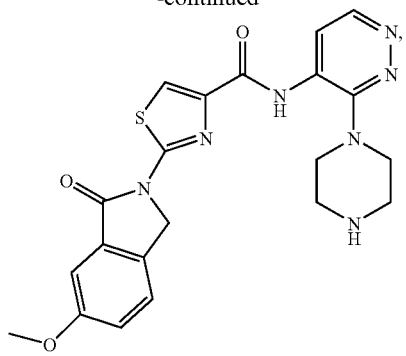
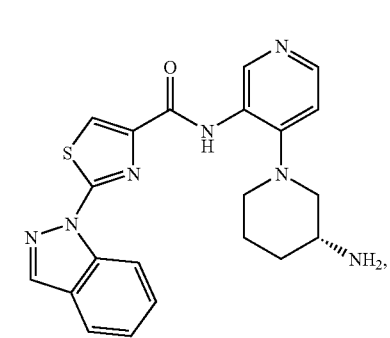
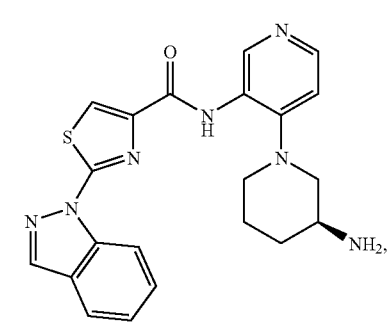
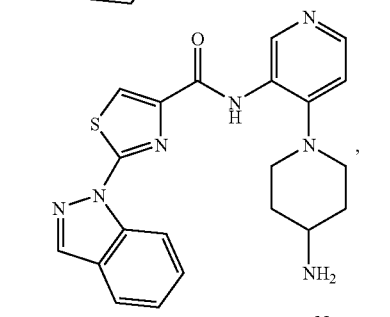
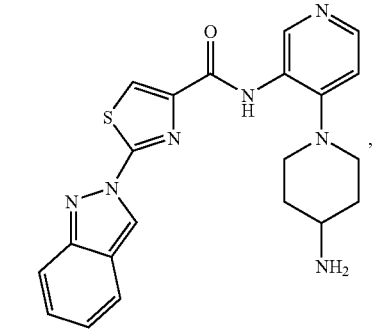

267
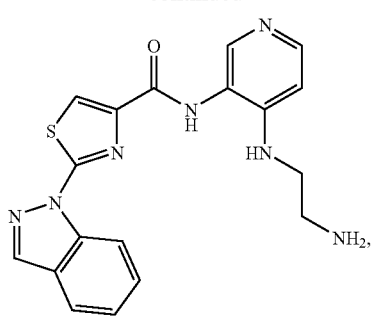
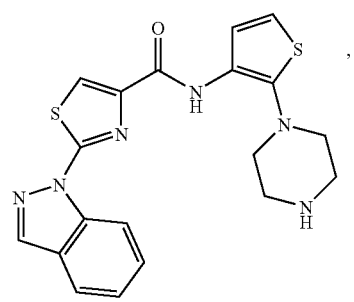
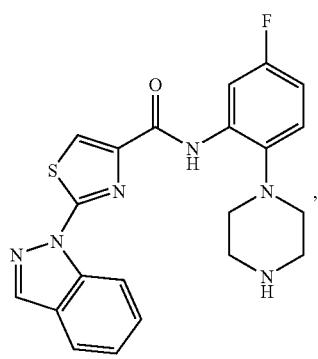
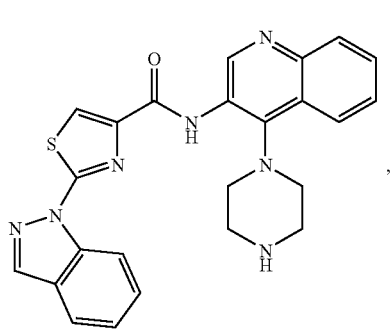
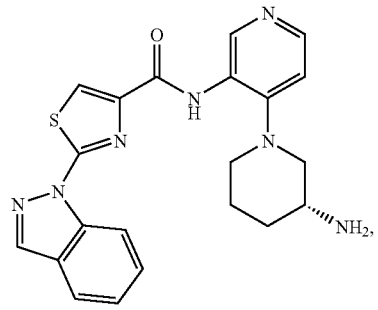
268
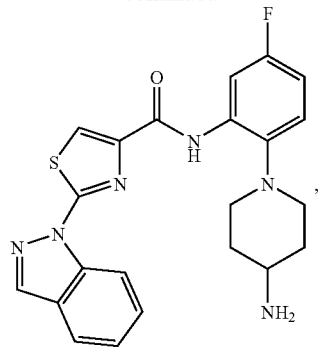
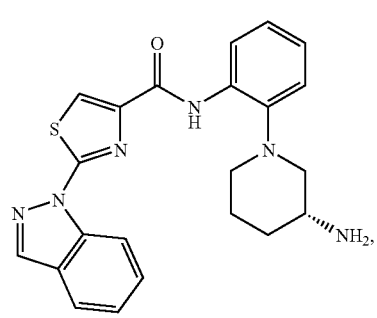
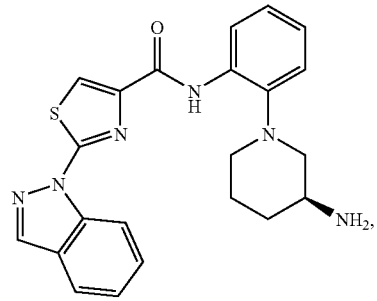
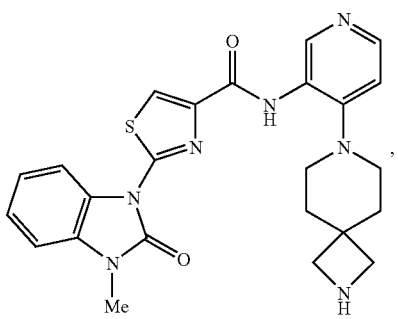
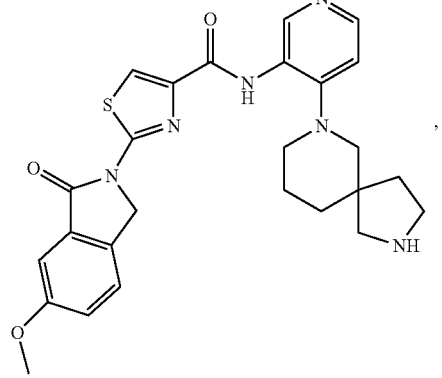

269
-continued
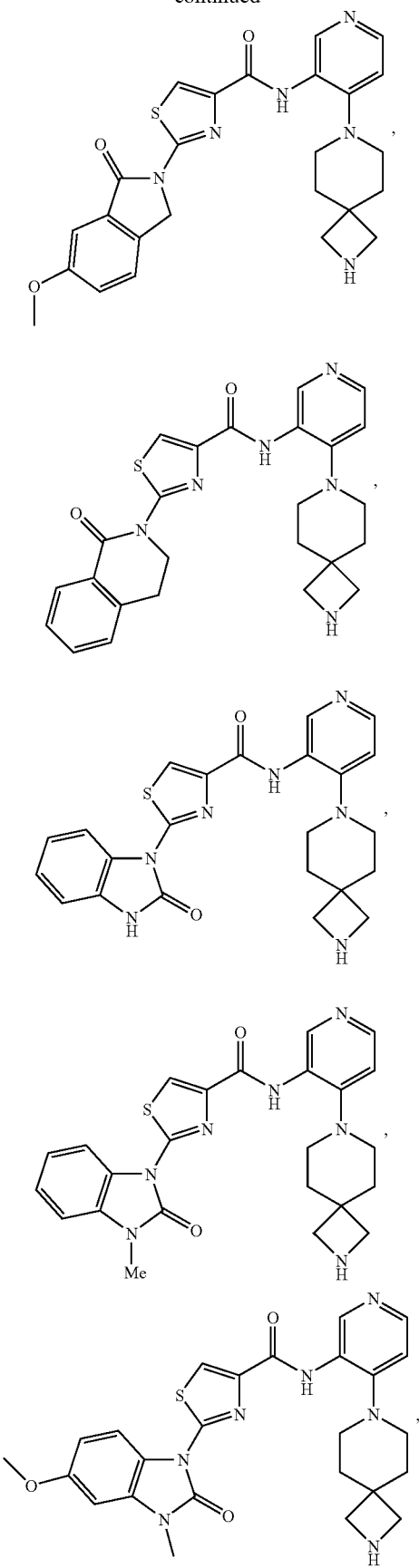
270
-continued
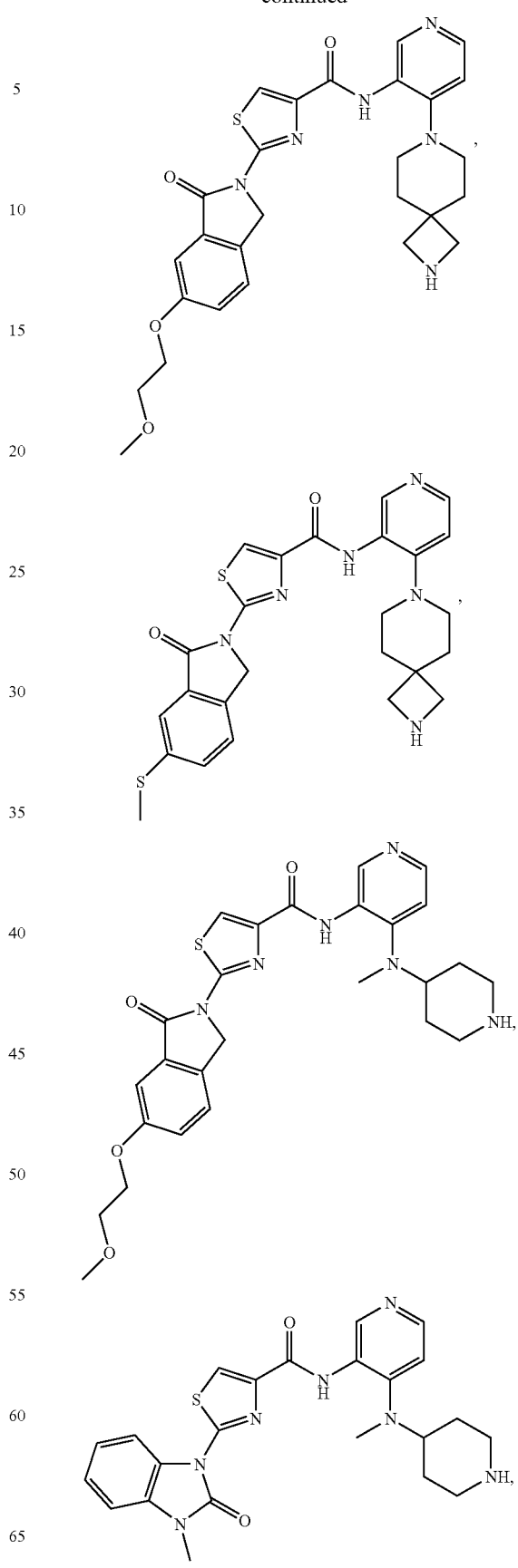

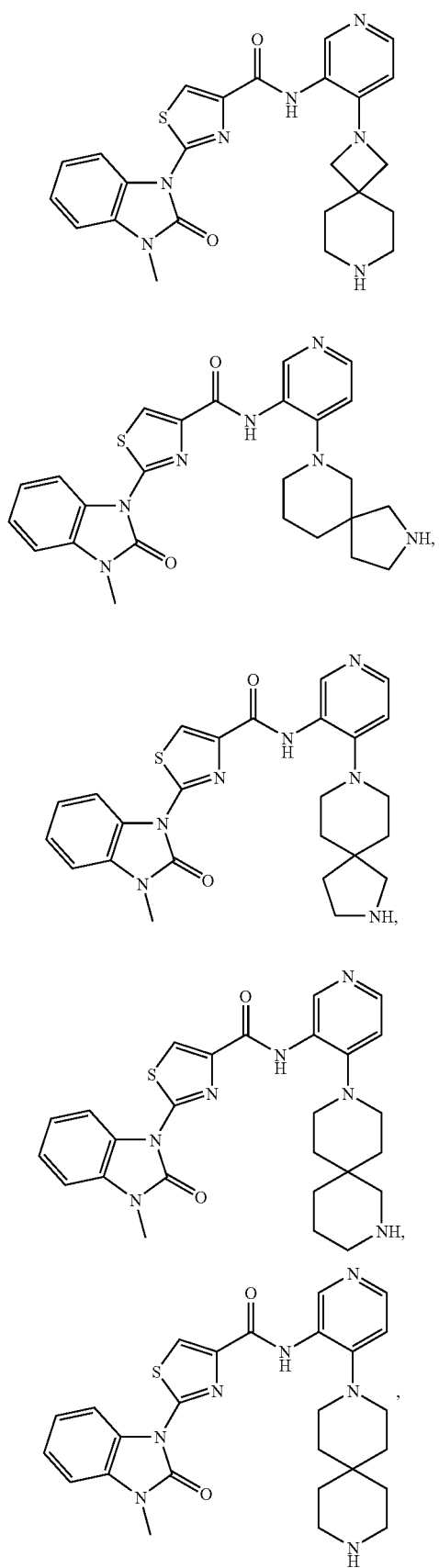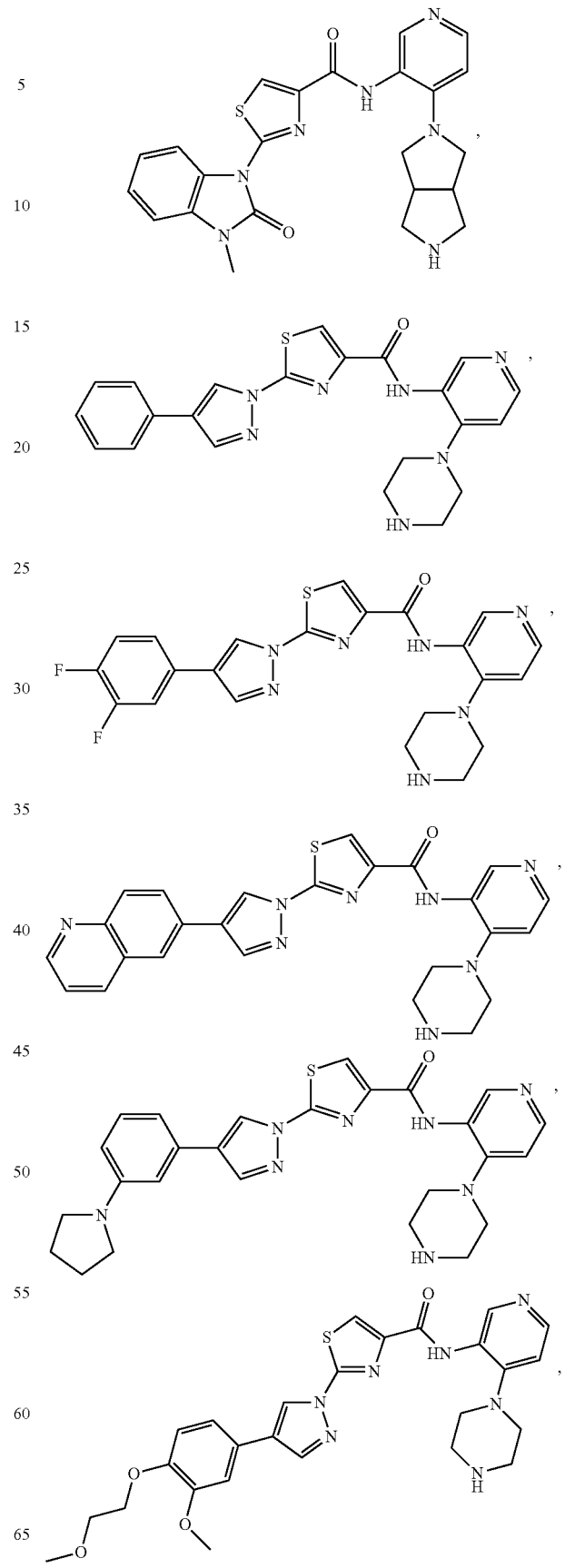

-continued
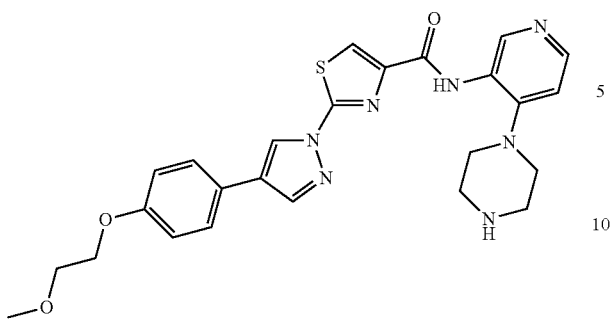
and
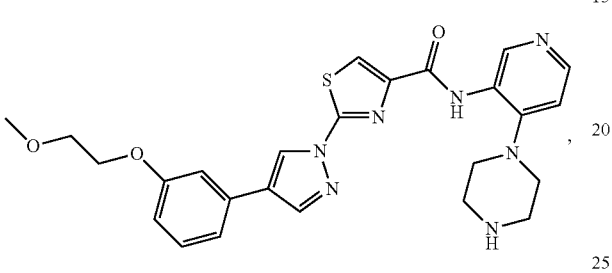
and pharmaceutically acceptable salts, solvates, esters, prodrugs and stereoisomers thereof.
In another embodiment, the present invention provides the following compounds:
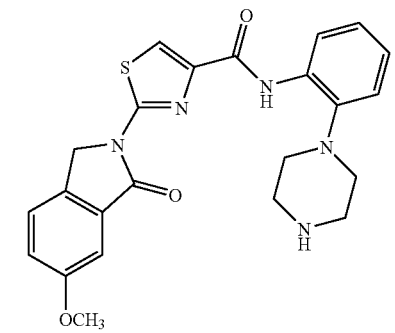
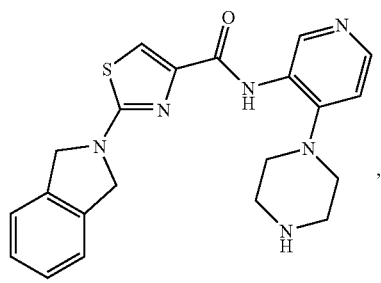
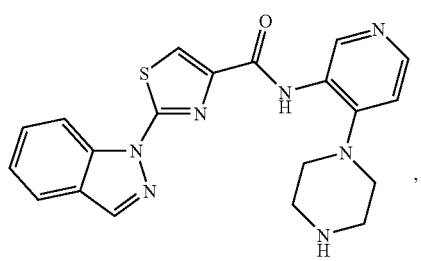
-continued
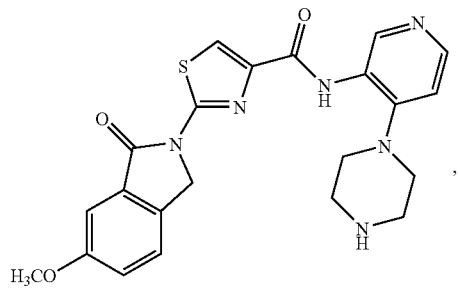
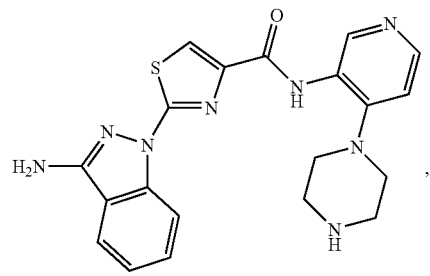
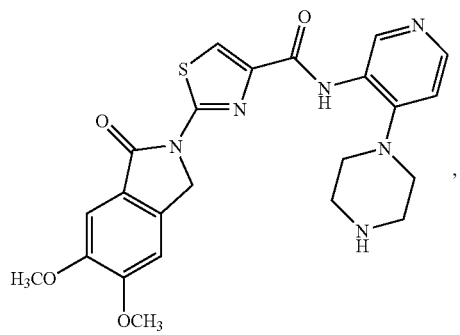
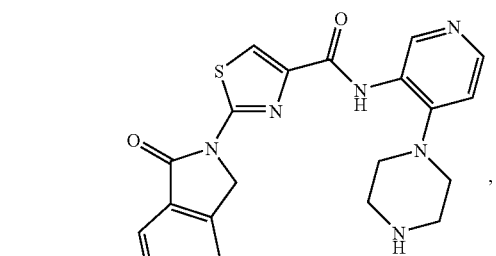
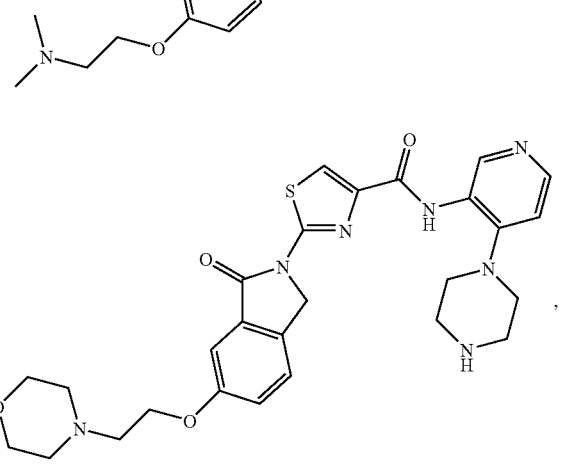

275
-continued
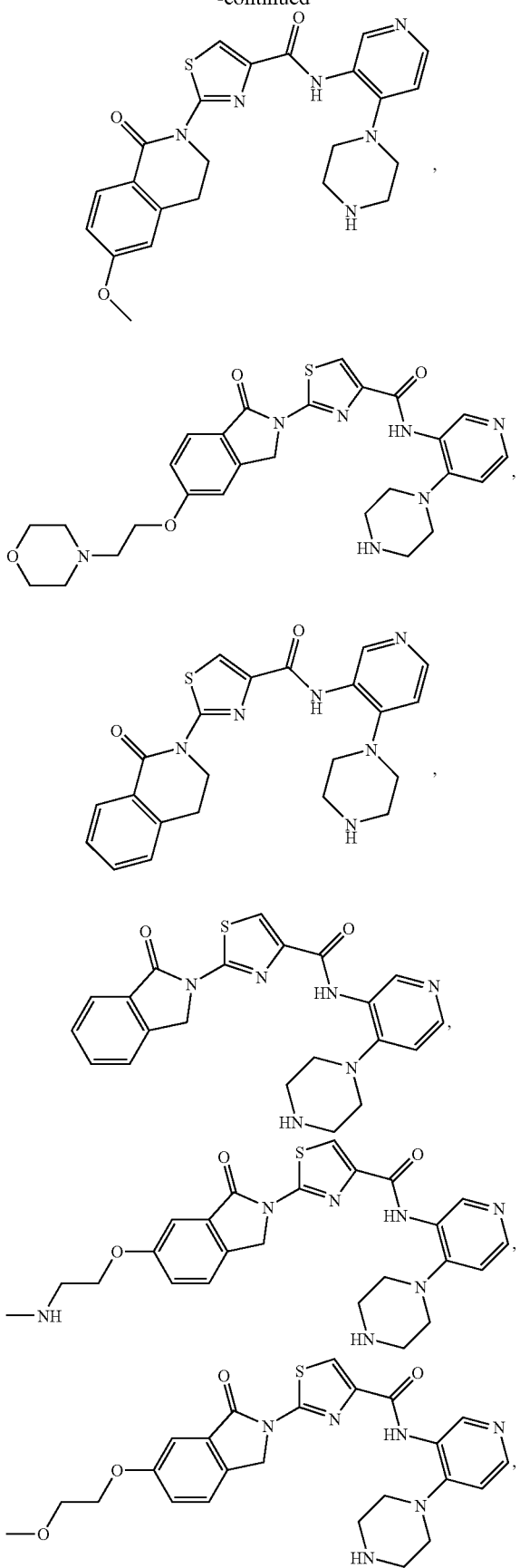
276
-continued
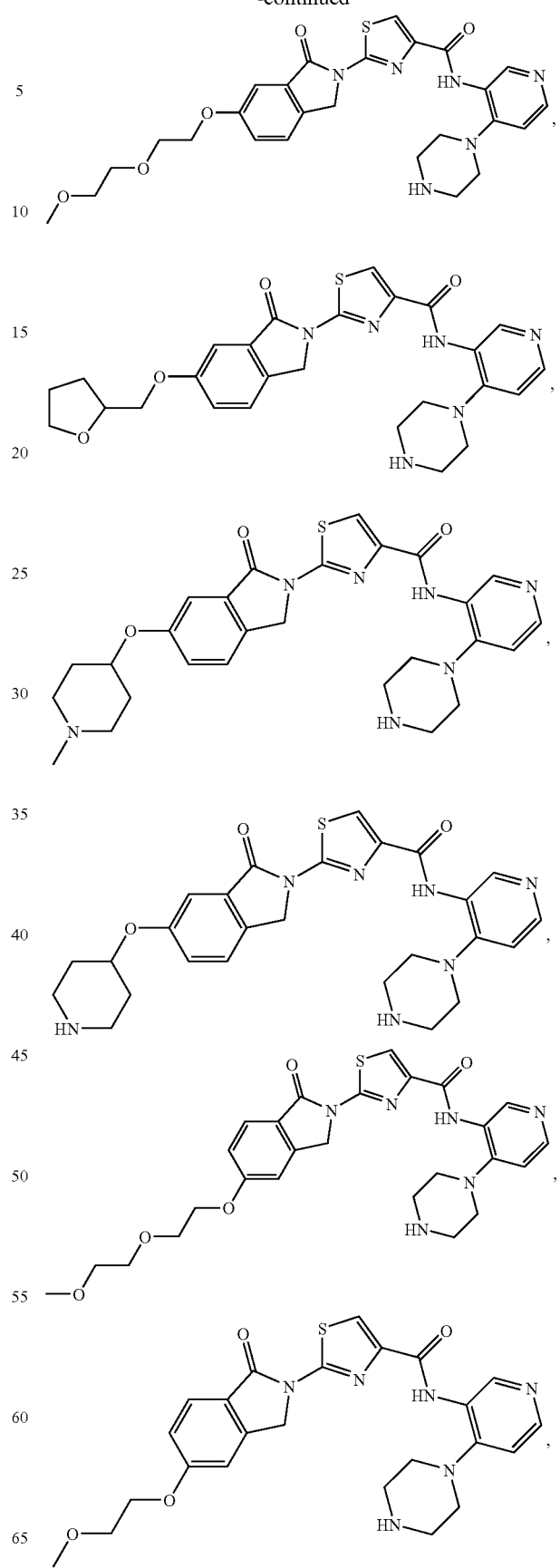

277
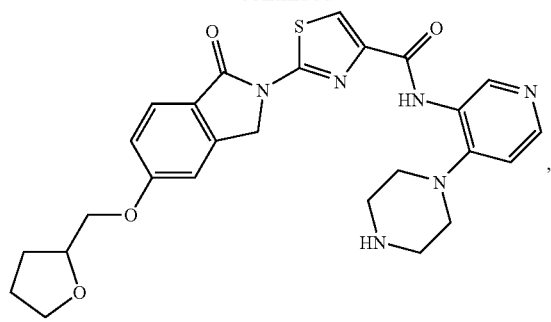
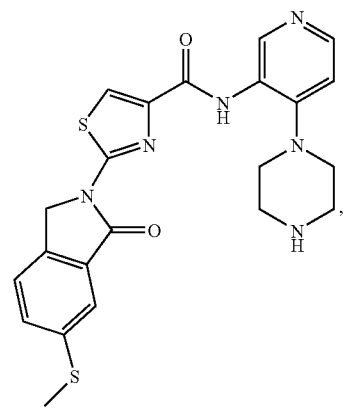
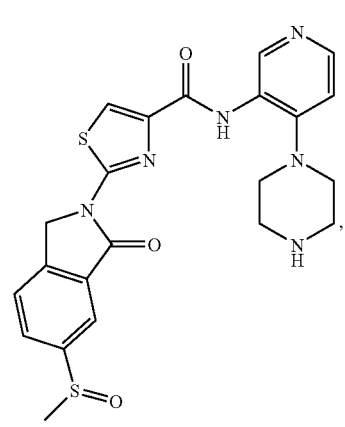
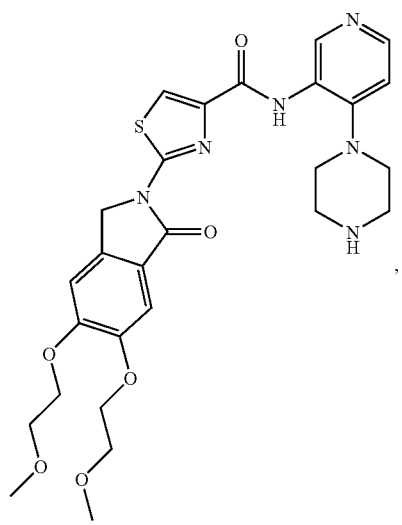
278
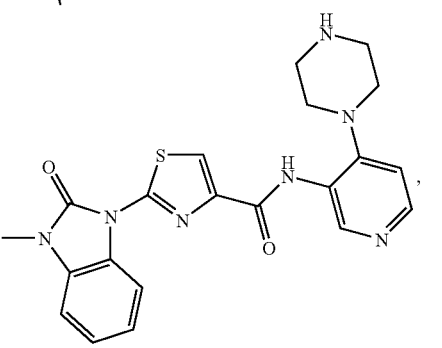
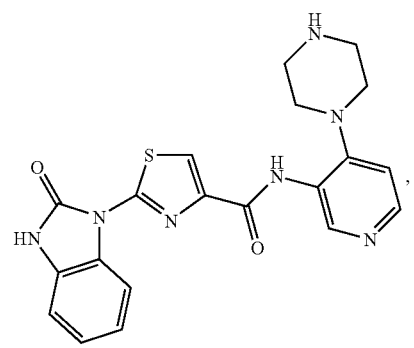
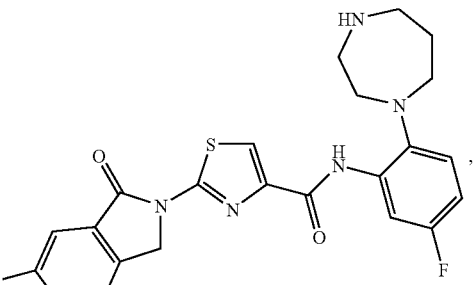
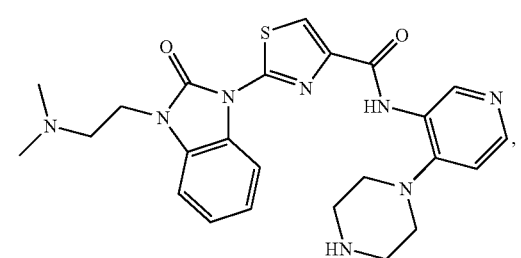
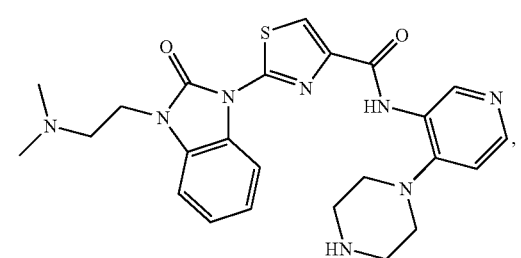
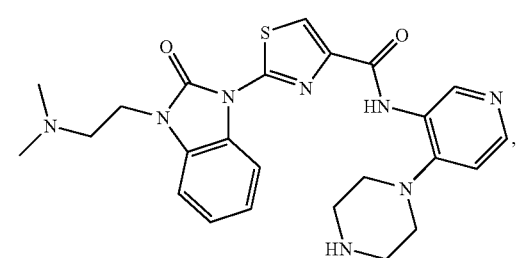

279
-continued
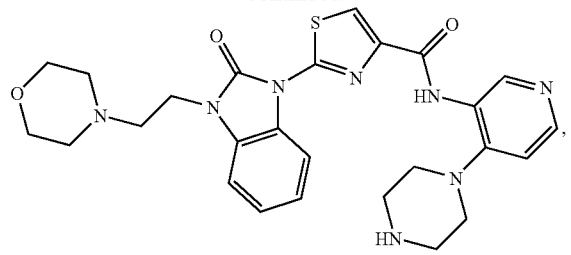
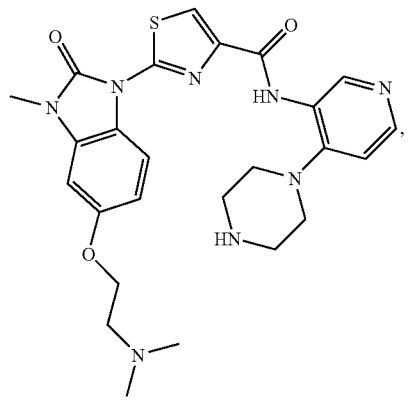
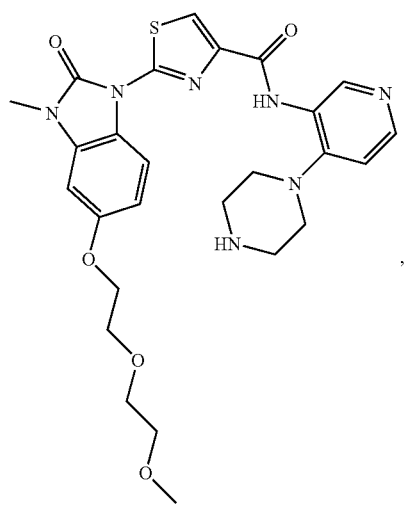
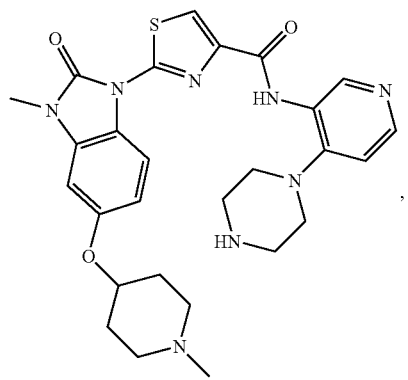
280
-continued
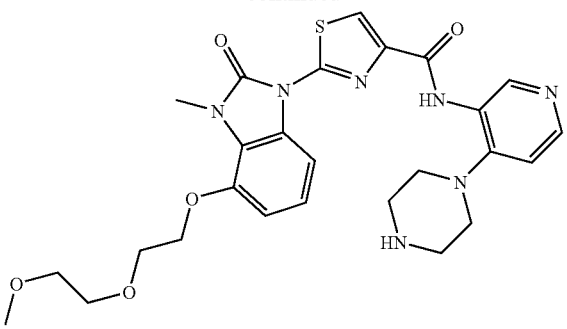
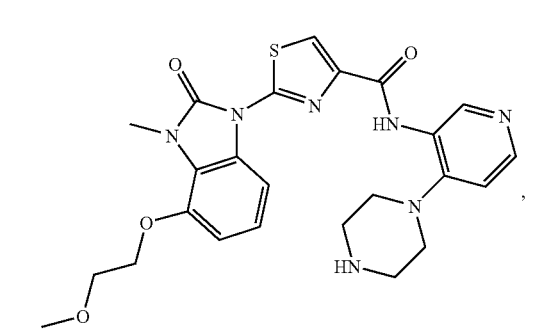
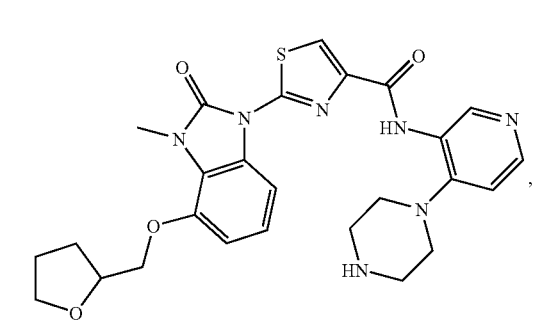
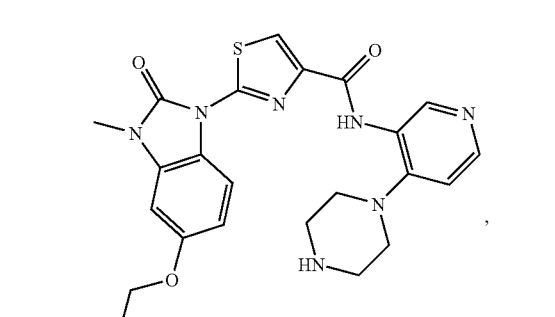
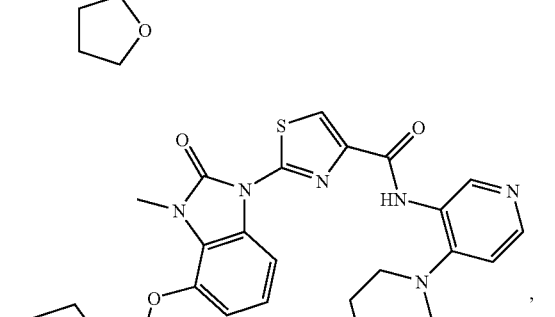

281
-continued
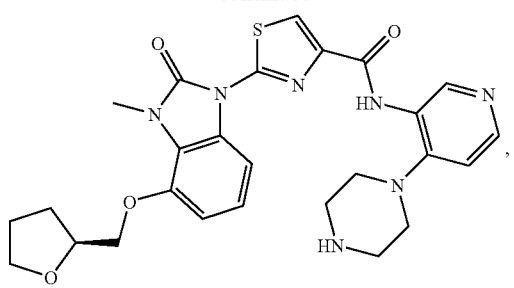
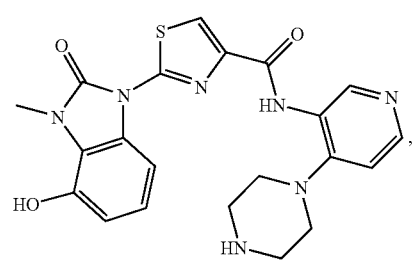
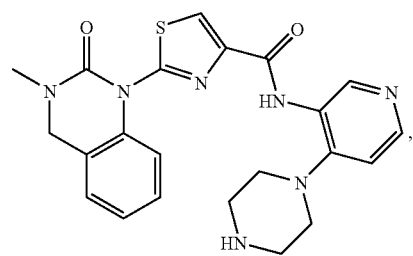
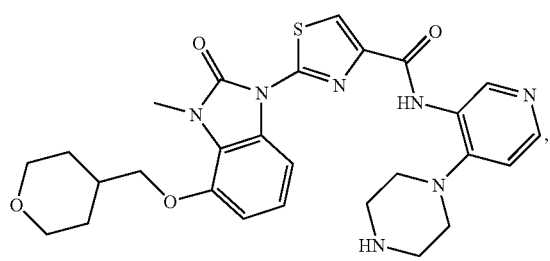
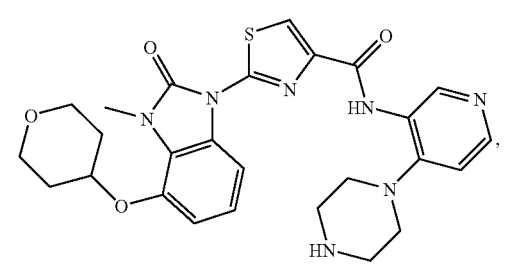
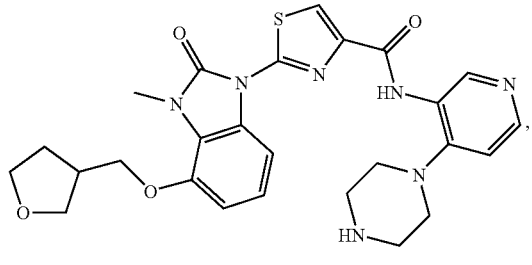
282
-continued
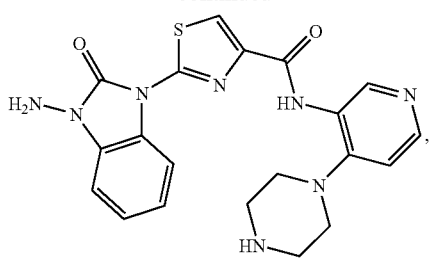
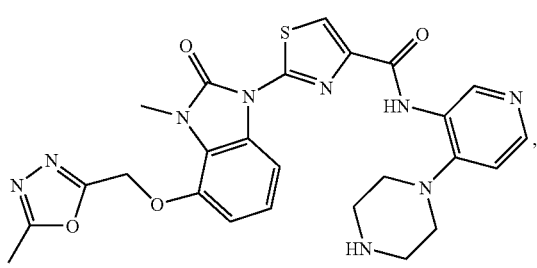
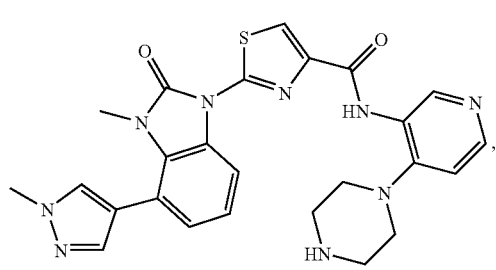
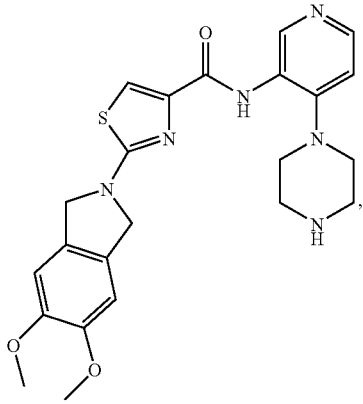
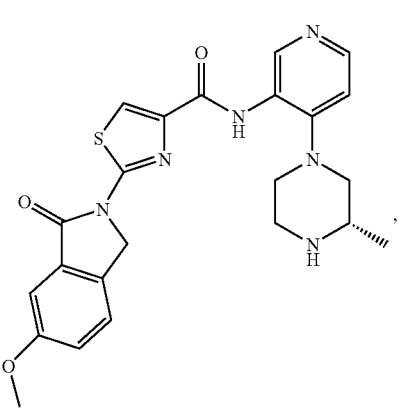

-continued
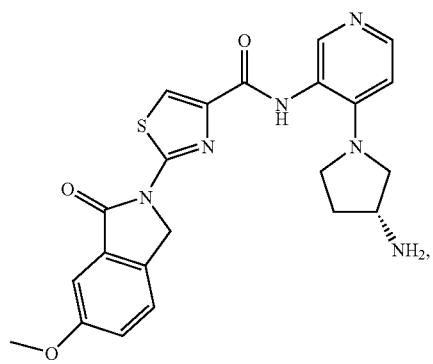
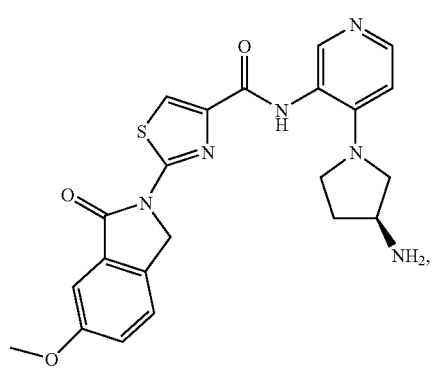
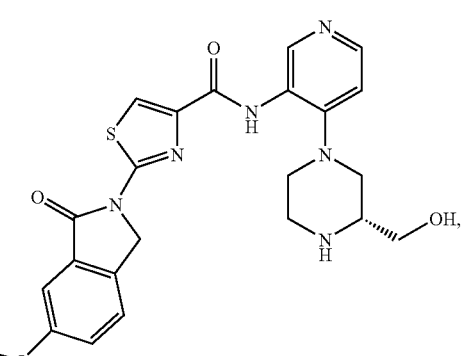
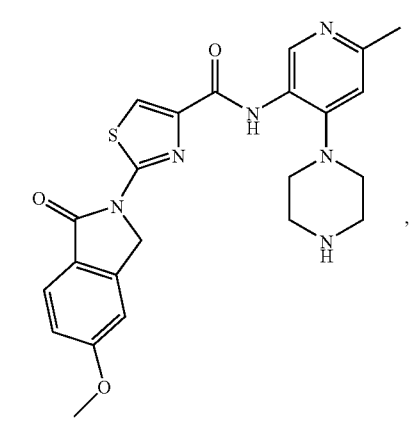
-continued
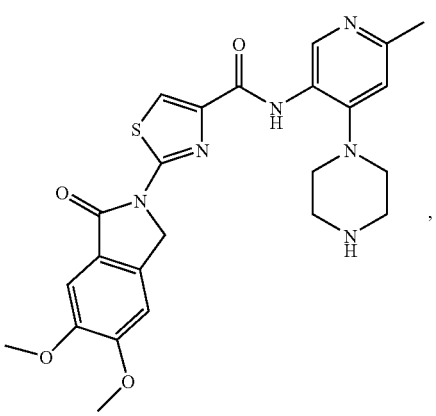
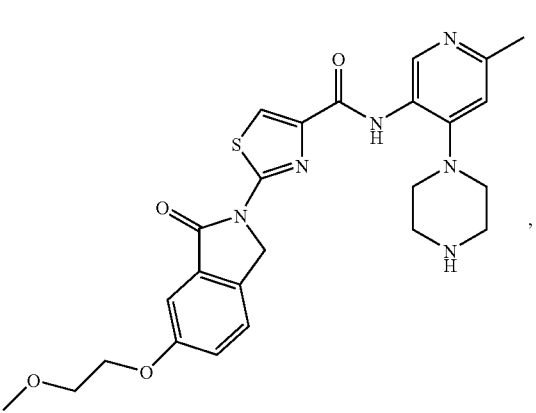
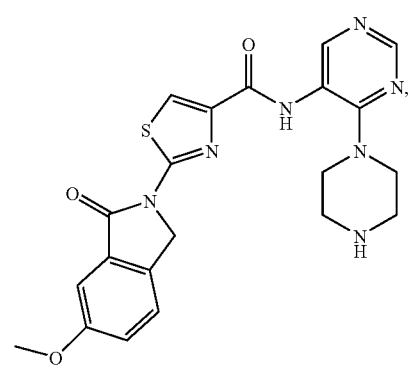
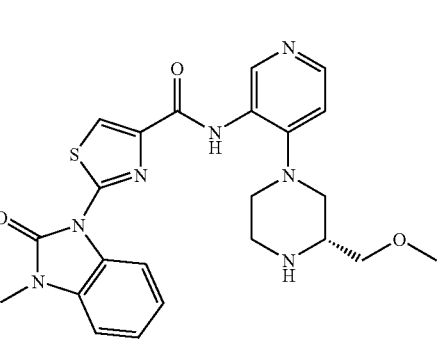

285
-continued
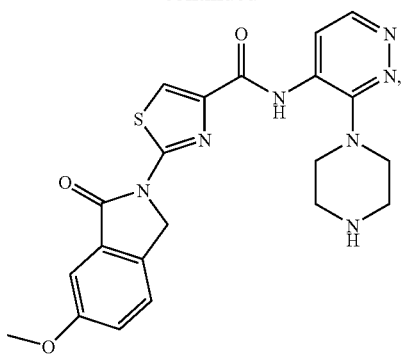
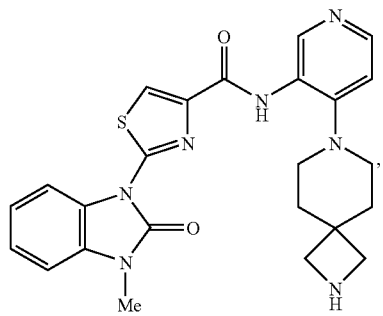
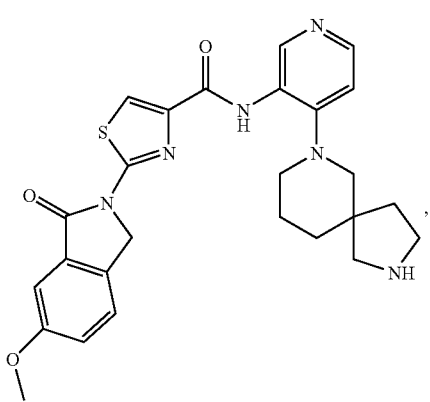
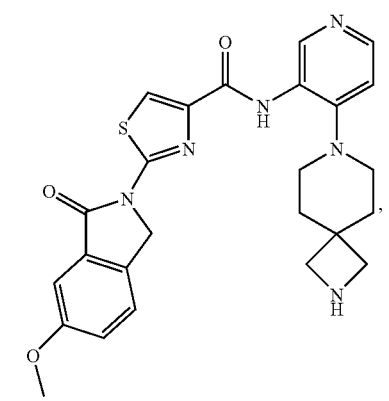
286
-continued
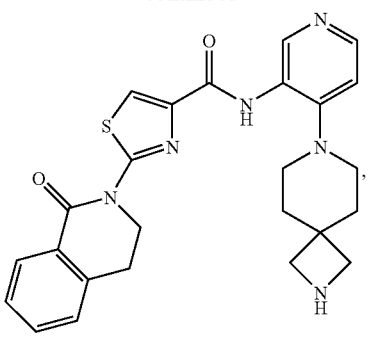
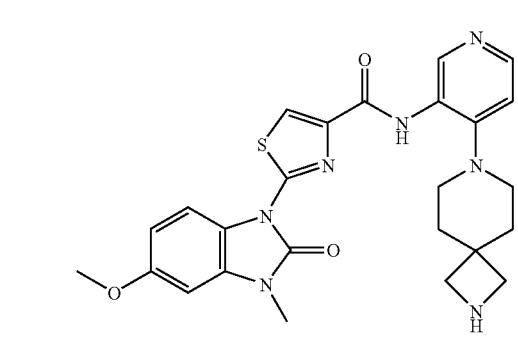
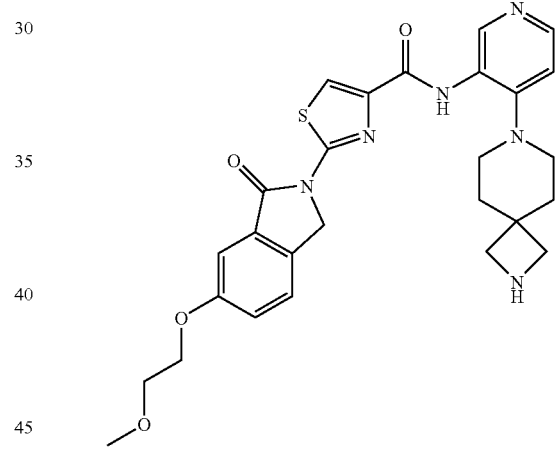
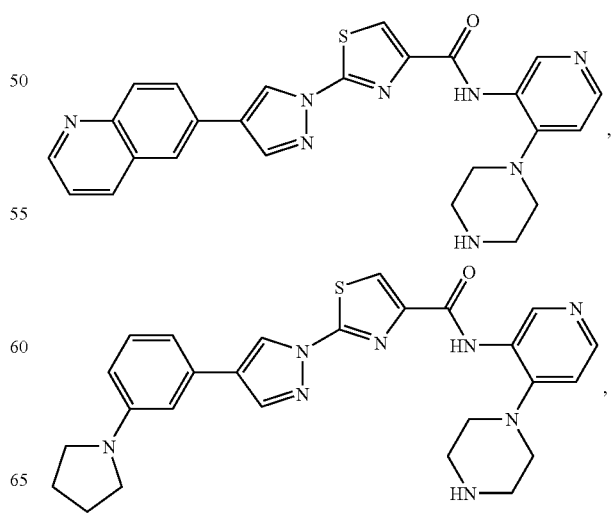

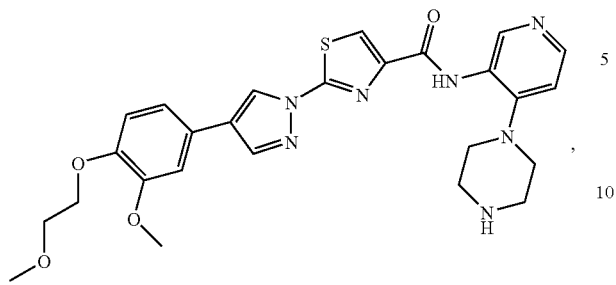

,

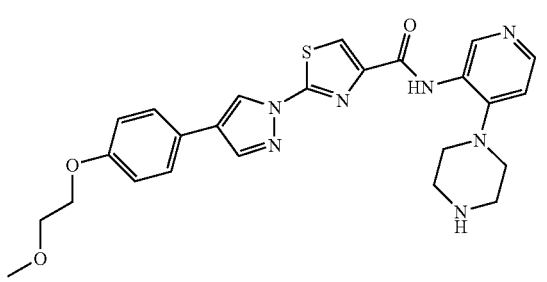

and

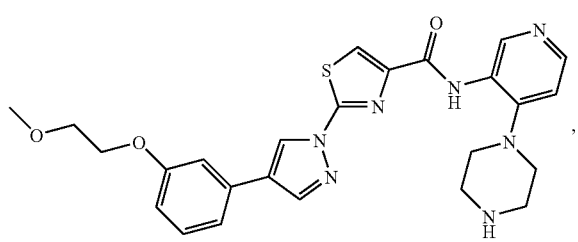

, and pharmaceutically acceptable salts, solvates, esters, prodrugs and stereoisomers thereof.

Methods for Making the Anilinopiperazine Derivatives

Methods useful for making the Anilinopiperazine Derivatives of formula (I) are set forth below in Schemes 1-9. Alternative mechanistic pathways and analogous structures will be apparent to those skilled in the art.

Scheme 1 illustrates a method for making the intermediate amine compounds of formula iv.

Scheme 1

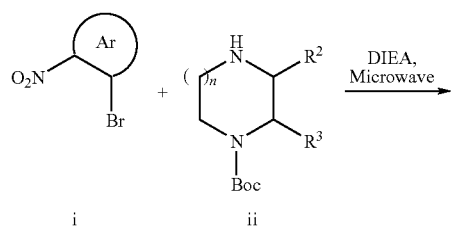

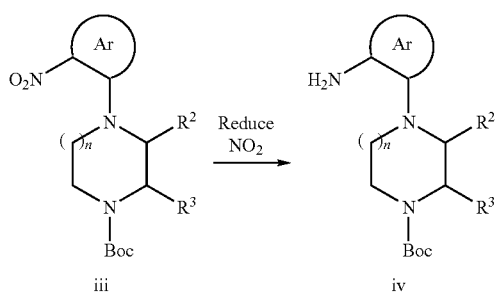

wherein $R^2$, $R^3$, Ar and n are as defined above for the compounds of formula (I).

A nitro-substituted aryl or heteroaryl derivative of formula i can be coupled with a piperizine compound of formula II in the presence of diisopropylethylamine using a microwave-assisted process to provide the coupled compound iii. The nitro group of a compound of formula iii can then be reduced using an appropriate method to provide the intermediate amine compounds of formula iv.

Scheme 2 illustrates a method for making the intermediate amine compounds of formula vii.

Scheme 2

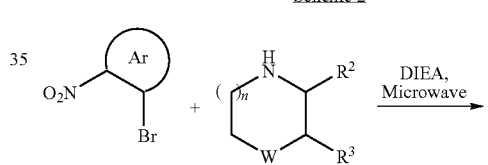

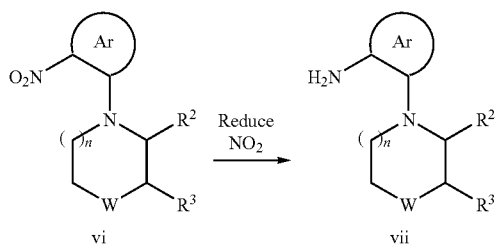

wherein $R^2$, $R^3$, W, Ar and n are as defined above for the compounds of formula (I).

A nitro-substituted aryl or heteroaryl derivative of formula i can be coupled with a cyclic amine of formula v to provide the coupled compound vi, using the DIEA coupling method described in Scheme 1. The nitro group of a compound of formula vi can then be reduced using an appropriate method to provide the intermediate amine compounds of formula vii.

Scheme 3 illustrates a method for making the intermediate amine compounds of formula xi.

Scheme 3

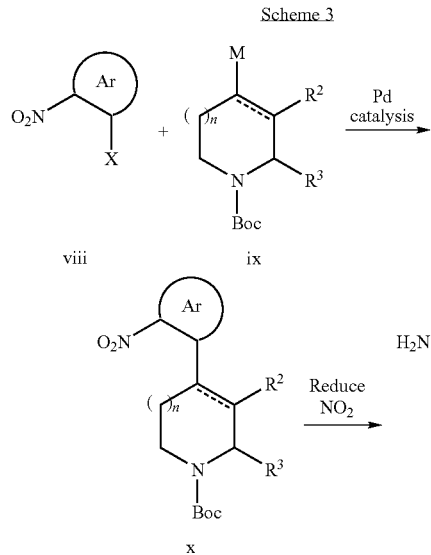

wherein X is —Cl, —Br or —OTf; M is B(OH)$_2$, ZnX or SnBu$_3$; and R$^2$, R$^3$, Ar and n are as defined above for the compounds of formula (I).

A nitro-substituted aryl or heteroaryl derivative of formula viii can be coupled with a piperidine compound of formula ix using a Pd-catalyzed coupling method (e.g., a Suzuki coupling or a Stille coupling) to provide the coupled compound x. The nitro group of a compound of formula x can then be reduced using an appropriate reduction method to provide the intermediate amine compounds of formula xi.

Scheme 4 illustrates a method for making the intermediate amine compounds of formula xiv.

Scheme 4

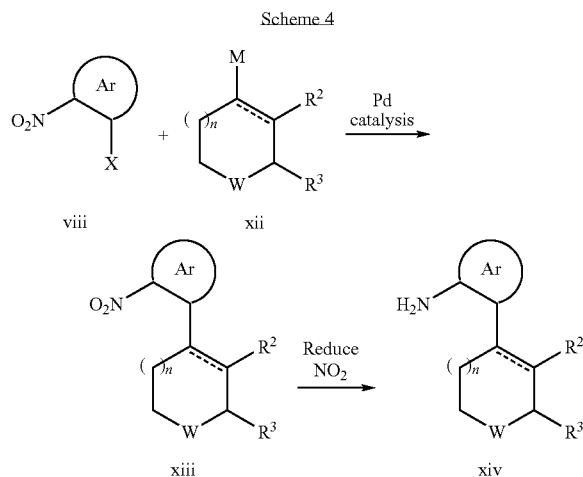

wherein X is —Cl, —Br or —OTf; M is B(OH)$_2$, ZnX or SnBu$_3$; and R$^2$, R$^3$, W, Ar and n are as defined above for the compounds of formula (I).

A nitro-substituted aryl or heteroaryl derivative of formula viii can be coupled with a compound of formula xii to provide a compound of formula xiii, using the Pd coupling method described in Scheme 3. The nitro group of a compound of formula xiii can then be reduced using an appropriate method to provide the intermediate amine compounds of formula xiv.

Scheme 5 illustrates a method for making the Anilinopiperazine Derivatives of formula (I), wherein W is —NH— and Z is N.

Scheme 5

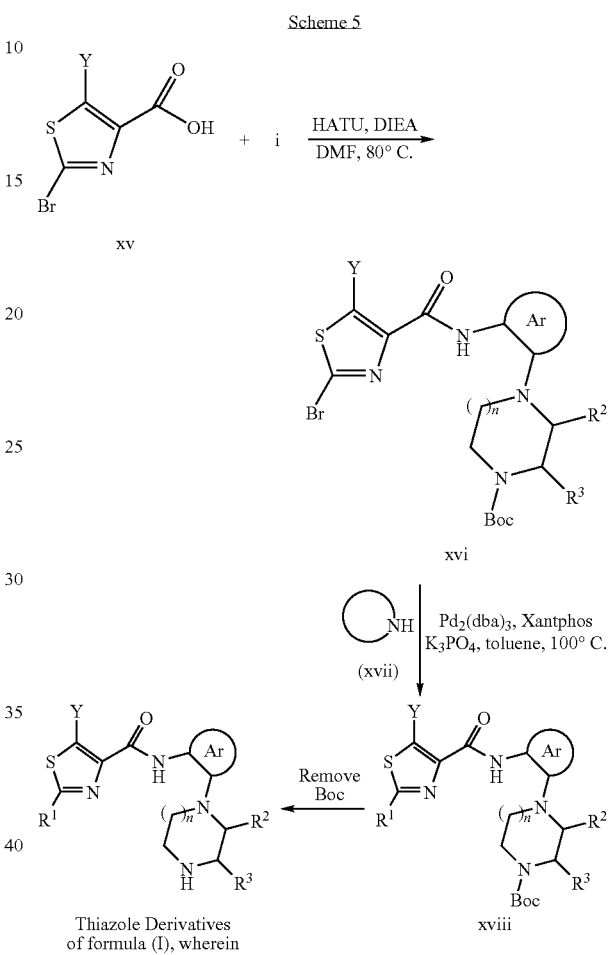

Thiazole Derivatives of formula (I), wherein W is NH and Z is N wherein R$^1$, R$^2$, R$^3$, Ar, n and Y are as defined above for the compounds of formula (I).

A 2-bromo-thiazole-4-carboxylic acid compound of formula xv can be coupled with an amine compound of formula i using 2-(1H-7-azabenzotriazol-1-yl)-1,1,3,3-tetramethyl uronium hexafluorophosphate (HATU) in the presence of N,N-diisopropylethylamine to provide the amido intermediates of formula xvi. A compound of formula xvi can then be coupled with a cyclic amine of formula xvii (which corresponds to R$^1$) using a palladium-catalyzed process to provide the compounds of formula xviii. Removal of the Boc protecting group from a compound of formula xviii using an acid, such as TFA or formic acid, provides the Anilinopiperazine Derivatives of formula (I), wherein W is —NH— and Z is N.

Scheme 6 illustrates a method for making the Anilinopiperazine Derivatives of formula (I), wherein W is —C(R$^4$)$_2$—; and Z is N.

Scheme 6

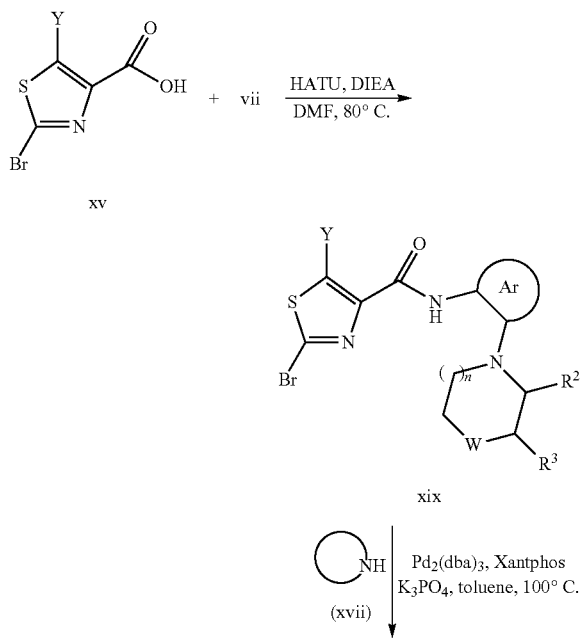
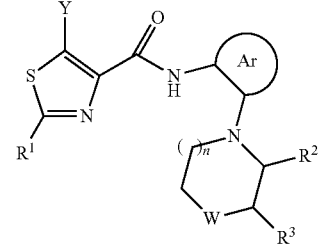

Thiazole Derivatives
of formula (I), wherein
W is —C($R^4$)$_2$— and Z is N wherein $R^1$, $R^2$, $R^3$, Ar, W, Y and n are as defined above for the compounds of formula (I).

A 2-bromo-thiazole-4-carboxylic acid compound of formula xv can be coupled with an amine intermediate of formula vii using the HATU coupling method set forth in Scheme 5 to provide the amido intermediates of formula xix. A compound of formula xix can then be coupled with a cyclic amine of formula xvii (which corresponds to $R^1$) using the Pd coupling method set forth in Scheme 5 to provide the Anilinopiperazine Derivatives of formula (I), wherein W is —C($R^4$)$_2$—; and Z is N.

Scheme 7 illustrates a method for making the Anilinopiperazine Derivatives of formula (I), wherein W is —NH— and Z is carbon.

Scheme 7

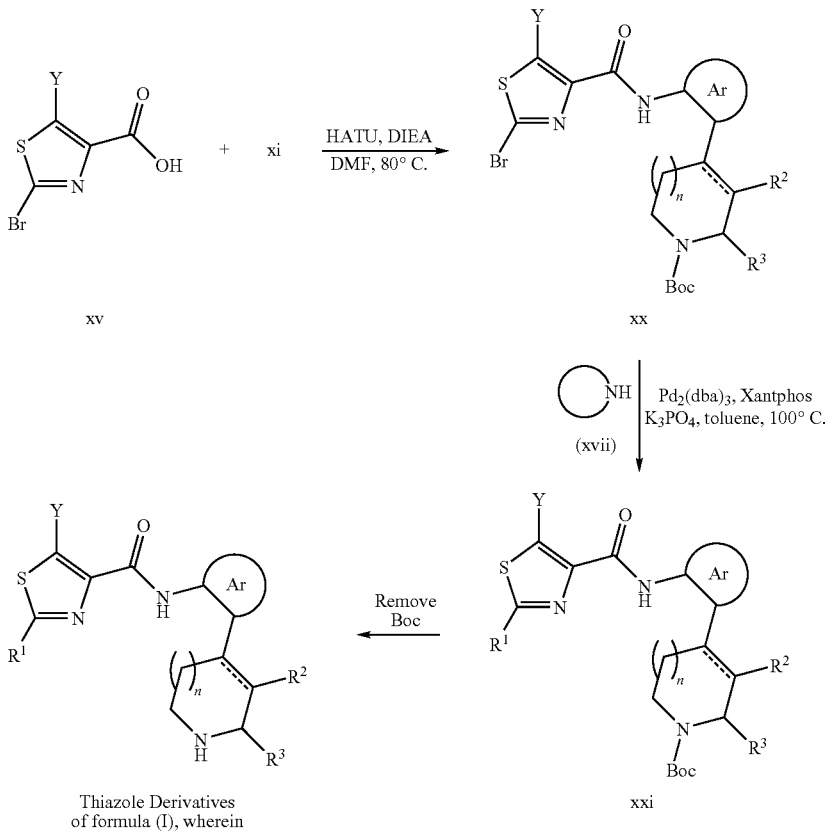

wherein $R^1$, $R^2$, $R^3$, Ar, Y and n are as defined above for the compounds of formula (I).

Using the method described in Scheme 5 and substituting intermediate amine compound xi for intermediate amine compound i, the Anilinopiperazine Derivatives of formula (I) can be prepared, wherein W is —NH— and Z is carbon.

Scheme 8 illustrates a method for making the Anilinopiperazine Derivatives of formula (I), wherein W is —C($R^4$)$_2$—; and Z is carbon.

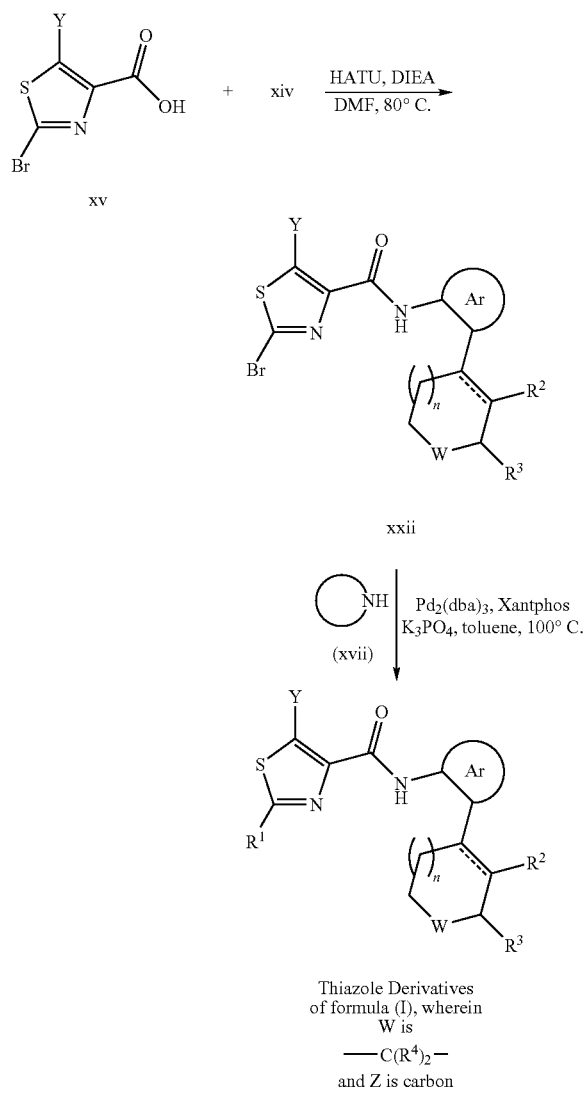

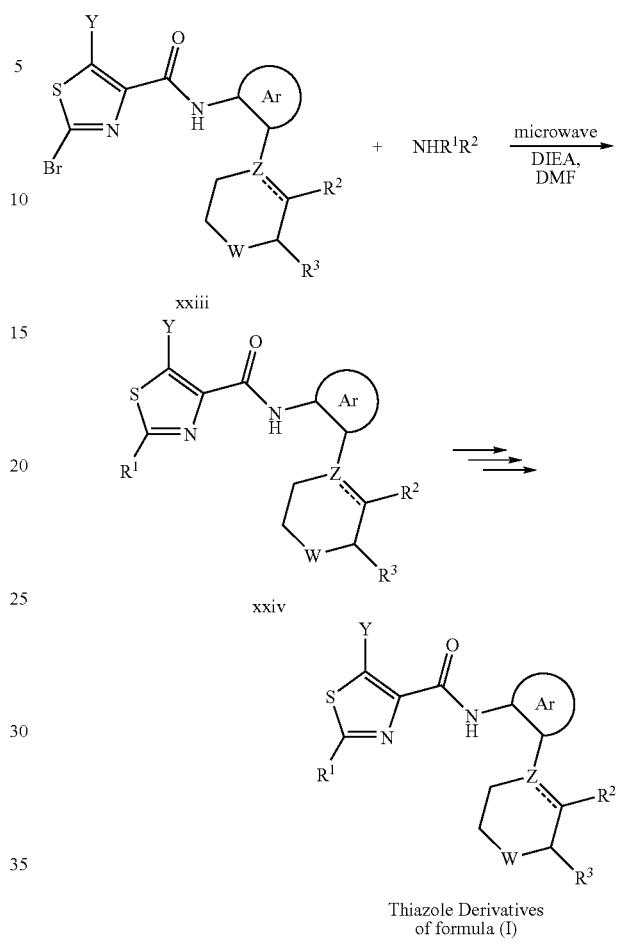

wherein $R^1$, $R^2$, $R^3$, Ar, W, Y, Z and n are as defined above for the compounds of formula (I).

An amido compound of formula xxiii (which is representative of compounds xvi, xix, xx and xxii) can be coupled with an amine of formula NHR$^1$R$^2$ in the presence of diisopropylethylamine using a microwave-assisted process to provide the amine compounds of formula 54. The compounds of formula 54 can then be further elaborated using the methods set forth above in Schemes 5-8 to provide the Anilinopiperazine Derivatives of formula (I).

EXAMPLES

General Methods

Solvents, reagents, and intermediates that are commercially available were used as received. Reagents and intermediates that are not commercially available were prepared in the manner as described below. $^1$H NMR spectra were obtained on a Varian AS-400 (400 MHz) and are reported as ppm down field from Me$_4$Si with number of protons, multiplicities, and coupling constants in Hz indicated parenthetically. Where LC/MS data are presented, analyses were performed using an Applied Biosystems API-100 mass spectrometer and Shimadzu SCL-10A LC column: Altech wherein $R^1$, $R^2$, $R^3$, Ar, Y and n are as defined above for the compounds of formula (I).

Using the method described in Scheme 6 and substituting intermediate amine compound xiv for intermediate amine compound vii, the Anilinopiperazine Derivatives of formula (I) can be prepared, wherein W is —C($R^4$)$_2$—; and Z is carbon.

Scheme 9 illustrates an alternative method for coupling an amine compound of formula xvii with an intermediate compound of formula xvi, xix, xx or xxii.

platinum C18, 3 micron, 33 mm×7 mm ID; gradient flow: 0 min—10% CH₃CN, 5 min—95% CH₃CN, 7 min—95% CH₃CN, 7.5 min—10% CH₃CN, 9 min—stop. MS data were obtained using Agilent Technologies LC/MSD SL or 1100 series LC/MSD mass spectrometer. Final compounds were purified by PrepLC using the column of Varian Pursuit XRs C18 10 μm 250×21.2 mm and an eluent mixture of mobile phase A and B. The mobile phase A is composed of 0.1% TFA in H₂O and the mobile phase B is composed of CH₃CN (95%)/H₂O (5%)/TFA (0.1%). The mixture of mobile phase A and B was eluted through the column at a flow rate of 20 mL/min at room temperature. The purity of all the final discrete compounds was checked by LCMS using a Higgins Haisil HL C18 5 μm 150×4.6 mm column and an eluent mixture of mobile phase A and B, wherein mobile phase A is composed of 0.1% TFA in H₂O and the mobile phase B is composed of CH₃CN (95%)/H₂O (5%)/TFA (0.1%). The column was eluted at a flow rate of 3 mL/min at a temperature of 60° C. Intermediate compounds were characterized by LCMS using a Higgins Haisil HL C18 5 μm 50×4.6 mm column and an eluent mixture of mobile phase A and B, wherein mobile phase A is composed of 0.1% TFA in H₂O and the mobile phase B is composed of CH₃CN (95%)/H₂O (5%)/TFA (0.1%). The column was eluted at a flow rate of 3 mL/min at a column temperature of 60° C.

Example 1

Preparation of Intermediate Compound A

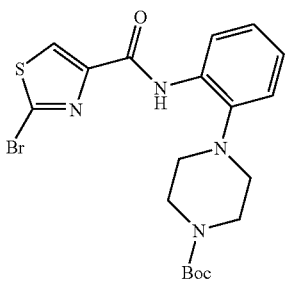

A

To a solution of 2-bromo-thiazole-4-carboxylic acid (2.0 mmol, 0.42 g), N,N-diisopropylethylamine (3.0 mmol, 0.52 mL) and HATU (2.0 mmol, 0.76 g) in DMF (10 mL) was added 4-(2-aminophenyl)-piperazine-1-carboxylic acid tert-butyl ester (2.0 mmol, 0.56 g). The reaction mixture was stirred at 80° C. for 3 h, and then concentrated in vacuo. The resulting residue was purified using flash column chromatography on silica gel (eluent: Hexane:EtOAc (4.5:1)) to provide Compound A as a yellow solid (0.67 g, 72%). ¹H NMR (400 MHz, CDCl₃) δ 10.38 (s, 1H), 8.49 (dd, J=8.0, 1.2 Hz, 1H), 8.14 (s, 1H), 7.23-7.10 (m, 3H), 3.72 (br s, 4H), 2.89-2.87 (m, 4H), 1.50 (s, 9H). HPLC-MS RT=2.39 min, mass calculated for formula $C_{19}H_{23}BrN_4O_3S$ 466.07, observed LCMS m/z 467.05 (M+H).

Example 2

Preparation of Compound 1

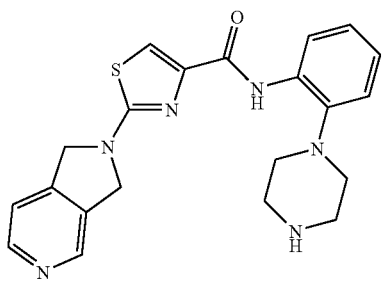

1

A solution of Compound A (0.050 mmol, 23 mg), N,N-diisopropylethylamine (0.20 mmol, 35 μL) and 2,3-dihydro-1H-pyrrolo[3,4-c]pyridine (0.1 mmol) in DMF (1 mL) was irradiated using microwave for 15 minutes at a temperature of 180° C. The reaction mixture was then concentrated in vacuo, and to the resulting residue was added TFA (0.5 mL). The resulting solution was allowed to stir at room temperature for 10 minutes and was then concentrated in vacuo. The resulting residue was purified using reverse phase HPLC to provide Compound 1.

Example 3

Preparation of Compound 2

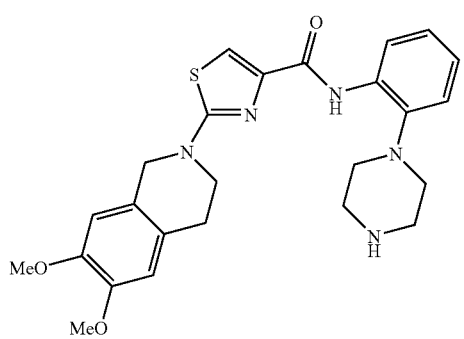

2

Using the method described in Example 2 and substituting 6,7-dimethoxy-1,2,3,4-tetrahydro-isoquinoline for 2,3-dihydro-1H-pyrrolo[3,4-c]pyridine, Compound 2 was prepared.

Example 4

Preparation of Compound 3

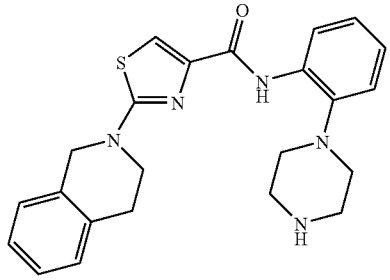

3

Using the method described in Example 2 and substituting 1,2,3,4-tetrahydro-isoquinoline for 2,3-dihydro-1H-pyrrolo[3,4-c]pyridine, Compound 3 was prepared.

Example 5

Preparation of Compound 4

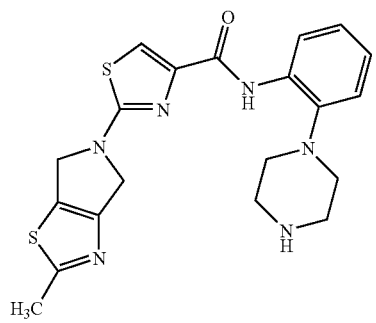

4

Using the method described in Example 2 and substituting 2-methyl-5,6-dihydro-4H-pyrrolo[3,4-d]thiazole for 2,3-dihydro-1H-pyrrolo[3,4-c]pyridine, Compound 4 was prepared.

Example 6

Preparation of Compound 5

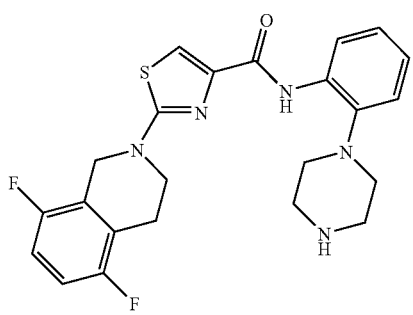

5

Using the method described in Example 2 and substituting 5,8-difluoro-1,2,3,4-tetrahydro-isoquinoline for 2,3-dihydro-1H-pyrrolo[3,4-c]pyridine, Compound 5 was prepared.

Example 7

Preparation of Compound 6

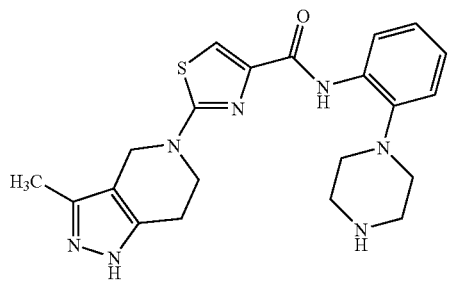

6

Using the method described in Example 2 and substituting 3-methyl-4,5,6,7-tetrahydro-1H-pyrazolo[4,3-c]pyridine for 2,3-dihydro-1H-pyrrolo[3,4-c]pyridine, Compound 6 was prepared.

Example 8

Preparation of Compound 7

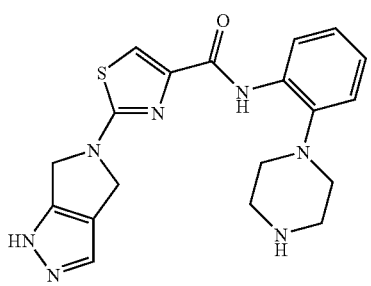

7

Using the method described in Example 2 and substituting 1,4,5,6-tetrahydro-pyrrolo[3,4-c]pyrazole for 2,3-dihydro-1H-pyrrolo[3,4-c]pyridine, Compound 7 was prepared.

Example 9

Preparation of Compound 8

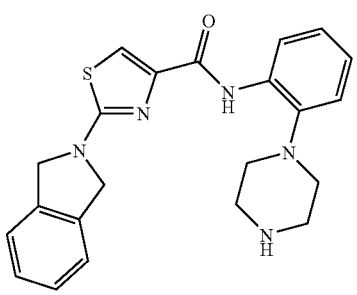

8

Using the method described in Example 2 and substituting 2,3-dihydro-1H-isoindole for 2,3-dihydro-1H-pyrrolo[3,4-c]pyridine, Compound 8 was prepared.

Example 10

Preparation of Compound 9

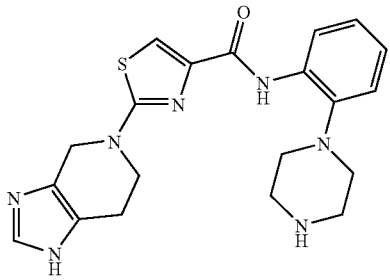

9

Using the method described in Example 2 and substituting 4,5,6,7-tetrahydro-1H-imidazo[4,5-c]pyridine for 2,3-dihydro-1H-pyrrolo[3,4-c]pyridine, Compound 9 was prepared.

Example 11

Preparation of Compound 10

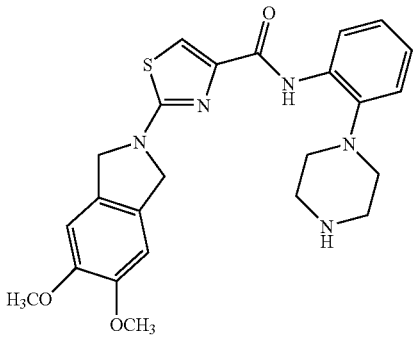

10

Using the method described in Example 2 and substituting 5,6-dimethoxy-2,3-dihydro-1H-isoindole for 2,3-dihydro-1H-pyrrolo[3,4-c]pyridine, Compound 10 was prepared.

Example 12

Preparation of Compound 11

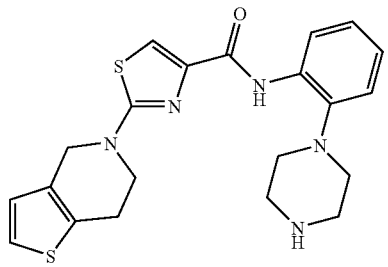

11

Using the method described in Example 2 and substituting 4,5,6,7-tetrahydro-1H-thieno[3,2-c]pyridine for 2,3-dihydro-1H-pyrrolo[3,4-c]pyridine, Compound 11 was prepared.

Example 13

Preparation of Compound 12

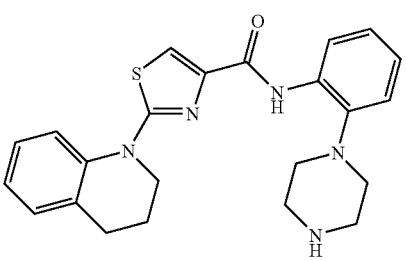

12

Using the method described in Example 2 and substituting 1,2,3,4-tetrahydroquinoline for 2,3-dihydro-1H-pyrrolo[3,4-c]pyridine, Compound 12 was prepared.

Example 14

Preparation of Compound 13

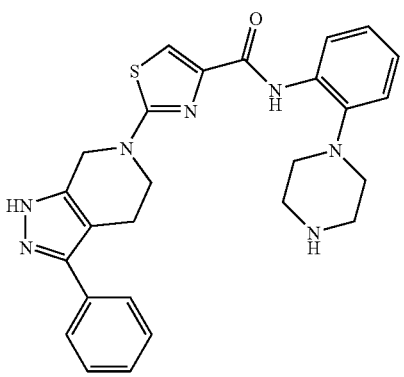

13

Using the method described in Example 2 and substituting 3-phenyl-4,5,6,7-tetrahydro-1H-pyrazolo[3,4-c]pyridine for 2,3-dihydro-1H-pyrrolo[3,4-c]pyridine, Compound 13 was prepared.

Example 15

Preparation of Compound 14

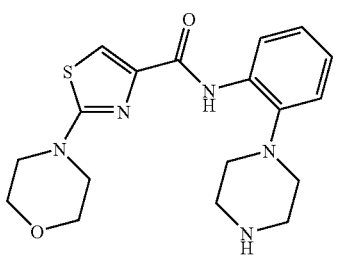

14

A tube containing a stir bar was charged with a solution of Compound A (0.050 mmol, 23 mg), $Pd_2(DBA)_3$ (5.0 μmol, 4.6 mg), and X-Phos (0.010 mmol, 4.8 mg) in dioxane (1 mL).

K₃PO₄ (0.10 mmol, 21 mg) was added to the solution and the resulting reaction was put under a nitrogen atmosphere. Morpholine (8.7 mg, 0.10 mmol) was added to the reaction mixture via a syringe under a N₂ atmosphere. The tube put into an oil bath at 100° C. and the reaction was allowed to stir at this temperature for about 15 hours, then cooled to room temperature. The reaction mixture was then diluted with acetonitrile (5 mL), the resulting solution was centrifuged for about 2 hours at a speed of about 1000 rpm, and the supernatant was collected and concentrated in vacuo. To the resulting residue was added TFA (0.5 mL) and the resulting solution was allowed to stand for 10 minutes, then concentrated in vacuo. The resulting residue was purified using reverse phase HPLC to provide Compound 14.

Example 16

Preparation of Compound 15

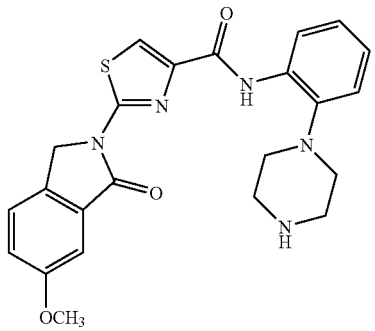

Using the method described in Example 15 and substituting 6-methoxy-2,3-dihydro-isoindol-1-one for morpholine, Compound 15 was prepared.

Example 17

Preparation of Compound 16

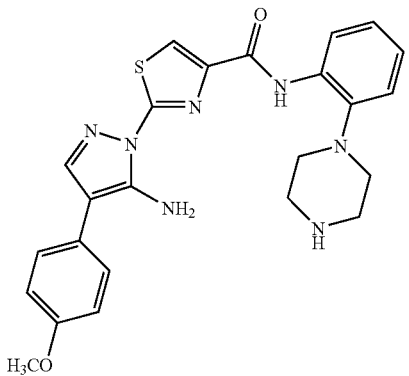

A tube containing a stir bar was charged with a solution of 4-(4-methoxy-phenyl)-2H-pyrazol-3-ylamine (0.10 mmol), Pd₂(DBA)₃ (5.0 µmol, 4.6 mg), Xantphos (0.010 mmol, 5.8 mg) and Compound A (0.050 mmol, 23 mg) in dioxane (1 mL). To the solution was then added K₃PO₄ (0.10 mmol, 21 mg) and the reaction tube was flushed with N₂ then sealed tightly. The resulting reaction was heated to 100° C. and allowed to stir at this temperature for about 15 hours, then cooled to room temperature. The reaction mixture was then diluted with acetonitrile (5 mL), the resulting solution was centrifuged for about 2 hours at a speed of about 1000 rpm, and the supernatant was collected and concentrated in vacuo. To the resulting residue was added TFA (0.5 mL) and the resulting solution was allowed to stand for 10 minutes, then concentrated in vacuo. The resulting residue was purified using reverse phase HPLC to provide Compound 16.

Example 18

Preparation of Compound 17

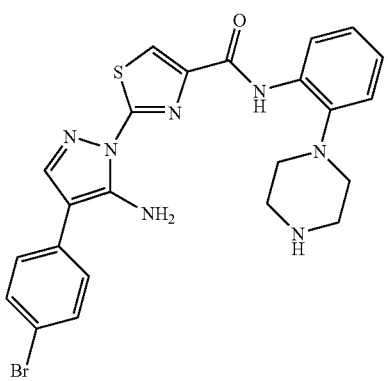

Using the method described in Example 17 and substituting 4-(4-bromo-phenyl)-2H-pyrazol-3-ylamine for 4-(4-methoxy-phenyl)-2H-pyrazol-3-ylamine, Compound 17 was prepared.

Example 19

Preparation of Compound 18

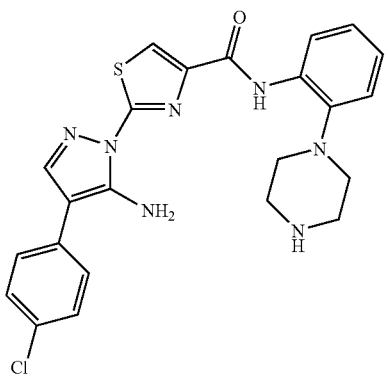

Using the method described in Example 17 and substituting 4-(4-chloro-phenyl)-2H-pyrazol-3-ylamine for 4-(4-methoxy-phenyl)-2H-pyrazol-3-ylamine, Compound 18 was prepared.

Example 20

Preparation of Compound 19

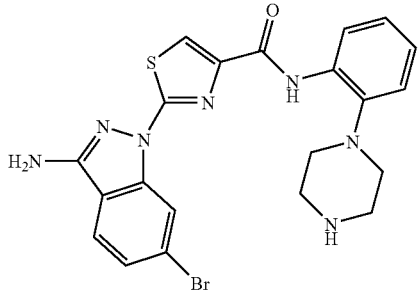

Using the method described in Example 17 and substituting 6-bromo-1H-indazol-3-ylamine for 4-(4-methoxy-phenyl)-2H-pyrazol-3-ylamine, Compound 19 was prepared.

Example 21

Preparation of Compound 20

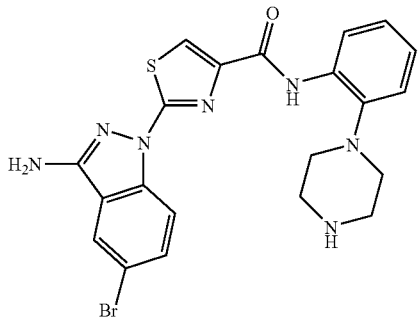

Using the method described in Example 17 and substituting 5-bromo-1H-indazol-3-ylamine for 4-(4-methoxy-phenyl)-2H-pyrazol-3-ylamine, Compound 20 was prepared.

Example 22

Preparation of Compound 21

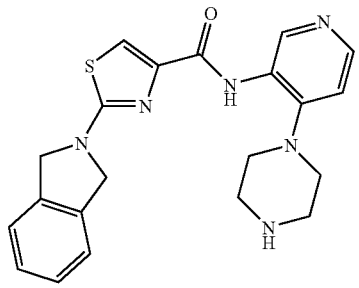

Step 1—Synthesis of Intermediate Compound B

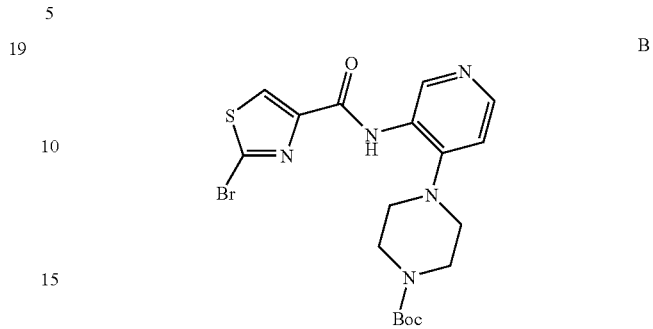

A solution of 4-chloro-3-nitro-pyridine (2.0 mmol, 0.32 g), triethylamine (3.0 mmol, 0.42 mL) and piperazine-1-carboxylic acid tert-butyl ester (2.5 mmol, 0.47 g) in dioxane (2 mL) was irradiated using microwave for 8 minutes at a temperature of 150° C. The solution was then cooled to room temperature and concentrated in vacuo and the resulting residue was purified using flash column chromatography on silica gel (eluent: ethyl acetate) to provide 4-(3-nitro-pyridin-4-yl)-piperazine-1-carboxylic acid tert-butyl ester as a yellow solid (633 mg, quantitative yield). $^1$H NMR (400 MHz, CDCl$_3$) δ 8.87 (s, 1H), 8.40 (d, J=5.6 Hz, 1H), 6.87 (d, J=6.0 Hz, 1H), 3.68-3.56 (m, 4H), 3.32-3.18 (m, 4H), 1.48 (s, 9H).

The 4-(3-nitro-pyridin-4-yl)-piperazine-1-carboxylic acid tert-butyl ester (633 mg) was then diluted with MeOH/EtOAc (1:1, 10 mL) and to the resulting solution was added Pd on carbon (5% Pd). The resulting reaction mixture was stirred under a hydrogen atmosphere at room temperature for about 15 hours. The reaction mixture was filtered through a pad of celite and the filtrate was concentrated in vacuo to provide 4-(3-amino-pyridin-4-yl)-piperazine-1-carboxylic acid tert-butyl ester as a solid form. HPLC-MS RT=1.10 min, mass calculated for formula $C_{14}H_{22}N_4O_2$ 278.17, observed LCMS m/z 279.28 (M+H).

To a solution of 2-bromo-thiazole-4-carboxylic acid (0.78 mmol, 0.16 g), N,N-diisopropylethylamine (1.5 mmol, 0.26 mL) and HATU (0.78 mmol, 0.30 g) in DMF (10 mL) was added 4-(3-amino-pyridin-4-yl)-piperazine-1-carboxylic acid tert-butyl ester (0.78 mmol, 0.22 g). The reaction mixture was heated to 80° C. and allowed to stir at this temperature for about 15 hours, after which time the reaction mixture was cooled to room temperature and concentrated in vacuo. The resulting crude residue was purified using flash column chromatography on silica gel (eluent: ethyl acetate) to provide Compound B as a yellow solid. HPLC-MS RT=1.40 min, mass calculated for formula $C_{18}H_{22}BrN_5O_3S$ 467.06, observed LCMS m/z 468.05 (M+H).

Step 2—Synthesis of Compound 21

Using the method described in Example 2 and substituting Compound B for Compound A, and 2,3-dihydro-1H-isoindole for 2,3-dihydro-1H-pyrrolo[3,4-c]pyridine, Compound 21 was prepared.

Example 23

Preparation of Compound 22

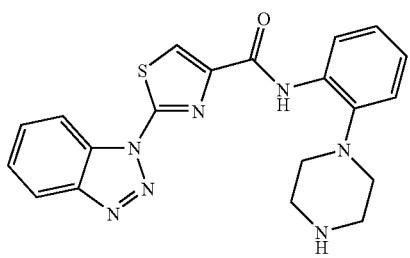

22

Step 1—Synthesis of Compound C

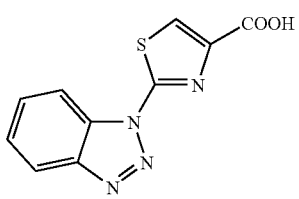

C

Benzotriazole (1.20 mmol, 143 mg), K$_3$PO$_4$ (1.5 mmol, 0.32 g), Pd$_2$(DBA)$_3$ (40.0 µmol, 36.6 mg), X-Phos (0.12 mmol, 57 mg) and 2-bromo-thiazole-5-carboxylic acid ethyl ester (1.00 mmol, 236 mg) were loaded into a Schlenk tube containing a stir bar. The Schlenk tube was capped with a rubber septum, evacuated and put under a nitrogen atmosphere. Toluene (2 mL) was added through the septum via a syringe, then the tube was sealed with a Teflon screw cap under a flow of nitrogen, and put into an oil bath at 100° C. The reaction was heated to 100° C. and allowed to stir at this temperature for about 15 hours, after which time, the reaction mixture was cooled to room temperature and filtered through a pad of celite. The filtrate was concentrated in vacuo and the resulting residue was purified using flash column chromatography on silica gel (eluent: Hexane/EtOAc (6:1)) to provide 2-benzotriazol-1-yl-thiazole-4-carboxylic acid ethyl ester as a white solid. $^1$H NMR (400 MHz, CDCl$_3$) δ 8.57 (d, J=8.4 Hz, 1H), 8.14 (d, J=8.0 Hz, 1H), 8.06 (s, 1H), 7.73-7.68 (m, 1H), 7.54-7.49 (m, 1H), 4.46 (q, J=7.2 Hz, 2H), 1.45 (t, J=7.2 Hz, 3H).

2-benzotriazol-1-yl-thiazole-4-carboxylic acid ethyl ester was diluted with concentrated aqueous hydrochloric acid and the resulting solution was heated to reflux and allowed to stir at this temperature for about 15 hours. The reaction mixture was then cooled to room temperature and lyophilized to provide Compound C as an ammonium chloride salt.

Step 2—Synthesis of Compound 22

To a solution of 2-benzotriazol-1-yl-thiazole-4-carboxylic acid (0.050 mmol, 14 mg), N,N-diisopropylethylamine (0.25 mmol, 44 µL) and HATU (0.050 mmol, 19 mg) in DMF (0.5 mL) was added 4-(2-aminophenyl)-piperazine-1-carboxylic acid tert-butyl ester (0.10 mmol, 28 mg). The reaction mixture was heated to 80° C. and allowed to stir at this temperature for about 15 hours, after which time the reaction mixture was cooled to room temperature and concentrated in vacuo. To the resulting solid residue was added TFA (0.5 mL) and the resulting solution was allowed to stand for 10 minutes, then was concentrated in vacuo. The resulting residue was purified using reverse phase HPLC to provide Compound 22.

Example 24

Preparation of Compound 23

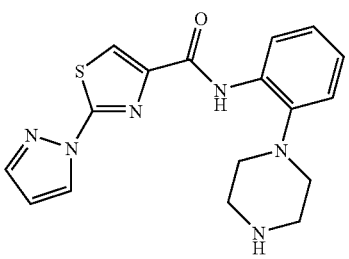

23

In 20 mL vial containing a stir bar (vial 1) is charged with a solution of 4-{2-[(2-bromo-thiazole-4-carbonyl)-amino]-phenyl}-piperazine-1-carboxylic acid tert-butyl ester acid (107 µmol, 50 mg) and 1,4-dioxane (1 mL). A second 20 mL vial containing a stir bar (vial 2) is charged with a solution of pyrazole (4 eq, 428 µmol, 29.1 mg) and 1,-4 dioxane (2 mL). To the solution in vial 2 is added NaH (60% dispersion in mineral oil, 4 eq, 428 µmol, 17.2 mg). The resulting reaction is allowed to stir for 15 minutes, then is added to the solution in vial 1. Vial 1 is sealed and the resulting reaction inside vial 1 is heated to 100° C. and allowed to stir at this temperature for about 18 hours. LC/MS analysis confirmed disappearance of the starting material and the reaction mixture was concentrated in vacuo. The resulting crude residue was diluted with dichloromethane (2 mL), filtered through celite and the filtrate was purified using flash column chromatography on silica gel (eluent: gradient from 100% hexanes to 60% ethyl acetate in hexanes) provided an intermediate white solid product. $^1$H NMR (400 MHz, CD$_3$CN) δ 10.35-10.25 (br s, 1H), 8.49-8.46 (dd, J=8, 1.6 Hz, 1H), 8.39-8.37 (d, J=2.8 Hz, 1H), 8.04 (s, 1H), 7.84-7.83 (d, J=1.6 Hz, 1H), 7.30-7.27 (dd, J=8, 1.6 Hz, 1H), 7.25-7.20 (td, J=8, 1.6 Hz, 1H), 7.18-7.13 (td, J=8, 1.6 Hz, 1H), 3.70-3.63 (br t, J=4.8 Hz, 4H), 2.91-2.86 (m, J=4.8 Hz, 4H), 1.48 (s, 9H). The intermediate white solid product was diluted with a 9:1 solution of TFA:H$_2$O (2 mL). The resultant solution was shaken for 2 hours at room temperature and the reaction mixture was concentrated in vacuo. The resulting residue was purified using reverse-phase HPLC and lyophilized with aqueous HCl (1 M) to provide Compound 23 as a dihydrochloride salt (15.43 mg).

The following illustrative compounds of the invention were prepared using this method with appropriate reactants:

| No. | Structure | LCMS MH+ m/z | HPLC MS $t_R$ |
|---|---|---|---|
| 118 | 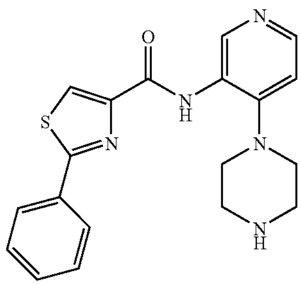 | 366.21 | 1.74 |
| 204 | 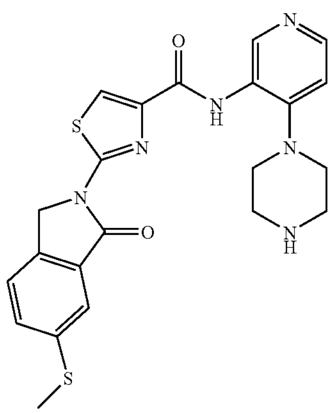 | 467.23 | 2.13 |
| 242 | 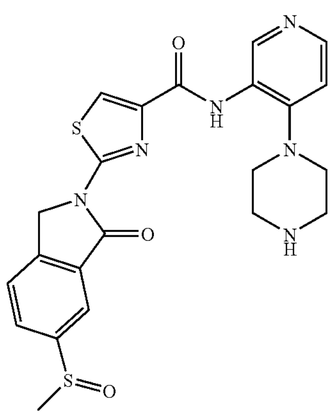 | 483.11 | 1.48 |
| 243 | 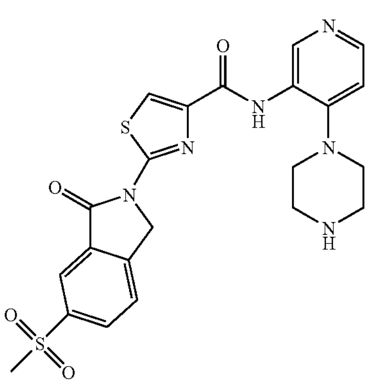 | 499.08 | 1.26 |
| 267 | | 445.69 (M + Na) | 0.749 |
| 269 | | 563.26 | 2.71 |
| 293 | | 569.37 | 2.07 |

-continued

| No. | Structure | LCMS MH+ m/z | HPLC MS $t_R$ |
|---|---|---|---|
| 333 | 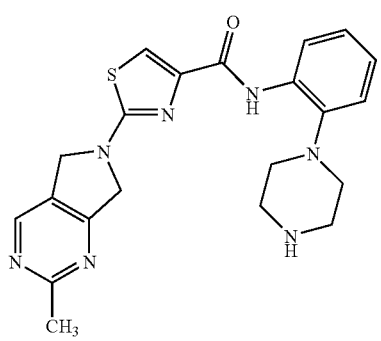 | 469.22 | 1.92 |

Example 25

Preparation of Compound 24

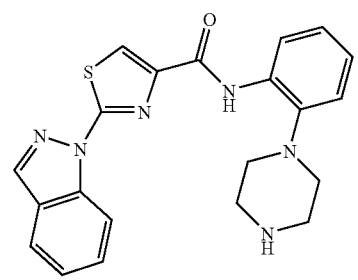

24

Using the method described in Example 24 and substituting indazole for pyrazole, Compound 24 was prepared as a dihydrochloride salt.

Example 26

Preparation of Compound 25

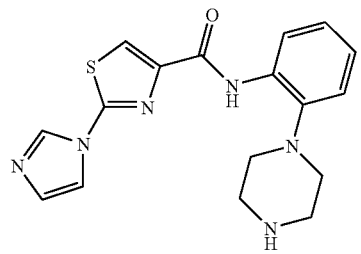

25

Using the method described in Example 24 and substituting imidazole for pyrazole, Compound 25 was prepared as a dihydrochloride salt.

Example 27

Preparation of Compound 26

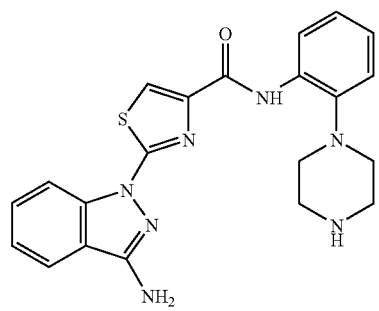

26

Using the method described in Example 24 and substituting 2-methyl-6,7-dihydro-5H-pyrrolo[3,4-d]pyrimidine dihydrochloride for pyrazole, Compound 26 was prepared as a dihydrochloride salt.

Example 28

Preparation of Compound 27

27

A 20 mL vial containing a stir bar was charged with 4-{2-[(2-bromo-thiazole-4-carbonyl)-amino]-phenyl}-piperazine-1-carboxylic acid tert-butyl ester (107 µmol, 50 mg), $Pd_2(DBA)_3$ (0.05 eq, 5.4 µmol, 4.9 mg), Xant-Phos (0.1 eq, 10.7 µmol, 6.2 mg), $K_3PO_4$ (2 eq, 214 µmol, 45.5 mg), 3-aminoindazole (2 eq, 214 µmol, 28.5 mg) and toluene (3 mL). The vial was flushed with argon, capped and sealed and then put in an oil bath at 140° C. The reaction was then allowed to stir at this temperature for about 18 hours. LC/MS confirms the presence of 2 products. The reaction mixture was concentrated in vacuo and the resulting residue was diluted with dichloromethane (2 mL) and filtered through celite. The filtrate was then purified using reverse-phase HPLC and the 2 separated products were characterized using LC/MS (the first product had a retention time=5.76 min, and m+1=520.24; the second product has a retention time=5.99 minutes, and m+1=520.35). The second product was diluted with a 9:1 mixture of TFA:$H_2O$ (2 mL) and the resulting solution was shaken for 2 hours at room temperature. The reaction mixture was concentrated in vacuo and the resulting residue was purified using reverse-phase HPLC and lyophilized with aqueous HCl (1M) to provide Compound 27 as a dihydrochloride salt.

Example 29

Preparation of Compound 28

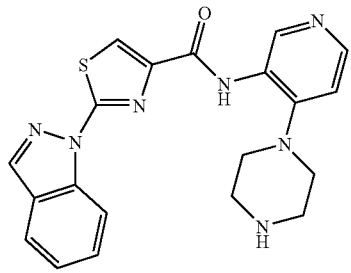

Using the method described in Example 24 and substituting 4-{3-[(2-Bromo-thiazole-4-carbonyl)-amino]-pyridin-4-yl}-1-Boc-piperazine for 4-{2-[(2-bromo-thiazole-4-carbonyl)-amino]-phenyl}-piperazine-1-carboxylic acid tert-butyl ester acid and indazole for pyrazole, Compound 28 was prepared as a dihydrochloride salt.

Example 30

Preparation of Compound 29

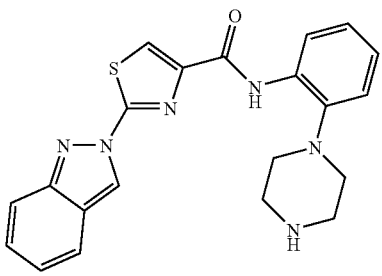

A 20 mL vial containing a stir bar (vial 1) was charged with a solution of 4-{2-[(2-bromo-thiazole-4-carbonyl)-amino]-phenyl}-piperazine-1-carboxylic acid tert-butyl ester acid (321 μmol, 150 mg). To this is added 2 mL 1,4-dioxane. A second 20 mL vial containing a stir bar (vial 2) was charged with a solution of indazole (3 eq, 963 μmol, 114 mg) and 4 mL 1,4-dioxane. To the solution in vial 2 was then added NaH (60% dispersion in mineral oil, 3 eq, 963 μmol, 38.5 mg). The resulting reaction was allowed to stir at room temperature for about 15 minutes, then the reaction mixture was added to the solution in vial 1. Vial 1 was then sealed, placed in an oil bath at 100° C. and the reaction mixture was allowed to stir at this temperature for about 5 hours. The reaction mixture was then concentrated in vacuo and the resulting residue was diluted with dichloromethane (2 mL) and filtered through celite. The resulting residue was purified using flash column chromatography on silica gel (eluent: gradient from 100% hexanes to 70% ethyl acetate in hexanes) provided a product which was collected and diluted with a 9:1 mixture of TFA:H$_2$O (3 mL) and the resulting solution was allowed to stir for 2 hours at room temperature. concentrated in vacuo and the resulting residue was purified by reverse-phase HPLC and shown to contain two products. The first product has a retention time of 3.73 minutes with a visible mass of m+1=405.23. This product was lyophilized with aqueous HCl to provide Compound 29 as a dihydrochloride salt (12.45 mg).

Example 31

Preparation of Compound 30

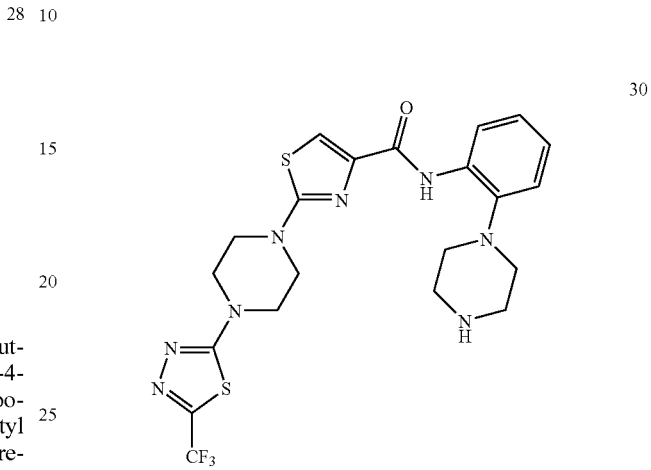

A 2 mL microwave vial was charged with a solution of 4-{2-[(2-bromo-thiazole-4-carbonyl)-amino]-phenyl}-piperazine-1-carboxylic acid tert-butyl ester (107 μmol, 50 mg) in acetonitrile (2 mL). To this solution was added a solution of 1-(5-Trifluoromethyl-[1,3,4]thiadiazol-2-yl)-piperazine (160 μmol, 38 mg) in DIEA (160 μmol, 28 μL) and the resulting reaction was microwaved at 180° C. for about 15 minutes. The reaction mixture was then concentrated in vacuo and the resulting residue was diluted with a 9:1 mixture of TFA:H$_2$O (2 mL) and the resulting solution was shaken for about 2 hours at room temperature. The reaction mixture was then concentrated in vacuo and the resulting residue was purified using reverse-phase HPLC and lyophilized with aqueous HCl to provide Compound 30 as a dihydrochloride salt (53.34 mg).

LCMS data and HPLC retention times for Illustrative Anilinopiperazine Derivatives are provided in the table below, wherein the compound numbers in Table 1 correspond to the compound numbering in the specification.

| Compound | Observed LCMS m/z (M + H) | HPLC-MS retention time (min) |
| --- | --- | --- |
| 1 | 407.28 | 2.56 |
| 2 | 480.33 | 4.06 |
| 3 | 420.40 | 4.24 |
| 4 | 427.23 | 3.72 |
| 5 | 456.29 | 4.37 |
| 6 | 424.28 | 2.93 |
| 7 | 396.29 | 3.27 |
| 8 | 406.26 | 4.13 |
| 9 | 410.29 | 2.36 |
| 10 | 466.26 | 3.91 |
| 11 | 426.26 | 4.11 |
| 12 | 420.27 | 4.21 |
| 13 | 486.26 | 3.82 |
| 14 | 374.25 | 3.28 |
| 15 | 450.12 | 3.72 |
| 16 | 476.32 | 3.75 |
| 17 | 524.26 | 4.11 |

| Compound | Observed LCMS m/z (M + H) | HPLC-MS retention time (min) |
|---|---|---|
| 18 | 480.32 | 4.05 |
| 19 | 498.22 | 3.84 |
| 20 | 498.25 | 3.81 |
| 21 | 407.28 | 2.70 |
| 22 | 406.21 | 3.48 |
| 23 | 355.33 | 3.20 |
| 24 | 405.28 | 3.89 |
| 25 | 355.27 | 2.31 |
| 26 | 422.27 | 3.28 |
| 27 | 420.10 | 3.45 |
| 28 | 406.12 | 2.31 |
| 29 | 405.23 | 3.73 |
| 30 | 525.21 | 3.85 |
| 31 | 487.5 | NA |

NA = not available

Example 32

Preparation of Compound 45

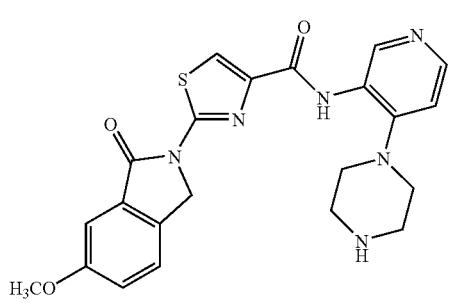

Using the method described in Example 24 and substituting 4-{3-[(2-Bromo-thiazole-4-carbonyl)-amino]-pyridin-4-yl}-1-Boc-piperazine for 4-{2-[(2-bromo-thiazole-4-carbonyl)-amino]-phenyl}-piperazine-1-carboxylic acid tert-butyl ester acid (compound B) and 6-methoxy-2,3-dihydro-isoindol-1-one, Compound 45 was prepared as a dihydrochloride salt.

Example 33

Preparation of Compound 43

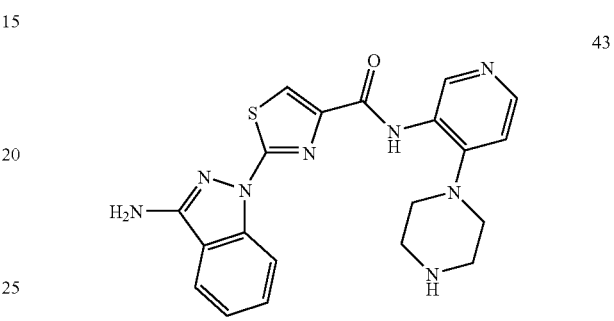

Using the method described in Example 24 and substituting 4-{3-[(2-Bromo-thiazole-4-carbonyl)amino]-pyridin-4-yl}-1-Boc-piperazine for 4-{2-[(2-bromo-thiazole-4-carbonyl)-amino]-phenyl}-piperazine-1-carboxylic acid tert-butyl ester acid and 3-amino indazole, Compound 43 was prepared as a trihydrochloride salt.

Using the same procedure and the appropriate reactants, the following compounds were prepared.

| No. | Structure | MS m/z (M + H) | HPLC MS $t_R$ |
|---|---|---|---|
| 84 | 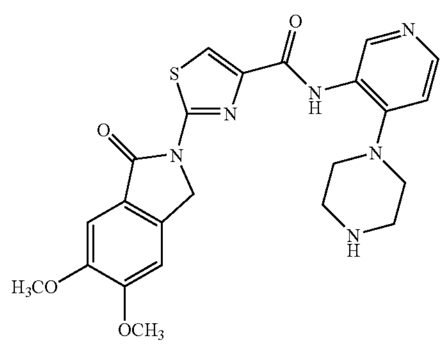 | 481.1 | 1.04 |
| 96 | 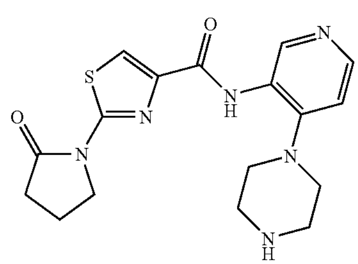 | 373.1 | 0.60 |

-continued

| No. | Structure | MS m/z (M + H) | HPLC MS t_R |
|---|---|---|---|
| 99 | 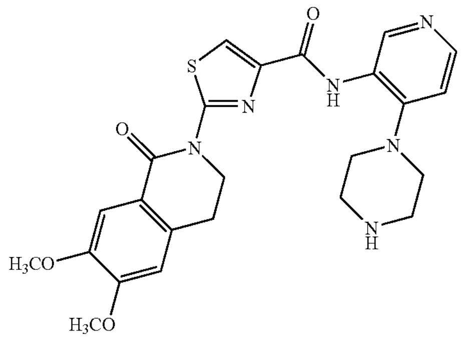 | 495.1 | 0.92 |
| 100 | 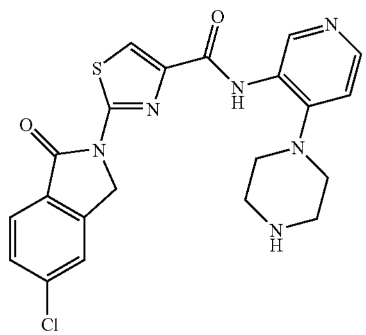 | 455.0 | 0.98 |
| 106 | 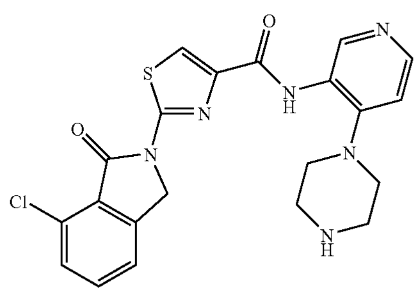 | 455.0 | 0.97 |
| 107 | 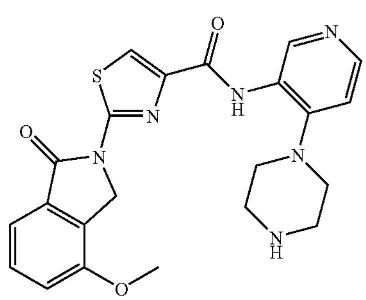 | 451.1 | 1.06 |
| 108 | 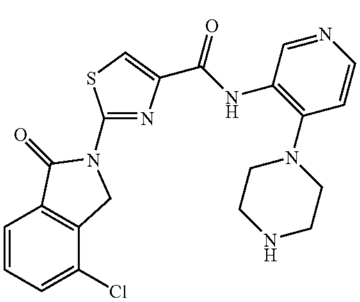 | 455.0 | 0.95 |

-continued

| No. | Structure | MS m/z (M + H) | HPLC MS $t_R$ |
|---|---|---|---|
| 109 | 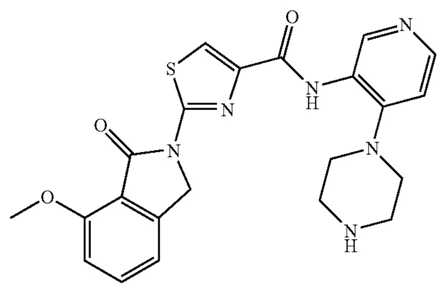 | 451.1 | 0.88 |
| 115 | 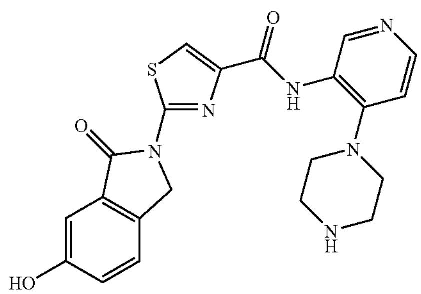 | 437.1 | 0.74 |
| 116 | 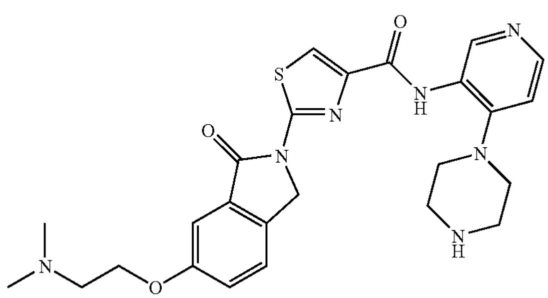 | 508.1 | 0.65 |
| 119 | 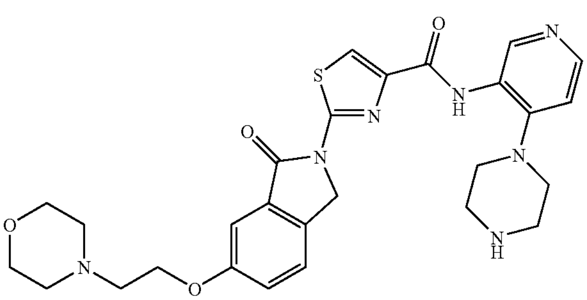 | 550.2 | 0.66 |
| 121 | 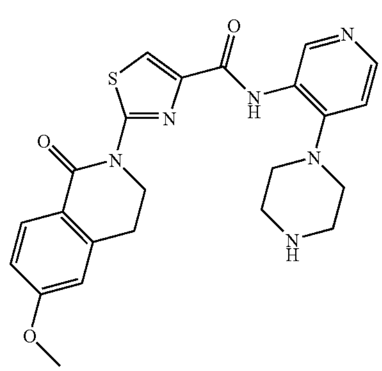 | 465.1 | 1.00 |

| No. | Structure | MS m/z (M + H) | HPLC MS $t_R$ |
|---|---|---|---|
| 86 | 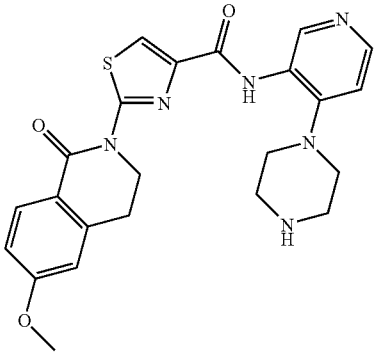 | 465.1 | 1.00 |
| 138 | 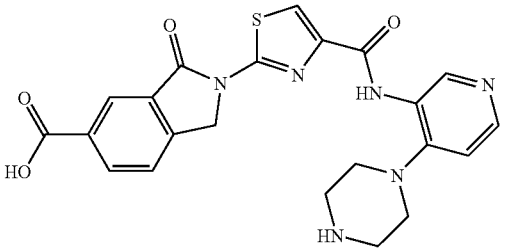 | 465.0 | 0.72 |
| 139 | 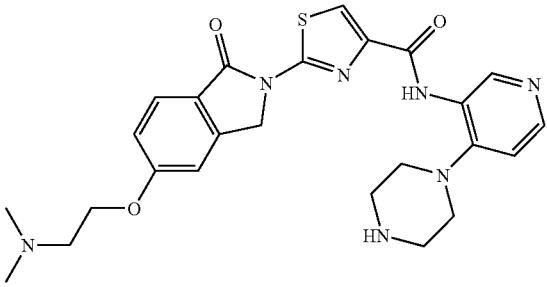 | 508.1 | 0.69 |
| 147 | 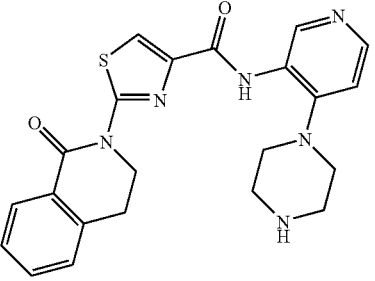 | 435.1 | 0.98 |
| 149 | 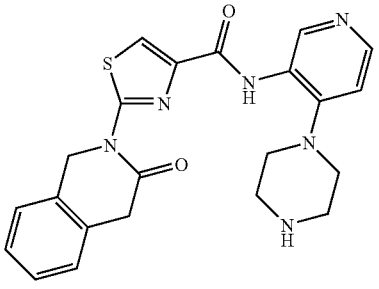 | 435.1 | 0.98 |

| No. | Structure | MS m/z (M + H) | HPLC MS $t_R$ |
|---|---|---|---|
| 150 | 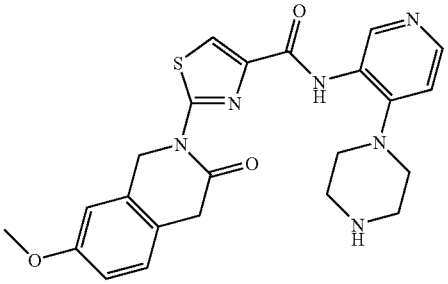 | 465.1 | 1.00 |
| 164 | 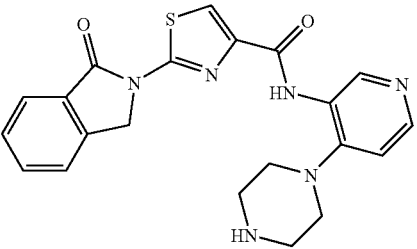 | 421.1 | 0.88 |
| 165 | 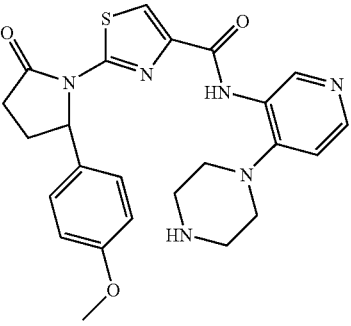 | 479.1 | 0.93 |
| 169 | 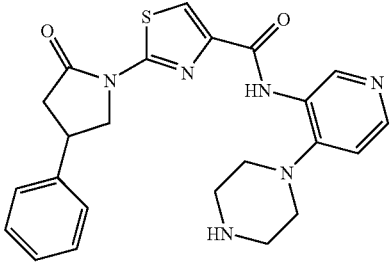 | 449.2 | 0.97 |
| 186 | 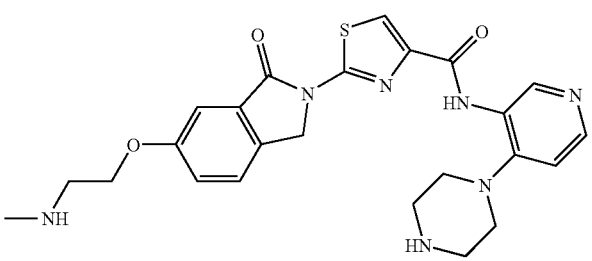 | 494.1 | 0.63 |

-continued

| No. | Structure | MS m/z (M + H) | HPLC MS $t_R$ |
|---|---|---|---|
| 187 | 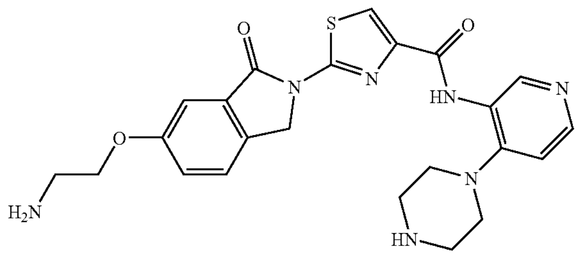 | 480.0 | 0.62 |
| 188 | 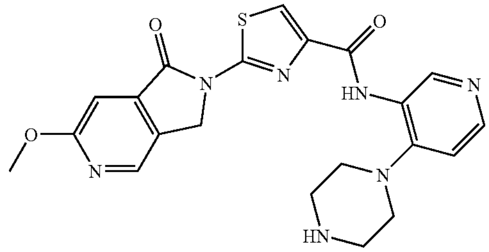 | 452.1 | 0.88 |
| 190 | 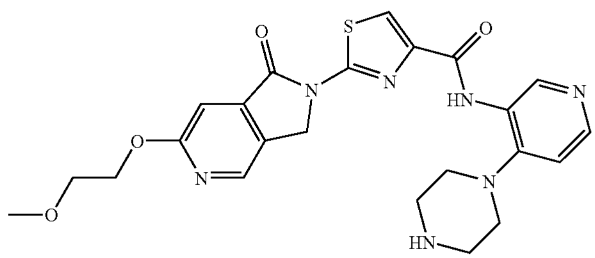 | 495.1 | 0.92 |
| 191 | 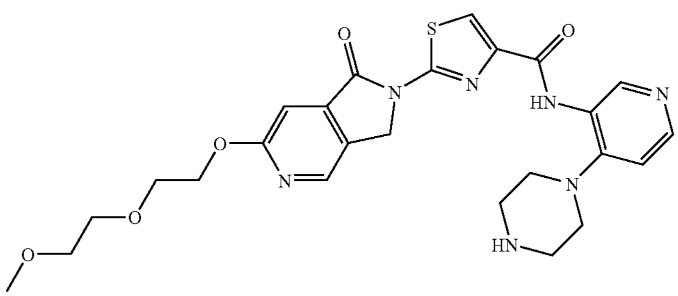 | 539.2 | 0.93 |
| 192 | 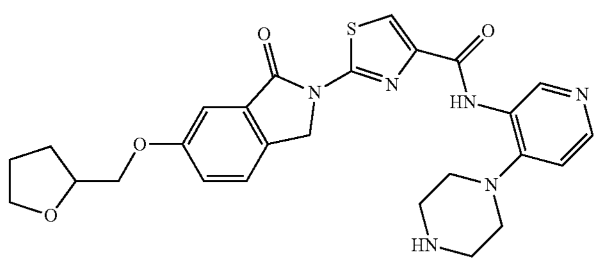 | 521.2 | 1.00 |

-continued

| No. | Structure | MS m/z (M + H) | HPLC MS t_R |
|---|---|---|---|
| 196 | 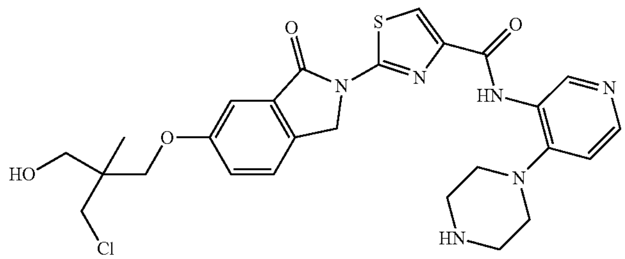 | 557.2 | 0.97 |
| 197 | 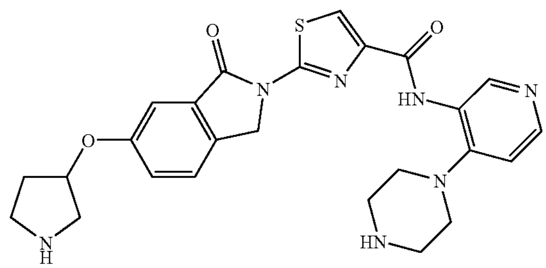 | 506.2 | 0.65 |
| 198 | 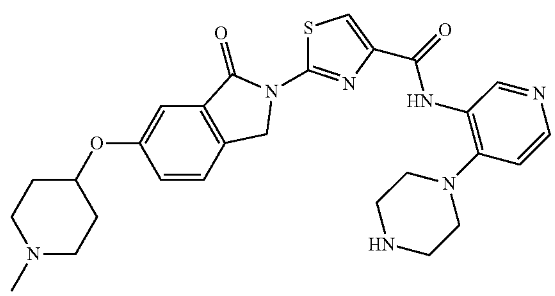 | 534.2 | 0.86 |
| 199 | 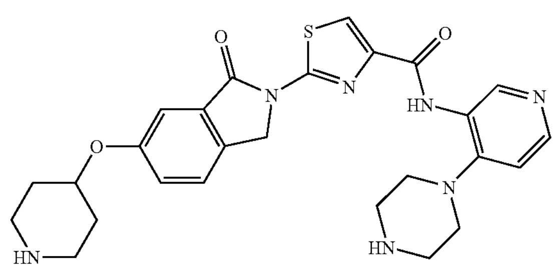 | 520.2 | 0.68 |
| 200 | 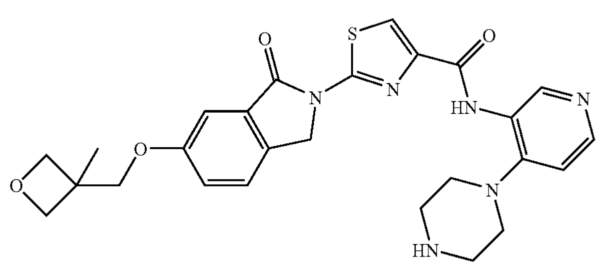 | 521.2 | 1.03 |

-continued

| No. | Structure | MS m/z (M + H) | HPLC MS t$_R$ |
|---|---|---|---|
| 205 | 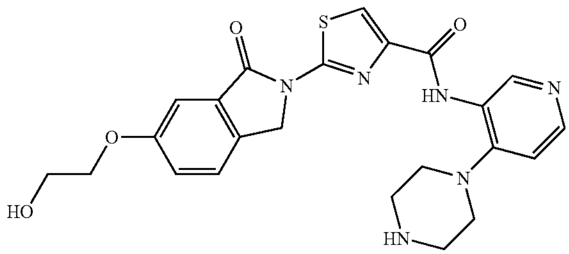 | 481.1 | 0.93 |
| 234 | 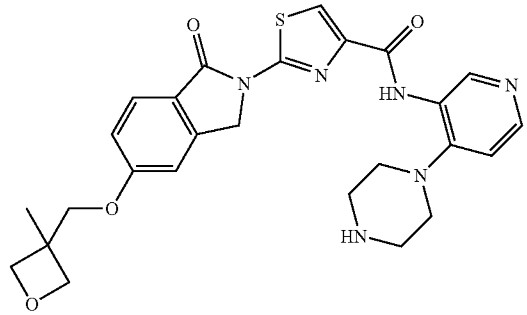 | 521.2 | 1.01 |
| 235 | 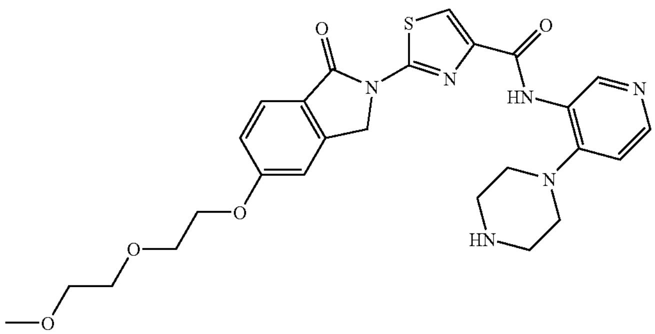 | 539.2 | 0.94 |
| 236 | 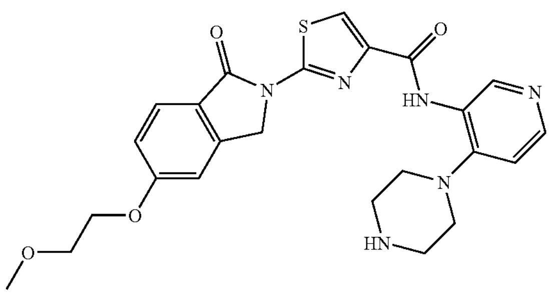 | 495.1 | 0.92 |
| 237 | 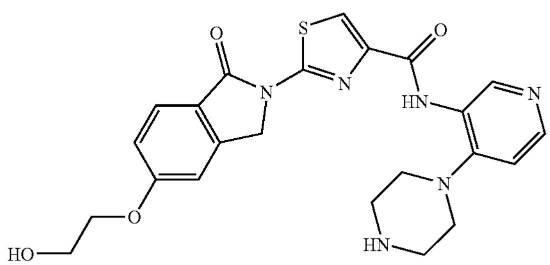 | 481.1 | 0.90 |

| No. | Structure | MS m/z (M + H) | HPLC MS $t_R$ |
|---|---|---|---|
| 238 | 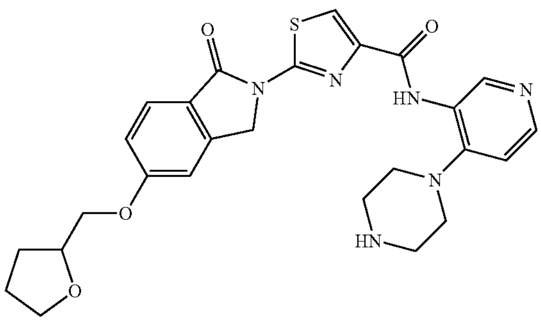 | 521.2 | 1.01 |
| 263 | 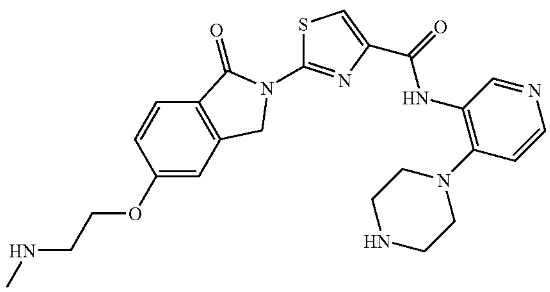 | 494.1 | 0.64 |
| 287 | 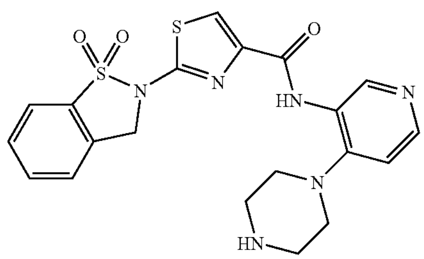 | 457.1 | 0.81 |

Example 34

Preparation of intermediate compound 34C

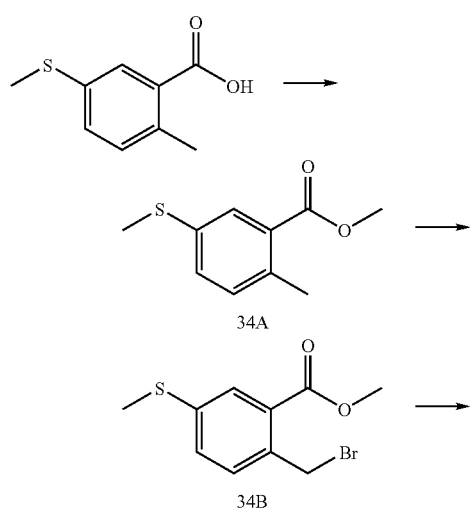

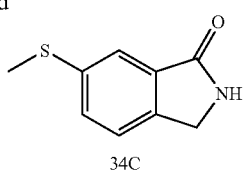

Into a solution of 2-Methyl-5-methylsulfanyl-benzoic acid (250 mg, 1.37 mmol) in 12 mL (1:1 benzene/methanol) mixture was added 2.74 mmol of (Trimethylsilyl)diazomethane. Reaction was stirred for 1.5 hours. Solvent was removed to yield 34A (2-Methyl-5-methylsulfanyl-benzoic acid methyl ester) as yellow oil which was used as is in subsequent step.

Into solution of 34A (1.034 g, 5.27 mmol) in 15 mL of carbon tetrachloride was added N-Bromosuccinimide (0.685 g, 3.85 mmol) and benzoyl peroxide (46.63 mg, 0.19 mmol). The reaction mixture was refluxed at 80° C. for 6 hours. Mixture was cooled and precipitate removed via filtration. Organic layer collected was concentrated under vacuo. Resulting crude compound 34B was dissolved in 7N $NH_3$ in methanol (20 mL) and heated to 85° C. in a sealed vessel for about 15 hours. Solvent was removed and crude was purified on flash silica column using ethyl acetate/hexane solvent system to provide 158 mg of compound 34A as a white powder. NMR (H¹) δ 2.51 (3H), 4.30 (2H), 7.45-7.47 (m, 3H).

Example 35

Preparation of Intermediate Compound 35A

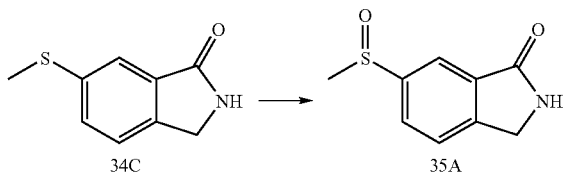

To solution of compound 34C (40 mg, 0.223 mmol) in 5 mL dichloromethane was added 3-chloroperoxybenzoic acid (55 mg, 0.223 mmol) and the reaction was stirred at room temperature for 3 hours. The reaction mixture was then cooled in an ice bath and the precipitated formed was removed via filtration. The filtrated was washed with water, dried over anhydrous sodium sulfate, filtered and concentrated in vacuo to provide compound 35A, which was used without further purification. NMR of crude indicate a shift of S—CH3 peak from 2.51 to 2.84 ppm Example 36

Preparation of Intermediate Compound 36A

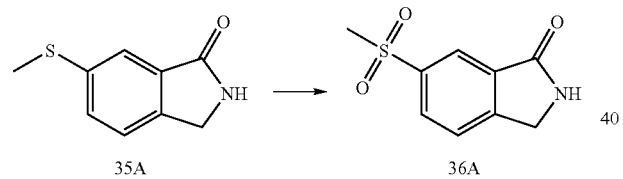

Using the method described in Example 35, compound 35A was converted to compound 36A.

Example 37

Preparation of Intermediate Compound 37A

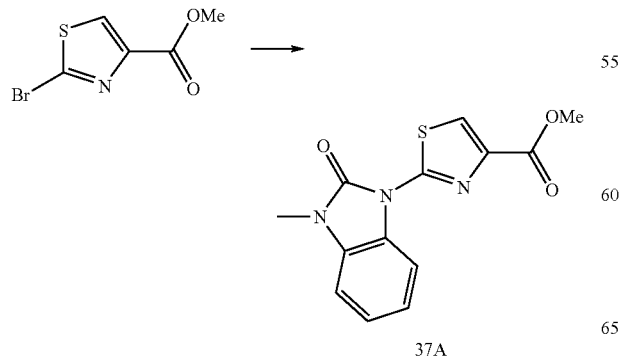

To a solution of 2-bromo-4-carbomethoxythiazole (1.5 g, 6.78 mmol) in dioxane (80 mL) at room temperature was added 1-methyl-2-benzimidazolone (1.0 g, 6.78 mmol) followed by CuI (0.13 g, 0.68 mmol), K₂CO₃ (1.0 g, 7.47 mmol), trans-N,N-dimethylcyclohexane (0.21 mL, 1.35 mmol). The mixture was degassed under house vacuum and filled with N₂ six times and heated to 90° C. The mixture was stirred for 12 hours, cooled to rt, and concentrated under reduced pressure. The crude product was purified using flash chromatography using a 20:1 mixture of CH₂Cl₂/MeOH to provide 1.8 g (92% yield) of the title compound as an off-white solid. LC-MS [M+H]=290.2; 98% purity.

Example 38

Preparation of Intermediate Compound 38A

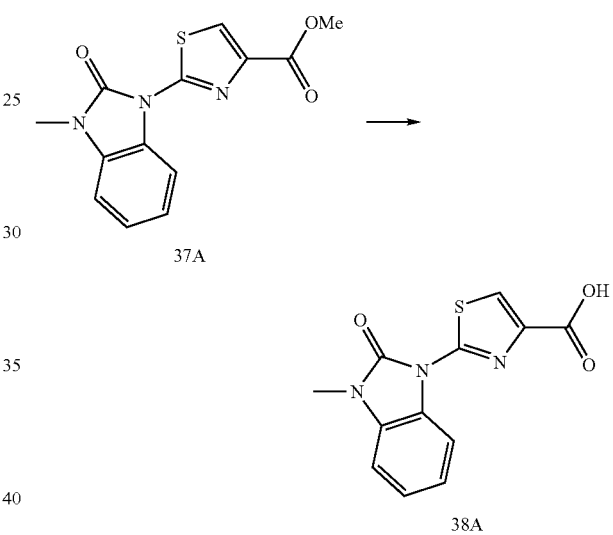

To a solution of compound 37A (0.18 g, 0.59 mmol) in THF (1.5 mL) at 0° C. was added dropwise a 1M solution of LiOH (1.18 mL). The resulting reaction was allowed to warm to room temperature and allowed to stir for 12 hours. The mixture was concentrated under reduced pressure and taken up in H₂O (2 mL). The mixture was treated with concentrated HCl until pH=4 was attained. The mixture was concentrated under reduced pressure to provide compound 38A (0.15 g, 92% yield) as an orange solid which was used without further purification. LC-MS [M+H]=276.2; 96% purity Example 39

Preparation of Intermediate Compound 39A

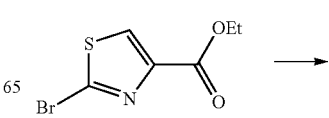

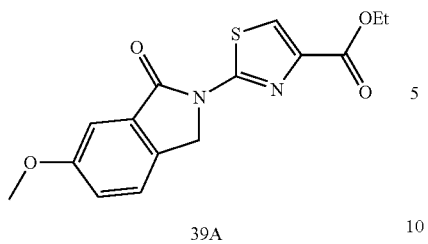

39A

To a pressure tube charged with 2-bromo-4-carboethoxythiazole (2.5 g, 10.6 mmol) and a stir bar was added 6-methoxyisoindolin-1-one (2.1 g, 12.7 mmol), $K_3PO_4$ (4.9 g, 23.3 mmol), $Pd_2(dba)_3$ (0.58 g, 0.64 mmol), Xant-Phos (0.62 g, 1.1 mmol). Dioxane (20 mL) was added and $N_2$ was bubbled thru the solution for 10 min before the vessel was capped. The mixture stirred at 105° C. for 12 h and was cooled to rt. The mixture was filtered thru a pad of Celite and was washed with $CH_2Cl_2$/MeOH (20:1; 2×10 mL). The resulting filtrate was concentrated under reduced pressure and place under high vacuum. The crude product was purified using flash chromatography using a gradient from $CH_2Cl_2$ to 97:3 $CH_2Cl_2$/acetone to provide 3.1 g (91% yield) of compound 39A as a brown solid. LC-MS [M+H]=400.2; 98% purity.

Example 40

Preparation of Intermediate Compound 40A

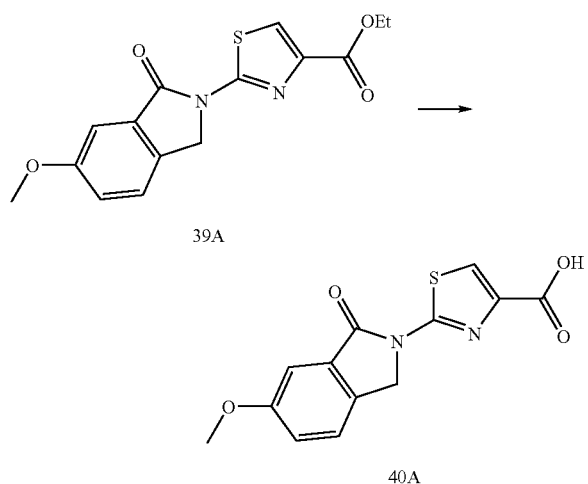

39A

40A

To a solution of the compound 39A (0.67 g, 2.1 mmol) in THF/MeOH/$H_2O$ (2:2:1; 12.5 mL total) at room temperature was added LiOH $H_2O$ (97 mg, 2.3 mmol) in one portion. The resulting solution was stirred at 40° C. for 12, cooled to rt, and concentrated under reduced pressure. The crude material and taken up in $H_2O$ (20 mL) and was treated with concentrated HCl until pH 3 was attained. The mixture was concentrated under reduced pressure to provide 0.58 g (95% yield) of compound 40A a pale white solid which was used without further purification. MS [M+H]=290.9

Example 41

Preparation of Intermediate Compound 41A

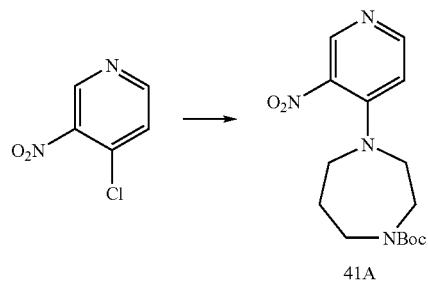

41A

To a solution of 4-chloro-3-nitropyridine (2.0 g, 12.5 mmol) in dioxane (25 mL) was added DIPEA (3.2 mL, 18.7 mmol) followed by Boc-homopiperazine (3.0 g, 15.0 mmol). The resulting mixture was stirred at 110° C. for 12 hours, cooled to rt, and concentrated to dryness. The mixture was partitioned between sat. aq $NaHCO_3$ (4 mL) and $CH_2Cl_2$ (15 mL) and the layers were separated. The aqueous layer was extracted with $CH_2Cl_2$ (2×15 mL) and the organic layers were combined. The organic layer was washed with brine (1×4 mL), dried ($Na_2SO_4$), filtered, and concentrated under reduced pressure. The crude product was purified using flash chromatography using a 50:1 mixture of $CH_2Cl_2$/MeOH as eluent to provide 3.7 g (93% yield) of compound 41A as a yellow solid. LC-MS [M+H]=323.2; 98% purity.

Example 42

Preparation of Intermediate Compounds 42A-42D

Intermediate compounds 42A-42D, shown in the table below, were prepared by reacting the indicated chloro derivatives with the indicated amines according to the method described in Example 41.

| Chloro derivative | Amine | Product | 1. Yield (%) 2. LC-MS (M + H) |
|---|---|---|---|
| ![3-nitro-4-chloropyridine] | HN(piperazine)NBoc | ![42A product] | 1. 98 2. 309.2 |

42A stirred for 12 h at room temperature and was purged to $N_2$. The reaction mixture was filtered through a pad of Celite which was washed with the MeOH/EtOAc (1:1; 3×25 mL). The resultant filtrate was concentrated under reduced pressure and placed under high vacuum to provide 3.2 g (99% yield) of compound 43A as a yellow semisolid. LC-MS [M+H]=293.2; 87% purity. This material was used without further purification.

Example 44

Preparation of Intermediate Compounds 44A-44C

Following the method described in Example 43, the indicated nitro derivatives were converted to the corresponding amino derivatives 44A-44C.

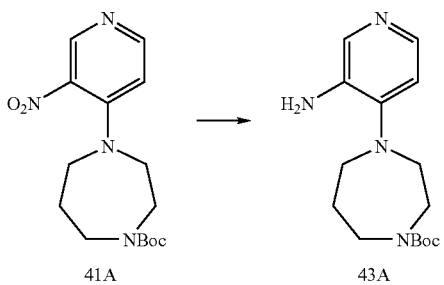

| Chloro derivative | Amine | Product | 1. Yield (%) 2. LC-MS (M + H) |
|---|---|---|---|
| | | 42B | 1. 80 2. 309.2 |
| | | 42C | 1. 94 2. 326.1 |
| | | 42D | 1. 98 2. 333.2 |

Example 43

Preparation of Intermediate Compound 43A

41A → 43A

To a mixture of compound 41A (3.5 g, 11.1 mmol) in MeOH/EtOAc (1:1; 100 mL) at room temperature was added 5% Pd/C (1.2 g). The resulting mixture was degassed and filled with $N_2$ and finally with $H_2$ (balloon). The mixture was

| Nitro derivative | Product | 1. Yield (%) 2. LC-MS (M + H) |
|---|---|---|
| | 44A | 1. 98 2. 309.2 |
| | 44B | 1. 80 2. 309.2 |
| | 44C | 1. 94 2. 326.1 |

Example 45

Preparation of Intermediate Compound 45A

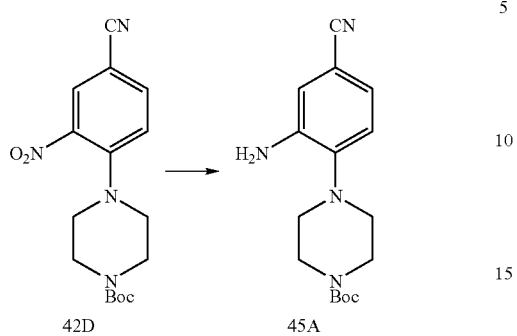

To a mixture of compound 42D (0.5 g, 1.5 mmol) in THF (15 mL) at room temperature was added ammonium formate (0.95 g, 15.1 mmol) followed by 10% Pd/C (50 mg). The resulting mixture heated to 65° C., stirred for 30 min, and was cooled to rt. The reaction mixture was filtered through a pad of Celite which was washed with the EtOH (2×5 mL) and $CH_2Cl_2$ (2×5 mL). The resultant filtrate was concentrated under reduced pressure and placed under high vacuum to provide 0.46 g (99% yield) of compound 45A as a yellow semisolid. LC-MS [M+H]=303.2; 99% purity. This material was used without further purification.

Example 46

Preparation of Intermediate Compound 46A

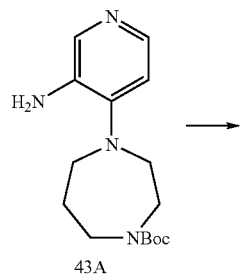

To a solution of compound 43A (1.1 g, 5.2 mmol) in DMF (10 mL) was added N,N-diisopropylethylamine (2.7 ml, 15.4 mmol) and HATU (2.2 g, 5.6 mmol) in DMF (10 mL) was added aniline (1.5 g, 5.2 mmol) from Preparative Example 10. The reaction mixture was stirred at room temperature for 72 h and then concentrated in vacuo. The crude residue was taken up in EtOAc (50 mL) and sat. aq $NaHCO_3$ (2 mL) was added. The layers were separated and the organic layer was washed with sat. aq. $NaHCO_3$ (1×2 mL) and brine (1×2 mL). The organic layer was dried ($Na_2SO_4$), filtered, and concentrated under reduced pressure. The crude product was purified using preparative thin-layer chromatography using a 40:1 mixture of $CH_2Cl_2$/MeOH as eluent to provide 1.9 g (75% yield) of compound 46A as a light yellow solid as the title compound. LC-MS [M+H]=483.2; 89% purity.

Example 47

Preparation of Intermediate Compounds 47A-47C

Following the method described in Example 46, utilizing 2-bromo-thiazole-4-carboxylic acid and the indicated amines, intermediate compounds 47A-47C were made.

| Amine | Product | 1. Yield (%)<br>2. LC-MS (M + H) |
|---|---|---|
| 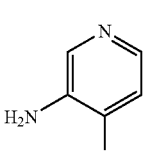 | 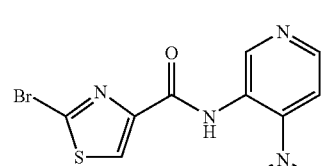 47A | 1. 63<br>2. 470.3 |

-continued

| Amine | Product | 1. Yield (%)<br>2. LC-MS (M + H) |
|---|---|---|
| 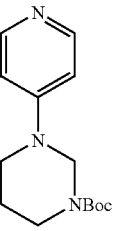 | 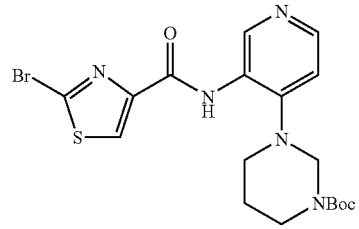 47B | 1. 35<br>2. 470.3 |
| 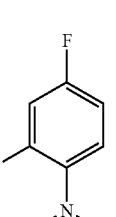 | 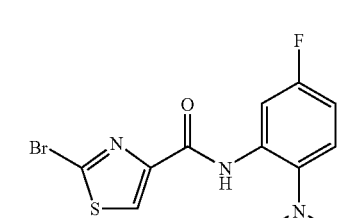 47C | 1. 67<br>2. 470.3 |

Example 48

Preparation of Intermediate Compound 48A

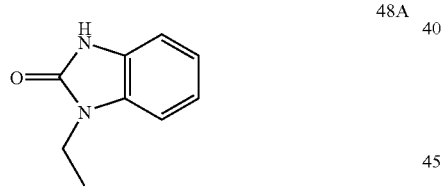

48A

Compound 48A was prepared using the method described in US Patent Publication No. 2007/0072928.

Example 49

Preparation of Intermediate Compound 49A

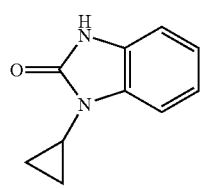

49A

Compound 49A was prepared using the method described in US Patent Publication No. 2007/0072928.

Example 50

Preparation of Intermediate Compound 50A

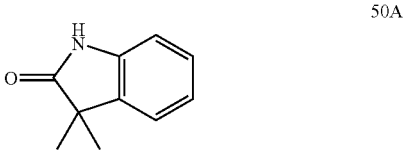

50A

Compound 50A was prepared using the method described in *J. Med. Chem.* 1986, 29, 1832.

Example 51

Preparation of Intermediate Compound 51A

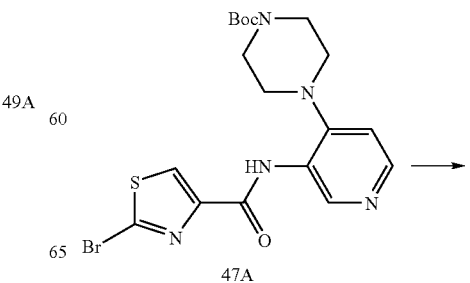

47A

-continued

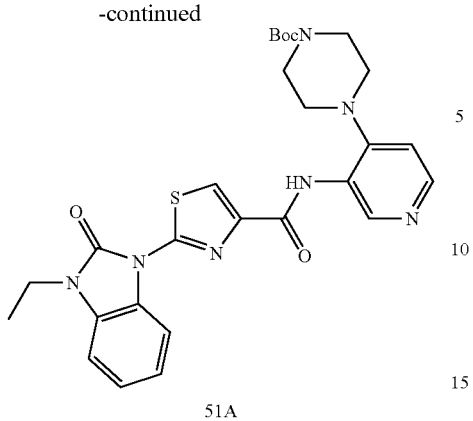

51A

To a solution of the compound 47A (0.35 g, 0.75 mmol) was added compound 48A (0.12 g, 0.75 mmol), CuI (14 mg, 0.075 mmol), K$_2$CO$_3$ (114 mg, 0.83 mmol), and trans-N,N-dimethylcyclohexane (23 μL, 0.15 mmol). The mixture was degassed under house vacuum and filled with N$_2$ six times and heated to 90° C. The mixture was stirred for 12 hours, cooled to rt, and concentrated under reduced pressure. The crude product was taken up in EtOAc (2 mL) and filtered. The resultant solid was washed with EtOAc (2×2 mL) and H$_2$O (2×2 mL), then dried under high vacuum to provide 0.25 g (61% yield) of compound 51A as a tan solid. MS (M+H)=550.2.

Example 52

Preparation of Intermediate Compound 52A

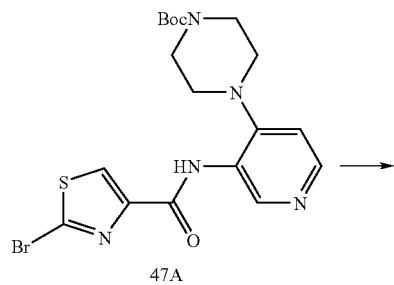

47A

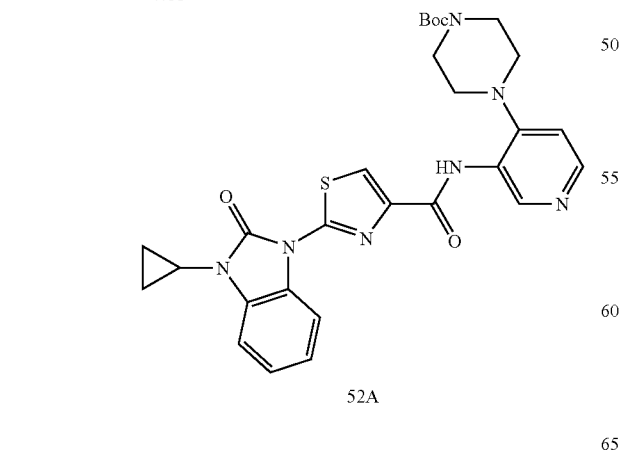

52A

Compound 47A (0.35 g, 0.75 mmol) was reacted with compound 49A (0.12 g, 0.75 mmol) according to the method described in Example 51 to provide 0.28 g (66% yield) of compound 52A as a light yellow solid. MS (M+H)=562.3.

Example 53

Preparation of Intermediate Compound 53A

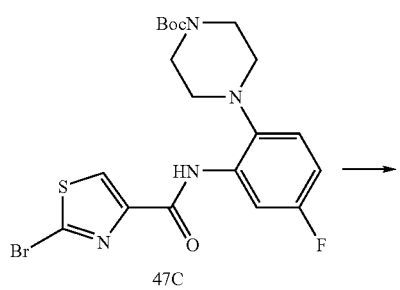

47C

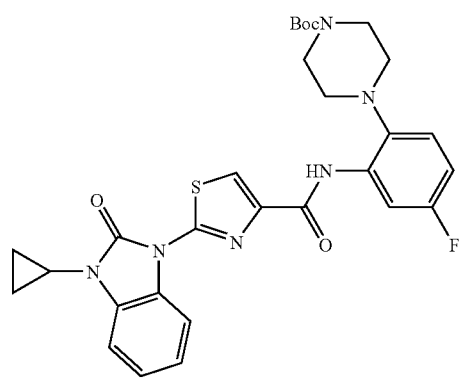

53A

Compound 47C (0.35 g, 0.72 mmol) was reacted with compound 49A (0.13 g, 0.72 mmol) according to the method described in Example 51 to provide 0.28 g (66% yield) of compound 53A as a gray solid. MS (M+H)=579.1.

Example 54

Preparation of Intermediate Compound 54A

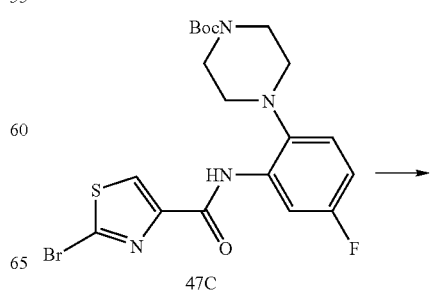

47C

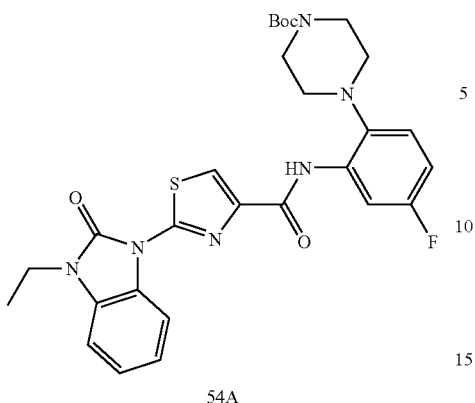

54A

Compound 47C (0.35 g, 0.72 mmol) was reacted with compound 48A (0.12 g, 0.72 mmol) according to the method described in Example 51 to provide 0.29 g (71% yield) of compound MA as an orange solid. MS (M+H)=567.1.

Example 55

Preparation of Intermediate Compound 55A

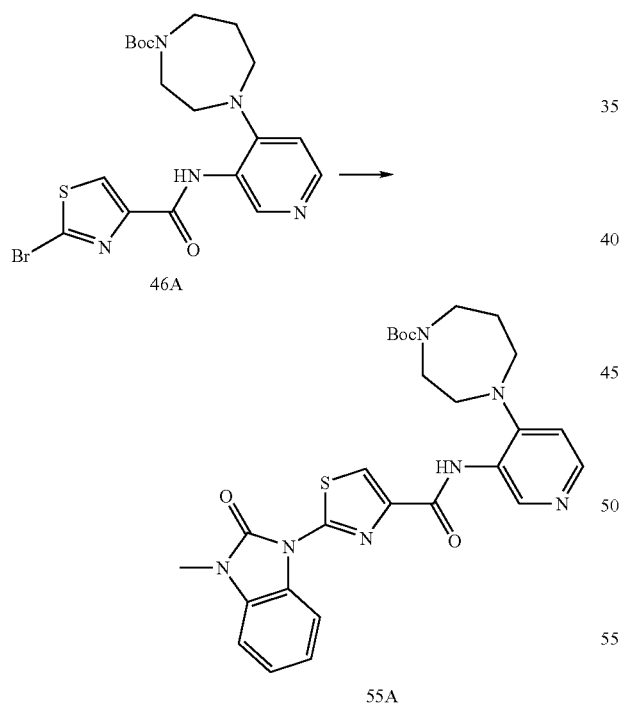

55A

Compound 46A (0.10 g, 0.21 mmol) was reacted with 1-methyl-2-benzimidazolone (31 mg, 0.21 mmol) according to the method described in Example 51 to provide 0.11 g (95% yield) of compound 55A as an orange solid. LC-MS [M+H]=550.3; 99% purity.

Example 56

Preparation of Intermediate Compound 56A

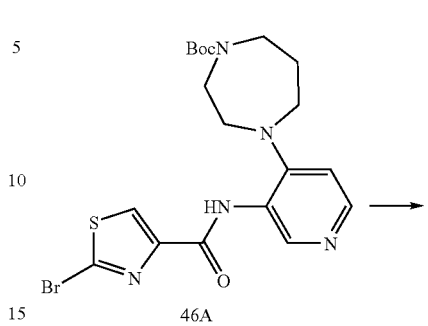

56A

Compound 46A (0.25 g, 0.52 mmol) was reacted 6-methoxyisoindolin-1-one (93 mg, 0.57 mmol) according to the method described in Example 51 to provide 0.28 g (96% yield) of compound 56A as an orange solid. LC-MS [M+H]= 565.3; 80% purity.

Example 57

Preparation of Intermediate Compound 57A

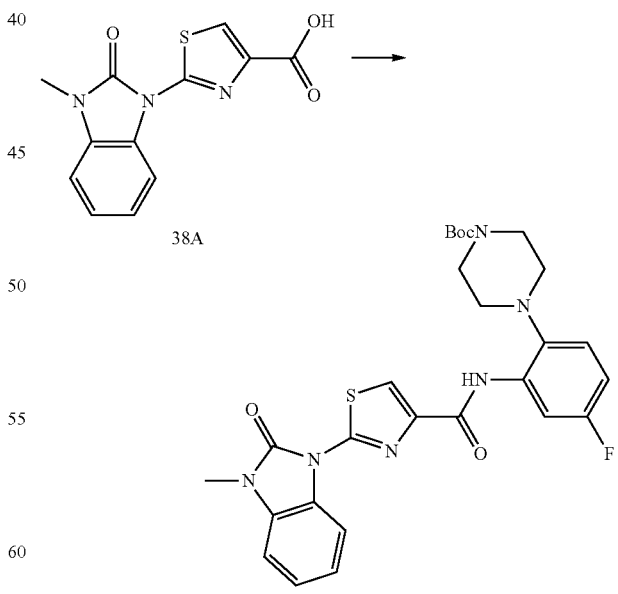

57A

Compound 38A (0.15 g, 0.55 mmol) was reacted with compound 44C (0.12 g, 0.72 mmol) according to the method described in Example 58 below to provide 0.29 g (71% yield) of compound 57A as an orange solid. MS (M+H)=567.1.

Example 58

Preparation of Intermediate Compound 58A

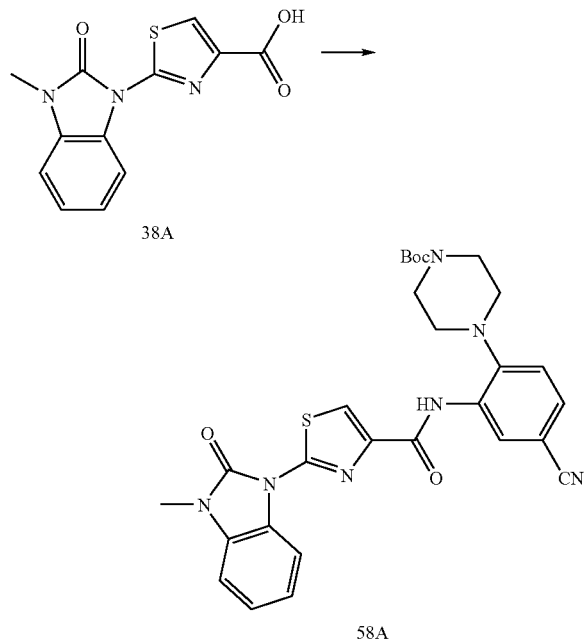

To a solution of compound 38A (0.10 g, 0.36 mmol) in CH$_2$Cl$_2$ (4 mL) at room temperature was added oxalyl chloride (61 µL, 0.72 mmol) followed by DMF (3 drops). The mixture was stirred for 1 h whereupon an addition portion of oxalyl chloride (61 µL, 0.72 mmol) and DMF (3 drops) were added. After an additional 1 hours, the mixture was concentrated under reduced pressure and redissolved in CH$_2$Cl$_2$ (3 mL). DIPEA (0.19 mL, 1.1 mmol) was added followed by addition of compound 45A (0.12 g, 0.42 mmol) and the mixture was stirred for 12 hours. The reaction mixture was concentrated to dryness and was partitioned between sat. aq NaHCO$_3$ (3 mL) and CH$_2$Cl$_2$ (10 mL). The layers were separated, the aqueous layer was extracted with CH$_2$Cl$_2$ (2×10 mL), and the organic layers were combined. The organic layer was washed with brine (1×4 mL), dried (Na$_2$SO$_4$), filtered, and concentrated under reduced pressure. The crude product was purified using flash chromatography using a 50:1 mixture of CH$_2$Cl$_2$/MeOH as eluent to provide 0.10 (50% yield) of compound 58A as a yellow semisolid. MS [M+H]=560.2.

Example 59

Preparation of Intermediate Compound 59A

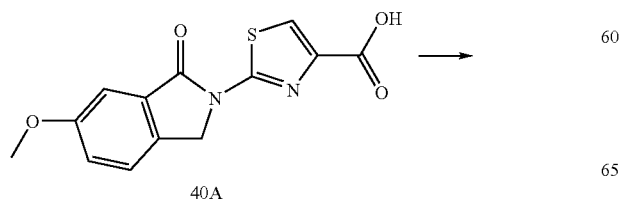

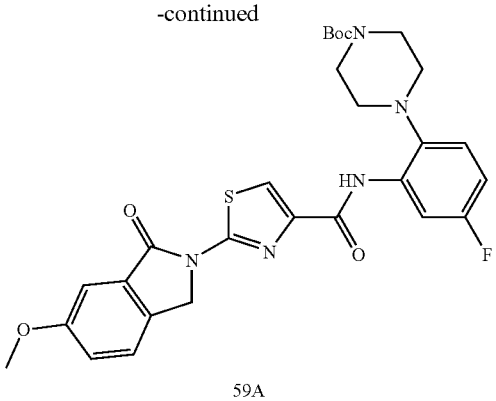

To a solution of compound 40A (0.15 g, 0.52 mmol) in DMF (2 mL) was added compound 44C (0.17 g, 0.57 mmol), followed by N-methylmorpholine (0.17 mL, 1.56 mmol) and PyBop (0.54 g, 1.1 mmol). The resulting mixture was stirred for 72 h at room temperature and concentrated under reduced pressure. The crude residue was taken up in EtOAc (8 mL) and sat. aq NaHCO$_3$ (3 mL) was added. The layers were separated and the aqueous layer was extracted with EtOAc (2×8 mL). The organic layers were combined and washed with brine (1×5 mL). The organic layer was dried (Na$_2$SO$_4$), filtered, and concentrated under reduced pressure. The crude product was purified using preparative thin-layer chromatography using a 2:1 mixture of hexanes/EtOAc as eluent to provide 40 mg (14% yield) of compound 59A a light yellow solid. LC-MS [M+H]=568.3; 89% purity.

Example 60

Preparation of Intermediate Compound 60A

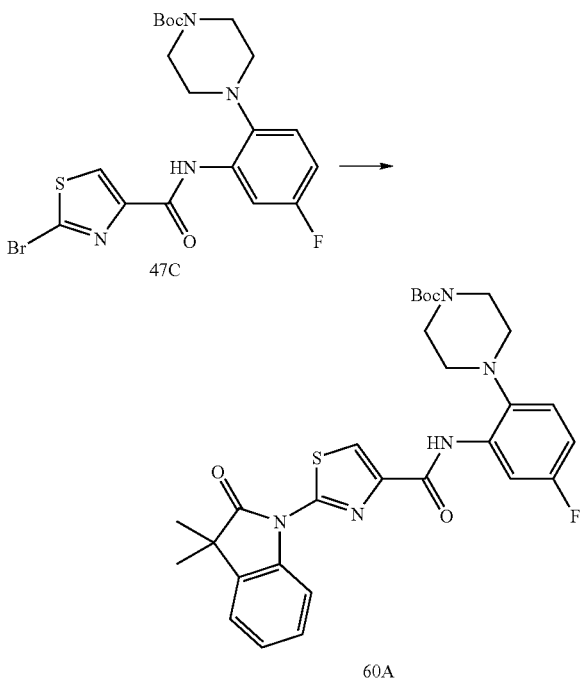

To a solution of compound 47C (0.30 g, 0.61 mmol) was added compound 50A (98 mg, 0.61 mmol), CuI (58 mg, 0.31 mmol), K$_3$PO$_4$ (263 mg, 1.24 mmol), and 1,2-trans-diamino cyclohexane (73 μL, 0.61 mmol). The mixture was diluted with dioxane (4 mL) and degassed under house vacuum and filled with N$_2$ six times. The reaction mixture was heated to 100° C., stirred for 12 hours, cooled to rt, and concentrated under reduced pressure. The crude product was taken up in a 20:1 mixture of CH$_2$Cl$_2$/MeOH (5 mL), filtered and concentrated under reduced pressure. The residue from the filtrate was purified using preparative thin-layer chromatography using a 3:1 mixture of hexanes/EtOAc as eluent to provide 125 mg (36% yield) of compound 60A as an off-white solid. LC-MS [M+H]=566.3; 98% purity.

Example 61

Preparation of Intermediate Compound 61A

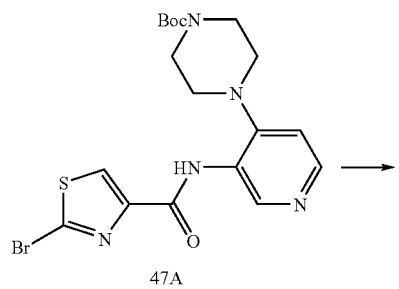

47A

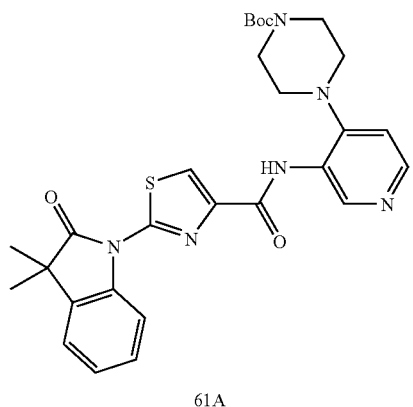

61A

Using the method described in Example 60, compound 47A (0.35 g, 0.75 mmol) was reacted with compound 50A (0.12 g, 0.75 mmol) to provide 0.15 g (36% yield) of compound 61A as a brown solid. LC-MS [M+H]=549.3; 90% purity.

Example 62

Preparation of Compound 258

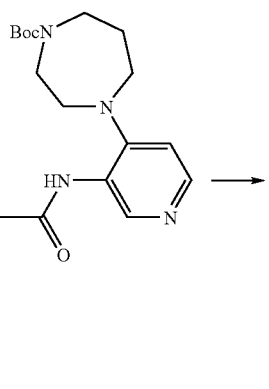

55A

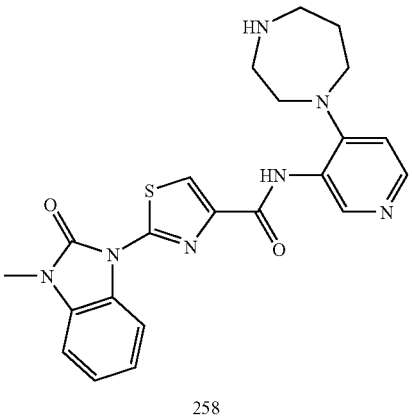

258

To a solution of compound 55A (42 mg, 0.08 mmol) in CH$_2$Cl$_2$ (3 mL) at room temperature was added TFA (1 mL). The mixture was stirred for 3 hours at room temperature and was concentrated under reduced pressure. The crude product was taken up in 7M NH$_3$ in MeOH (5 mL), stirred for 2 hours, and concentrated under reduced pressure. The crude product was purified using preparative thin-layer chromatography using a 12:1 mixture of CH$_2$Cl$_2$/MeOH (7M NH$_3$) as eluent to provide 29 mg (85% yield) of compound 258 as a pale yellow solid. mp 152-155° C., LC-MS [M+H]=450.1; 95% purity.

Example 63

Preparation of Compounds 229-232, 239, 256, 288, 301 and 313

Using the methods described in Examples 60 and 62, and utilizing the Boc adducts indicated, the following illustrative compounds of the invention were made.

| Boc adduct | Product | 1. Yield (%)  2. LC-MS  3. mp (° C.) |
|---|---|---|
| 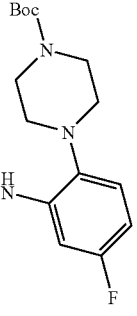 | 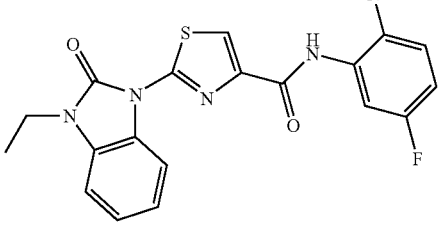  255 | 1. 90  2. 467.3  3. 242-244 |
| 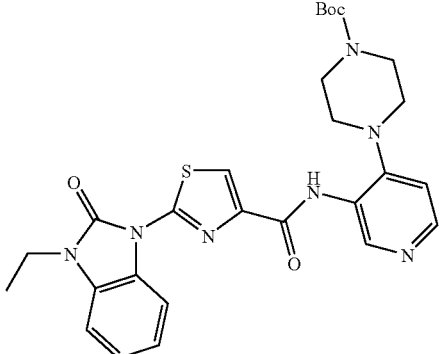 | 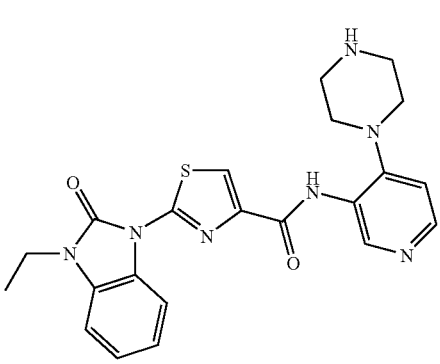  239 | 1. 73  2. 450.2  3. 172-175 |
| 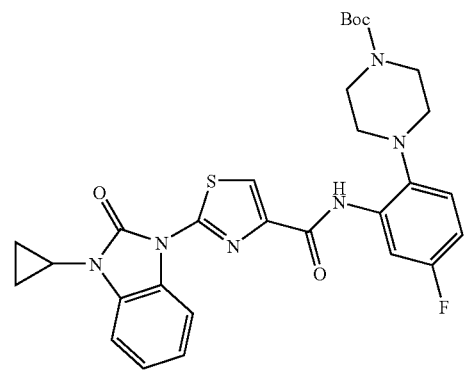 | 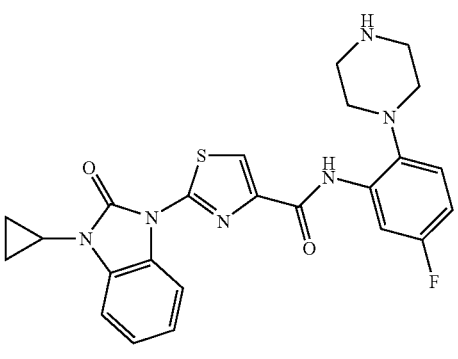  256 | 1. 92  2. 479.3  3. 220-223 |
| 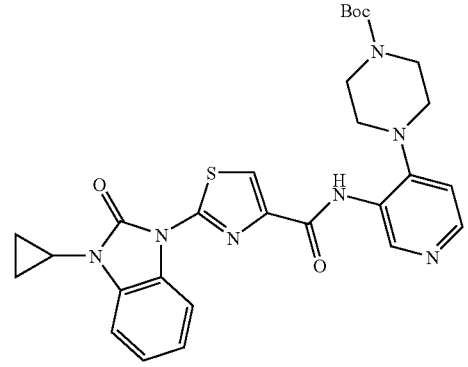 | 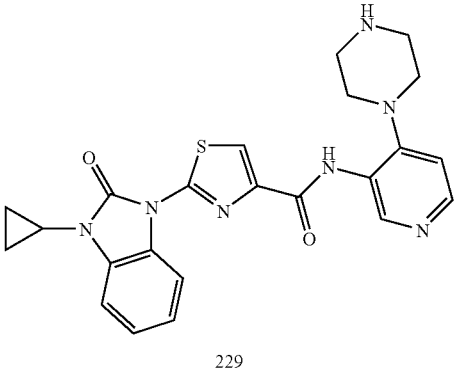  229 | 1. 67  2. 462.3  3. 180-183 |

-continued
| Boc adduct | Product | 1. Yield (%) 2. LC-MS 3. mp (° C.) |
|---|---|---|
| 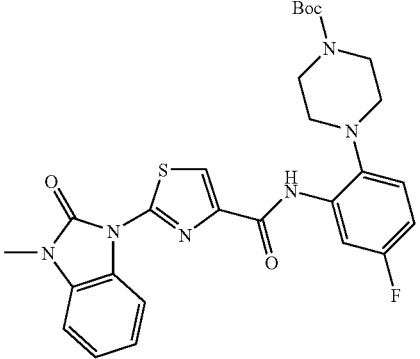 | 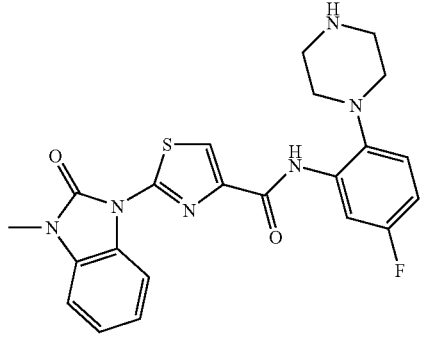 232 | 1. 62 2. 453.2 3. 140-142 |
| 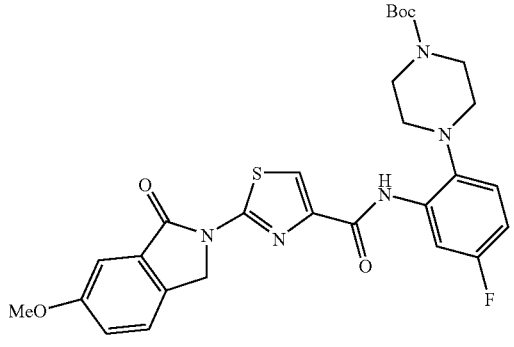 | 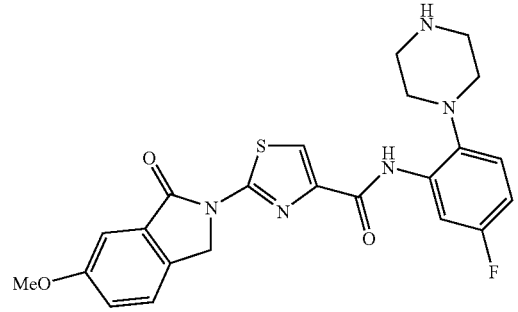 230 | 1. 86 2. 468.3 3. 168-171 |
| 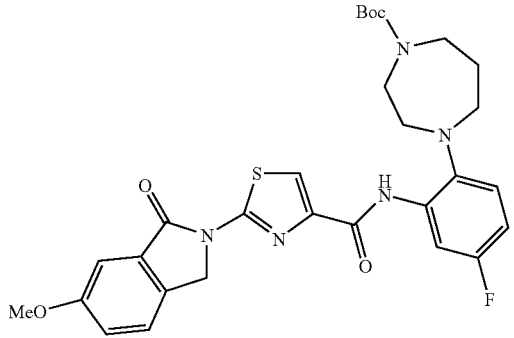 | 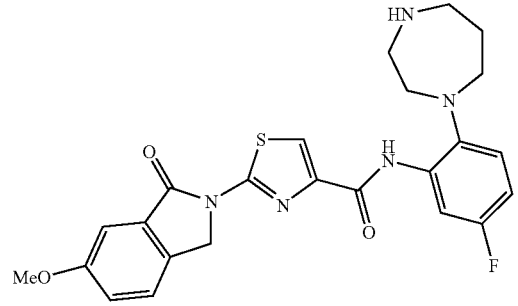 231 | 1. 90 2. 465.3 3. 133-135 |
| 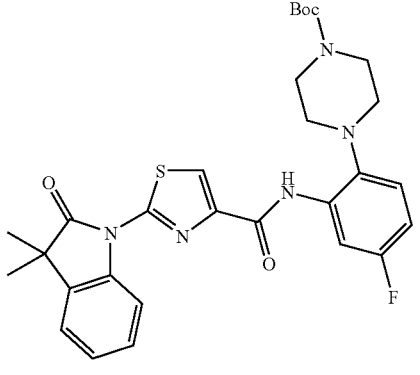 | 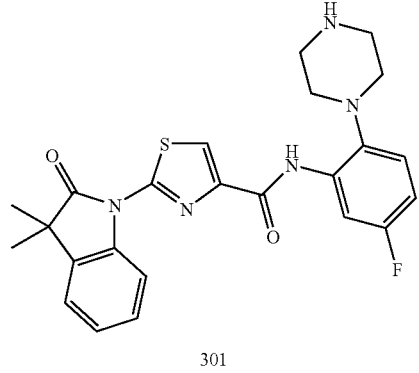 301 | 1. 87 2. 466.3 3. 167-170 |

-continued

| Boc adduct | Product | 1. Yield (%)<br>2. LC-MS<br>3. mp (° C.) |
|---|---|---|
| 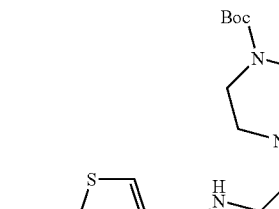 | 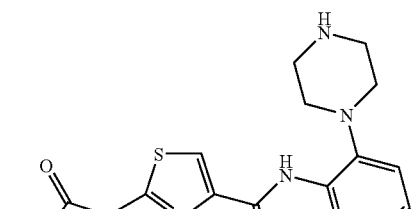　313 | 1. 92<br>2. 449.2<br>3. 200-205 |
| 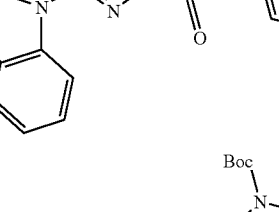 | 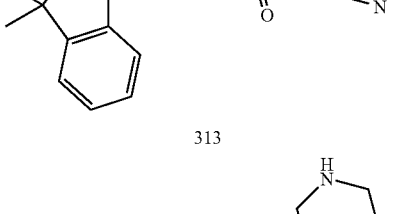　288 | 1. 57<br>2. 460.2<br>3. 168-171 |

Example 64

Preparation of Compound 64A

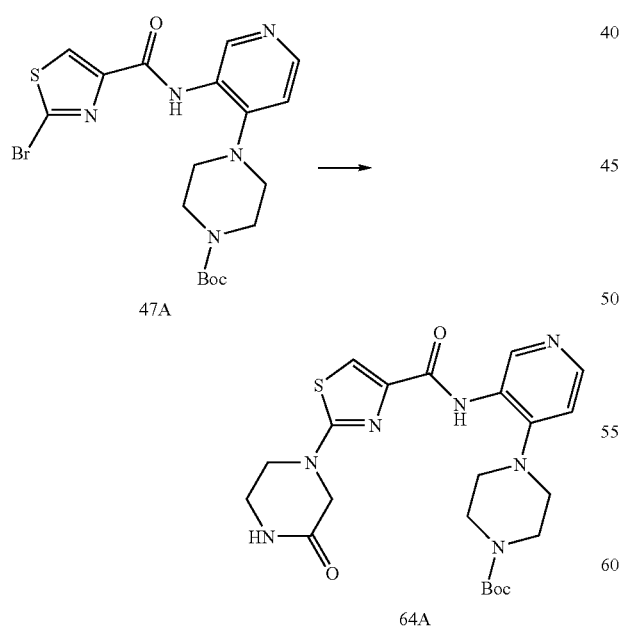

Using the methods described in Examples 60 and 62, compound 47A (0.15 g, 0.32 mmol) was reacted with piperazin-2-one (96 mg, 0.96 mmol) in dioxane (2 mL) to provide 84 mg (54% yield) of compound 64A as a light yellow solid. LC-MS [M+H]=488.3; 98% purity.

Example 65

Preparation of Compound 112

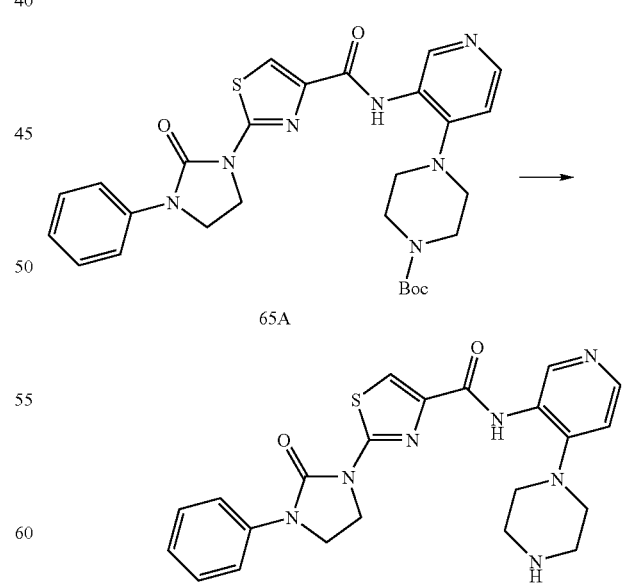

To a solution of compound 65A (0.13 g, 0.22 mmol) in $CH_2Cl_2$ (3 mL) at room temperature was added TFA (1 mL).

The mixture was stirred for 2 hours at room temperature and was concentrated under reduced pressure. The crude product was taken up in 2M ammonia in MeOH (3 mL), stirred for 2 hours, then concentrated under reduced pressure. The crude product was purified using preparative thin-layer chromatography using a 11:1 mixture of CH$_2$Cl$_2$/MeOH (7M NH$_3$) as eluent to provide 63 mg (64% yield) of compound 112 a pale yellow solid. mp 116-118° C., LC-MS [M+H]=450.2; 95% purity.

Using the method described above, the indicated Boc adducts were deprotected to provide illustrative compounds of the invention 96, 101 and 111 as shown in the table below.

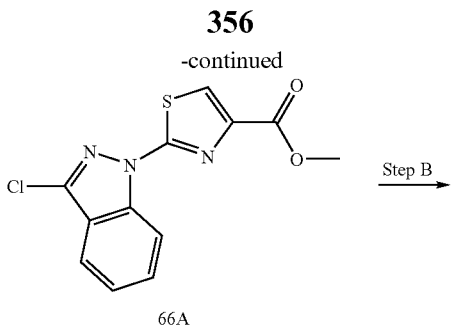

66A

| Boc adduct | Product | 1. Yield (%) 2. LC-MS 3. mp (° C.) |
|---|---|---|
| 96 | | 1. 45 2. 373.2 3. 122-124 |
| 101 | | 1. 71 2. 359.2 3. 179-181 |
| 111 | | 1. 77 2. 388.2 3. 215-218 |

Example 66

Preparation of Compound 82

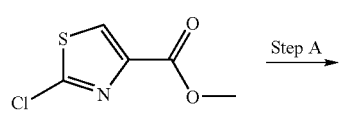

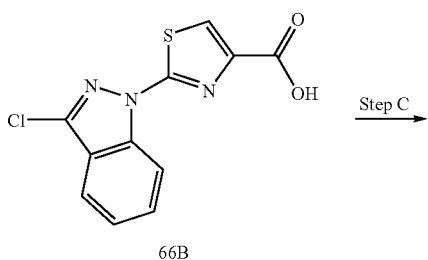

66B

357

-continued

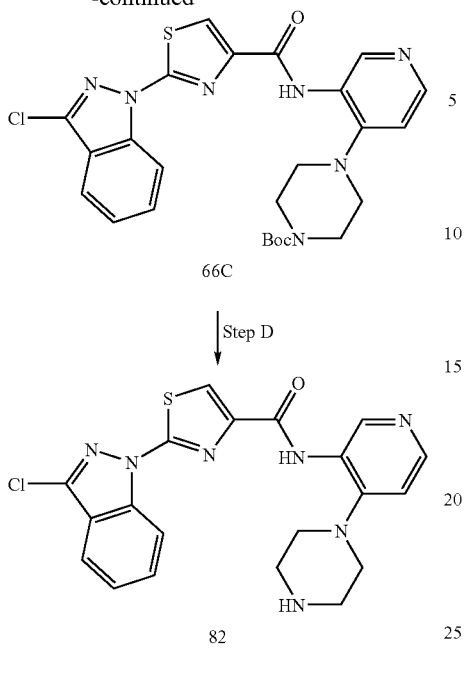

66C

|Step D

82

Step A:

3-Chloroindazole (305 mg, 2.0 mmol) and 2-chlorothiazole (355 mg, 2.0 mmol) were taken up in DMF (20 mL). NaH (80 mg, 60% in oil, 2.0 mmol) was added carefully and the resulting mixture was heated to 60° C. and stirred for 3 hours. After cooling to room temperature, NH$_4$Cl (aq.) was added carefully and the resulting solution was extracted with EtOAc (60 mL×3). The organics was dried over Na$_2$SO$_4$, concentrated under vacuum, and purified using flash column chromatography on silica gel (EtOAc/Hexane=30:70) to provide compound 66A (503 mg) as brown solid. HPLC-MS t$_R$=2.24 min (UV$_{254\ nm}$); mass calculated for formula C$_{12}$H$_8$ClN$_3$O$_2$S 293.0, observed LCMS m/z 294.0 (M+H).

Step B:

Compound 66A (503 mg, 1.7 mmol) was diluted with THF (10 mL) and to the resulting solution was added LiOH (1N, 3.0 mL). The mixture was stirred at room temperature for about 15 hours. The solvent was removed under vacuum, and the residue obtained was diluted with H$_2$O (5 mL). 1N HCl was added to adjust the pH to 5 and the solid formed was collected by filtration, then washed with water and air-dried to provide compound 66B, which was used in the next step without further purification. HPLC-MS t$_R$=1.71 min (UV$_{254\ nm}$); mass calculated for formula C$_{11}$H$_6$ClN$_3$O$_2$S 279.0, observed LCMS m/z 280.0 (M+H).

Step C:

Compound 66C was synthesized from compound 66B using the method described in Example 59. HPLC-MS t$_R$=1.75 min (UV$_{254\ nm}$); mass calculated for formula C$_{25}$H$_{26}$ClN$_7$O$_3$S 539.2, observed LCMS m/z 540.1 (M+H).

Step D:

Compound 82 was prepared from compound 66C using the method described in Example 62. HPLC-MS t$_R$=1.10 min (UV$_{254\ nm}$); mass calculated for formula C$_{20}$H$_{18}$ClN$_7$OS 439.1, observed LCMS m/z 440.0 (M+H).

358

Example 67

Preparation of Compound 78

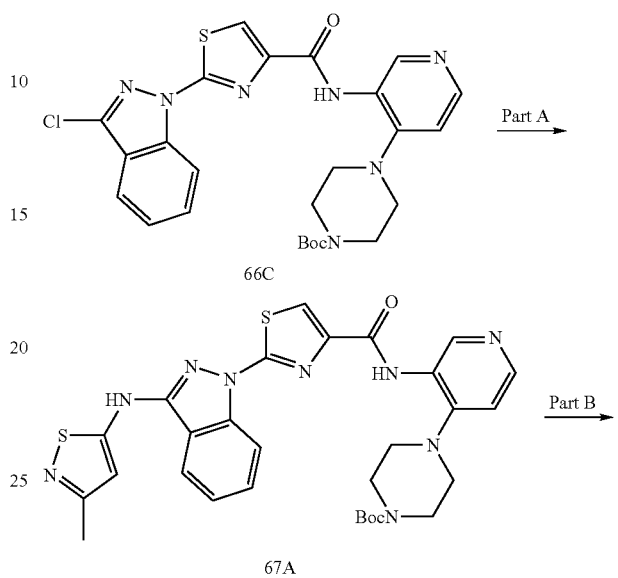

66C

67A

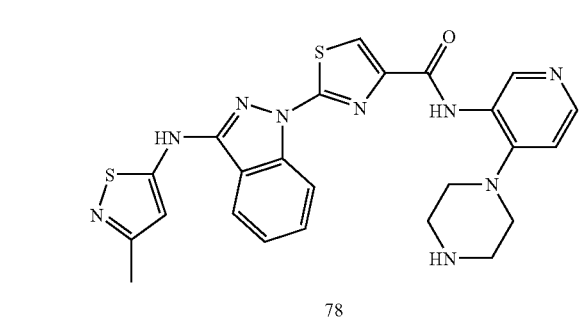

78

Step A:

To a 25 ml round bottom flask charged with compound 66C (270 mg, 0.5 mmol), isothiazole HCl salt (300 mg, 2.0 mmol), Pd$_2$(dba)$_3$ (45 mg, 0.05 mmol), 2-di-t-butylphosphino-2',4',6'-tri-1-propyl-1,1-biphenyl (42 mg, 0.1 mmol) and K$_3$PO$_4$ (616 mg, 3.0 mmol) was added toluene (10 mL). The mixture was thoroughly degassed by alternately connected the flask to vacuum and Argon. This resulting mixture was then heated to 90° C. and stirred for about 15 hours, then was diluted by EtOAc (40 mL) and washed with brine. After concentration, the residue obtained was purified using Preparative liquid chromatography to provide compound 67A. HPLC-MS t$_R$=1.49 min (UV$_{254\ nm}$); mass calculated for formula C$_{29}$H$_{31}$N$_9$O$_3$S$_2$ 617.2, observed LCMS m/z 618.1 (M+H).

Step B:

Compound 78 was prepared by removing the Boc protecting group from compound 67A using the method described in Example 62. HPLC-MS t$_R$=0.97 min (UV$_{254\ nm}$); mass calculated for formula C24H$_{23}$N$_9$OS$_2$ 517.1, observed LCMS m/z 518.1 (M+H).

Example 68

Preparation of Compound 90

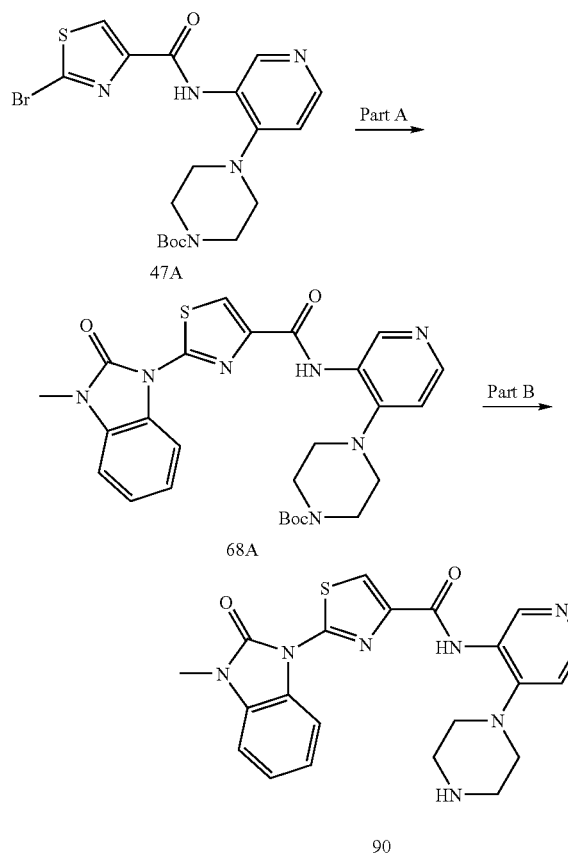

Step A:

To a 25 mL round bottom flask charged with compound 47A (100 mg, 0.22 mmol), benzimidazolone (45 mg, 0.3 mmol), CuI (10 mg, 0.05 mmol), trans-1,2-dimethylaminocyclohexane (13 mg, 0.1) and $K_2CO_3$ (51 mg, 0.3 mmol) was added dioxane (10 mL). The mixture was thoroughly degassed by alternately connected the flask to vacuum and Argon. This resulting mixture was then heated at 80° C. for about 15 hours. After cooling to room temperature, the solvent was removed under vacuum. The residue obtained was diluted with $H_2O$ (5 mL) and the crude solid compound 68A was collected by filtration and used directly in the next step without further purification. HPLC-MS $t_R$=1.42 min ($UV_{254\ nm}$); mass calculated for formula $C_{26}H_{29}N_7O_4S$ 535.2, observed LCMS m/z 536.2 (M+H).

Step B:

Compound 90 was prepared by removing the Boc protecting group from compound 68A using the method described in Example 62. HPLC-MS $t_R$=0.83 min ($UV_{254\ nm}$); mass calculated for formula $C_{21}H_{21}N_7O_2S$ 435.1, observed LCMS m/z 436.1 (M+H).

Using the method described in Steps A and B above, and using the appropriate coupling partners in Step A, the following illustrative compounds of the invention were made.

| Compound | MS m/z (M + H) | HPLC MS $t_R$ |
|---|---|---|
| 89 | 388.1 | 0.74 |
| 93 | 422.1 | 0.71 |

-continued
| Compound | MS m/z (M + H) | HPLC MS $t_R$ |
|---|---|---|
| 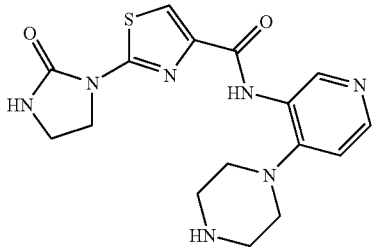 97 | 374.2 | 0.47 |
| 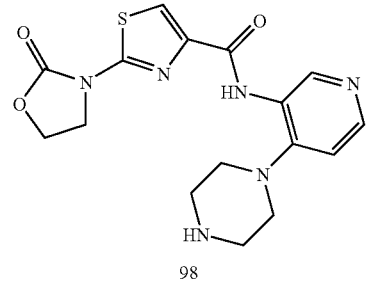 98 | 375.1 | 0.55 |
| 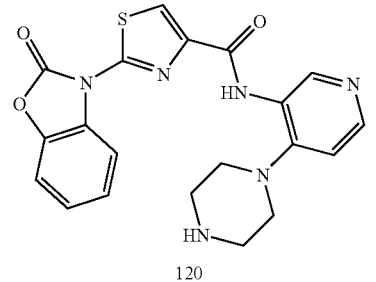 120 | 423.1 | 0.88 |
| 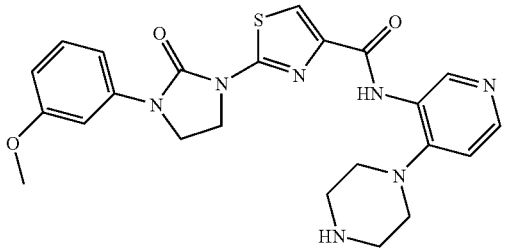 127 | 480.1 | 1.00 |
| 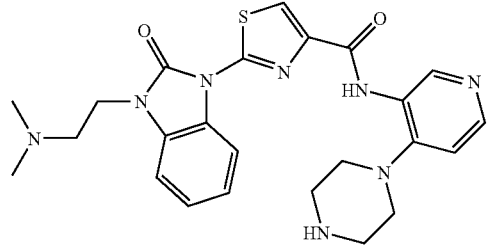 136 | 493.1 | 0.58 |

-continued
| Compound | MS m/z (M + H) | HPLC MS t_R |
|---|---|---|
| 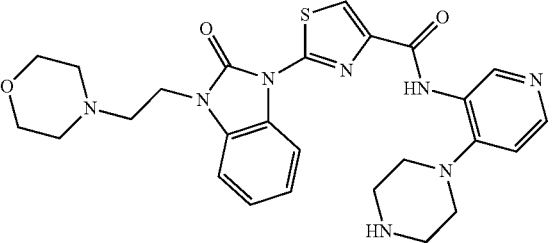  137 | 535.1 | 0.61 |
| 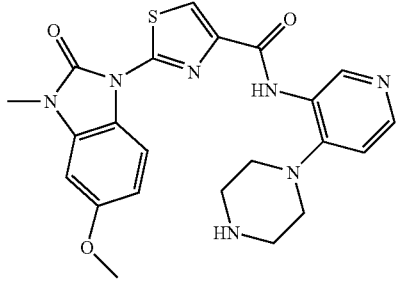  166 | 466.1 | 0.86 |
| 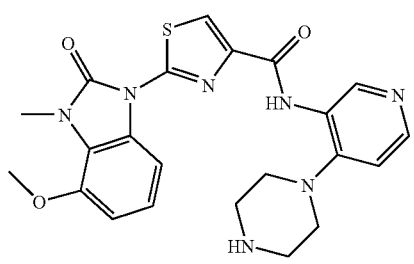  185 | 466.1 | 0.97 |
| 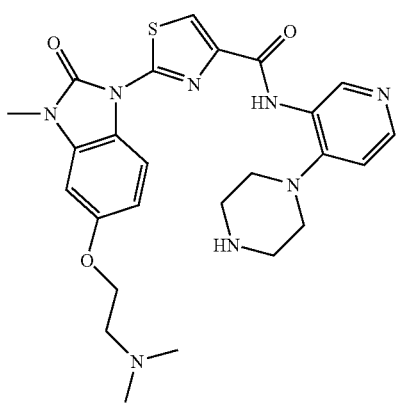  189 | 523.1 | 0.63 |

| Compound | MS m/z (M + H) | HPLC MS $t_R$ |
|---|---|---|
| 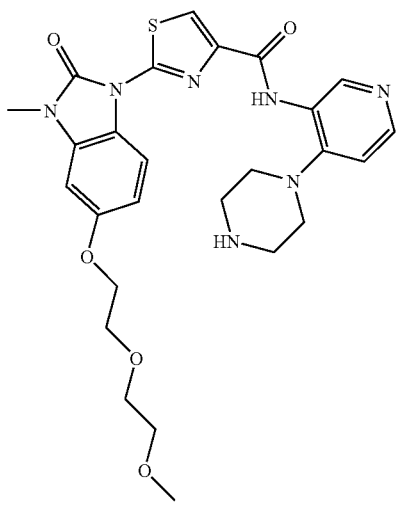 194 | 554.2 | 0.93 |
| 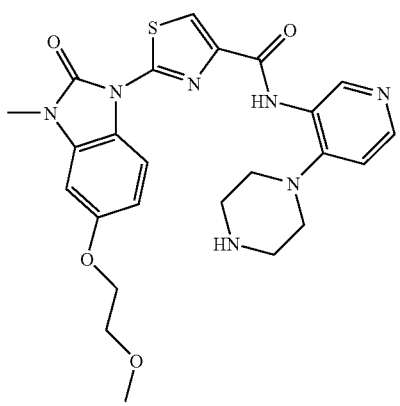 195 | 510.1 | 0.90 |
| 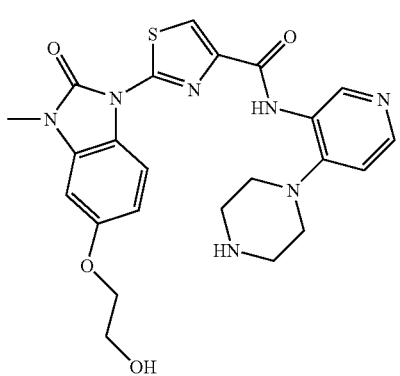 206 | 496.2 | 0.97 |

-continued
| Compound | MS m/z (M + H) | HPLC MS t_R |
|---|---|---|
| 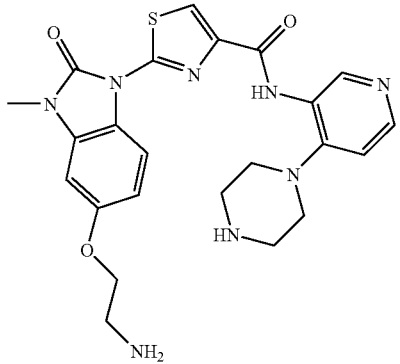 207 | 495.1 | 0.68 |
| 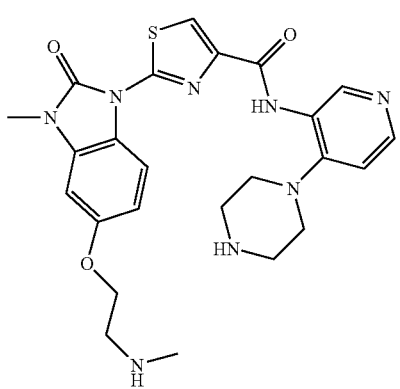 208 | 509.2 | 0.69 |
| 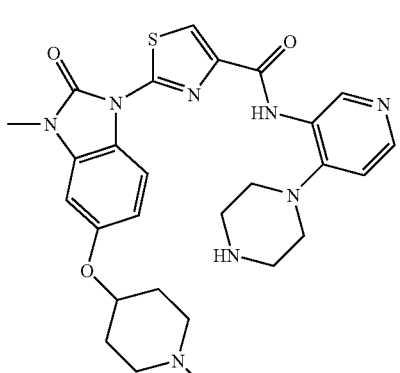 222 | 549.2 | 0.75 |

| Compound | MS m/z (M + H) | HPLC MS t$_R$ |
|---|---|---|
| 223 | 554.2 | 1.15 |
| 224 | 510.2 | 1.13 |
| 225 | 536.2 | 1.21 |
| 226 | 536.2 | 1.17 |

| Compound | MS m/z (M + H) | HPLC MS $t_R$ |
|---|---|---|
| 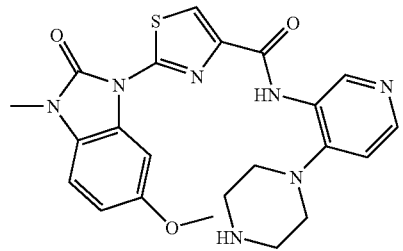 228 | 466.1 | 0.91 |
| 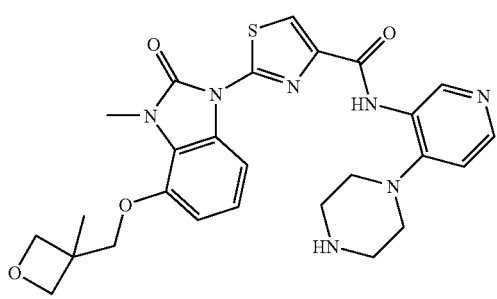 259 | 536.3 | 0.98 |
| 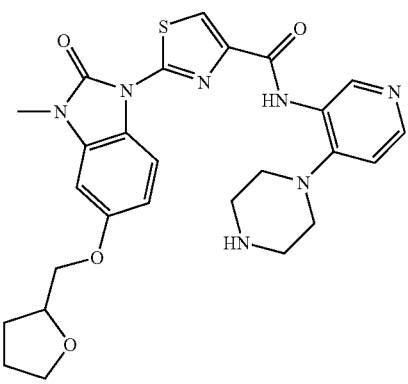 260 | 536.2 | 1.23 |
| 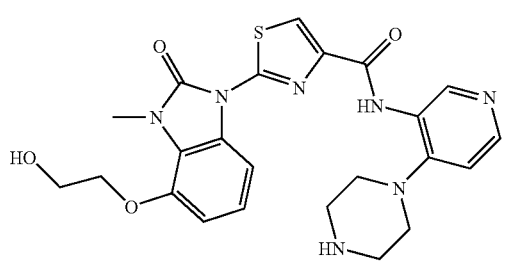 261 | 496.1 | 0.90 |

| Compound | MS m/z (M + H) | HPLC MS $t_R$ |
|---|---|---|
| 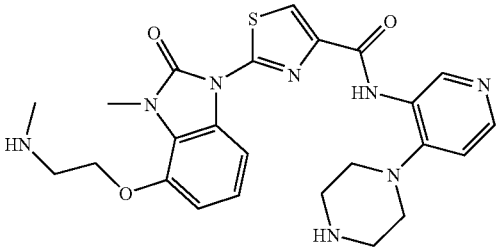 262 | 509.2 | 0.67 |
| 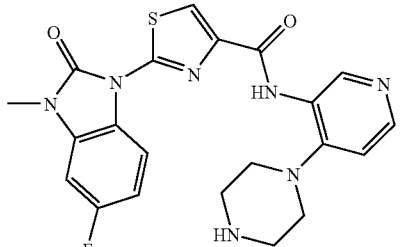 264 | 454.1 | 1.02 |
| 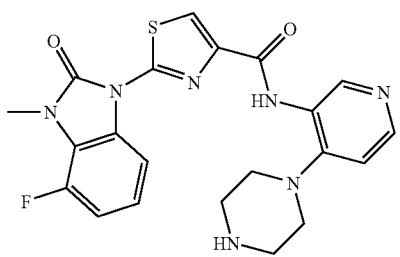 270 | 454.1 | 0.93 |
| 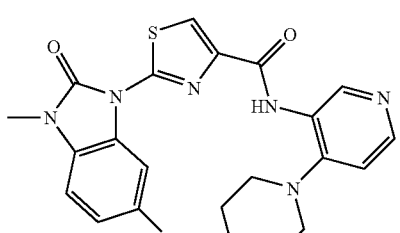 273 | 454.1 | 1.02 |
| 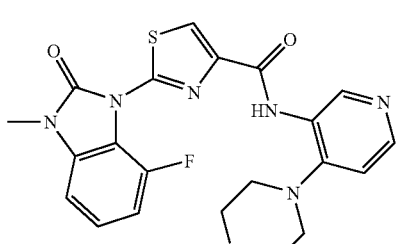 274 | 454.1 | 1.02 |

| Compound | MS m/z (M + H) | HPLC MS $t_R$ |
|---|---|---|
| 275 | 437.2 | 0.64 |
| 278 | 437.2 | 0.93 |
| 279 | 536.2 | 1.22 |
| 280 | 536.2 | 1.25 |
| 286 | 452.2 | 1.12 |

-continued
| Compound | MS m/z (M + H) | HPLC MS $t_R$ |
|---|---|---|
| 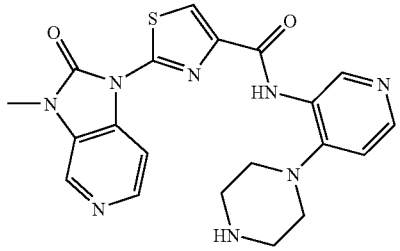 289 | 437.1 | 0.19 |
| 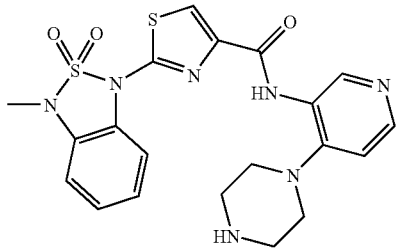 290 | 472.1 | 0.94 |
| 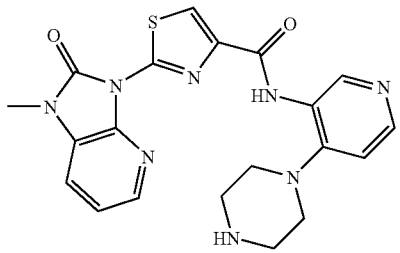 294 | 437.0 | 0.92 |
| 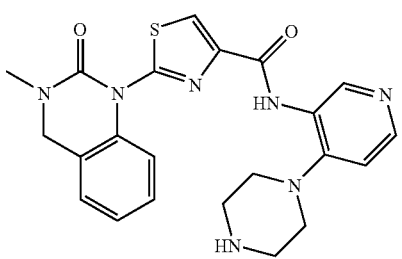 295 | 450.1 | 1.06 |
| 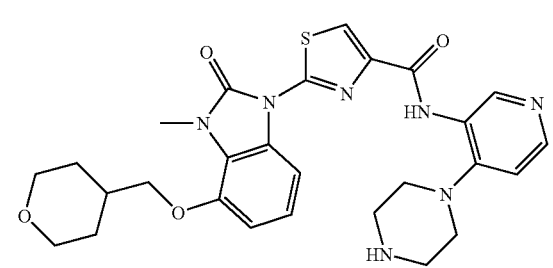 32 | 550.2 | 1.09 |

-continued
| Compound | MS m/z (M + H) | HPLC MS $t_R$ |
|---|---|---|
| 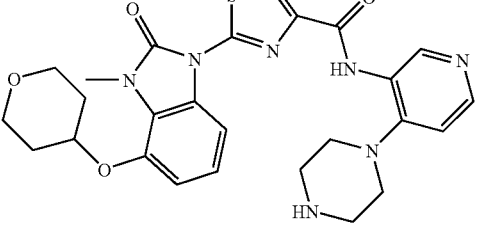 299 | 536.2 | 1.06 |
| 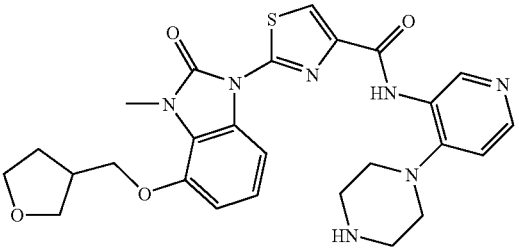 300 | 536.2 | 1.06 |
| 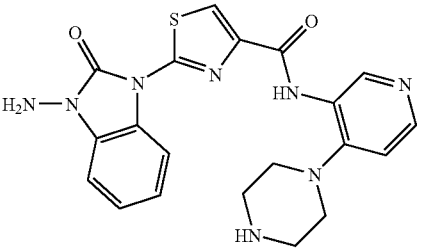 329 | 437.1 | 0.72 |
| 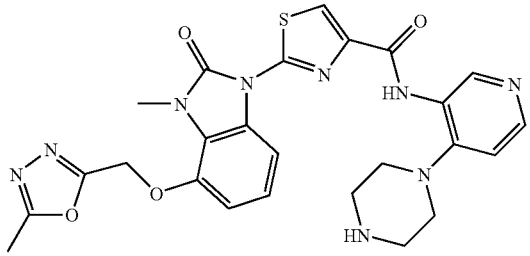 330 | 548.2 | 1.11 |
| 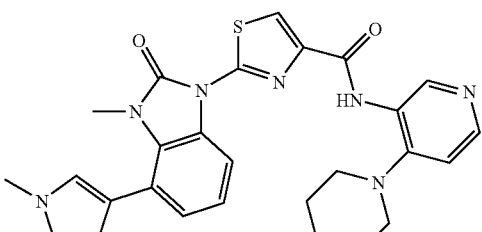 331 | 516.1 | 0.93 |

-continued

| Compound | MS m/z (M + H) | HPLC MS $t_R$ |
|---|---|---|
| 332 | 513.1 | 0.92 |

Example 69

Preparation of Compound 69B

Step A:
A solution of 4-chloro-3-nitro-pyridine (2.0 mmol, 0.32 g), diethylisopropyl amine (3.0 mmol, 0.52 mL) and 2(s)-methyl-piperazine-1-carboxylic acid tert-butyl ester (2.5 mmol, 0.50 g) in dioxane (2 mL) was irradiated using microwave for 20 minutes at a temperature of 120° C. The reaction mixture was concentrated in vacuo, and the resulting residue was purified using flash column chromatography on silica gel (eluent: ethyl acetate) to provide compound 69A as a yellow solid in quantitative yield. HPLC-MS RT=1.42 min, mass calculated for formula $C_{15}H_{22}N_4O_4$ 322.16, observed LCMS m/z 323.1 (M+H).

Step B:
To a solution of compound 69A (600 mg) in Ethanol/EtOAc (1:1, 10 mL) was added Pd on carbon (5% Pd). The reaction mixture was stirred under a hydrogen atmosphere at room temperature for about 15 hours, then filtered through a pad of celite. The filtrate was concentrated in vacuo to provide Compound 69B as a solid. HPLC-MS RT=1.10 min, mass calculated for formula $C_{15}H_{24}N_4O_2$ 292.19, observed LCMS m/z 293.20 (M+H).

Using the methods described in Steps A and B above, and using the appropriate reactants, the following intermediate compounds were made:

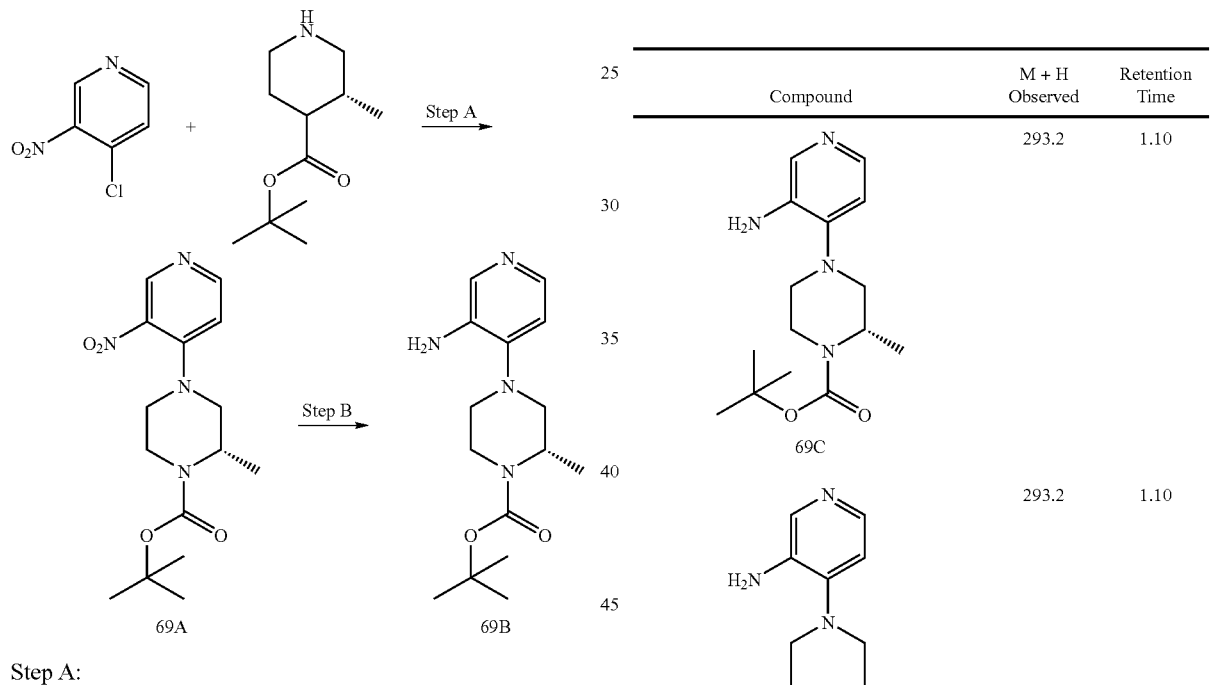

| Compound | M + H Observed | Retention Time |
|---|---|---|
| 69C | 293.2 | 1.10 |
| 69D | 293.2 | 1.10 |
| 69E | 307.3 | 1.0 |

-continued
| Compound | M + H Observed | Retention Time |
|---|---|---|
| 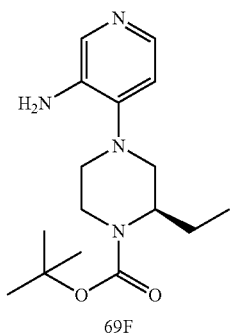 69F | 307.3 | 1.0 |
| 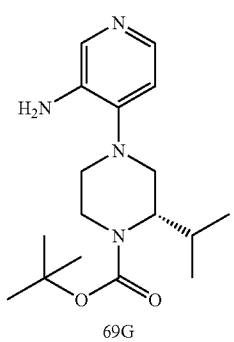 69G | 321.2 | 1.15 |
| 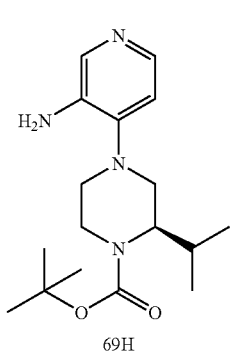 69H | 321.2 | 1.15 |
| 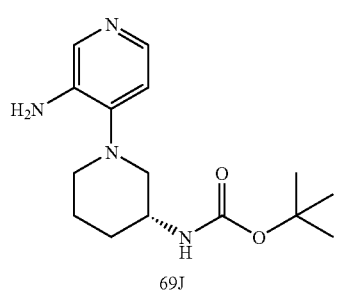 69J | 293.2 | 0.09 |
-continued
| Compound | M + H Observed | Retention Time |
|---|---|---|
| 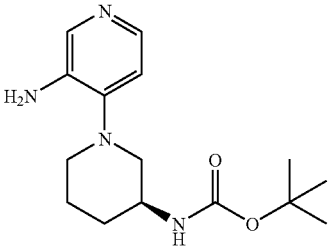 69K | 293.2 | 0.09 |
| 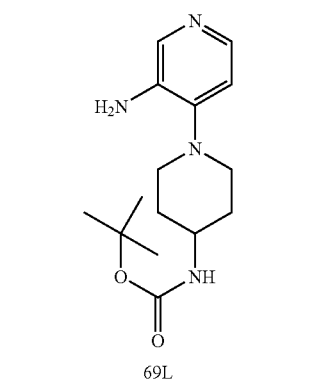 69L | 293.3 | 1.0 |
| 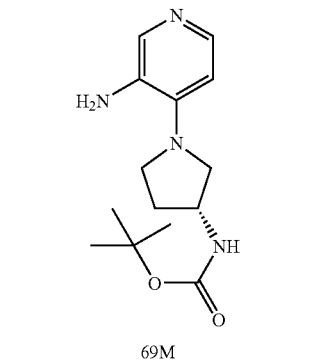 69M | 279.1 | 0.85 |
| 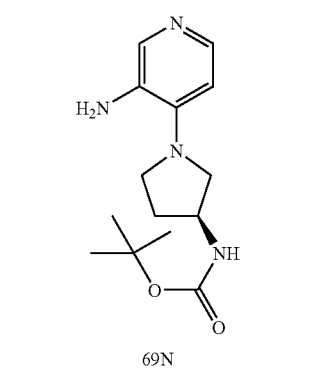 69N | 279.1 | 0.85 |

385
-continued

| Compound | M + H Observed | Retention Time |
|---|---|---|
| 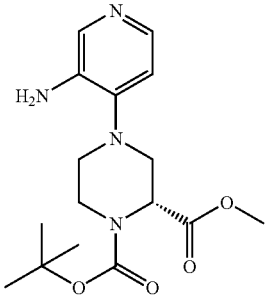 69P | 337.12 | 0.95 |
| 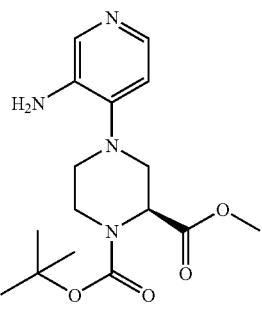 69Q | 337.12 | 0.95 |
| 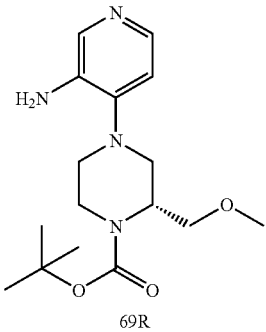 69R | 323.2 | 1.05 |

Example 70

Preparation of Compound 70B

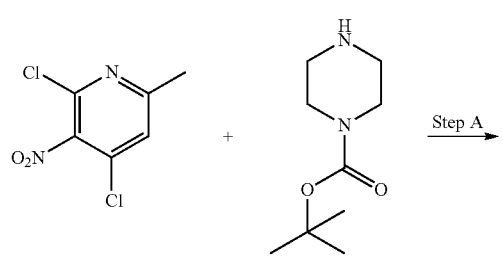

386
-continued

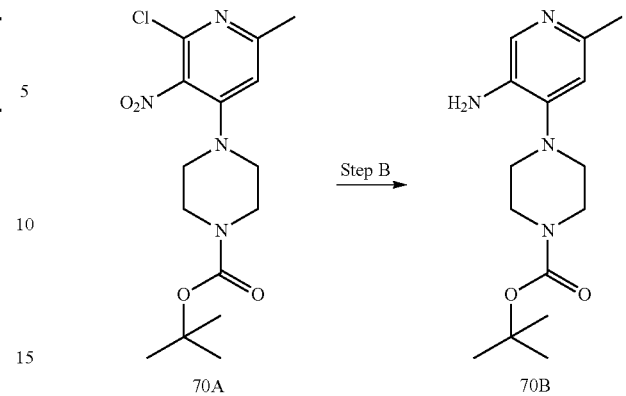

Step A:

A solution of 2,4-dichloro-6-methyl-3-nitro-pyridine (2.0 mmol, 0.42 g), diethylisopropyl amine (3.0 mmol, 0.52 mL) and piperazine-1-carboxylic acid tert-butyl ester (2. mmol, 0.372 g) in dichloromethane (5 mL) was stirred at room temperature for 12 hours. The reaction mixture was concentrated in vacuo, and the resulting residue was purified using flash column chromatography on silica gel (eluent: Hexane and ethyl acetate) to provide compound 70A as a yellow solid in quantitative yield. HPLC-MS RT=2.1 min, mass calculated for formula $C_{15}H_{21}ClN_4O_4$ 356.13, observed LCMS m/z 357.1 (M+H).

Step B:

To a solution of compound 70A (600 mg) in Ethanol/EtOAc (1:1, 10 mL) was added Pd on carbon (5% Pd). The reaction mixture was stirred under a hydrogen atmosphere at 40 psi for about 15 hours, then filtered through a pad of celite. The filtrate was concentrated. in vacuo to provide Compound 70B as a solid. HPLC-MS RT=1.10 min, mass calculated for formula $C_{15}H_{24}N_4O_2$ 292.19, observed LCMS m/z 293.20 (M+H).

Using the methods described in Steps A and B above, and using the appropriate reactants, the following intermediate compounds were made:

| Starting material | Product | M + H Observed | Retention Time |
|---|---|---|---|
| 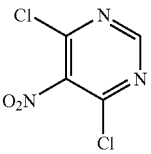 | 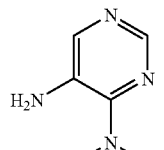 70C | 280.3 | 0.9 |

387

-continued

| Starting material | Product | M + H Observed | Retention Time |
|---|---|---|---|
| | | 284.1 | 1.5 |
| | | 296.2 | 2.0 |
| | | 329.2 | 1.2 |

70D

70E

70F

Example 71

Preparation of Compound 71D

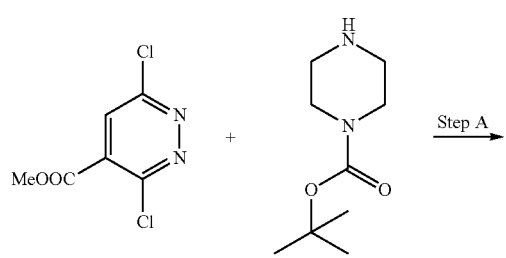

388

-continued

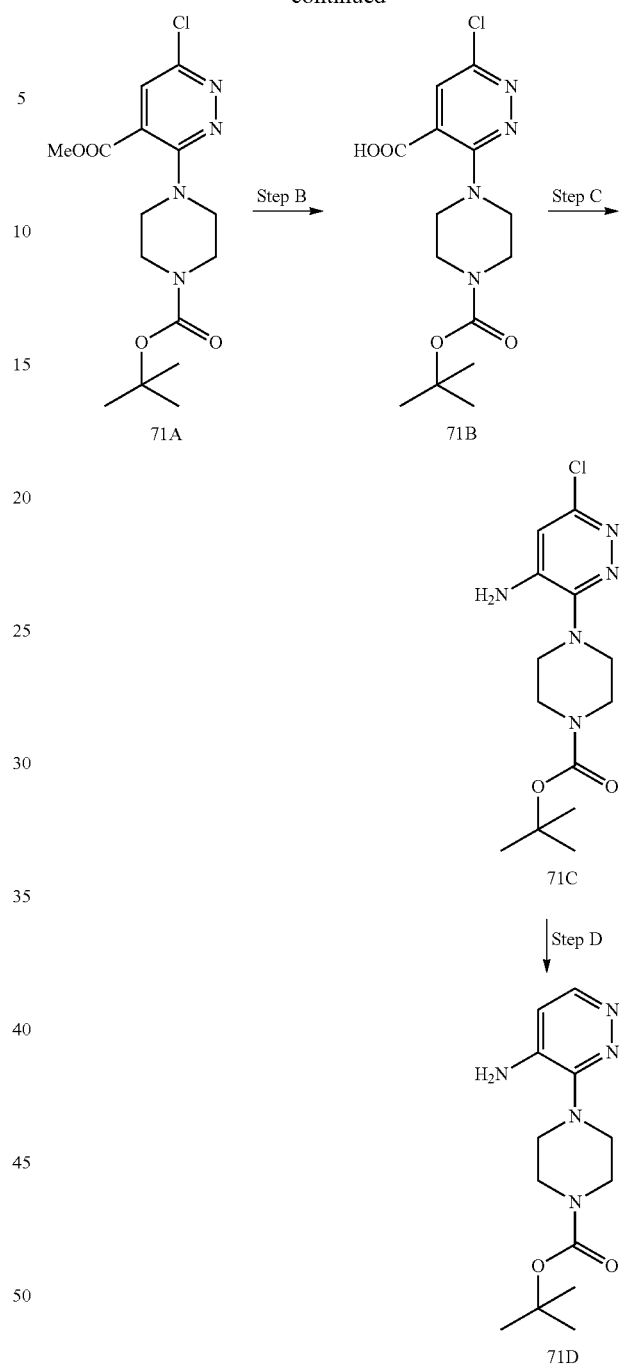

Step A:

A solution of 3,6-dichloro pyridazine-4-carboxylic acid methyl ester (2.0 mmol, 0.41 g), diethylisopropyl amine (3.0 mmol, 0.52 mL) and piperazine-1-carboxylic acid tert-butyl ester (2 mmol, 0.37 g) in dioxane (2 mL) was irradiated using microwave for 20 minutes at a temperature of 80° C. The reaction mixture was concentrated in vacuo, and the resulting residue was purified using flash column chromatography on silica gel (eluent: ethyl acetate) to provide compound 71A as a yellow solid in quantitative yield. HPLC-MS RT=1.9 min, mass calculated for formula $C_{15}H_{21}ClN_4O_4$ 356.13, observed LCMS m/z 357.1 (M+H).

Step B:

To a solution of compound 71A (2.0 mmol. 0.714 g) in 4 ml of THF was added 1N. LiOH solution in water 4 mL and stirred for about 15 hours at room temperature. THF is removed and acidified to pH to 2. Aqueous layer is extracted with ethyl acetate, washed with brine, dried over anhydrous sodium sulfate. Filtered and concentrated to get compound 71B. HPLC-MS RT=1.3 min, mass calculated for formula $C14H_{19}ClN_4O_4$ 342.11, observed LCMS m/z 343.1 (M+H).

Step C:

To a solution of Compound 71B (1 mmol, 0.34 g.) in DMF (5 mL) was added DPPA (1 mmol, 0.275 g.) and triethylamine (1.1 mmol, 0.16 mL) and stirred under Ar for 4 hours then added 1 ml of water and heated to 65° C. for 1 hour. Cooled to room temperature and pH was adjusted to 9 by adding potassium carbonate. Extracted with Ethyl acetate, washed with brine, dried over sodium sulfate, filtered and concentrated to obtain compound 71C. HPLC-MS RT=1.35 min, mass calculated for formula $C_{13}H_{20}ClN_5O_2$ 313.13, observed LCMS m/z 314.2 (M+H).

Step D:

To a solution of compound 71C (150 mg) in Ethanol/EtOAc (1:1, 10 mL) was added Pd on carbon (5% Pd). The reaction mixture was stirred under a hydrogen atmosphere at 40 psi for about 15 hours, then filtered through a pad of celite. The filtrate was concentrated. in vacuo to provide Compound 71D as a solid. HPLC-MS RT=1.0 min, mass calculated for formula $C_{13}H_{21}N5O_2$ 279.17, observed LCMS m/z 280.30 (M+H).

Example 72

Preparation of Compound 72B

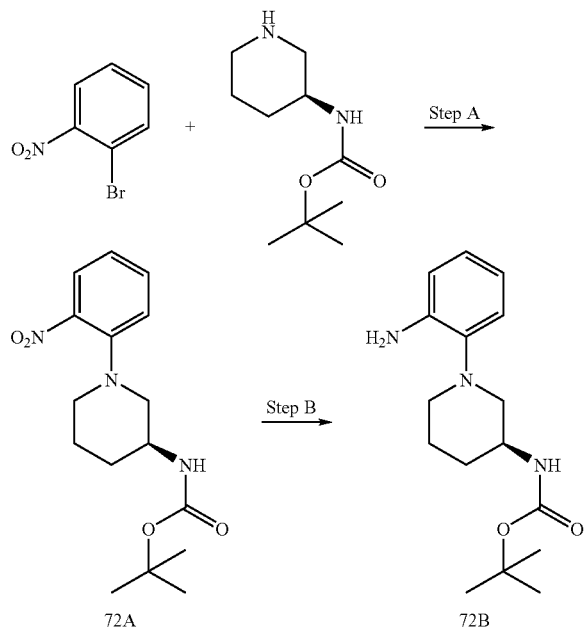

Step A:

A solution of 1-bromo-2-nitro-benzene (2.0 mmol, 0.4 g), diethylisopropyl amine (3.0 mmol, 0.52 mL) and Compound (2.5 mmol, 0.50 g) in dimethylacetamide (2 mL) was irradiated using microwave for 30 minutes at a temperature of 200° C. The reaction mixture was concentrated in vacuo, and the resulting residue was purified using flash column chromatography on silica gel (eluent: ethyl acetate) to provide compound 72A as a solid. HPLC-MS RT=2.15 min, mass calculated for formula $C_{16}H_{23}N_3O_4$ 321.17, observed LCMS m/z 322.2 (M+H).

Step B:

To a solution of compound 72A (400 mg) in Ethanol/EtOAc (1:1, 10 mL) was added Pd on carbon (5% Pd). The reaction mixture was stirred under a hydrogen atmosphere at room temperature for about 15 hours, then filtered through a pad of celite. The filtrate was concentrated in vacuo to provide Compound 72B as a solid. HPLC-MS RT=1.70 min, mass calculated for formula $C_{16}H_{25}N3O_2$ 291.19, observed LCMS m/z 292.20 (M+H).

Using the methods described in Steps A and B above, and utilizing the enantiomer of compound 72B, the following intermediate compound was made:

| Compound | M + H Observed | Retention Time |
|---|---|---|
| 72C | 292.20 | 1.70 |

Example 73

Preparation of Intermediate Compounds 73A-73Q

Using the methods described in Example 46 above, and using the appropriate reactants, the following intermediate compounds were made:

| Compound | M + H Observed |
|---|---|
| 73A | 482.1 |

| Compound | M + H Observed |
|---|---|
| 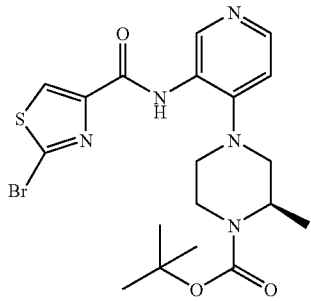<br>73B | 482.1 |
| 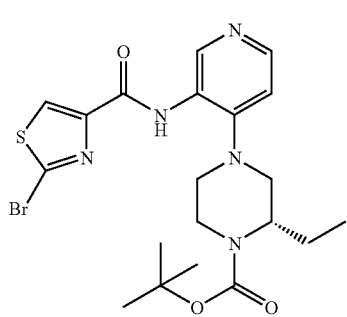<br>73C | 496.1 |
| 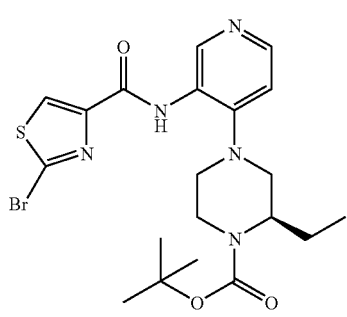<br>73D | 496.1 |
| 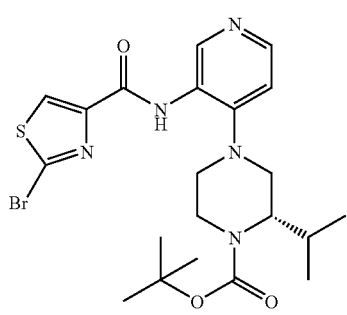<br>73E | 510.1 |
| Compound | M + H Observed |
|---|---|
| 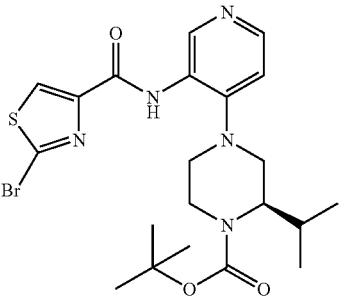<br>73F | 510.1 |
| 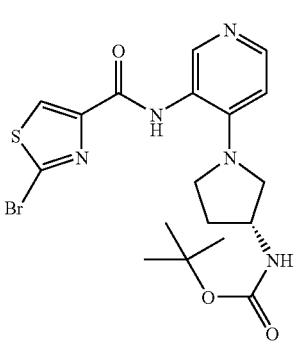<br>73G | 468.1 |
| 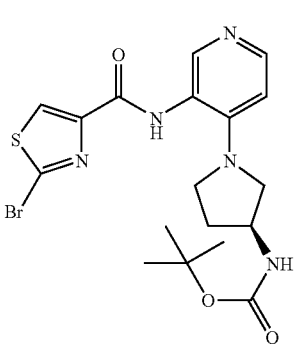<br>73H | 468.1 |
| 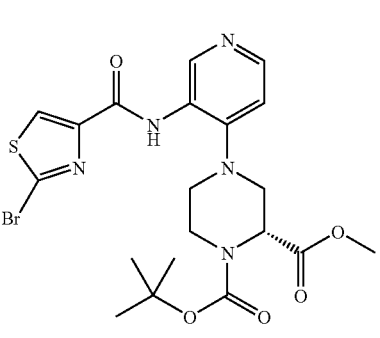<br>73J | 526.1 |

-continued

| Compound | M + H Observed |
|---|---|
| 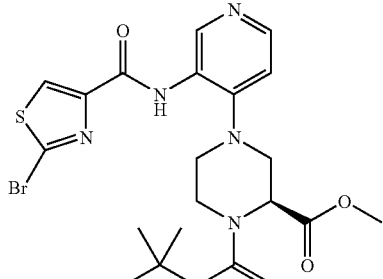 73K | 526.1 |
| 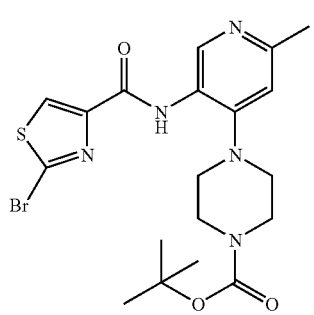 73L | 482.1 |
| 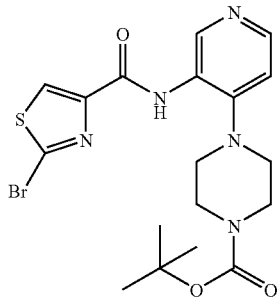 73M | 469.1 |
| 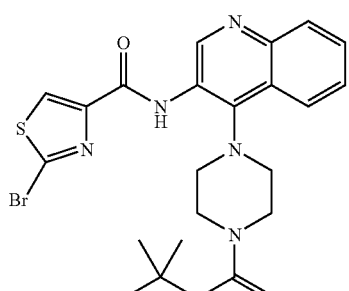 73N | 518.1 |

-continued

| Compound | M + H Observed |
|---|---|
| 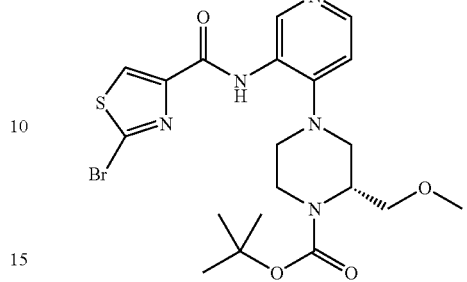 73P | 512.1 |
| 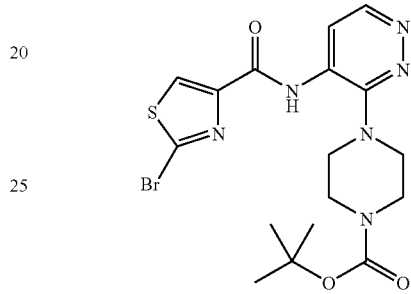 73Q | 469.1 |

Example 74

Preparation of Compound 74A

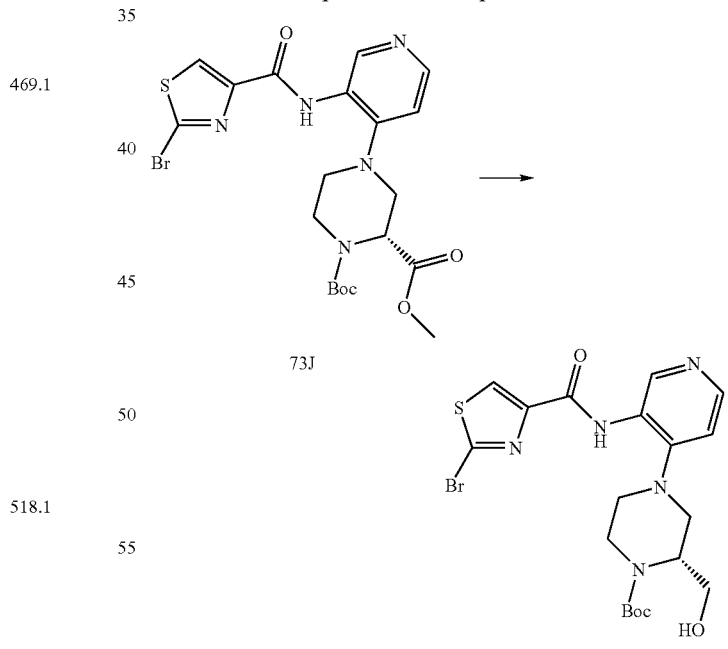

To a solution of compound 73J (0.2 mmol, 0.1 g.) in Ethanol 2 mL added sodiumboro hydride (0.8 mmol, 0.03 g.) and stirred for about 15 hours. Water is added and extracted with ethylacetate. Ethylacetate layer is washed with water, brine, dried over anhydrous sodium sulfate, filtered and concentrated in vacuo to provide product 75A. HPLC-MS RT=1.10 min, mass calculated for formula $C_{19}H_{24}BrN_5O_4S$ 497.07, observed LCMS m/z 498.1 (M+H).

Using this procedure, compound 74B was synthesized from compound 73K.
| Compound | M + H Observed |
|---|---|
| 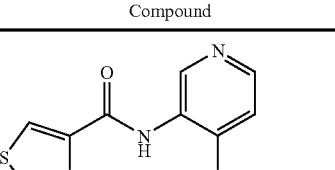 74B | 498.31 |
Example 75
Preparation of Compounds 65, 71, 75, 81, 83, 86, 87, 151-153, 201, 202, 240, 241, 257, 317, 320-322 and 324
The compounds of the present invention depicted below were made using the method described in Example 51 and utilizing the appropriate reactants.
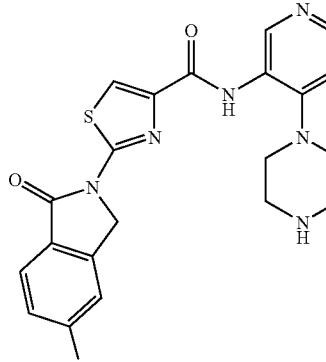
| Compound | M + H Observed | Retention Time |
|---|---|---|
| 83 | 451.14 | 2.07 |
| 65 | 467.2 | 0.5 |

| Compound | M + H Observed | Retention Time |
|---|---|---|
| 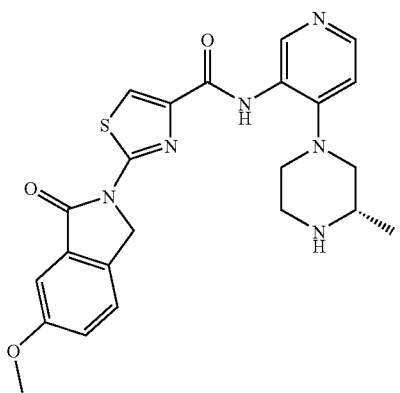 202 | 465.1 | 0.75 |
| 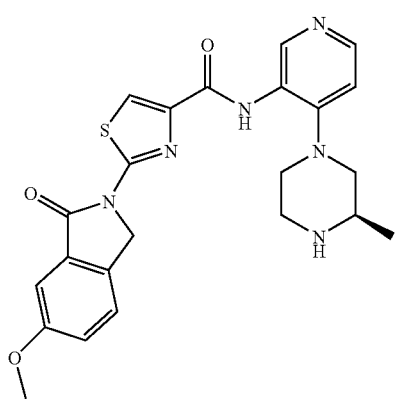 201 | 465.1 | 0.8 |
| 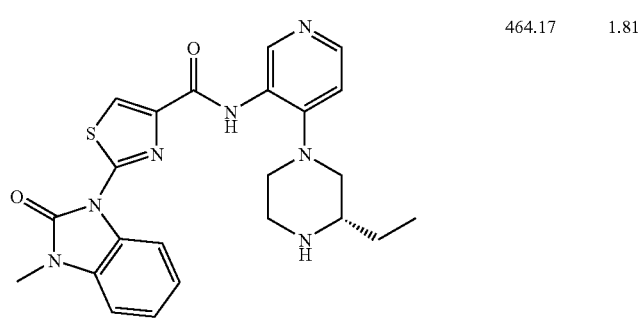 320 | 464.17 | 1.81 |

-continued
| Compound | M + H Observed | Retention Time |
|---|---|---|
| 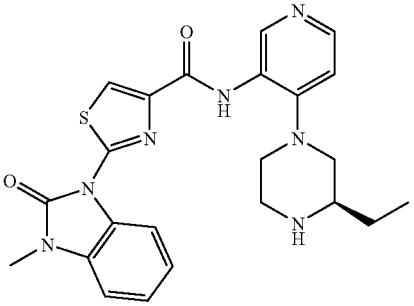 324 | 464.17 | 1.92 |
| 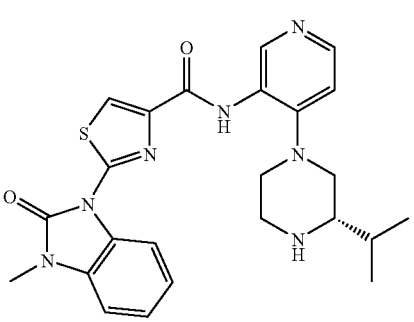 322 | 478.19 | 1.93 |
| 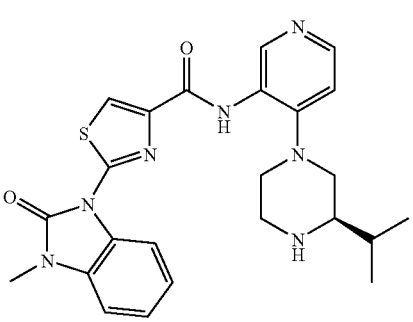 321 | 478.19 | 1.86 |
| 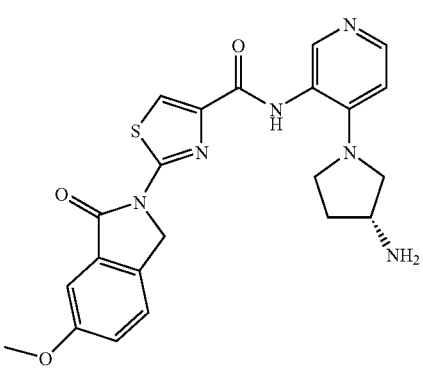 153 | 451.1 | 2.1 |

| Compound | M + H Observed | Retention Time |
|---|---|---|
| 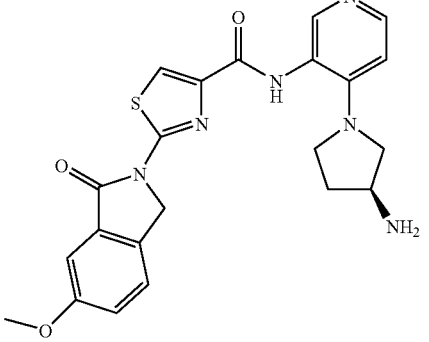<br>152 | 451.1 | 2.1 |
| 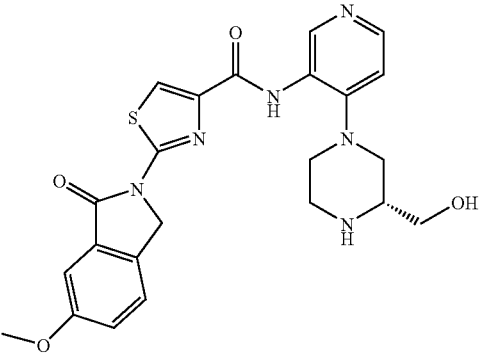<br>241 | 481.15 | 1.71 |
| 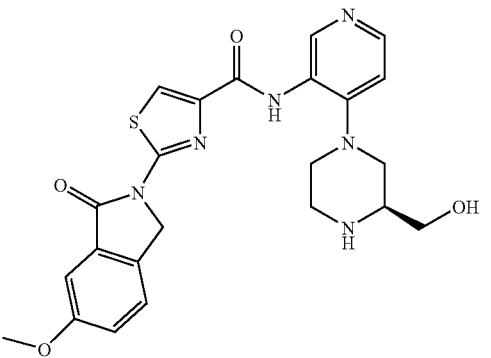<br>240 | 481.15 | 1.74 |
| 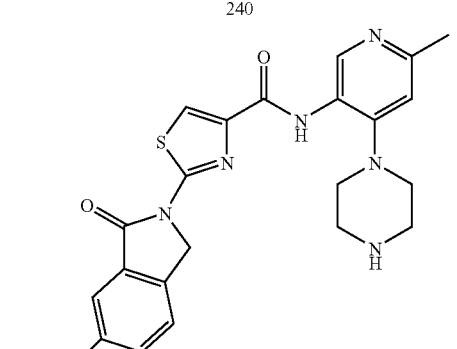<br>81 | 465.16 | 2.14 |

| Compound | M + H Observed | Retention Time |
|---|---|---|
| 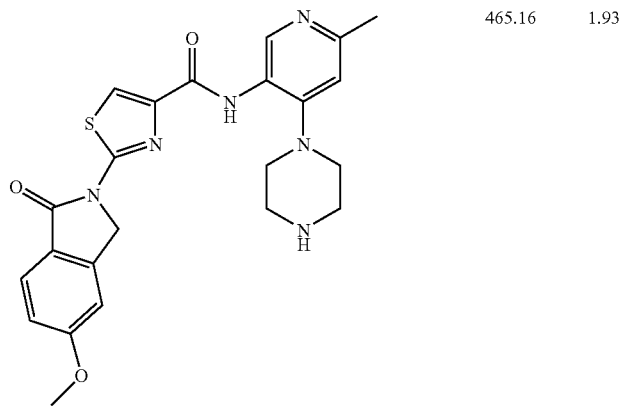<br>86 | 465.16 | 1.93 |
| 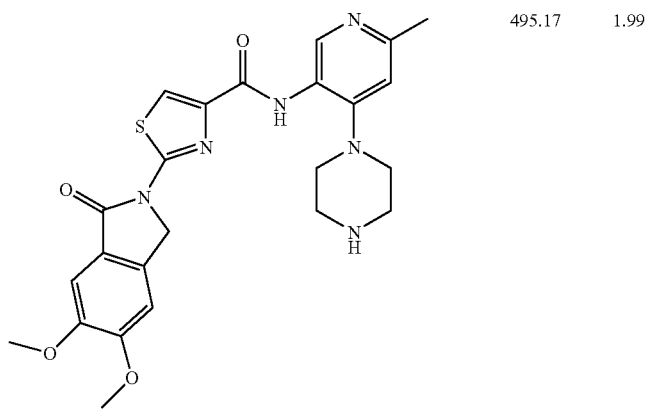<br>87 | 495.17 | 1.99 |
| 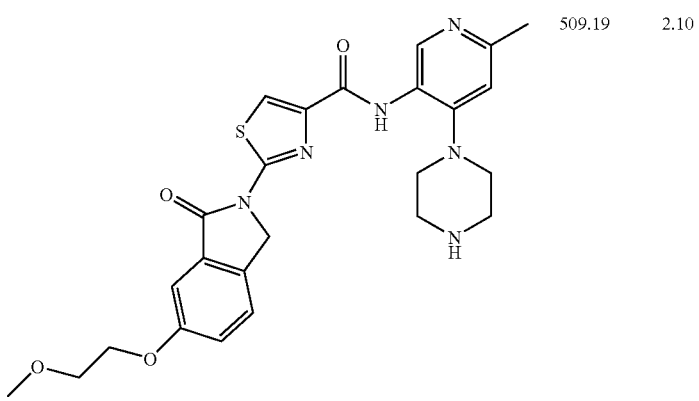<br>257 | 509.19 | 2.10 |

-continued
| Compound | M + H Observed | Retention Time |
|---|---|---|
| 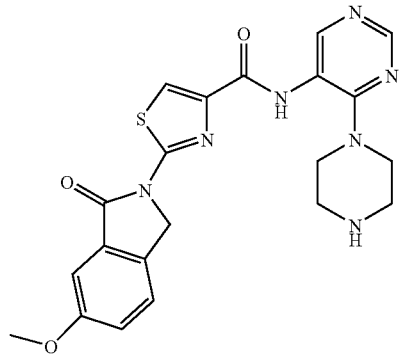<br>71 | 452.1 | 2.45 |
| 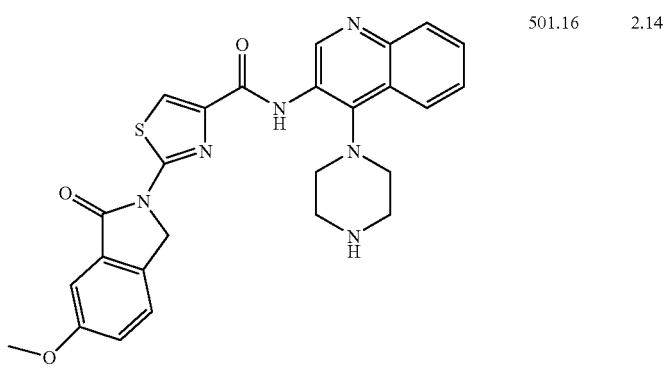<br>75 | 501.16 | 2.14 |
| 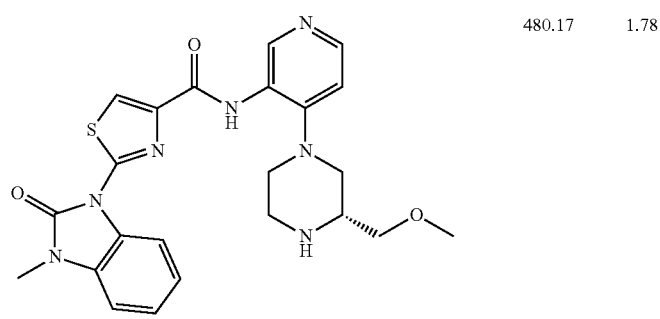<br>317 | 480.17 | 1.78 |

| Compound | M + H Observed | Retention Time |
|---|---|---|
| 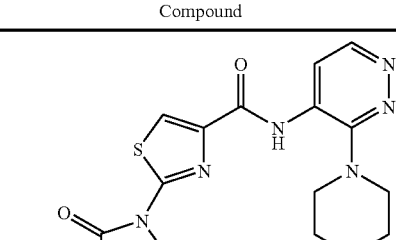 151 | 452.15 | 2.76 |

Example 76

Preparation of Compound 76A and 76B

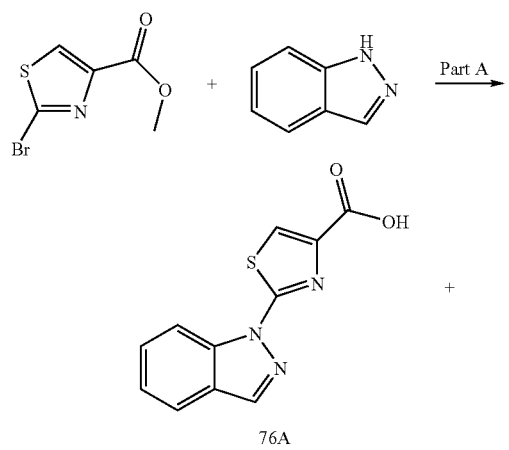

To a suspension of NaH (60% dispersion in oil, 10 mmol, 0.48 g.) in anhydrous dioxane (5 mL) was added a solution of indazole (10 mmol, 1.18 g) in dioxane (5 mL) and the resulting reaction was allowed to stir for 30 minutes. A solution of 2-bromo-thiazole-4-carboxylic acid methyl ester (10.0 mmol, 2.22 g) in dioxane (5 mL) was then added dropwise and the reaction mixture was heated to 100° C. for 4 hrs. The reaction mixture was cooled to room temperature, quenched with water, and the solution was adjusted to pH 2 using 1N HCl. The resulting basic solution was extracted with ethyl acetate and the organic phase was washed with water and brine, dried over anhydrous sodium sulfate, then filtered and concentrated. LCMS of the resulting residue showed two peaks for the acid indicating the formation of two regioisomers (Compounds 76A and 76B). HPLC-MS RT=1.35 and 1.45 min, mass calculated for formula $C_{11}H_7N_3O_2S$ 245.03, observed LCMS m/z 246.1 (M+H).

Example 77

Preparation of Compounds 33, 40, 53, 59, 60, 76, 173, 176 and 179

The compounds of the present invention depicted below were made by reacting compound 76A or 76B with the appropriate coupling partner using the method described in Steps C and D of Example 66.

| Compound | M + H Observed | Retention Time |
|---|---|---|
| 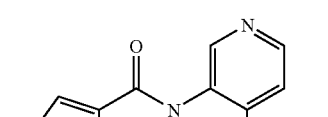 173 | 420.1 | 2.07 |

409
-continued
| Compound | M + H Observed | Retention Time |
|---|---|---|
| 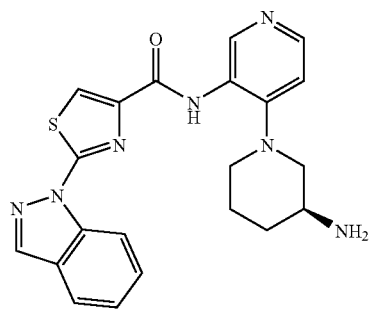<br>171 | 420.1 | 2.07 |
| 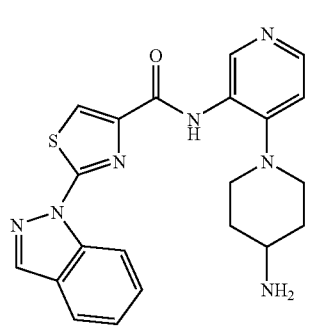<br>59 | 420.15 | 2.22 |
| 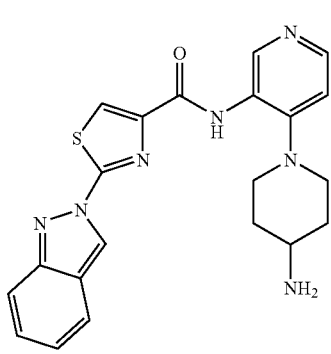<br>60 | 420.15 | 2.16 |
| 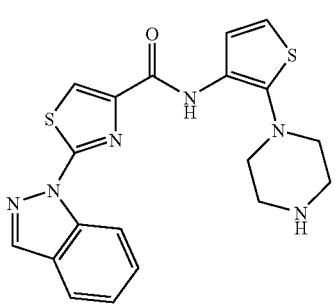<br>33 | 411.09 | 3.34 |
410
-continued
| Compound | M + H Observed | Retention Time |
|---|---|---|
| 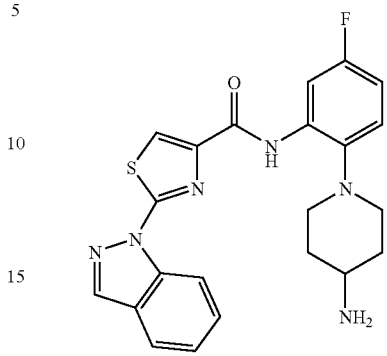<br>40 | 423.1 | 3.75 |
| 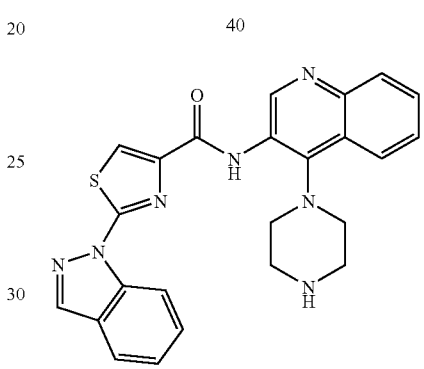<br>76 | 456.15 | 2.31 |
| 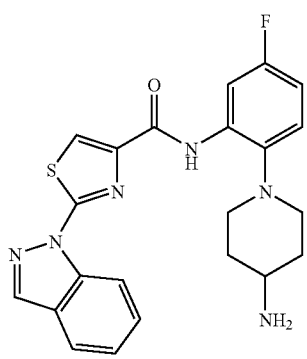<br>53 | 437.2 | 4.0 |
| 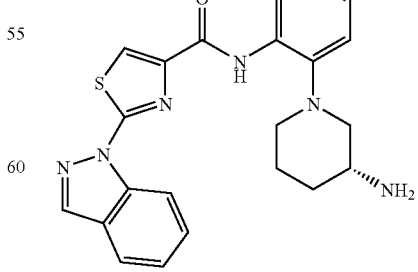<br>179 | 419.15 | 3.57 |

411
-continued

| Compound | M + H Observed | Retention Time |
|---|---|---|
| 176 | 419.15 | 3.54 |

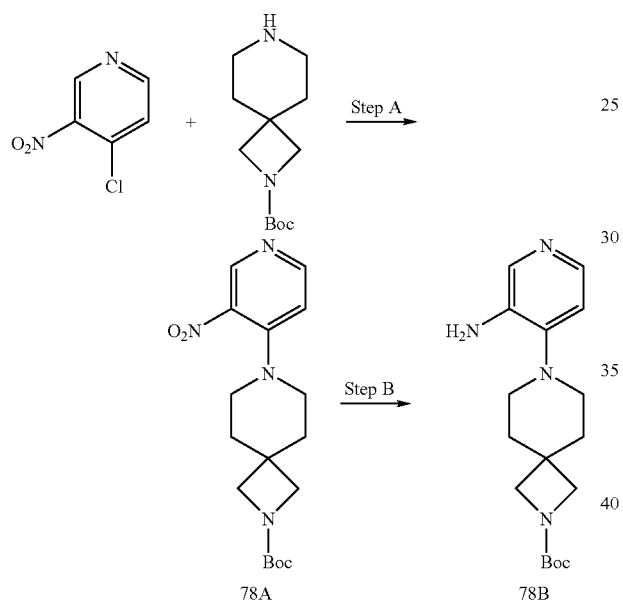

412

Step A:

To a vial were added 4-chloro-3-nitro pyridine (2 mmol) and spirocyclic amine (2 mmol). The starting materials were dissolved in 4 mL of dichloromethane followed by the addition of DIPEA (6 mmol). The reaction was stirred at 60° for about 15 hours, then the reaction mixture was concentrated and using preparative liquid chromatography (0-5% methanol in ethyl acetate) to provide compound 78A. Recovered 1.6 mmol (80%) of 274. Mass calculated for formula $C_{17}H_{24}N_4O_4$ 348.18, observed LCMS m/z 348.20 (M+H).

Step B:

To a round-bottom flask was added a solution of compound 78A in ethyl acetate. Next, Pd/C was added to the mixture. The flask was sealed with a septum and evacuated. The mixture was hydrogenated using a balloon for about 15 hours. Product was confirmed by LCMS. The Pd/C was filtered off using Celite and the filtrate was concentrated in vacuo to provide compound 78B in quantitative yield. Mass calculated for formula $C_{17}H_{26}N_4O_2$ 318.21, observed LCMS m/z 319.20 (M+H). LCMS calculated for 275: 318.21.

Using the methods described in Steps A and B above, and using the appropriate reactants, the following intermediate compounds were made:

| Starting Material | Product | M + 1 | Retention time (min) |
|---|---|---|---|
| | 78C | 319.2 | 0.95 |

-continued
| Starting Material | Product | M + 1 | Retention time (min) |
|---|---|---|---|
| 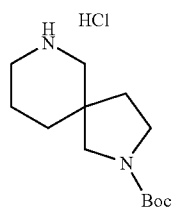 | 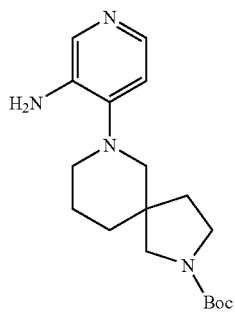
78D | 333.2 | 1.11 |
| 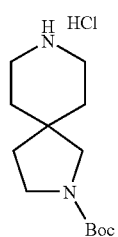 | 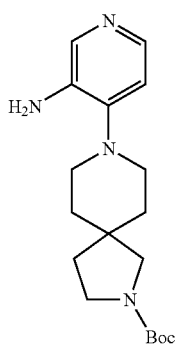
78E | 333.3 | 1.21 |
| 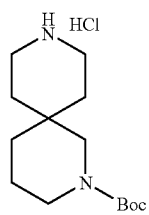 | 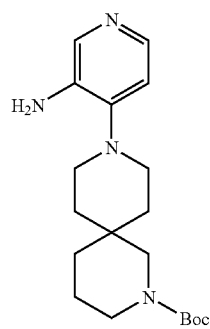
78F | 347.2 | 1.12 |
| 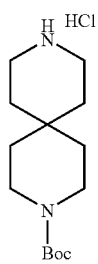 | 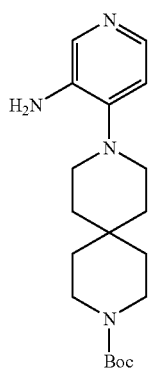
78G | 347.2 | 1.05 |

| Starting Material | Product | M + 1 | Retention time (min) |
|---|---|---|---|
| 78H | | 307.3 | 0.99 |

Example 79

Preparation of Compound 79A

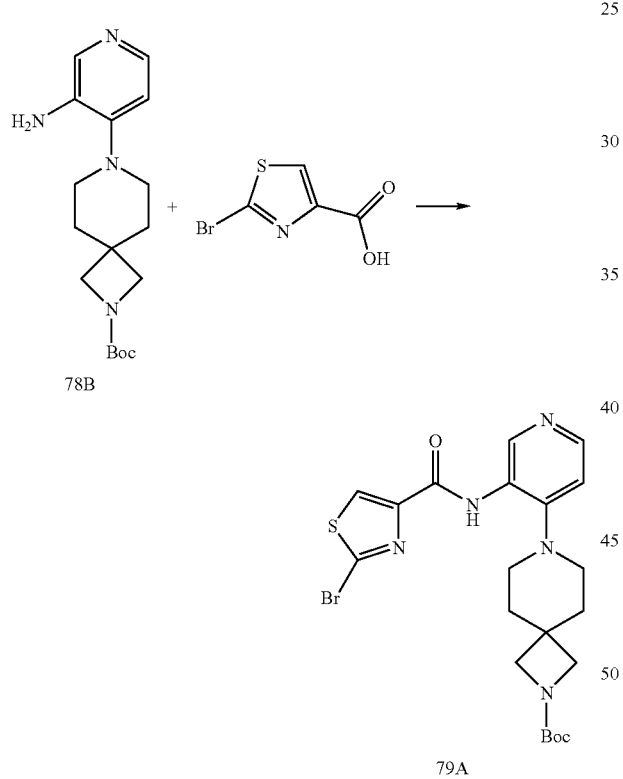

To a solution of 2-bromo thiazole-5 carboxylic acid (0.57 mmol) and HATU (0.68 mmol) in 1 mL of DMF, was added DIPEA (3 equivalents, 1.6 mmol) and the resulting reaction was stirred for 10 minutes at room temperature. To the reaction mixture was then added a solution of compound 78B (0.57 mmol) in 0.5 mL of DMF and the resulting reaction was stirred at room temperature for an additional 2 hours. The reaction mixture was then concentrated in vacuo and the residue obtained was purified using preparative liquid chromatography (5-10% methanol in dichloromethane) to provide 0.54 mmol (95%) of compound 79A.

Example 80

Preparation of Compound 221

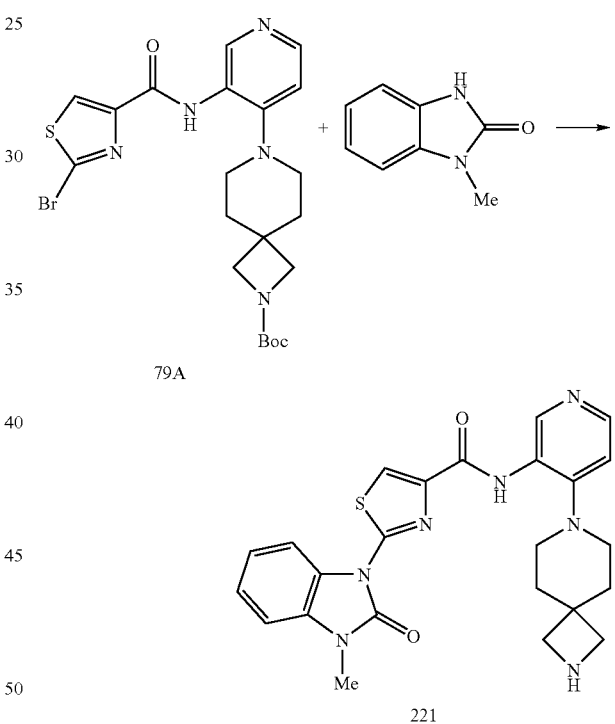

Compound 79A (0.15 mmol), 1-methyl-1,3-dihydro-benzimidazole-2-one (0.1 mmol), $Pd_2$ $dba_3$ (0.01 mmol), Xantphos (0.02 mmol), and $K_3PO_4$ (0.3 mmol) were placed in vial and diluted with dioxane (1 mL). The resulting solution was degassed and flushed with argon, then capped, and sonicated. The reaction was heated to 90° C. and allowed to stir at this temperature for 2 hours, then the reaction mixture was cooled to room temperature and diluted with ethyl acetate. The organic layer was sequentially washed with saturated $NaHCO_3$ (aq), brine, and water. The organic layer was then dried with sodium sulfate, filtered and concentrated in vacuo and the crude residue obtained was purified using preparative liquid chromatography (5-10% methanol in dichloromethane). The product obtained was then lyophilized and the solid material obtained was treated with excess 2M HCl in dioxane to provide compound 221.
Using the method described above, the following illustrative compounds of the invention were made:
| Compound | M + (m/z) | M + H | Retention time (minutes) |
|---|---|---|---|
| 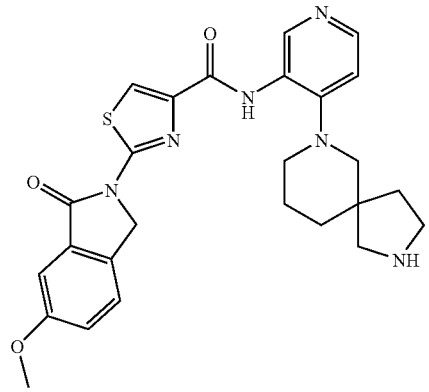 77 | 504.20 | 505.20 | 2.75 |
| 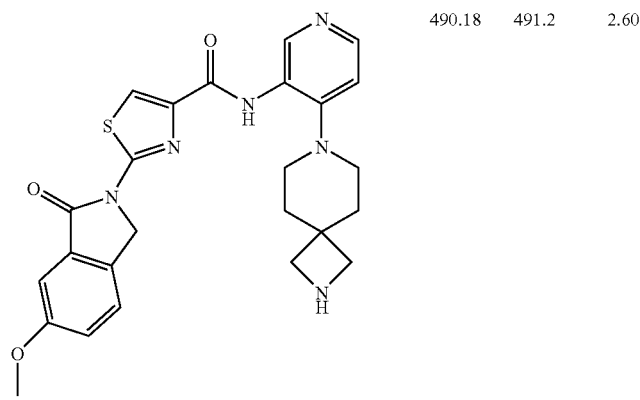 170 | 490.18 | 491.2 | 2.60 |
| 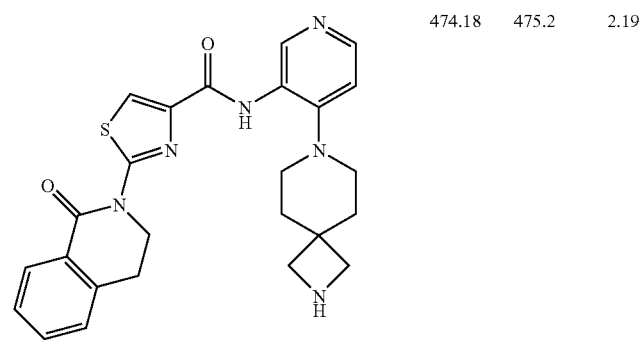 219 | 474.18 | 475.2 | 2.19 |

-continued

| Compound | M + (m/z) | M + H | Retention time (minutes) |
|---|---|---|---|
| 220 | 461.16 | 462.1 | 1.84 |
| 233 | 505.19 | 506.1 | 2.26 |
| 268 | 534.21 | 535.2 | 2.66 |

-continued
| Compound | M + (m/z) | M + H | Retention time (minutes) |
|---|---|---|---|
| 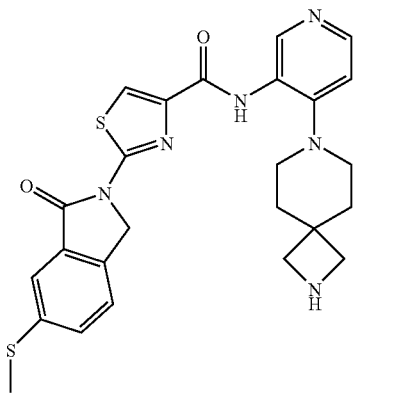 276 | 506.16 | 507.1 | 2.48 |
| 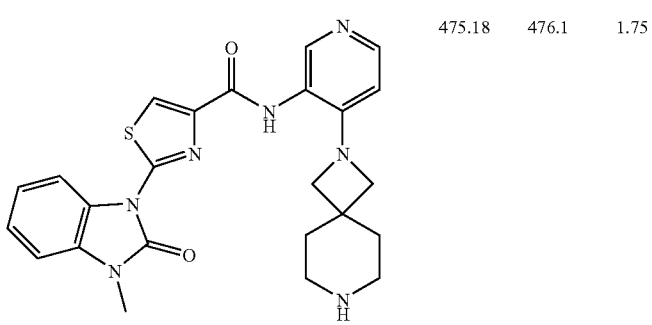 309 | 475.18 | 476.1 | 1.75 |
| 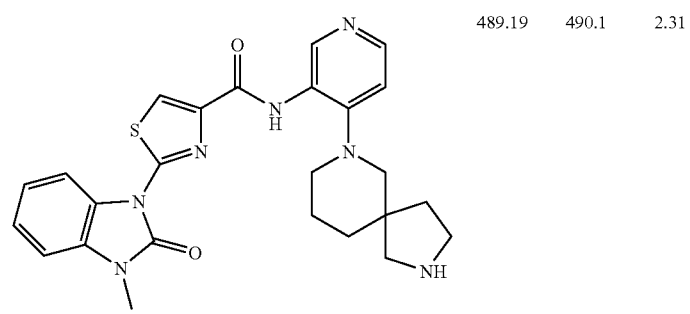 315 | 489.19 | 490.1 | 2.31 |

-continued

| Compound | M + (m/z) | M + H | Retention time (minutes) |
|---|---|---|---|
| 316 | 489.19 | 490.1 | 2.39 |
| 319 | 503.21 | 504.3 | 2.18 |
| 323 | 503.21 | 504.3 | 2.15 |

Example 81

Preparation of Compound 81B

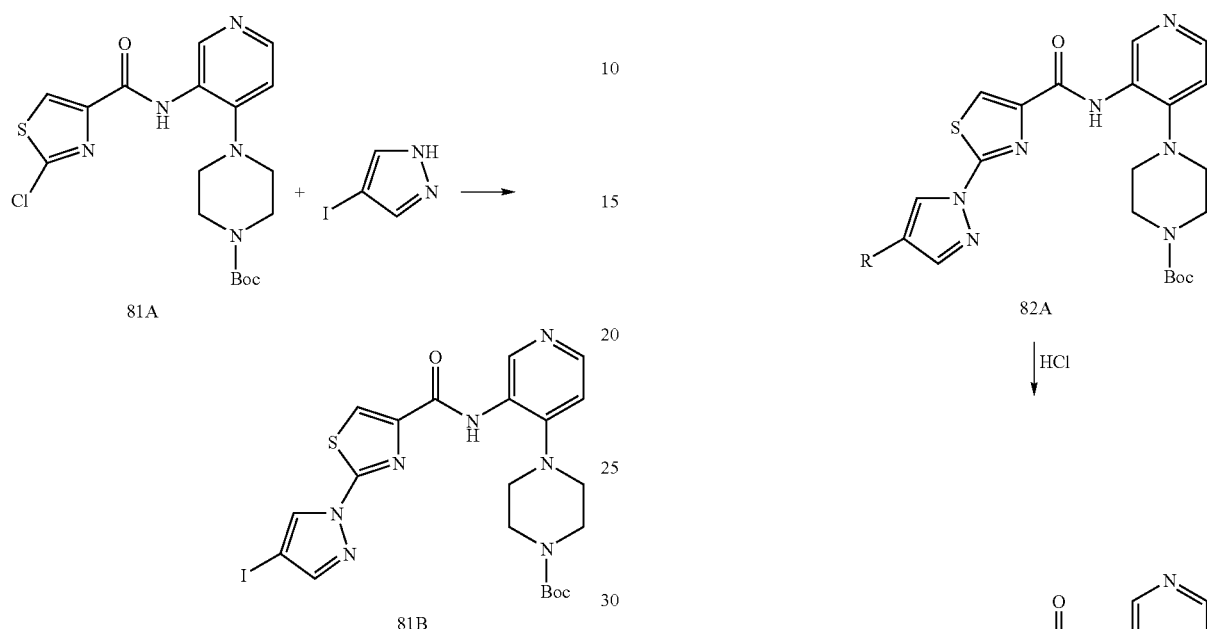

Using the method described in Example 24, compound 81A was reacted with 4-iodopyrazole to prepare compound 81B. Mass calculated for formula $C_{21}H_{24}N_7O_2SI$ 581.0, observed LCMS m/z 582.20 (M+H).

Example 82

Preparation of Compounds 62, 63, 66, 70, 272, 277 and 283

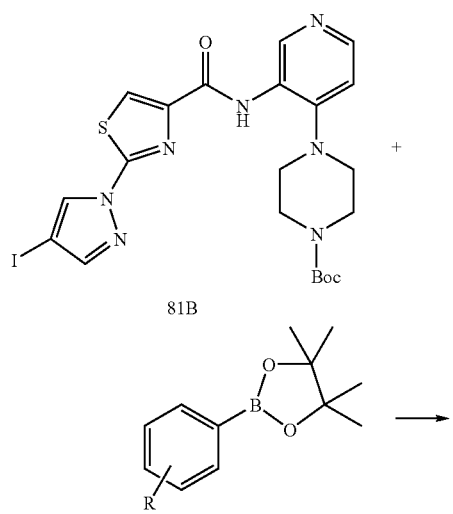

General Procedure:

Compound 81B (0.30 mmol), a representative boronic acid or ester (0.34 mmol), Pd(dppf)Cl$_2$ (0.034 mmol), and K$_3$PO$_4$ (0.9 mmol) are dissolved in 2 mL of dioxane and 300 µL of water. The resulting solution is degassed and flushed with argon, then heated to 90° C. and allowed to stir at this temperature for about 2 hours. The reaction is then diluted with ethyl acetate and the organic phase is washed sequentially with saturated aqueous NaHCO$_3$ and water. The organic layer is then dried over Na$_2$SO$_4$, filtered and concentrated in vacuo. The residue obtained can be purified using preparative HPLC to provide a compound of formula 82A, which is subsequently lyophilized and the purified product is then treated with 4N HCl to remove the Boc group and afforded the desired product 82B.

Using this method, the following illustrative compounds of the invention were made.

| Compound | M + H Observed | Ret time (min) |
|---|---|---|
| 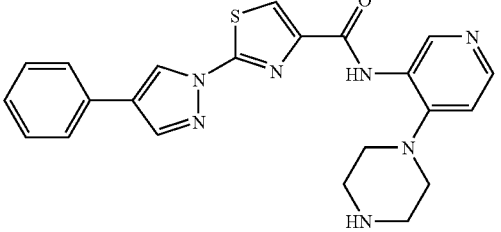 62 | 432.15 | 2.60 |
| 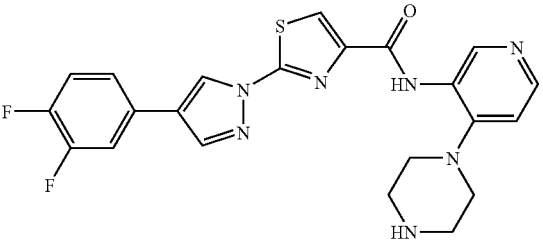 63 | 468.1 | 2.49 |
| 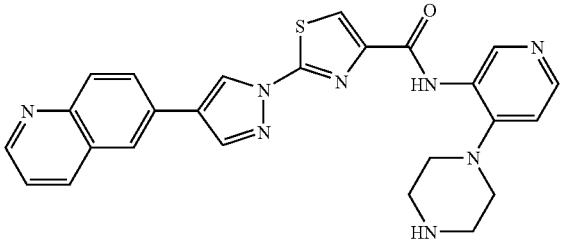 66 | 483.1 | 1.69 |
| 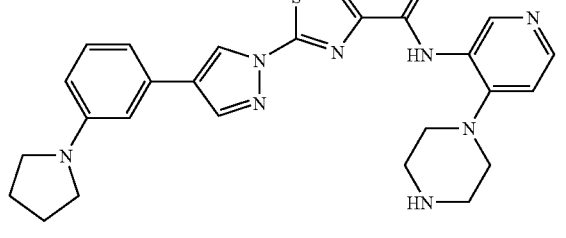 70 | 501.2 | 2.63 |
| 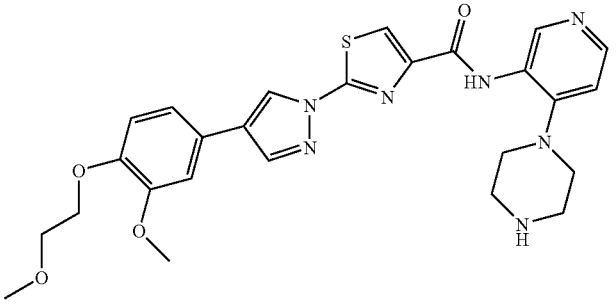 | 536.2 | 2.86 |

| Compound | M + H Observed | Ret time (min) |
|---|---|---|
| 277 | 506.2 | 2.96 |
| 283 | 506.2 | 2.95 |

Example 83

Preparation of Compound 128

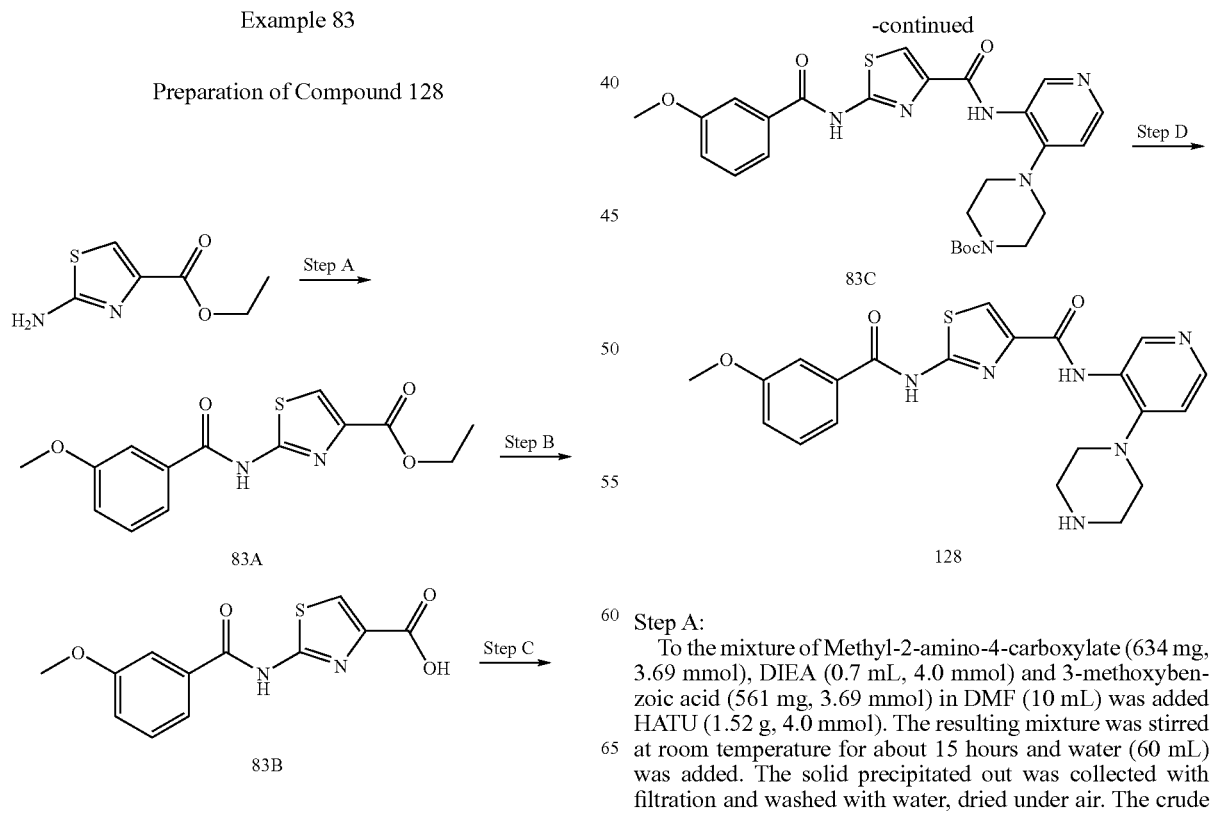

Step A:
To the mixture of Methyl-2-amino-4-carboxylate (634 mg, 3.69 mmol), DIEA (0.7 mL, 4.0 mmol) and 3-methoxybenzoic acid (561 mg, 3.69 mmol) in DMF (10 mL) was added HATU (1.52 g, 4.0 mmol). The resulting mixture was stirred at room temperature for about 15 hours and water (60 mL) was added. The solid precipitated out was collected with filtration and washed with water, dried under air. The crude product 83A was used in the next step directly without any further purification. HPLC-MS $t_R$=1.71 min (UV$_{254\ nm}$); mass calculated for formula $C_{14}H_{14}N_2O_4S$ 306.1, observed LCMS m/z 307.1 (M+H).

Step B:

The compound 83B was prepared by hydrolyzing compound 83A using the method described in Example 50 above. HPLC-MS $t_R$=1.45 min (UV$_{254\ nm}$); mass calculated for formula $C_{12}H_{10}N_2O_4S$ 278.0, observed LCMS m/z 279.1 (M+H).

Step C:

Compound 83C was prepared by reacting compound 83B with the appropriate coupling partner according to the method described in Example 58 above. HPLC-MS $t_R$=1.50 min (UV$_{254\ nm}$); mass calculated for formula $C_{26}H_{30}N_6O_5S$ 538.2, observed LCMS m/z 539.2 (M+H).

Step D:

Compound 128 was prepared by deprotecting compound 83C using the method described in Example 62 above. HPLC-MS $t_R$=0.94 min (UV$_{254\ nm}$); mass calculated for formula $C_{21}H_{22}N_6O_3S$ 438.1, observed LCMS m/z 439.1 (M+H).

Example 84

CHK1 SPA Assay

An in vitro assay was developed that utilizes recombinant His-CHK1 expressed in the baculovirus expression system as an enzyme source and a biotinylated peptide based on CDC25C as substrate (biotin-RSGLYRSPSMPENLNRPR).

Materials and Reagents:

1) CDC25C Ser 216 C-term Biotinylated peptide substrate (25 mg), stored at −20° C., Custom Synthesis by Research Genetics: biotin-RSGLYRSPSMPENLNRPR 2595.4 MW
2) His-CHK1 In House lot P976, 235 μg/mL, stored at −80° C.
3) D-PBS (without CaCl and MgCl): GIBCO, Cat. #14190-144
4) SPA beads: Amersham, Cat. # SPQ0032: 500 mg/vial
   Add 10 mL of D-PBS to 500 mg of SPA beads to make a working concentration of 50 mg/mL. Store at 4° C. Use within 2 week after hydration.
5) 96-Well White Microplate with Bonded GF/B filter: Packard, Cat. #6005177
6) Top seal-A 96 well Adhesive Film: Perkin Elmer, Cat. #6005185
7) 96-well Non-Binding White Polystyrene Plate: Corning, Cat. #6005177
8) $MgCl_2$: Sigma, Cat. #M-8266
9) DTT: Promega, Cat. #V3155
10) ATP, stored at 4° C.: Sigma, Cat. #A-5394
11) $\gamma^{33}$P-ATP, 1000-3000 Ci/mMol: Amersham, Cat. #AH9968
12) NaCl: Fisher Scientific, Cat. #BP358-212
13) $H_3PO_4$ 85% Fisher, Cat. #A242-500
14) Tris-HCL pH 8.0: Bio-Whittaker, Cat. #16-015V
15) Staurosporine, 100 μg: CALBIOCHEM, Cat. #569397
16) Hypure Cell Culture Grade Water, 500 mL: HyClone, Cat. #SH30529.02

Reaction Mixtures:

1) Kinase Buffer: 50 mM Tris pH 8.0; 10 mM $MgCl_2$; 1 mM DTT
2) His-CHK1, In House Lot P976, MW ~30 KDa, stored at −80° C.

6 nM is required to yield positive controls of ~5,000 CPM. For 1 plate (100 rxn): dilute 8 μL of 235 μg/mL (7.83 μM) stock in 2 mL Kinase Buffer. This makes a 31 nM mixture. Add 20 μL/well. This makes a final reaction concentration of 6 nM.

3) CDC25C Biotinylated peptide.

Dilute CDC25C to 1 mg/mL (385 μM) stock and store at −20° C. For 1 plate (100 rxn): dilute 10 μL of 1 mg/mL peptide stock in 2 mL Kinase Buffer. This gives a 1.925 μM mix. Add 20 μL/rxn. This makes a final reaction concentration of 385 nM.

4) ATP Mix.

For 1 plate (100 rxn): dilute 10 μL of 1 mM ATP (cold) stock and 2 μL fresh P33-ATP (20 μCi) in 5 mL Kinase Buffer. This gives a 2 μM ATP (cold) solution; add 50 μL/well to start the reaction. Final volume is 100 μL/rxn so the final reaction concentrations will be 1 μM ATP (cold) and 0.2 μCi/rxn.

5) Stop Solution:

For 1 plate add: To 10 mL Wash Buffer 2 (2M NaCl 1% $H_3PO_4$): 1 mL SPA bead slurry (50 mg); Add 100 pt/well
6) Wash buffer 1: 2 M NaCl
7) Wash buffer 2: 2 M NaCl, 1% $H_3PO_4$ Assay Procedure:

| Assay Component | Final Concentration | Volume |
| --- | --- | --- |
| CHK1 | 6 nM | 20 μl/rxn |
| Compound (10% DMSO) | — | 10 μl/rxn |
| CDC25C | 0.385 μM | 20 μl/rxn |
| $\gamma^{33}$P-ATP | 0.2 μCi/rxn | 50 μl/rxn |
| Cold ATP | 1 μM | |
| Stop solution SPA beads | 0.5 mg/rxn | 100 μl/rxn* |
| | | 200 μl/rxn** |

*Total reaction volume for assay.
**Final reaction volume at termination of reaction (after addition of stop solution).

1) Dilute compounds to desired concentrations in water/10% DMSO—this will give a final DMSO concentration of 1% in the rxn. Dispense 10 μL/rxn to appropriate wells. Add 10 μL 10% DMSO to positive (CHK1+CDC25C+ATP) and negative (CHK1+ATP only) control wells.
2) Thaw enzyme on ice—dilute enzyme to proper concentration in kinase buffer (see Reaction Mixtures) and dispense 20 μL to each well.
3) Thaw the Biotinylated substrate on ice and dilute in kinase buffer (see Reaction Mixtures). Add 20 μL/well except to negative control wells. Instead, add 20 μL Kinase Buffer to these wells.
4) Dilute ATP (cold) and P33-ATP in kinase buffer (see Reaction Mixtures). Add 50 μL/well to start the reaction.
5) Allow the reaction to run for 2 hours at room temperature.
6) Stop reaction by adding 100 μL of the SPA beads/stop solution (see Reaction Mixtures) and leave to incubate for 15 minutes before harvest
7) Place a blank Packard GF/B filter plate into the vacuum filter device (Packard plate harvester) and aspirate 200 mL water through to wet the system.
8) Take out the blank and put in the Packard GF/B filter plate.
9) Aspirate the reaction through the filter plate.
10) Wash: 200 mL each wash; 1× with 2M NaCl; 1× with 2M NaCl/1% $H_3PO_4$
11) Allow filter plate to dry 15 min.
12) Put TopSeal-A adhesive on top of filter plate.

13) Run filter plate in Top Count
   Settings: Data mode: CPM
   Radio nuclide: Manual SPA:P33
   Scintillator: Liq/plast
   Energy Range Low IC$_{50}$ DETERMINATIONS: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate IC$_{50}$ values, the dose-response curves were then fitted to a standard sigmoidal curve and IC$_{50}$ values were derived by nonlinear regression analysis. IC$_{50}$ values for illustrative compounds of the present invention determined according to the above method are set forth in the table below, wherein the compound numbers in the table correspond to the compound numbering in the specification.

Selected Anilinopiperazine Derivatives of the present invention, when tested using this assay provided IC$_{50}$ values ranging from about 1 nM to about 10 μM.

Example 85

CDK2 Assay

BACULOVIRUS CONSTRUCTIONS: Cyclin E was cloned into pVL1393 (Pharmingen, La Jolla, Calif.) by PCR, with the addition of 5 histidine residues at the amino-terminal end to allow purification on nickel resin. The expressed protein was approximately 45 kDa. CDK2 was cloned into pVL1393 by PCR, with the addition of a haemaglutinin epitope tag at the carboxy-terminal end (YDVPDYAS). The expressed protein was approximately 34 kDa in size.

ENZYME PRODUCTION: Recombinant baculoviruses expressing cyclin E and CDK2 were co-infected into SF9 cells at an equal multiplicity of infection (MOI=5), for 48 hrs. Cells were harvested by centrifugation at 1000 RPM for 10 minutes, then pellets lysed on ice for 30 minutes in five times the pellet volume of lysis buffer containing 50 mM Tris pH 8.0, 150 mM NaCl, 1% NP40, 1 mM DTT and protease inhibitors (Roche Diagnostics GmbH, Mannheim, Germany). Lysates were spun down at 15000 RPM for 10 minutes and the supernatant retained. 5 mL of nickel beads (for one liter of SF9 cells) were washed three times in lysis buffer (Qiagen GmbH, Germany). Imidazole was added to the baculovirus supernatant to a final concentration of 20 mM, then incubated with the nickel beads for 45 minutes at 4° C. Proteins were eluted with lysis buffer containing 250 mM imidazole. Eluate was dialyzed overnight in 2 liters of kinase buffer containing 50 mM Tris pH 8.0, 1 mM DTT, 10 mM MgCl$_2$, 100 μM sodium orthovanadate and 20% glycerol. Enzyme was stored in aliquots at −70° C.

Example 86

In Vitro Cyclin E/CDK2 Kinase Assay

Cyclin E/CDK2 kinase assays were performed in low protein binding 96-well plates (Corning Inc, Corning, N.Y.). Enzyme was diluted to a final concentration of 50 μg/mL in kinase buffer containing 50 mM Tris pH 8.0, 10 mM MgCl$_2$, 1 mM DTT, and 0.1 mM sodium orthovanadate. The substrate used in these reactions was a biotinylated peptide derived from Histone H1 (from Amersham, UK). The substrate was thawed on ice and diluted to 2 μM in kinase buffer. Compounds were diluted in 10% DMSO to desirable concentrations. For each kinase reaction, 20 μL of the 50 μg/mL enzyme solution (1 μg of enzyme) and 20 μl of the 2 substrate solution were mixed, then combined with 10 μL of diluted compound in each well for testing. The kinase reaction was started by addition of 50 μL of 2 ATP and 0.1 μCi of 33P-ATP (from Amersham, UK). The reaction was allowed to run for 1 hour at room temperature. The reaction was stopped by adding 200 μL of stop buffer containing 0.1% Triton X-100, 1 mM ATP, 5 mM EDTA, and 5 mg/mL streptavidine coated SPA beads (from Amersham, UK) for 15 minutes. The SPA beads were then captured onto a 96-well GF/B filter plate (Packard/Perkin Elmer Life Sciences) using a Filtermate universal harvester (Packard/Perkin Elmer Life Sciences.). Non-specific signals were eliminated by washing the beads twice with 2M NaCl then twice with 2 M NaCl with 1% phosphoric acid. The radioactive signal was then measured using a Top-Count 96 well liquid scintillation counter (from Packard/Perkin Elmer Life Sciences).

IC$_{50}$ DETERMINATIONS: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate IC$_{50}$ values, the dose-response curves were then fitted to a standard sigmoidal curve and IC$_{50}$ values were derived by nonlinear regression analysis.

Example 87

MEK1 Kinase Assay

Full-length active phosphorylated MEK1 was expressed as a 6× histidine tagged protein (His$_6$-MEK1) by baculovirus infection of Hi-Five cells co-infected with a baculovirus expressing untagged constitutively active Raf-1. Several milligrams of active His$_6$-MEK1 was then purified by Ni-NTA affinity chromatography followed by gel filtration chromatography. Full-length murine catalytically inactive ERK2KR, which had the lysine in subdomain II mutated to arginine was used as a substrate. ERK2KR was expressed from vector pET32aRC in IPTG-induced BL21D3 *E. coli* as a biotinylated, 6× histidine and thioredoxin tagged fusion protein and purified by Ni-NTA affinity chromatography followed by Mono Q ion exchange chromatography. Kinase reactions were performed in duplicate in a 96-well plate, 33 μL per well at 25° C. for 15 mins, and consisted of 20 nM His$_6$-MEK1, 2 μM ERK2KR, 2 μM ATP, 10 μCi/μL [γ-$^{33}$P]-ATP, 10 mM MgCl$_2$, 0.01% β-octylglucoside, 1 mM DTT, 20 mM HEPES pH 7.5, 3% DMSO and test compounds ranging from 20 μM down to 0.08 nM. Kinase reactions were stopped by addition of 30 μL of 1.5% o-phosphoric acid, transferred to Millipore Multiscreen-PH plates and incubated for 5 minutes to allow ERK2KR binding. Non-specific activity was estimated from pre-inactivated reactions wherein 30 μL of 1.5% o-phosphoric acid was added per well before addition of enzyme. Stopped plates were washed three times by vacuum filtration with 0.75% o-phosphoric acid followed by two washes with 100% ethanol and air dried. 504 of scintillation cocktail was added to each well and $^{33}$P incorporated into ERK2KR was detected using a Wallac Microbeta 1450 JET scintillation counter. Percentage inhibition, IC$_{50}$ and Hill slope values were calculated using ActivityBase software.

Selected Anilinopiperazine Derivatives of the present invention, when tested using this assay, provided IC$_{50}$ values ranging from about 10 nM to about 100 μM.

Example 88

General Procedure for MEK1 TdF Assays

1 µM protein was mixed with micromolar concentrations (usually 1-50 µM) of compounds in 20 µl of assay buffer (25 mM HEPES, pH 7.4, 300 mM NaCl, 1 mM DTT, 2% DMSO, Sypro Orange 5x) in a white 96-well PCR plate. The plate is sealed by clear strips and placed in a thermocycler (Chromo4, BioRad). The fluorescence intensities are monitored at every 0.5° C. increment during melting from 25° C. to 95° C. The data are exported into an excel sheet and subject to a custom curve fitting algorithm to derive TdF Kd values. All TdF Kd values have an error margin of ~50% due to uncertainty with the enthalpy change of binding.

Selected Anilinopiperazine Derivatives of the present invention, when tested using this assay, provided $K_d$ values ranging from about 1 µM to about 100 µM.

Example 89

General Procedure for MEK1 Delfia Enzyme Activity Assay

The inhibitory effect of compounds was determined with a DELFIA (Perkin-Elmer) based enzyme assay in which both compound individual percent inhibitions and dose response curves (IC50 determinations) were run. Activated recombinant human MEK1 (5 nanomolar final concentration) in buffer containing Hepes, magnesium chloride, dithiothreitol and ATP (2 micromolar final concentration) was preincubated for 10 minutes, before starting the reaction by addition of the recombinant MEK1 substrate ERK (1 micromolar final concentration), which contains a biotin label. The reaction was run at 20 degrees centigrade for 60 minutes, at which time the reaction was stopped by transfer of reaction aliquots to ROCHE streptavidin microplates (Perkin-Elmer #11734776001) containing DELFIA assay buffer (Perkin-Elmer #4002-0010). After one hour of binding at room temperature with agitation the plates were washed with DELFIA wash buffer (Perkin-Elmer #4010-0010) following which DELFIA assay buffer containing a phosphotyrosine specific antibody (Perkin Elmer #AD0040) was added to the plate and incubated as above for one hour. After a second wash, the plates were developed by addition of Perkin-Elmer enhancement solution (#4001-0010), followed by a 10 minute incubation with agitation. Europium fluorescence was read on a Victor 1420 fluorescent plate reader. Percent inhibition and IC50 determinations were made by comparison of compound containing assays to reaction controls.

Selected Anilinopiperazine Derivatives of the present invention, when tested using this assay, provided $IC_{50}$ values ranging from about 10 nM to about 100 µM.

Example 90

In Vitro Aurora TdF Assays

Aurora A Assay

Aurora A kinase assays were performed in low protein binding 384-well plates (Corning Inc). All reagents were thawed on ice. Test compounds were diluted in 100% DMSO to desirable concentrations. Each reaction consisted of 8 nM enzyme (Aurora A, Upstate cat #14-511), 100 nM Tamra-PKAtide (Molecular Devices, 5TAMRA-GRTGRRNSI-COOH), 25 µM ATP (Roche), 1 mM DTT (Pierce), and kinase buffer (10 mM Tris, 10 mM MgCl2, 0.01% Tween 20). For each reaction, 14 µl containing TAMRA-PKAtide, ATP, DTT and kianse buffer were combined with 1 µl diluted compound. The kinase reaction was started by the addition of 5 µl diluted enzyme. The reaction was allowed to run for 2 hours at room temperature. The reaction was stopped by adding 60 µl IMAP beads (1:400 beads in progressive (94.7% buffer A: 5.3% buffer B) 1× buffer, 24 mM NaCl). After an additional 2 hours, fluorescent polarization was measured using an Analyst AD (Molecular devices).

Aurora B Assay

Aurora A kinase assays were performed in low protein binding 384-well plates (Corning Inc). All reagents were thawed on ice. Compounds were diluted in 100% DMSO to desirable concentrations. Each reaction consisted of 26 nM enzyme (Aurora B, Invitrogen cat #pv3970), 100 nM Tamra-PKAtide (Molecular Devices, 5TAMRA-GRTGRRNSI-COOH), 50 µM ATP (Roche), 1 mM DTT (Pierce), and kinase buffer (10 mM Tris, 10 mM $MgCl_2$, 0.01% Tween 20). For each reaction, 14 µl containing TAMRA-PKAtide, ATP, DTT and kianse buffer were combined with 1 µl diluted compound. The kinase reaction was started by the addition of 5 µl diluted enzyme. The reaction was allowed to run for 2 hours at room temperature. The reaction was stopped by adding 60 µl IMAP beads (1:400 beads in progressive (94.7% buffer A: 5.3% buffer B) 1× buffer, 24 mM NaCl). After an additional 2 hours, fluorescent polarization was measured using an Analyst AD (Molecular devices).

$IC_{50}$ Determinations

Dose-response curves were plotted from inhibition data generated each in duplicate, from 8-point serial dilutions of test compounds. Concentration of compound was plotted against kinase activity, calculated by degree of fluorescent polarization. To generate $IC_{50}$ values, the dose-response curves were then fitted to a standard sigmoidal curve and $IC_{50}$ values were derived by nonlinear regression analysis.

Selected Anilinopiperazine Derivatives of the present invention, when tested using this assay, provided $K_d$ values ranging from about 1 nM to about 100 µM.

Uses of the Anilinopiperazine Derivatives

The Anilinopiperazine Derivatives can be useful for treating or preventing a Condition in a patient.

Specific diseases and disorders treatable by administration of an effective amount of at least one Anilinopiperazine Derivative include, but are not limited to, those disclosed in U.S. Pat. No. 6,413,974, which is incorporated by reference herein.

Treatment or Prevention of a Cardiovascular Disease

The Anilinopiperazine Derivatives are useful for treating or preventing a cardiovascular disease in a patient.

Accordingly, in one embodiment, the present invention provides a method for treating a cardiovascular disease in a patient, comprising administering to the patient an effective amount of one or more Anilinopiperazine Derivatives.

Illustrative examples of cardiovascular diseases treatable or preventable using the present methods, include, but are not limited to atherosclerosis, congestive heart failure, cardiac arrhythmia, myocardial infarction, atrial fibrillation, atrial flutter, circulatory shock, left ventricular hypertrophy, ventricular tachycardia, supraventricular tachycardia, coronary artery disease, angina, infective endocarditis, non-infective endocarditis, cardiomyopathy, peripheral artery disease, Reynaud's phenomenon, deep venous thrombosis, aortic stenosis, mitral stenosis, pulmonic stenosis and tricuspid stenosis.

In one embodiment, the cardiovascular disease is atherosclerosis.

In another embodiment, the cardiovascular disease is congestive heart failure.

In another embodiment, the cardiovascular disease is coronary artery disease.

Treatment or Prevention of a CNS Disorder

The Anilinopiperazine Derivatives are useful for treating or preventing a central nervous system (CNS) disorder in a patient.

Accordingly, in one embodiment, the present invention provides a method for treating a CNS disorder in a patient, comprising administering to the patient an effective amount of one or more Anilinopiperazine Derivatives.

Illustrative examples of CNS disorders treatable or preventable using the present methods, include, but are not limited to hypoactivity of the central nervous system, hyperactivity of the central nervous system, a neurodegenerative disease, Alzheimer's disease, amyotrophic lateral sclerosis (ALS), Creutzfeldt-Jakob disease, Huntington disease, multiple sclerosis, Lewy body disorder, a tic disorder, Tourette's Syndrome, Parkinson disease, Pick's disease, a prion disease or schizophrenia, epilepsy, migraine, anxiety, bipolar disorder, depression, attention deficit hyperactivity disorder (ADHD) and dementia.

In one embodiment, the CNS disorder is Alzheimer's disease.

In another embodiment, the CNS disorder is Parkinson disease.

In another embodiment, the CNS disorder is ALS.

Treatment or Prevention of a Viral Disease

The Anilinopiperazine Derivatives are useful for treating or preventing a viral disease in a patient.

Accordingly, in one embodiment, the present invention provides a method for treating a viral disease in a patient, comprising administering to the patient an effective amount of one or more Anilinopiperazine Derivatives.

Illustrative examples of viral diseases treatable or preventable using the present methods include, but are not limited to, HIV, human papilloma virus (HPV), herpesvirus, poxvirus, Epstein-Barr virus, Sindbis virus and adenovirus.

In one embodiment the viral disease is HIV.

In another embodiment the viral disease is HPV.

Treatment or Prevention of a Fungal Infection

The Anilinopiperazine Derivatives are useful for treating or preventing a fungal infection in a patient.

Accordingly, in one embodiment, the present invention provides a method for treating a fungal infection in a patient, comprising administering to the patient an effective amount of one or more Anilinopiperazine Derivatives.

Illustrative examples of fungal infections treatable or preventable using the present methods include, but are not limited to, aspergillosis, blastomycosis, candidiasis, coccidioidomycosis, cryptococcosis, histomplamosis, an opportunistic fungi (including yeasts and molds), mucormycosis, mycetoma, paracoccidioidomycosis and sporotrichosis.

In one embodiment the fungal infection is candidiasis.

Treating or Preventing a Disease Related to the Activity of a Protein Kinase

The Anilinopiperazine Derivatives can be inhibitors, regulators or modulators of protein kinases and are useful for treating or preventing a disease related to the activity of a protein kinase in a patient.

Accordingly, in one embodiment, the present invention provides a method for treating a disease related to the activity of a protein kinase in a patient, comprising administering to the patient an effective amount of one or more Anilinopiperazine Derivatives.

Illustrative examples of diseases related to the activity of a protein kinase that are treatable or preventable using the present methods include, but are not limited to, cyclin-dependent kinases (CDKs) such as CDK1, CDK2, CDK3, CDK4, CDK5, CDK6 and CDK7, CDK8; aurora kinases such as Aurora-A, Aurora-B and Aurora-C; mitogen activated protein kinase (MAPK/ERK); glycogen synthase kinase 3 (GSK3beta); c-Met kinases, such as c-Met; Pim-1 kinases; checkpoint kinases, such as Chk1 and Chk2; tyrosine kinases, such as the HER subfamily (including, for example, EGFR (HER1), HER2, HER3 and HER4), the insulin subfamily (including, for example, INS-R, IGF-IR, IR, and IR-R), the PDGF subfamily (including, for example, PDGF-alpha and beta receptors, CSFIR, c-kit and FLK-II), the FLK family (including, for example, kinase insert domain receptor (KDR), fetal liver kinase-1 (FLK-1), fetal liver kinase-4 (FLK-4) and the fms-like tyrosine kinase-1 (flt-1)); non-receptor protein tyrosine kinases, for example LCK, Src, Frk, Btk, Csk, Abl, Zap70, Fes/Fps, Fak, Jak, Ack, and LIMK; and growth factor receptor tyrosine kinases such as VEGF-R2, FGF-R, TEK, Akt kinases and the like.

In one embodiment, the present invention provides a method of inhibiting one or more Checkpoint kinases in a patient in need thereof, comprising administering to the patient a therapeutically effective amount of at least one Anilinopiperazine Derivative or a pharmaceutically acceptable salt, solvate, ester, prodrug or stereoisomer thereof.

In another embodiment, the present invention provides a method of treating, or slowing the progression of, a disease associated with one or more Checkpoint kinases in a patient in need thereof, comprising administering a therapeutically effective amount of at least one Anilinopiperazine Derivative or a pharmaceutically acceptable salt, solvate, ester, prodrug or stereoisomer thereof.

In another embodiment, the present invention provides a method of treating one or more diseases associated with Checkpoint kinase, comprising administering to a patient in need of such treatment at least one Anilinopiperazine Derivative, or a pharmaceutically acceptable salt, solvate, ester, prodrug or stereoisomer thereof; and at least one additional anticancer agent, wherein the amounts of the at least one Anilinopiperazine Derivative and the at least one anticancer agent result in a therapeutic effect.

In still another embodiment, the present invention provides a method of treating, or slowing the progression of, a disease associated with one or more Checkpoint kinases in a patient in need thereof, comprising administering a therapeutically effective amount of a pharmaceutical composition comprising in combination at least one pharmaceutically acceptable carrier and at least one Anilinopiperazine Derivative, or a pharmaceutically acceptable salt, solvate, ester, prodrug or stereoisomer thereof.

In one embodiment, the checkpoint kinase to be inhibited, modulated or regulated is Chk1. In another embodiment, the checkpoint kinase to be inhibited, modulated or regulated is Chk2.

In one embodiment, the present invention provides a method of inhibiting one or more tyrosine kinases in a patient in need thereof, comprising administering to the patient a therapeutically effective amount of at least one Anilinopiperazine Derivative or a pharmaceutically acceptable salt, solvate, ester, prodrug or stereoisomer thereof.

In another embodiment, the present invention provides a method of treating, or slowing the progression of, a disease associated with one or more tyrosine kinases in a patient in need thereof, comprising administering a therapeutically effective amount of at least one Anilinopiperazine Derivative or a pharmaceutically acceptable salt, solvate, ester, prodrug or stereoisomer thereof.

In another embodiment, the present invention provides a method of treating one or more diseases associated with tyrosine kinase, comprising administering to a patient in need of such treatment at least one Anilinopiperazine Derivative, or a pharmaceutically acceptable salt, solvate, ester, prodrug or stereoisomer thereof; and at least one additional anticancer agent, wherein the amounts of the at least one Anilinopiperazine Derivative and the at least one anticancer agent result in a therapeutic effect.

In still another embodiment, the present invention provides a method of treating, or slowing the progression of, a disease associated with one or more tyrosine kinases in a patient in need thereof, comprising administering a therapeutically effective amount of a pharmaceutical composition comprising in combination at least one pharmaceutically acceptable carrier and at least one Anilinopiperazine Derivative or a pharmaceutically acceptable salt, solvate, ester, prodrug or stereoisomer thereof.

In specific embodiments, the tyrosine kinase being inhibited, modulated or regulated is VEGFR (VEGF-R2), EGFR, HER2, SRC, JAK or TEK, or a combination thereof.

In one embodiment, the present invention provides a method of inhibiting one or more Pim-1 kinases in a patient in need thereof, comprising administering to the patient a therapeutically effective amount of at least one Anilinopiperazine Derivative or a pharmaceutically acceptable salt, solvate, ester, prodrug or stereoisomer thereof.

In another embodiment, the present invention provides a method of treating, or slowing the progression of, a disease associated with one or more Pim-1 kinases in a patient in need thereof, comprising administering a therapeutically effective amount of at least one Anilinopiperazine Derivative or a pharmaceutically acceptable salt, solvate, ester, prodrug or stereoisomer thereof.

In another embodiment, the present invention provides a method of treating one or more diseases associated with Pim-1 kinase, comprising administering to a patient in need of such treatment at least one Anilinopiperazine Derivative, or a pharmaceutically acceptable salt, solvate, ester, prodrug or stereoisomer thereof; and at least one additional anticancer agent, wherein the amounts of the at least one Anilinopiperazine Derivative and the at least one anticancer agent result in a therapeutic effect.

In still another embodiment, the present invention provides a method of treating, or slowing the progression of, a disease associated with one or more Pim-1 kinases in a patient in need thereof, comprising administering a therapeutically effective amount of a pharmaceutical composition comprising in combination at least one pharmaceutically acceptable carrier and at least one Anilinopiperazine Derivative or a pharmaceutically acceptable salt, solvate, ester, prodrug or stereoisomer thereof.

In one embodiment, the present invention provides a method of treating one or more diseases associated with an Aurora kinase, comprising administering to a patient in need of such treatment at least one Anilinopiperazine Derivative, or a pharmaceutically acceptable salt, solvate, ester, prodrug or stereoisomer thereof; and at least one additional anticancer agent, wherein the amounts of the at least one Anilinopiperazine Derivative and the at least one anticancer agent result in a therapeutic effect.

In another embodiment, the present invention provides a method of treating, or slowing the progression of, a disease associated with one or more Aurora kinases in a patient in need thereof, comprising administering a therapeutically effective amount of a pharmaceutical composition comprising in combination at least one pharmaceutically acceptable carrier and at least one Anilinopiperazine Derivative or a pharmaceutically acceptable salt, solvate, ester, prodrug or stereoisomer thereof.

In one embodiment, the present invention provides a method of treating one or more diseases associated with a cyclin dependent kinase, comprising administering to a patient in need of such treatment an amount of a first compound, which is an Anilinopiperazine Derivative, or a pharmaceutically acceptable salt, solvate, ester, prodrug or stereoisomer thereof; and an amount of at least one second compound, the second compound being an anticancer agent different from the Anilinopiperazine Derivative, wherein the amounts of the first compound and the second compound result in a therapeutic effect.

The Anilinopiperazine Derivatives can also be useful for inhibiting oncogenes that encode for protein kinases. Non-limiting examples of such oncogenes include C-Met.

Treatment or Prevention of a Proliferative Disorder

The Anilinopiperazine Derivatives are useful for treating or preventing a proliferative disorder in a patient.

Accordingly, in one embodiment, the present invention provides a method for treating a proliferative disorder in a patient, comprising administering to the patient an effective amount of one or more Anilinopiperazine Derivatives.

Illustrative examples of proliferative disorders treatable or preventable using the present methods include, but are not limited to, cancer, atherosclerosis, benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, idiopathic pulmonary fibrosis, scleroderma and cirrhosis of the liver.

Induction or Inhibition of Apoptosis

The Anilinopiperazine Derivatives are useful for inducing or inhibiting apoptosis in a patient.

Accordingly, in one embodiment, the present invention provides a method for inducing or inhibiting apoptosis in a patient, comprising administering to the patient an effective amount of one or more Anilinopiperazine Derivatives.

The apoptotic response is aberrant in a variety of human diseases and the Anilinopiperazine Derivatives, as modulators of apoptosis, can be useful for the treatment of cancer, a viral infection, prevention of AIDS development in HIVinfected individuals, an autoimmune disease (including but not limited to systemic lupus, erythematosus, autoimmune mediated glomerulonephritis, rheumatoid arthritis, psoriasis, inflammatory bowel disease, and autoimmune diabetes mellitus), a neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), a myelodysplastic syndrome, aplastic anemia, an ischemic injury associated with myocardial infarction, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Treatment or Prevention of Cancer

The Anilinopiperazine Derivatives are useful for treating or preventing cancer in a patient.

Accordingly, in one embodiment, the present invention provides a method for treating cancer in a patient, comprising administering to the patient an effective amount of one or more Anilinopiperazine Derivatives.

Illustrative examples of cancers treatable or preventable using the present methods include, but are not limited to cancers of the bladder, breast, colon, rectum, kidney, liver, lung (including small cell lung cancer, non-small cell lung cancer, mesothelioma, and giant cell cancer), head and neck, esophagus, gall bladder, ovary, pancreas, stomach, cervix, thyroid, prostate or skin (including squamous cell carcinoma and melanoma); hematopoietic tumors of lymphoid lineage (including but not limited to, a leukemia such as acute lymphocytic leukemia, chronic lymphocytic leukemia or acute lymphoblastic leukemia; a lymphoma, such as B-cell lymphoma, T-cell lymphoma, Hodgkins lymphoma, non-Hodgkins lymphoma, hairy cell lymphoma, mantle cell lymphoma, myeloma or Burkett's lymphoma); a cancer of unknown origin; hematopoietic tumors of myeloid lineage, including but not limited to, acute and chronic myelogenous leukemias, myelodysplastic syndrome and promyelocytic leukemia; tumors of mesenchymal origin, including but not limited to, fibrosarcoma and rhabdomyosarcoma; tumors of the central and peripheral nervous system, including but not limited to brain tumors such as an astrocytoma, a neuroblastoma, a glioma (such as glioblastoma multiforme) or a schwannoma; and other tumors, including seminoma, teratocarcinoma, osteosarcoma, xenoderoma pigmentosum, keratoctanthoma, thyroid follicular cancer and Kaposi's sarcoma. The Anilinopiperazine Derivatives are useful for treating primary and/or metastatic cancers.

The Anilinopiperazine Derivatives may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The Anilinopiperazine Derivatives may also be useful in inhibiting tumor angiogenesis and metastasis.

In one embodiment, the cancer treated or prevented is selected from: breast cancer, colorectal cancer, lung cancer, prostate cancer, ovarian cancer, pancreatic cancer, skin cancer, a leukemia and a lymphoma.

In another embodiment, the cancer treated or prevented is selected from: breast cancer, colorectal cancer, lung cancer and prostate cancer.

In one embodiment, the cancer treated or prevented is breast cancer.

In another embodiment, the cancer treated or prevented is lung cancer.

In another embodiment, the cancer treated or prevented is colorectal cancer.

In still another embodiment, the cancer treated or prevented is prostate cancer.

In still another embodiment, the cancer treated or prevented is a leukemia.

In still another embodiment, the cancer treated or prevented is a lymphoma.

In one embodiment, the cancer treated or prevented is a solid tumor.

In another embodiment, the cancer treated or prevented is a cancer of the blood or lymph.

In one embodiment, the cancer treated or prevented is a primary cancer.

In another embodiment, the cancer treated or prevented is a metastatic cancer.

In a further embodiment, the patient is being treated for both primary and metastatic cancer.

Combination Therapy

In one embodiment, the present invention provides methods for treating a Condition in a patient, the method comprising administering to the patient one or more Anilinopiperazine Derivatives, or a pharmaceutically acceptable salt, solvate, ester or prodrug thereof and at least one additional therapeutic agent that is not an Anilinopiperazine Derivative, wherein the amounts administered are together effective to treat or prevent a Condition.

Additional therapeutic agents useful in the present methods include, but are not limited to, an anticancer agent, an agent useful for treating a cardiovascular disease, an agent useful for treating a CNS disorder, an antiviral agent, an antifungal agent, an anti-proliferative agent, an anti-alopecia agent, an anti-inflammatory agent, an agent useful for the treatment of a protein kinase-related disorder, an anti-ischemic agent or any combination of two or more of these agents.

In another embodiment, the other therapeutic agent is an agent useful for reducing any potential side effect of an Anilinopiperazine Derivative. Such potential side effects include, but are not limited to, nausea, vomiting, headache, fever, lethargy, muscle aches, diarrhea, general pain, and pain at an injection site.

When administering a combination therapy to a patient in need of such administration, the therapeutic agents in the combination, or a composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Anilinopiperazine Derivatives are administered during a time when the additional therapeutic agent(s) exert their prophylactic or therapeutic effect, or vice versa.

In another embodiment, the one or more Anilinopiperazine Derivatives and the additional therapeutic agent(s) are administered in doses commonly employed when such agents are used as monotherapy for treating a Condition.

In another embodiment, the one or more Anilinopiperazine Derivatives and the additional therapeutic agent(s) are administered in doses lower than the doses commonly employed when such agents are used as monotherapy for treating a Condition.

In still another embodiment, the one or more Anilinopiperazine Derivatives and the additional therapeutic agent(s) act synergistically and are administered in doses lower than the doses commonly employed when such agents are used as monotherapy for treating a Condition.

In one embodiment, the one or more Anilinopiperazine Derivatives and the additional therapeutic agent(s) are present in the same composition. In one embodiment, this composition is suitable for oral administration. In another embodiment, this composition is suitable for intravenous administration.

The one or more Anilinopiperazine Derivatives and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Anilinopiperazine Derivatives and the additional therapeutic agent(s) may inhibit the resistance of a Condition to one or more of these agents.

In one embodiment, the additional therapeutic agent is used at its known therapeutically effective dose. In another embodiment, the additional therapeutic agent is used at its normally prescribed dosage. In another embodiment, the additional therapeutic agent is used at less than its normally prescribed dosage or its known therapeutically effective dose.

The doses and dosage regimen of the other agents used in the combination therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When administered in combination, the Anilinopiperazine Derivative(s) and the other agent(s) for treating diseases or conditions listed above can be administered simultaneously or sequentially. This particularly useful when the components of the combination are given on different dosing schedules, e.g., one component is administered once daily and another every six hours, or when the compositions are different, e.g. one is a tablet and one is a capsule. A kit comprising the separate dosage forms is therefore advantageous.

Generally, a total daily dosage of the one or more Anilinopiperazine Derivatives and the additional therapeutic agent(s) can when administered as combination therapy, range from about 0.1 to about 2000 mg per day, although variations will necessarily occur depending on the target of the therapy, the patient and the route of administration. In one embodiment, the dosage is from about 0.2 to about 100 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

Combination Therapy for the Treatment of Cancer

The compounds of this invention may also be useful in combination (administered together or sequentially in any order) with one or more separate anticancer treatments such as surgery, radiation therapy, biological therapy (e.g., anticancer vaccine therapy) and/or the administration of at least one additional anticancer agent different from the Anilinopiperazine Derivatives, in order to treat or prevent cancer in a patient. The compounds of the present invention can be present in the same dosage unit as the additional anticancer agent(s) or in separate dosage units.

Non-limiting examples of additional anticancer agents (also known as anti-neoplastic agents) suitable for use in combination with the compounds of the present invention include cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide or teniposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other useful additional anticancer agents include but are not limited to Uracil mustard, Chlormethine, Ifosfamide, Melphalan, Chlorambucil, Pipobroman, Triethylenemelamine, ara-C, adriamycin, cytoxan, Clofarabine (Clolar® from Genzyme Oncology, Cambridge, Mass.), cladribine (Leustat® from Janssen-Cilag Ltd.), aphidicolon, rituxan (from Genentech/Biogen Idec), sunitinib (Sutent® from Pfizer), dasatinib (or BMS-354825 from Bristol-Myers Squibb), tezacitabine (from Aventis Pharma), Sml1, fludarabine (from Trigan Oncology Associates), pentostatin (from BC Cancer Agency), triapine (from Vion Pharmaceuticals), didox (from Bioseeker Group), trimidox (from ALS Therapy Development Foundation), amidox, 3-AP (3-aminopyridine-2-carboxaldehyde thiosemicarbazone), MDL-101,731 ((E)-2'-deoxy-2'-(fluoromethylene)cytidine) and gemcitabine.

Other useful additional anticancer agents include but are not limited to Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Oxaliplatin, Aroplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Herceptin, Bexxar, Velcade, Zevalin, Trisenox, Xeloda, Vinorelbine, Profimer, Erbitux, Liposomal, Thiotepa, Altretamine, Melphalan, Trastuzumab, Lerozole, Fulvestrant, Exemestane, Fulvestrant, Ifosfomide, Rituximab, C225 and Campath.

In one embodiment, the other anticancer agent is selected from: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Herceptin, Bexxar, Velcade, Zevalin, Trisenox, Xeloda, Vinorelbine, Profimer, Erbitux, Liposomal, Thiotepa, Altretamine, Melphalan, Trastuzumab, Lerozole, Fulvestrant, Exemestane, Ifosfomide, Rituximab, C225, Doxil, Ontak, Deposyt, Mylotarg, Campath, Celebrex, Sutent, Aranesp, Neupogen, Neulasta, Kepivance, SU11248, and PTK787.

In one embodiment, the other anticancer agent is a platinum-based agent, such as cisplatin, carboplatin or oxaliplatin.

In another embodiment, the other anticancer agent is an alkylating agent.

In another embodiment, the other anticancer agent is a vinca alkaloid, such as vincristine or vinblastine.

In still another embodiment, the other anticancer agent is a topoisomerase I inhibitor.

In another embodiment, the other anticancer agent is a topoisomerase II inhibitor.

In a further embodiment, the other anticancer agent is an antimetabolite.

In another embodiment, the other anticancer agent is a spindle poison.

In another embodiment, the other anticancer agent is an antitumor antibiotic.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.,* (1995) 108, 2897. Anilinopiperazine Derivatives may also be administered sequentially with known anticancer or cytotoxic agents when a combination formulation is inappropriate. The invention is not limited in the sequence of administration; Anilinopiperazine Derivatives may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research,* (1997) 57, 3375. Such techniques are within the skills of persons skilled in the art as well as attending physicians.

Accordingly, in an aspect, this invention includes methods for treating cancer in a patient, comprising administering to the patient an amount of at least one Anilinopiperazine Derivative, or a pharmaceutically acceptable salt, solvate, ester, prodrug or stereoisomer thereof, and one or more other anticancer treatment modalities, wherein the amounts of the Anilinopiperazine Derivative(s)/other treatment modality result in the desired therapeutic effect. In one embodiment, the at least one Anilinopiperazine Derivative and the one or more other treatment modalities act synergistically. In another embodiment, the at least one Anilinopiperazine Derivative and the one or more other treatment modalities act additively.

In one embodiment, the other treatment modality is surgery.

In another embodiment, the other treatment modality is radiation therapy.

In another embodiment, the other treatment modality is biological therapy, such as hormonal therapy or anticancer vaccine therapy.

The pharmacological properties of the compounds of this invention may be confirmed by a number of pharmacological assays. The exemplified pharmacological assays which are described herein below have been carried out with compounds according to the invention and their salts, solvates, esters or prodrugs.

Compositions and Administration

This invention is also directed to pharmaceutical compositions which comprise at least one Anilinopiperazine Derivative, or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously or intrathecally or some suitable combination(s) thereof.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 500 mg. In one embodiment, the quantity of active compound in a unit dose of preparation is from about 0.01 mg to about 250 mg. In another embodiment, the quantity of active compound in a unit dose of preparation is from about 0.1 mg to about 100 mg. In another embodiment, the quantity of active compound in a unit dose of preparation is from about 1.0 mg to about 100 mg. In another embodiment, the quantity of active compound in a unit dose of preparation is from about 1.0 mg to about 50 mg. In still another embodiment, the quantity of active compound in a unit dose of preparation is from about 1.0 mg to about 25 mg.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.01 mg/day to about 2000 mg/day of the Anilinopiperazine Derivatives. In one embodiment, a daily dosage regimen for oral administration is from about 1 mg/day to 1000 mg/day. In another embodiment, a daily dosage regimen for oral administration is from about 1 mg/day to 500 mg/day. In another embodiment, a daily dosage regimen for oral administration is from about 100 mg/day to 500 mg/day. In another embodiment, a daily dosage regimen for oral administration is from about 1 mg/day to 250 mg/day. In another embodiment, a daily dosage regimen for oral administration is from about 100 mg/day to 250 mg/day. In still another embodiment, a daily dosage regimen for oral administration is from about 1 mg/day to 100 mg/day. In still another embodiment, a daily dosage regimen for oral administration is from about 50 mg/day to 100 mg/day. In a further embodiment, a daily dosage regimen for oral administration is from about 1 mg/day to 50 mg/day. In another embodiment, a daily dosage regimen for oral administration is from about 25 mg/day to 50 mg/day. In a further embodiment, a daily dosage regimen for oral administration is from about 1 mg/day to 25 mg/day. The daily dosage may be administered in a single dosage or can be divided into from two to four divided doses.

Kits

In one aspect, the present invention provides a kit comprising an effective amount of one or more Anilinopiperazine Derivatives, or a pharmaceutically acceptable salt, solvate, ester or prodrug thereof, and a pharmaceutically acceptable carrier.

In another aspect the present invention provides a kit comprising an amount of one or more Anilinopiperazine Derivatives, or a pharmaceutically acceptable salt, solvate, ester or prodrug thereof, and an amount of at least one additional therapeutic agent listed above, wherein the combined amounts are effective for treating or preventing a Condition in a patient.

When the components of a combination therapy regimen are to be administered in more than one composition, they can be provided in a kit comprising a single package containing one or more containers, wherein one container contains one or more Anilinopiperazine Derivatives in a pharmaceutically acceptable carrier, and a second, separate container comprises an additional therapeutic agent in a pharmaceutically acceptable carrier, with the active components of each composition being present in amounts such that the combination is therapeutically effective.

In another aspect the present invention provides a kit comprising an amount of at least one Anilinopiperazine Derivative, or a pharmaceutically acceptable salt, solvate, ester or prodrug of said compound and an amount of at least one anticancer therapy and/or additional anticancer agent listed above, wherein the amounts of the two or more ingredients result in the desired therapeutic effect.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

What is claimed is:

1. A compound having the formula:

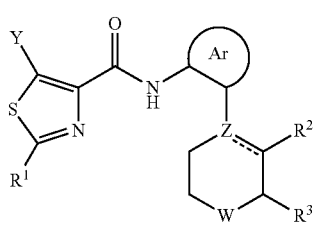

or a pharmaceutically acceptable salt, ester, prodrug or stereoisomer thereof, wherein the dashed line indicates an optional and additional bond, and wherein:

$R^1$ is nitrogen-containing heteroaryl, nitrogen-containing heterocyclyl, nitrogen-containing benzofused heteroaryl or nitrogen-containing benzofused heterocyclyl, wherein $R^1$ is joined to the rest of the compound of formula (I) via a ring nitrogen atom, and wherein one or more ring carbon atoms of the nitrogen-containing heteroaryl, nitrogen-containing heterocyclyl, nitrogen-containing benzofused heteroaryl or nitrogen-containing benzofused heterocyclyl group can be substituted with up to 5 substituents, which may be the same or different, and are independently selected from alkyl, aryl, halo, —OH, —O-alkyl, —O-aryl, —N($R^8$)$_2$— $CF_3$, —$NO_2$, —C(O)$R^8$, —C(O)O$R^8$, —C(O)N($R^8$)$_2$, —OC(O)$R^8$ or —NHC(O)$R^8$;

$R^2$ is —H, -alkyl, —$NH_2$ or —$CH_2NH_2$;

$R^3$ is —H, -alkyl, —$NH_2$ or —$CH_2NH_2$;

each occurrence of $R^4$ is independently —H, -alkyl, —$NH_2$, —OH, -alkylene-OH, —$CH_2NH_2$, —C(O)$R^5$, —C(O)$NH_2$, —C(O)NH-alkyl, —C(O)N(alkyl)$_2$, —NHC(O)$R^6$ or —NHS(O)$_2R^6$;

$R^5$ is —H, -alkyl, -aryl, -heteroaryl, —NHOH;

$R^6$ is —H, -alkyl or —$CF_3$;

$R^7$ is —H, —OH, —$C_1$-$C_6$ alkyl, —O—($C_1$-$C_6$ alkyl), or —$CF_3$;

$R^8$ is —H, alkyl, aryl, heterocyclyl, heteroaryl or cycloalkyl;

Ar is -arylene- or -heteroarylene-, wherein the arylene or heteroarylene is joined via 2 of its adjacent ring carbon atoms, and wherein the -arylene- or -heteroarylene- can be substituted with up to 4 substituents, which may be the same or different, and are independently selected from -halo, alkyl, alkoxy, aryloxy, —S$R^8$, —S(O)$R^8$, —S(O)$_2R^8$, —C(O)$R^8$, —C(O)O$R^8$, —C(O)N($R^8$)$_2$, —NHC(O)$R^8$, —$CF_3$, —CN or $NO_2$, and such that when Ar is tetrahydronaphthylene, $R^1$ and $R^2$ cannot both be hydrogen W is —NH— or —C($R^4$)$_2$—, wherein both $R^4$ groups and the carbon atom to which they are attached can combine to form a five to seven membered heterocyclyl or heteroaryl group;

Y is —H, -halo, -alkyl or —CN; and

Z is —$CR^7$— or —N—, when the optional additional bond is absent, and —C— when the optional additional bond is present.

2. The compound of claim 1, wherein $R^1$ is nitrogen-containing heteroaryl.

3. The compound of claim 1, wherein $R^1$ is nitrogen-containing heterocyclyl.

4. The compound of claim 1, wherein $R^1$ is nitrogen-containing benzofused heteroaryl.

5. The compound of claim 1, wherein $R^1$ is nitrogen-containing benzofused heterocyclyl.

6. The compound of claim 1, wherein $R^1$ is

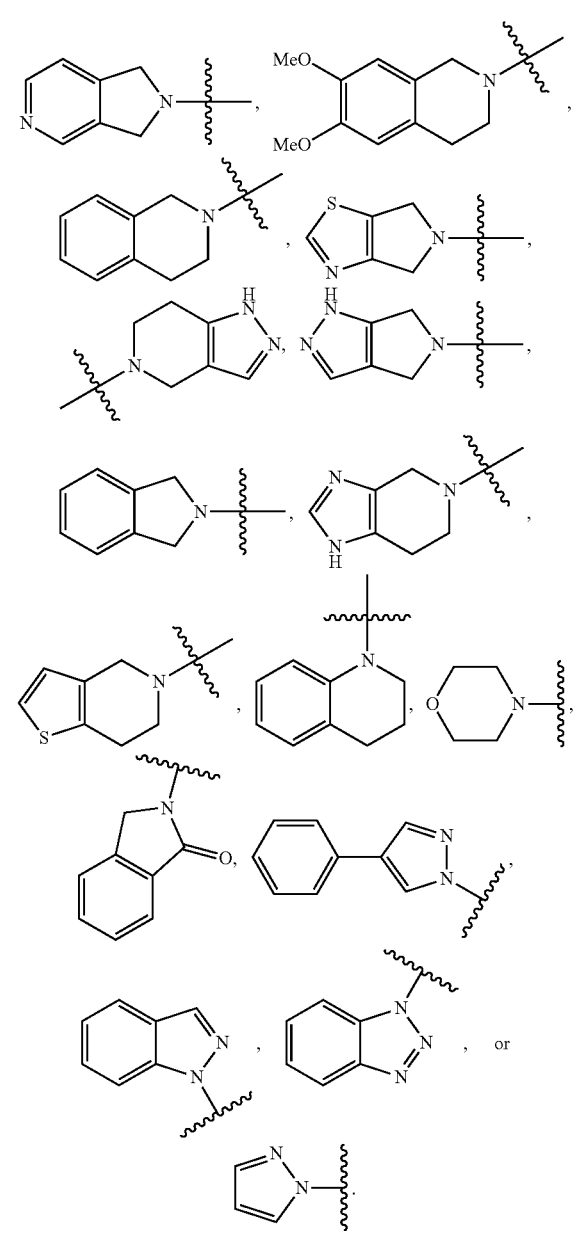

7. The compound of claim 1, wherein $R^2$ and $R^3$ are each —H; and Z is —N—.

8. The compound of claim 7, wherein W is —(C$R^4$)$_2$—.

9. The compound of claim 7, wherein W is NH.

10. The compound of claim 1, wherein Ar is:

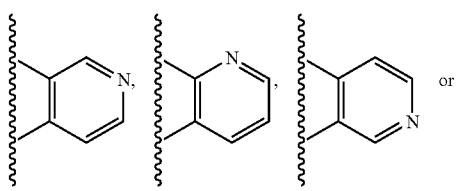

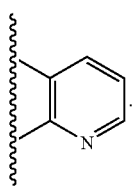

11. The compound of claim 8, wherein Ar is:

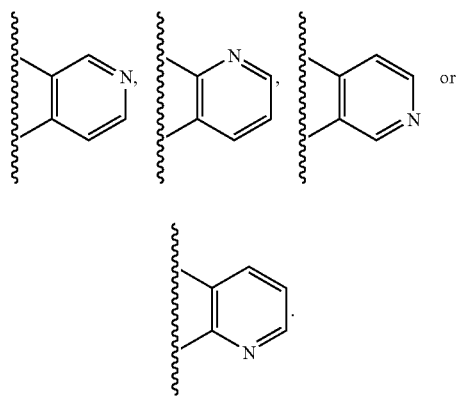

12. The compound of claim 1 having the formula:

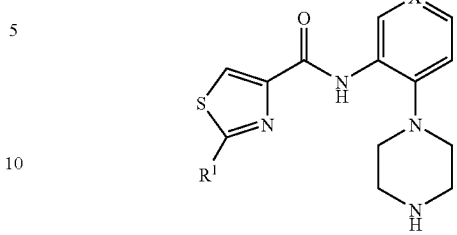

or a pharmaceutically acceptable salt, ester, prodrug or stereoisomer thereof, wherein X is N or CH; and $R^1$ is as defined in claim 1.

13. The compound of claim 12, wherein X is N.

14. A compound of claim 1 in purified form.

15. A pharmaceutical composition comprising an effective amount of at least one compound of claim 1 or a pharmaceutically acceptable salt, ester, prodrug or stereoisomer thereof, and a pharmaceutically acceptable carrier.

16. A pharmaceutical composition comprising an effective amount of at least one compound of claim 1 or a pharmaceutically acceptable salt, ester, prodrug or stereoisomer thereof, and a pharmaceutically acceptable carrier, further comprising an effective amount of at least one anticancer agent, wherein the anticancer agent is different from the compound of claim 1.

* * * * *